US009611485B2

(12) United States Patent
Li et al.

(10) Patent No.: US 9,611,485 B2
(45) Date of Patent: Apr. 4, 2017

(54) POLYNUCLEOTIDE AND POLYPEPTIDE SEQUENCES ASSOCIATED WITH HERBICIDE TOLERANCE

(75) Inventors: Bailin Li, Hockessin, DE (US); Kevin A. Fengler, Wilmington, DE (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 1331 days.

(21) Appl. No.: 13/013,139

(22) Filed: Jan. 25, 2011

(65) Prior Publication Data
US 2011/0185444 A1    Jul. 28, 2011

Related U.S. Application Data

(60) Provisional application No. 61/298,528, filed on Jan. 26, 2010, provisional application No. 61/298,523, filed on Jan. 26, 2010, provisional application No. 61/371,392, filed on Aug. 6, 2010, provisional application No. 61/371,454, filed on Aug. 6, 2010.

(51) Int. Cl.
| A01H 1/00 | (2006.01) |
|---|---|
| A01H 5/00 | (2006.01) |
| C07H 21/04 | (2006.01) |
| C12Q 1/68 | (2006.01) |
| C12N 15/82 | (2006.01) |

(52) U.S. Cl.
CPC ....... *C12N 15/8274* (2013.01); *C12Q 1/6895* (2013.01); *C12Q 2600/13* (2013.01); *C12Q 2600/156* (2013.01); *C12Q 2600/172* (2013.01)

(58) Field of Classification Search
USPC ....................................................... 800/300
See application file for complete search history.

(56) References Cited

U.S. PATENT DOCUMENTS

| 4,761,373 | A | 8/1988 | Anderson et al. |
|---|---|---|---|
| 5,013,659 | A | 5/1991 | Bedbrook et al. |
| 5,141,870 | A | 8/1992 | Bedbrook et al. |
| 5,304,732 | A | 4/1994 | Anderson et al. |
| 5,331,107 | A | 7/1994 | Anderson et al. |
| 5,378,824 | A | 1/1995 | Bedbrook et al. |
| 5,489,520 | A | 2/1996 | Adams et al. |
| 5,550,318 | A | 8/1996 | Adams et al. |
| 5,561,236 | A | 10/1996 | Leemans et al. |
| 5,605,011 | A | 2/1997 | Bedbrook et al. |
| 5,646,024 | A | 7/1997 | Leemans et al. |
| 5,648,477 | A | 7/1997 | Leemans et al. |
| 5,731,180 | A | 3/1998 | Dietrich |
| 5,767,361 | A | 6/1998 | Dietrich |
| 5,767,373 | A | 6/1998 | Ward et al. |
| 5,874,265 | A | 2/1999 | Adams et al. |
| 5,879,903 | A | 3/1999 | Strauch |
| 5,919,675 | A | 7/1999 | Adams et al. |
| 5,928,937 | A | 7/1999 | Kakefuda et al. |
| 5,969,213 | A | 10/1999 | Adams et al. |
| 6,069,115 | A | 5/2000 | Pallet et al. |
| 6,177,616 | B1 | 1/2001 | Bartsch et al. |
| 6,245,968 | B1 | 6/2001 | Boudec et al. |
| 6,268,549 | B1 | 7/2001 | Sailland et al. |
| 6,282,837 | B1 | 9/2001 | Ward et al. |
| 6,288,306 | B1 | 9/2001 | Ward et al. |
| 6,307,129 | B1 | 10/2001 | Ward et al. |
| 6,448,472 | B1 * | 9/2002 | Thomas et al. ............... 800/278 |
| 2003/0143586 | A1 * | 7/2003 | Chao et al. ........................ 435/6 |
| 2005/0112571 | A1 * | 5/2005 | Gielen et al. ...................... 435/6 |
| 2007/0128597 | A1 * | 6/2007 | Schwers et al. .................. 435/6 |

FOREIGN PATENT DOCUMENTS

| WO | WO 96/33270 | 10/1996 |
|---|---|---|
| WO | WO 99/23886 | 5/1999 |
| WO | WO 01/12825 | 2/2001 |
| WO | WO 2005/107437 | 11/2005 |
| WO | WO 2006/017840 | 2/2006 |
| WO | WO 2010/011803 | 1/2010 |

OTHER PUBLICATIONS

Schmutz et al, Genome Sequence of the Palaeopolyploid Soybean, Nature (2010) 463:178-183, disclosing the complete genome sequence of Glycine max; published Jan. 14, 2010; GenBank Accession No. ACUP00000000.*
Moller et al, A Plastidic ABC Protein Involved in Intercompartmental Communication of Light Sighting, Genes and Dev. (2001) 15:90-103.*
Conte S, Lloyd A.M, Exploring Multiple Drug and Herbicide Resistance in Plants—Spotlight on Transporter Proteins, Plant Science (2011) 180:196-203.*
Choi, et al., "A soybean transcript map: Gene distribution, haplotype and single nucleotide polymorphism analysis", Genetics, vol. 176, pp. 685-696 (2007).
Cregan, P.B., et al., "An integrated genetic linkage map of the soybean genome", Crop Science, vol. 39, pp. 1464-1490 (1990).
(Continued)

*Primary Examiner* — Mykola V Kovalenko

(57) ABSTRACT

This invention relates generally to the detection of genetic differences among soybeans. More particularly, soybean quantitative trait loci (QTL) associated with herbicide tolerance, including tolerance to one or more of an HPPD-inhibitor herbicide, such as mesotrione and isoxazole herbicides, and/or a PPO inhibitor herbicide; soybean plants possessing these QTLs; and genetic markers that are indicative of phenotypes associated with such herbicide tolerance are provided. Methods and compositions for use of these markers in genotyping of soybean and selection are also disclosed, as are methods and compositions for use of herbicides for weed control. Also disclosed are isolated polynucleotides and polypeptides relating to such tolerance or sensitivity and methods of introgressing such tolerance into a plant by breeding or transgenically, or by a combination thereof. Plant cells, plants, and seeds produced are also provided.

10 Claims, 30 Drawing Sheets

(56) References Cited

OTHER PUBLICATIONS

Dayan et al., "Soybean (*Glycine max*) cultivar differences in response to sulfentrazone", Weed Science, vol. 45, pp. 634-641 (1997).
Henikoff, et al., "Amino acid substitution matrices from protein blocks" Proc. Natl. Acad. Sci. USA, vol. 89, pp. 10915-10919 (1992).
Herman, et al., "A Three-component Dicamba O-Demethylase from Pseudomonas maltophilia, Strain DI-6: Gene Isolation . . . ", J. Biol. Chem., vol. 280, pp. 24759-24767 (2005).
Hulting, et al., "Soybean (*Glycine max* (L.) Merr.) cultivar tolerance to sulfehtrazone", Science Direct, vol. 20, pp. 679-683 (2001).
Li, Z., et al., "Physiological basis for the differential tolerance of *Glycine max* to sulfentrazone during seed germination", Weed Science, vol. 48, pp. 281-285 (2000).
Li, Z., et al., "Using electrolyte leakage to detect soybean (*Glycine max*) cultivars sensitive to sulfentrazone", Weed Technology, vol. 14, pp, 699-704 (2000).
Needleman, et al., "A general method applicable to the search for similarities in the amino acid sequence of two proteins", J. Mol. Biol., vol. 48, pp. 443-453 (1970).
Retzinger, et al., "Classification of herbicides by site of action for weed resistance management strategies", Weed Technology, vol. 11, pp. 383-393 (1997).
Shoemaker, et al., "Molecular linkage map of soybean (*Glycine max* L, Merr.)", pp. 6.131-6.138 (1993), in S.J. O'Brien (ed.) Genetic Maps: Locus Maps of Complex Genomes . . . .
Shoemaker, R.C., "RFLP map of soybean", pp. 299-309 (1994), In R. L. Phillips and I.K. Vasil (eds.) DNA based markers in plants. Kluwer Academic Pres Dordrecht, Netherlands.
Swantek, J.M., et al., "Evaluation of soybean injury from sulfentrazone and inheritance of tolerance", Weed Science, vol. 46, p. 271-277 (1998).
Taylor-Lovell, et al., "Phytoxic response and yield of soybean (*Glycine max*) varieties treated with sulfentrazone or flumioxazin", Weed Technology, vol. 15, pp. 95-102 (2001).
International Search Report in PCT/US2009/051483, mailed Oct. 13, 2009.
Copending U.S. Appl. No. 12/506,498, filed Jul. 21, 2009.
Copending U.S. Appl. No. 12/694,255, filed Jan. 26, 2010.
Copending U.S. Appl. No. 13/013,332, filed Jan. 25, 2011.
Eichhorn, H., et al., "Isolation of a novel ABC-transporter gene from soybean induced by salicylic acid", J. Exp. Botany, 2006, pp. 2193-2201, vol. 57, No. 10.

\* cited by examiner

FIG. 1A

| Marker | Linkage Group | Position | Type |
|---|---|---|---|
| SATT495 | L | 0.00 | SSR |
| SATT723 | L | 0.44 | SSR |
| SAT_408 | L | 1.00 | SSR |
| S08102-1-Q1 | L | | SNP |
| S08103-1-Q1 | | | |
| S08104-1-Q1 | | | |
| S08106-1-Q1 | | | |
| S08107-1-Q1 | | | |
| S08107-1-Q1 | | | |
| S08109-1-Q1 | | | |
| S08110-1-Q1 | | | |
| S08111-1-Q1 | | | |
| S08115-2-Q1 | | | |
| S08117-1-Q1 | | | |
| S08119-1-Q1 | | | |
| S08116-1-Q1 | | | |
| S08112-1-Q1 | | | |
| S08108-1-Q1 | | | |
| S08101-4-Q1 | | | |
| S08101-1-Q1 | | | |
| S08101-2-Q1 | | | |
| S08101-3-Q1 | | | |
| S08118-1-Q1 | | | |
| S08114-1-Q1 | | | |
| S08113-1-Q1 | | | |
| S03859-1-A | | | |
| Sat_301 | L | 10.31 | SSR |
| SATT446 | L | 11.13 | SSR |
| P10649C-3 | L | 12.5 | ASH |
| SATT232 | L | 12.55 | SSR |
| S08105-1-Q1 | L | | SNP |
| SATT182 | L | 13.90 | SSR |
| S08010-1-Q1 | L | | SNP |
| S08010-2-Q1 | | | |
| SATT238 | L | 19.41 | SSR |
| Sat_071 | L | 20.04 | SSR |
| SATT388 | L | 21.61 | SSR |
| SATT497 | L | 26.06 | SSR |
| SATT313 | L | 27.35 | SSR |
| SATT143 | L | 28.16 | SSR |
| Sat_397 | L | 28.26 | SSR |
| SATT418 | L | 28.57 | SSR |
| Sat_134 | L | 28.66 | SSR |

| | | | |
|---|---|---|---|
| SATT652 | L | 28.67 | SSR |
| SATT711 | L | 28.67 | SSR |
| Sat_187 | L | 28.68 | SSR |
| Sat_195 | L | 28.68 | SSR |
| Sat_388 | L | 28.71 | SSR |
| SATT694 | L | 28.71 | SSR |
| SATT398 | L | 28.90 | SSR |
| Sat_191 | L | 29.19 | SSR |
| Sat_405 | L | 29.40 | SSR |
| Sat_320 | L | 29.74 | SSR |
| SATT523 | L | 30.18 | SSR |
| SATT278 | L | 30.34 | SSR |
| SATT613 | L | 32.64 | SSR |

FIG. 1B

| Linked Markers | | | | | |
|---|---|---|---|---|---|
| Satt495 | Satt723 | Sat_408 | A169_1 | EV2_1 | Sle3_4s |
| BLT010_2 | BLT007_1 | Satt232 | Sat_301 | Satt446 | Satt182 |
| R176_1 | JUBC090 | Satt238 | Sat_071 | BLT039_1 | Bng071_1 |
| Satt388 | A264_1 | RGA_7 | RGA7 | Satt523 | Sat_134 |
| LbA | i8_2 | A450_2 | A106_1 | Sat_405 | Satt143 |
| B124_2 | A459_1 | Satt398 | Satt694 | Sat_195 | Sat_388 |
| Satt652 | Satt711 | Sat_187 | Satt418 | Satt278 | Sat_397 |
| Sat_191 | Sat_320 | O109_1 | A204_2 | Satt497 | G214_17 |
| Satt313 | B164_1 | G214_16 | Satt613 | A023_1 | Satt284 |
| AW508247 | Satt462 | L050_7 | E014_1 | A071_5 | B046_1 |
| L1 | B162_2 | S00224-1 | S01659-1 | | |

FIG. 2

| Marker Name | PCR Primers | Allele Probes |
|---|---|---|
| P10649C-3<br>LG-L | Primer Seq 1 (SEQ ID NO. 1):<br>GAGGGCTATGTTTCTCTCCCAGATGTGAG<br>Primer Seq 2 (SEQ ID NO. 2):<br>AAGGTCGGCTTGGTGGTTAAAGGCAG | Allele 1 Probe (SEQ ID NO. 3):<br>TCATcTgTGATAA<br>Allele 2 Probe (SEQ ID NO. 4):<br>TCATgTgTGATAA<br>Allele 3 Probe (SEQ ID NO. 5):<br>TCATcTcTGATAA |
| S00224-1<br>LG-L | Primer Seq 1 (F) (SEQ ID NO. 6):<br>CTGGACCTACCCGGGATGAAAA<br>Primer Seq 2 (R) (SEQ ID NO. 7):<br>TCTTCCTCTCCCTTCCTCTCGC | Allele 1 Probe (PF1) (SEQ ID NO. 8):<br>CGCGAcTCTCCTC<br>Allele 2 Probe (PV1) (SEQ ID NO. 9):<br>CGCGAgTCTCCTC |
| P5467-1<br>LG-N | Primer Seq 1 (SEQ ID NO. 10):<br>TCCCAGGTTAGATTTTCTGAACGAAGA<br>Primer Seq 2 (SEQ ID NO. 11):<br>CATCAGCACAAAAGGGCATCCTCA | Allele 1 Probe (SEQ ID NO. 12):<br>CACTCCTTAAGgTAAT<br>Allele 2 Probe (SEQ ID NO. 13):<br>CACTCCTTAAGaTAAT |
| S08101-1-Q1<br>LG-L | Primer Seq 1 (F) (SEQ ID NO. 14):<br>gttatcgtcaccaccacaa<br>Primer Seq 2 (R) (SEQ ID NO. 15):<br>Cacaaacacgagttagccgtagg | Allele 1 Probe (PF1) (SEQ ID NO. 16)<br>aacggAtcatcacaac<br>Allele 2 Probe (PV1) (SEQ ID NO. 17)<br>aacggCtcatcacaa |
| S08101-2-Q1<br>LG-L | Primer Seq 1 (F) (SEQ ID NO. 18):<br>cgacaatggcctttacacct<br>Primer Seq 2 (R) (SEQ ID NO. 19):<br>tcgatatggacgaaggagga | Allele 1 Probe (PF1) (SEQ ID NO. 20)<br>acaaccAtttttcatcc<br>Allele 2 Probe (PV1) (SEQ ID NO. 21)<br>acaccCttttcatcc |
| S08101-3-Q1<br>LG-L | Primer Seq 1 (F) (SEQ ID NO. 22):<br>GCAATCACATTTGCATTCCTTA<br>Primer Seq 2 (R) (SEQ ID NO. 23):<br>TCTGAACGAGTTGTGCAAGAA | Allele 1 Probe (PF1) (SEQ ID NO. 24)<br>actgctGcttgtcta<br>Allele 2 Probe (PV1) (SEQ ID NO. 25)<br>ctactgctActttgtc |

FIG. 3A

| Marker Name | PCR Primers | Allele Probes |
|---|---|---|
| S08101-4-Q1 LG-L | Primer Seq 1 (F) (SEQ ID NO. 26): acctcgtattggtgtggtg<br>Primer Seq 2 (R) (SEQ ID NO. 27): gaatgttcagtgcgagcaac | Allele 1 Probe (PF1) (SEQ ID NO. 28) acttccctcGtttcg<br>Allele 2 Probe (PV1) (SEQ ID NO. 29) cttccctcAtttcg |
| S08102-1-Q1 LG-L | Primer Seq 1 (F) (SEQ ID NO. 30): caaaaggaaaagaaccgtgt<br>Primer Seq 2 (R) (SEQ ID NO. 31): tccaacctatgtgttggttg | Allele 1 Probe (PF1) (SEQ ID NO. 32) atgattgaagcagGaaa<br>Allele 2 Probe (PV1) (SEQ ID NO. 33) tcatgattgaagcagCaa |
| S08103-1-Q1 LG-L | Primer Seq 1 (F) (SEQ ID NO. 34): gggagacttgacttaaagagaaagaaaa<br>Primer Seq 2 (R) (SEQ ID NO. 35): cggaaagaaaaacaatagatgaatg | Allele 1 Probe (PF1) (SEQ ID NO. 36) cttgttctagactgatCat<br>Allele 2 Probe (PV1) (SEQ ID NO. 37) ctagactgatAattca |
| S08104-1-Q1 LG-L | Primer Seq 1 (F) (SEQ ID NO. 38): tcattcaagactacatgaaagacaaa<br>Primer Seq 2 (R) (SEQ ID NO. 39): caagggaagagcaatccttga | Allele 1 Probe (PF1) (SEQ ID NO. 40) atagtctcCcaaaacac<br>Allele 2 Probe (PV1) (SEQ ID NO. 41) atagtctcTcaaacacc |
| S08105-1-Q1 LG-L | Primer Seq 1 (F) (SEQ ID NO. 42): gaaactttccatttgccctc<br>Primer Seq 2 (R) (SEQ ID NO. 43): agaacgcaggggagaagc | Allele 1 Probe (PF1) (SEQ ID NO. 44) ccttcttCcactcttac<br>Allele 2 Probe (PV1) (SEQ ID NO. 45) ccttcttAcactcttac |
| S08106-1-Q1 LG-L | Primer Seq 1 (F) (SEQ ID NO. 46): tgatatgacactctaagatgtgttg<br>Primer Seq 2 (R) (SEQ ID NO. 47): tgattcatccgcaaacttga | Allele 1 Probe (PF1) (SEQ ID NO. 48) cactctcctaTattgtc<br>Allele 2 Probe (PV1) (SEQ ID NO. 49) ctctccctaCattgtca |
| S08107-1-Q1 LG-L | Primer Seq 1 (F) (SEQ ID NO. 50): agatccttgttccaaattccaa<br>Primer Seq 2 (R) (SEQ ID NO. 51): ccttggcttaatgggtgtgt | Allele 1 Probe (PF1) (SEQ ID NO. 52) ccaacacaatcTaact<br>Allele 2 Probe (PV1) (SEQ ID NO. 53) ccaacacaatcGaa |

FIG. 3B

| Marker Name | PCR Primers | Allele Probes |
|---|---|---|
| S08108-1-Q1 LG-L | Primer Seq 1 (F) (SEQ ID NO. 54): atggaggcaagctgtgttt<br>Primer Seq 2 (R) (SEQ ID NO. 55): catgctaccagcatctgcaa | Allele 1 Probe (PF1) (SEQ ID NO. 56): cttcataaaCgccaaag<br>Allele 2 Probe (PV1) (SEQ ID NO. 57): cataaaTgccaaagca |
| S08109-1-Q1 LG-L | Primer Seq 1 (F) (SEQ ID NO. 58): aatgagcaaggaggaggaca<br>Primer Seq 2 (R) (SEQ ID NO. 59): tcgccgctgctatttaattt | Allele 1 Probe (PF1) (SEQ ID NO. 60): aagcacTactttcaattg<br>Allele 2 Probe (PV1) (SEQ ID NO. 61): aagcacCactttca |
| S08110-1-Q1 LG-L | Primer Seq 1 (F) (SEQ ID NO. 62): agatgccttgctcagtggac<br>Primer Seq 2 (R) (SEQ ID NO. 63): atgatgaatgtgttgagccaat | Allele 1 Probe (PF1) (SEQ ID NO. 64): ccccaTcaccatac<br>Allele 2 Probe (PV1) (SEQ ID NO. 65): accccaCcaccata |
| S08111-1-Q1 LG-L | Primer Seq 1 (F) (SEQ ID NO. 66): agaaaccttccaaagctcttgg<br>Primer Seq 2 (R) (SEQ ID NO. 67): tagggaggcacttgacaacc | Allele 1 Probe (PF1) (SEQ ID NO. 68): caacatcCgagtcca<br>Allele 2 Probe (PV1) (SEQ ID NO. 69): caacatcAgagtcca |
| S08112-1-Q1 LG-L | Primer Seq 1 (F) (SEQ ID NO. 70): ttttgaccccagagagttg<br>Primer Seq 2 (R) (SEQ ID NO. 71): ttgcaagcctaaaggatggt | Allele 1 Probe (PF1) (SEQ ID NO. 72): ctatctcTacacgatgtgt<br>Allele 2 Probe (PV1) (SEQ ID NO. 73): ctatctcCacacgatg |
| S08115-2-Q1 LG-L | Primer Seq 1 (F) (SEQ ID NO. 74): tcccacttgatcttgcagaa<br>Primer Seq 2 (R) (SEQ ID NO. 75): tacggtgggtggattattcg | Allele 1 Probe (PF1) (SEQ ID NO. 76): cctccaatGgcatac<br>Allele 2 Probe (PV1) (SEQ ID NO. 77): cctccaatAgcatacat |
| S08116-1-Q1 LG-L | Primer Seq 1 (F) (SEQ ID NO. 78): agaaaagcagcagaaagaggac<br>Primer Seq 2 (R) (SEQ ID NO. 79): cttcatgaatccaacatcaga | Allele 1 Probe (PF1) (SEQ ID NO. 80): ctctaattCcacatctg<br>Allele 2 Probe (PV1) (SEQ ID NO. 81): cctctaattTcacatctg |

FIG. 3C

| Marker Name | PCR Primers | Allele Probes |
|---|---|---|
| S08117-1-Q1 LG-L | Primer Seq 1 (F) (SEQ ID NO. 82): tcaaaccattigtttccagt Primer Seq 2 (R) (SEQ ID NO. 83): tgctagcctttgaataccaac | Allele 1 Probe (PF1) (SEQ ID NO. 84) ttgcattgtattCtct Allele 2 Probe (PV1) (SEQ ID NO. 85) ttgcattgtattTtc |
| S08118-1-Q1 LG-L | Primer Seq 1 (F) (SEQ ID NO. 86): gtctcaggcagtgaatctgct Primer Seq 2 (R) (SEQ ID NO. 87): cagccttaccatcaacatcg | Allele 1 Probe (PF1) (SEQ ID NO. 88) ttccgTgaagatc Allele 2 Probe (PV1) (SEQ ID NO. 89) atgcttccgCgaaga |
| S08119-1-Q1 LG-L | Primer Seq 1 (F) (SEQ ID NO. 90): ggtagcagtacttigtgatgtaagc Primer Seq 2 (R) (SEQ ID NO. 91): catgcaattaaaatcaaaacca | Allele 1 Probe (PF1) (SEQ ID NO. 92) tactgaTcacaggttat Allele 2 Probe (PV1) (SEQ ID NO. 93) tactgaCcacaggttat |
| S04867-1-A LG-L | Primer Seq 1 (F) (SEQ ID NO. 94): ttgctttggaaaggactcca Primer Seq 2 (R) (SEQ ID NO. 95): Cctcatcaactcctgctgct | Allele 1 Probe (PF1) (SEQ ID NO. 96) ctcggtgctgtTtt Allele 2 Probe (PV1) (SEQ ID NO. 97) ctcggtgctgtCtt |
| S03859-1-A LG-L | Primer Seq 1 (F) (SEQ ID NO. 98): gaaaccaatttgatgtgaagga Primer Seq 2 (R) (SEQ ID NO. 99): aagtgagaggggtgcaaaga | Allele 1 Probe (PF1) (SEQ ID NO. 100) cagccctAtctcac Allele 2 Probe (PV1) (SEQ ID NO. 101) agccctGtctact |
| S08010-1-Q1 LG-L | Primer Seq 1 (F) (SEQ ID NO. 102): gcaaatgagaaggctgaagct Primer Seq 2 (R) (SEQ ID NO. 103): gctgtccctcagtccatcc | Allele 1 Probe (PF1) (SEQ ID NO. 104) cggtatcgctcgTca Allele 2 Probe (PV1) (SEQ ID NO. 105) tatcgctcgCcaacg |
| S08010-2-Q1 LG-L | Primer Seq 1 (F) (SEQ ID NO. 106): atccacttgcaagataggacact Primer Seq 2 (R) (SEQ ID NO. 107): gtgtaagtactgatgtgcagttttga | Allele 1 Probe (PF1) (SEQ ID NO. 108) ctttgacattaagact.atcc Allele 2 Probe (PV1) (SEQ ID NO. 109) agactAatccttaaacaag |

FIG. 3D

| Marker Name | PCR Primers | Allele Probes |
|---|---|---|
| S08114-1-Q1 LG-L | Primer Seq 1 (F) (SEQ ID NO: 110): tcaacaggttatgaatatacaggtcaa<br>Primer Seq 2 (R) (SEQ ID NO: 111): catcaccaattgtttgcagttc | Allele 1 Probe (PF1) (SEQ ID NO: 112) ctattactcTccgttattt<br>Allele 2 Probe (PV1) (SEQ ID NO: 113) ctattactcCccgttatt |
| S08113-1-Q1 LG-L | Primer Seq 1 (F) (SEQ ID NO: 114): ttgttgaatgggggcact<br>Primer Seq 2 (R) (SEQ ID NO: 115): ctcgagcaaatctcgatggt | Allele 1 Probe (PF1) (SEQ ID NO: 116) ttgaatgCttactctct<br>Allele 2 Probe (PV1) (SEQ ID NO: 117) ttgaatgTttactctctt |
| S08007-1-Q1 LG-L | Primer Seq 1 (F) (SEQ ID NO: 118): ctgtggaggagagcttgag<br>Primer Seq 2 (R) (SEQ ID NO: 119): acaagtcacaaccgtcaatgat | Allele 1 Probe (PF1) (SEQ ID NO: 120) agtcttgttttctctTtt<br>Allele 2 Probe (PV1) (SEQ ID NO: 121) agtcttgttttctctCtt |

FIG. 3E

```
SEQ128 (Tol)  MHADGLDWFLMIFGLFGAIGDGIGTPLVLFITSKIMNNIGGFSSNIGSTF  50
              ||||||||||||| ||||||||||||||||||||||||||||||||||||
SEQ129 (Sus)  MHADGLDWFLMIFGLFGAIGDGIGTPLVLFITSKIMNNIGGFSSNIGSTF  50

IHSINENAVVLLYLAGGSFIACFLEGYCWTRTGERQAARMRVRYLKAVLR  100
              ||||||||||||||||||||||||||||||||||||||||||||||||||
              IHSINENAVVLLYLAGGSFIACFLEGYCWTRTGERQAARMRVRYLKAVLR  100

QEVAYFDLHVTSTSEVITSVSNDSLVIQDCLSEKVPNFLMNASMFVGSYI  150
              ||||||||||||||||||||||||||||||||||||||||||||||||||
              QEVAYFDLHVTSTSEVITSVSNDSLVIQDCLSEKVPNFLMNASMFVGSYI  150

VAFALLWRLAIVGFPFVALLVIPGFMYGRTLMGLASKIREEYNKAGTIAE  200
              ||||||||||||||||||||||||||||||||||||||||||||||||||
              VAFALLWRLAIVGFPFVALLVIPGFMYGRTLMGLASKIREEYNKAGTIAE  200

QAISSIRTVYSFVGESKTIDAFSEALQGSVELGLRQGLAKGLAIGSNGVV  250
              ||||||||||||||||||||||||||||||||||||||||||||||||||
              QAISSIRTVYSFVGESKTIDAFSEALQGSVELGLRQGLAKGLAIGSNGVV  250

FAIWAFMSYYGSRLVMYHGAKGGTVFAVGAAIALGGLALGAGLSNVKYFS  300
              ||||||||||||||||||||||||||||||||||||||||||||||||||
              FAIWAFMSYYGSRLVMYHGAKGGTVFAVGAAIALGGLALGAGLSNVKYFS  300

EASTAGERIMEVIKRVPKIDSDSMAEEILENVSGEVEFNHVDFVYPSRPD  350
              ||||||||||||||||||||||||||||||||||||||||||||||||||
              EASTAGERIMEVIKRVPKIDSDSMAEEILENVSGEVEFNHVDFVYPSRPD  350

SVILNDFCLKIPAGKTVALVGGSGSGKSTVISLLQRFYDPIEGEIFLDGV  400
              ||||||||||||||||||||||||||||||||||||||||||||||||||
              SVILNDFCLKIPAGKTVALVGGSGSGKSTVISLLQRFYDPIEGEIFLDGV  400

AIHKLQLKWLRSQMGLVSQEPALFATSIKENILFGREDATQEEVVEAAKA  450
              ||||||||||||||||||||||||||||||||||||||||||||||||||
              AIHKLQLKWLRSQMGLVSQEPALFATSIKENILFGREDATQEEVVEAAKA  450

SNAHNFISQLPQGYDTQVGERGVQMSGGQKQRIAIARAIIKKPRILLLDE  500
              |||||||||||||||||||||||||| |||||||||||||||||||||||
              SNAHNFISQLPQGYDTQVGERGVQMSGEQKQRIAIARAIIKKPRILLLDE  500

ATSALDSESERVVQEALDKAAVGRTTIIAHRLSTIRNANVIAVVQSGKI  550
              ||||||||||||||||||| ||||||||||||||||||||||||||||
              ATSALDSESERVVQEALDKVAVGRTTTIIAHRLSTIRNANVIAVVQSGKI  550

MEMGSHHELIQNDNGLYTSLVRLQQAKNEKEDTIFHPTPPSSISNKDNHN  600
              |||||||||||||||||||||||||||||||| |||||||||||||||||
              MEMGSHHELIQNDNGLYTSLVRLQQAKNEKEDTLFHPTPPSSISNKDNHN  600

TSSRRLSVVMIRSSSTNSIPRIGGGDDNNIVEEVVEDNKPPLPSFRRLLA  650
              |||||||||| |||||||||||||||||||||||||||||||||||||||
              TSSRRLSVVMSRSSSTNSIPRIGGGDDNNIVEEVVEDNKPPLPSFRRLLA  650
```

FIG. 6A

```
LNIPEWKQACLGCLNAVLFGAIQPVYAFAMGSVISVYFLPDHNEIKKKTM 700
|||||||||||||||||||||||||||||||||||||||||||||||||
LNIPEWKQACLGCLNAVLFGAIQPVYAFAMGSVISVYFLPDHNEIKKKTM 700

IYSLCFLGLAVFSLVVNILQHYNFAYIGEYLTKRIRERMFSKILTFEVGW 750
|||||||||||||||||||||||||||||||||||||||||||||||||
IYSLCFLGLAVFSLVVNILQHYNFAYIGEYLTKRIRERMFSKILTFEVGW 750

FDQDENSTGAVCSRLAKEANVVRSLVGDRMALVVQTISAVVIAFTMGLII 800
|||||||||||||||||||||||||||||||||||||||||||||||||
FDQDENSTGAVCSRLAKEANVVRSLVGDRMALVVQTISAVVIAFTMGLII 800

AWRLAIVMIAVQPIIIACFYTRRVLLKSMSSKAIKAQDESSKIAVEAVSN 850
|||||||||||||||||||||||||||||||||||||||||||||||||
AWRLAIVMIAVQPIIIACFYTRRVLLKSMSSKAIKAQDESSKIAVEAVSN 850

LRTITAFSSQDRILKMLEKAQEGPSRESIRQSWFAGIGLACSQSLTFCTW 900
|||||||||||||||||||||||||||||||||||||||||||||||||
LRTITAFSSQDRILKMLEKAQEGPSRESIRQSWFAGIGLACSQSLTFCTW 900

ALDFWYGGKLVFQGFINAKALFETFMILVSTGRVIADAGSMTNDLAKGAD 950
|||||||||||||||||||||||||||||||||||||||||||||||||
ALDFWYGGKLVFQGFINAKALFETFMILVSTGRVIADAGSMTNDLAKGAD 950

AVGSVFAILDRYTKIEPDDDIDGYKPEKLTGKIELHDVHFAYPARPNVMI 1000
|||||||||||:|||||||||||||||||||||||||||||||||||||
AVGSVFAILDKYTKIEPDDDIDGYKPEKLTGKIELHDVHFAYPARPNVMI 1000

FQGFSIKIDAGRSTALVGQSGSGKSTIIGLIERFYDPMKGIVTIDGRDIK 1050
||||:||||||||||||||||||||||||||||||||||||:|||||||
FQGFSIKIDAGRSTALVGQSGSGKSTIIGLIERFYDPLKGIVTIDGRDIK 1050

SYHLRSLRKHIALVSQEPTLFGGTIRENIAYGASNNNNKVDETEIIEAAR 1100
|||||||||||||||||||||||||||||||||||||||||||||||||
SYHLRSLRKHIALVSQEPTLFGGTIRENIAYGASNNNNKVDETEIIEAAR 1100

AANAHDFIASLKDGYDTSCRDRGVQLSGGQKQRIAIARAILKNPEVLLLD 1150
||||||||||||||||||| |||||||||||||||||||||||||||||
AANAHDFIASLKDGYDTSCGDRGVQLSGGQKQRIAIARAILKNPEVLLLD 1150

EATSALDSQSEKLVQDALERVMVGRTSVVVAHRLSTIQNCDLIAVLDKGK 1200
|||||||||||||||||||||||||||||||||||||||||||||||||
EATSALDSQSEKLVQDALERVMVGRTSVVVAHRLSTIQNCDLIAVLDKGK 1200

VVEKGTHSSLLAHGPGGAYYSLISLQRRPAN 1231
|||||||||||||||||||||||||||||||
VVEKGTHSSLLAHGPGGAYYSLISLQRRPAN 1231
```

FIG. 6B

```
SEQ125 (Sus)  TGGCTCTCTTCGGTCTATTTTCATGCATGCTGATGGCTTAGACTGGTTCC  50
              ||||||||||||||||||||||||||||||||||||||||||||||||||
SEQ124 (Tol)  TGGCTCTCTTCGGTCTATTTTCATGCATGCTGATGGCTTAGACTGGTTCC  50

TCATGATTTTTGGTCTCTTTGGGGCCATTGGTGATGGCATAGGCACCCCT  100
              ||||||||||||||||||||||||||||||||||||||||||||||||||
              TCATGATTTTTGGTCTCTTTGGGGCCATTGGTGATGGCATAGGCACCCCT  100

TTGGTGTTGTTTATCACCAGCAAAATTATGAACAATATTGGTGGTTTTTC  150
              ||||||||||||||||||||||||||||||||||||||||||||||||||
              TTGGTGTTGTTTATCACCAGCAAAATTATGAACAATATTGGTGGTTTTTC  150

TAGCAACATAGGCAGCACTTTCATCCACAGCATCAATGAGAATGCCGTGG  200
              ||||||||||||||||||||||||||||||||||||||||||||||||||
              TAGCAACATAGGCAGCACTTTCATCCACAGCATCAATGAGAATGCCGTGG  200

TTTTGTTATATTTGGCTGGTGGGTCTTTCATTGCTTGTTTCCTAGAGGGT  250
              ||||||||||||||||||||||||||||||||||||||||||||||||||
              TTTTGTTATATTTGGCTGGTGGGTCTTTCATTGCTTGTTTCCTAGAGGGT  250

TATTGTTGGACAAGAACAGGAGAAAGGCAAGCTGCAAGAATGAGAGTTAG  300
              ||||||||||||||||||||||||||||||||||||||||||||||||||
              TATTGTTGGACAAGAACAGGAGAAAGGCAAGCTGCAAGAATGAGAGTTAG  300

GTACCTTAAAGCAGTTCTCAGGCAAGAAGTAGCATACTTTGATTTGCATG  350
              ||||||||||||||||||||||||||||||||||||||||||||||||||
              GTACCTTAAAGCAGTTCTCAGGCAAGAAGTAGCATACTTTGATTTGCATG  350

TCACAAGCACATCGGAGGTCATCACCAGCGTCTCTAATGATAGCCTCGTA  400
              ||||||||||||||||||||||||||||||||||||||||||||||||||
              TCACAAGCACATCGGAGGTCATCACCAGCGTCTCTAATGATAGCCTCGTA  400

ATTCAAGATTGTCTTAGTGAAAAGGTCCCAAACTTTTTGATGAATGCGTC  450
              ||||||||||||||||||||||||||||||||||||||||||||||||||
              ATTCAAGATTGTCTTAGTGAAAAGGTCCCAAACTTTTTGATGAATGCGTC  450

CATGTTTGTTGGGAGCTACATAGTGGCTTTTGCATTATTGTGGAGATTGG  500
              ||||||||||||||||||||||||||||||||||||||||||||||||||
              CATGTTTGTTGGGAGCTACATAGTGGCTTTTGCATTATTGTGGAGATTGG  500

CCATTGTGGGGTTCCCTTTTGTGGCCCTACTTGTGATCCCCGGTTTCATG  550
              ||||||||||||||||||||||||||||||||||||||||||||||||||
              CCATTGTGGGGTTCCCTTTTGTGGCCCTACTTGTGATCCCCGGTTTCATG  550

TATGGGAGGACATTAATGGGGTTGGCTAGCAAGATAAGAGAAGAGTACAA  600
              ||||||||||||||||||||||||||||||||||||||||||||||||||
              TATGGGAGGACATTAATGGGGTTGGCTAGCAAGATAAGAGAAGAGTACAA  600

TAAAGCAGGCACAATAGCAGAACAAGCAATATCCTCCATCAGAACCGTTT  650
              ||||||||||||||||||||||||||||||||||||||||||||||||||
              TAAAGCAGGCACAATAGCAGAACAAGCAATATCCTCCATCAGAACCGTTT  650

ATTCTTTTGTGGGGGAAAGCAAGACTATTGATGCTTTCTCTGAAGCCCTA  700
              ||||||||||||||||||||||||||||||||||||||||||||||||||
              ATTCTTTTGTGGGGGAAAGCAAGACTATTGATGCTTTCTCTGAAGCCCTA  700
```

FIG. 7A

```
CAAGGGTCTGTTGAGTTGGGACTGAGACAAGGCTTAGCAAAAGGTTTAGC  750
||||||||||||||||||||||||||||||||||||||||||||||||||
CAAGGGTCTGTTGAGTTGGGACTGAGACAAGGCTTAGCAAAAGGTTTAGC  750

TATTGGAAGCAATGGTGTTGTCTTTGCTATATGGGCATTCATGTCCTATT  800
||||||||||||||||||||||||||||||||||||||||||||||||||
TATTGGAAGCAATGGTGTTGTCTTTGCTATATGGGCATTCATGTCCTATT  800

ATGGTAGCAGATTGGTCATGTACCATGGAGCTAAAGGTGGGACTGTATTT  850
||||||||||||||||||||||||||||||||||||||||||||||||||
ATGGTAGCAGATTGGTCATGTACCATGGAGCTAAAGGTGGGACTGTATTT  850

GCAGTTGGAGCAGCCATAGCTCTTGGAGGATTGGCACTAGGTGCTGGTTT  900
||||||||||||||||||||||||||||||||||||||||||||||||||
GCAGTTGGAGCAGCCATAGCTCTTGGAGGATTGGCACTAGGTGCTGGTTT  900

GTCGAACGTGAAGTACTTCTCAGAAGCAAGTACCGCAGGAGAACGCATAA  950
||||||||||||||||||||||||||||||||||||||||||||||||||
GTCGAACGTGAAGTACTTCTCAGAAGCAAGTACCGCAGGAGAACGCATAA  950

TGGAAGTGATAAAAAGGGTTCCAAAGATTGATTCTGATAGCATGGCTGAG  1000
||||||||||||||||||||||||||||||||||||||||||||||||||
TGGAAGTGATAAAAAGGGTTCCAAAGATTGATTCTGATAGCATGGCTGAG  1000

GAGATTCTGGAGAACGTTTCAGGGAAGTTGAATTCAACCATGTGGACTT  1050
||||||||||||||||||||||||||||||||||||||||||||||||||
GAGATTCTGGAGAACGTTTCAGGGAAGTTGAATTCAACCATGTGGACTT  1050

TGTGTACCCATCAAGGCCAGACAGTGTTATTCTGAATGATTTCTGCCTAA  1100
||||||||||||||||||||||||||||||||||||||||||||||||||
TGTGTACCCATCAAGGCCAGACAGTGTTATTCTGAATGATTTCTGCCTAA  1100

AGATTCCAGCAGGGAAAACAGTGGCTTTGGTTGGAGGGAGTGGCTCTGGA  1150
||||||||||||||||||||||||||||||||||||||||||||||||||
AGATTCCAGCAGGGAAAACAGTGGCTTTGGTTGGAGGGAGTGGCTCTGGA  1150

AAATCCACTGTGATATCACTTTTGCAGAGGTTTTATGACCCAATTGAGGG  1200
||||||||||||||||||||||||||||||||||||||||||||||||||
AAATCCACTGTGATATCACTTTTGCAGAGGTTTTATGACCCAATTGAGGG  1200

AGAGATATTTCTTGATGGTGTGGCCATTCACAAGTTGCAACTCAAGTGGT  1250
||||||||||||||||||||||||||||||||||||||||||||||||||
AGAGATATTTCTTGATGGTGTGGCCATTCACAAGTTGCAACTCAAGTGGT  1250

TGAGGTCTCAAATGGGTTTGGTCAGCCAAGAGCCTGCACTGTTTGCAACT  1300
||||||||||||||||||||||||||||||||||||||||||||||||||
TGAGGTCTCAAATGGGTTTGGTCAGCCAAGAGCCTGCACTGTTTGCAACT  1300

AGCATTAAAGAGAATATACTTTTTGGAAGAGAAGATGCCACTCAAGAAGA  1350
||||||||||||||||||||||||||||||||||||||||||||||||||
AGCATTAAAGAGAATATACTTTTTGGAAGAGAAGATGCCACTCAAGAAGA  1350

GGTTGTGGAGGCAGCAAAAGCTTCCAATGCTCATAATTTCATTTCACAGT  1400
||||||||||||||||||||||||||||||||||||||||||||||||||
GGTTGTGGAGGCAGCAAAAGCTTCCAATGCTCATAATTTCATTTCACAGT  1400
```

FIG. 7B

```
TGCCACAAGGATATGATACTCAGGTTGGGGAGAGAGGAGTTCAAATGTCA 1450
||||||||||||||||||||||||||||||||||||||||||||||||||
TGCCACAAGGATATGATACTCAGGTTGGGGAGAGAGGAGTTCAAATGTCA 1450

GGTGAACAAAAGCAAAGAATTGCAATAGCACGAGCAATAATAAAAAGCC 1500
||||  ||||||||||||||||||||||||||||||||||||||||||||
GGTGGACAAAAGCAAAGAATTGCAATAGCACGAGCAATAATAAAAAGCC 1500

ACGGATTCTTCTATTAGATGAAGCAACAAGTGCACTAGATTCTGAATCTG 1550
||||||||||||||||||||||||||||||||||||||||||||||||||
ACGGATTCTTCTATTAGATGAAGCAACAAGTGCACTAGATTCTGAATCTG 1550

AACGAGTTGTGCAAGAAGCATTAGACAAAGTAGCAGTAGGGCGCACAACA 1600
|||||||||||||||||||||||||||||| |||||||||||||||||||
AACGAGTTGTGCAAGAAGCATTAGACAAAGCAGCAGTAGGGCGCACAACA 1600

ATCATCATTGCACATAGATTATCCACCATAAGGAATGCAAATGTGATTGC 1650
||||||||||||||||||||||||||||||||||||||||||||||||||
ATCATCATTGCACATAGATTATCCACCATAAGGAATGCAAATGTGATTGC 1650

TGTTGTGCAAAGTGGGAAAATCATGGAGATGGGATCACACCATGAACTAA 1700
||||||||||||||||||||||||||||||||||||||||||||||||||
TGTTGTGCAAAGTGGGAAAATCATGGAGATGGGATCACACCATGAACTAA 1700

TCCAAAACGACAATGGCCTTTACACCTCACTAGTTCGTCTCCAACAAGCA 1750
||||||||||||||||||||||||||||||||||||||||||||||||||
TCCAAAACGACAATGGCCTTTACACCTCACTAGTTCGTCTCCAACAAGCA 1750

AAAAATGAAAAAGAAGACACCCTTTTTCATCCTACTCCTCCTTCGTCCAT 1800
||||||||||||||||||||| ||||||||||||||||||||||||||||
AAAAATGAAAAAGAAGACACCATTTTTCATCCTACTCCTCCTTCGTCCAT 1800

ATCGAACAAAGACAATCACAACACGAGTAGCCGTAGGCTCTCTGTTGTGA 1850
||||||||||||||||||||||||||||||||||||||||||||||||||
ATCGAACAAAGACAATCACAACACGAGTAGCCGTAGGCTCTCTGTTGTGA 1850

TGAGCCGTTCTAGCTCCACCAACTCGATACCTCGTATTGGTGGTGGTGAC 1900
||| ||||||||||||||||||||||||||||||||||||||||||||||
TGATCCGTTCTAGCTCCACCAACTCGATACCTCGTATTGGTGGTGGTGAC 1900

GATAACAATATTGTTGAAGAAGTAGTGGAAGATAACAAGCCACCACTTCC 1950
||||||||||||||||||||||||||||||||||||||||||||||||||
GATAACAATATTGTTGAAGAAGTAGTGGAAGATAACAAGCCACCACTTCC 1950

CTCATTTCGAAGGTTGCTCGCACTGAACATTCCCGAGTGGAAGCAAGCAT 2000
|||  |||||||||||||||||||||||||||||||||||||||||||||
CTCGTTTCGAAGGTTGCTCGCACTGAACATTCCCGAGTGGAAGCAAGCAT 2000

GTTTAGGGTGTTTGAATGCGGTGTTGTTTGGTGCAATTCAGCCTGTGTAT 2050
|||||||||||||||||||||||||||||||||||||||||||||||||||
GTTTAGGGTGTTTGAATGCGGTGTTGTTTGGTGCAATTCAGCCTGTGTAT 2050

GCATTTGCAATGGGGTCAGTGATATCTGTTACTTCCTCCCAGACCATAA 2100
||||||||||||||||||||||||||||||||||||||||||||||||||
GCATTTGCAATGGGGTCAGTGATATCTGTTACTTCCTCCCAGACCATAA 2100
```

FIG. 7C

```
TGAGATAAAGAAGAAAACTATGATCTATTCACTTTGTTTCCTAGGGTTGG 2150
||||||||||||||||||||||||||||||||||||||||||||||||||
TGAGATAAAGAAGAAAACTATGATCTATTCACTTTGTTTCCTAGGGTTGG 2150

CTGTGTTCTCCTTAGTGGTTAATATCCTCCAGCATTACAACTTTGCTTAC 2200
||||||||||||||||||||||||||||||||||||||||||||||||||
CTGTGTTCTCCTTAGTGGTTAATATCCTCCAGCATTACAACTTTGCTTAC 2200

ATAGGAGAGTACTTGACTAAAAGGATCAGAGAAAGAATGTTTTCCAAGAT 2250
||||||||||||||||||||||||||||||||||||||||||||||||||
ATAGGAGAGTACTTGACTAAAAGGATCAGAGAAAGAATGTTTTCCAAGAT 2250

ACTCACTTTTGAAGTTGGATGGTTTGATCAAGATGAAAATTCCACAGGTG 2300
||||||||||||||||||||||||||||||||||||||||||||||||||
ACTCACTTTTGAAGTTGGATGGTTTGATCAAGATGAAAATTCCACAGGTG 2300

CTGTTTGTTCTAGACTTGCCAAAGAAGCCAATGTGGTAAGGTCTTTAGTG 2350
||||||||||||||||||||||||||||||||||||||||||||||||||
CTGTTTGTTCTAGACTTGCCAAAGAAGCCAATGTGGTAAGGTCTTTAGTG 2350

GGAGATAGAATGGCTCTAGTGGTACAAACCATTTCAGCAGTGGTAATAGC 2400
||||||||||||||||||||||||||||||||||||||||||||||||||
GGAGATAGAATGGCTCTAGTGGTACAAACCATTTCAGCAGTGGTAATAGC 2400

TTTTACAATGGGCCTAATCATTGCATGGAGGTTGGCCATTGTTATGATAG 2450
||||||||||||||||||||||||||||||||||||||||||||||||||
TTTTACAATGGGCCTAATCATTGCATGGAGGTTGGCCATTGTTATGATAG 2450

CAGTTCAACCCATTATCATAGCATGTTTCTACACAAGGCGTGTCCTTCTC 2500
||||||||||||||||||||||||||||||||||||||||||||||||||
CAGTTCAACCCATTATCATAGCATGTTTCTACACAAGGCGTGTCCTTCTC 2500

AAGAGCATGTCTAGTAAGGCCATCAAGGCCCAAGATGAAAGTAGCAAGAT 2550
||||||||||||||||||||||||||||||||||||||||||||||||||
AAGAGCATGTCTAGTAAGGCCATCAAGGCCCAAGATGAAAGTAGCAAGAT 2550

AGCTGTTGAAGCTGTTTCCAACCTCAGAACAATCACAGCATTTTCTTCCC 2600
||||||||||||||||||||||||||||||||||||||||||||||||||
AGCTGTTGAAGCTGTTTCCAACCTCAGAACAATCACAGCATTTTCTTCCC 2600

AAGATAGGATCCTTAAAATGCTCGAAAAGGCCCAAGAAGGCCCGAGCCGT 2650
||||||||||||||||||||||||||||||||||||||||||||||||||
AAGATAGGATCCTTAAAATGCTCGAAAAGGCCCAAGAAGGCCCGAGCCGT 2650

GAAAGCATTCGACAATCATGGTTTGCGGGCATTGGGCTTGCATGTTCCCA 2700
||||||||||||||||||||||||||||||||||||||||||||||||||
GAAAGCATTCGACAATCATGGTTTGCGGGCATTGGGCTTGCATGTTCCCA 2700

AAGCCTTACATTTGCACTTGGGCTTTGGACTTTTGGTATGGAGGCAAGC 2750
||||||||||||||||||||||||||||||||||||||||||||||||||
AAGCCTTACATTTGCACTTGGGCTTTGGACTTTTGGTATGGAGGCAAGC 2750

TTGTGTTTCAGGGCTTCATAAATGCCAAAGCATTGTTTGAGACCTTCATG 2800
|||||||||||||||||||||||| |||||||||||||||||||||||||
TTGTGTTTCAGGGCTTCATAAACGCCAAAGCATTGTTTGAGACCTTCATG 2800
```

FIG. 7D

```
ATTTTAGTGAGCACAGGTAGGGTTATTGCAGATGCTGGTAGCATGACCAA 2850
||||||||||||||||||||||||||||||||||||||||||||||||||
ATTTTAGTGAGCACAGGTAGGGTTATTGCAGATGCTGGTAGCATGACCAA 2850

TGACCTAGCTAAAGGGGCTGATGCTGTGGGCTCAGTTTTTGCAATCTTAG 2900
||||||||||||||||||||||||||||||||||||||||||||||||||
TGACCTAGCTAAAGGGGCTGATGCTGTGGGCTCAGTTTTTGCAATCTTAG 2900

ATAAGTACACAAAAATTGAGCCAGATGATGACATAGATGGGTACAAGCCT 2950
|||  |||||||||||||||||||||||||||||||||||||||||||||
ATAGGTACACAAAAATTGAGCCAGATGATGACATAGATGGGTACAAGCCT 2950

GAAAAGCTAACAGGGAAAATAGAGCTTCATGATGTCCATTTTGCATACCC 3000
||||||||||||||||||||||||||||||||||||||||||||||||||
GAAAAGCTAACAGGGAAAATAGAGCTTCATGATGTCCATTTTGCATACCC 3000

AGCTAGGCCCAATGTGATGATCTTCCAAGGCTTCTCAATCAAAATTGATG 3050
||||||||||||||||||||||||||||||||||||||||||||||||||
AGCTAGGCCCAATGTGATGATCTTCCAAGGCTTCTCAATCAAAATTGATG 3050

CAGGCAGATCAACAGCATTGGTCGGGCAAAGTGGCTCTGGAAAATCAACA 3100
||||||||||||||||||||||| ||||||||||||||||||||||||||
CAGGCAGATCAACAGCATTGGTTGGGCAAAGTGGCTCTGGAAAATCAACA 3100

ATCATAGGCTTAATTGAGAGATTCTATGACCCTCTAAAAGGGATTGTGAC 3150
||||||||||||||||||||||||||||||||||| ||||||||||||||
ATCATAGGCTTAATTGAGAGATTCTATGACCCTATGAAAGGGATTGTGAC 3150

CATTGATGGTAGAGACATAAAATCATACCACCTTAGGTCACTAAGGAAGC 3200
||||||||||||||||||||||||||||||||||||||||||||||||||
CATTCATGGTAGAGACATAAAATCATACCACCTTAGGTCACTAAGGAAGC 3200

ATATTGCTCTTGTAAGCCAAGAGCCAACATTGTTTGGTGGGACCATAAGG 3250
||||||||||||||||||||||||||||||||||||||||||||||||||
ATATTGCTCTTGTAAGCCAAGAGCCAACATTGTTTGGTGGGACCATAAGG 3250

GAAAATATTGCATATGGGGCATCTAATAATAATAACAAGGTTGATGAAAC 3300
||||||||||||||||||||||||||||||||||||||||||||||||||
GAAAATATTGCATATGGGGCATCTAATAATAATAACAAGGTTGATGAAAC 3300

TGAGATCATAGAAGCAGCTAGGGCAGCTAATGCTCATGATTTCATTGCAA 3350
||||||||||||||||||||||||||||||||||||||||||||||||||
TGAGATCATAGAAGCAGCTAGGGCAGCTAATGCTCATGATTTCATTGCAA 3350

GCCTAAAGGATGGTTATGACACATCGTGTGGAGATAGAGGAGTGCAACTC 3400
|||||||||||||||||||||||||| |||||||||||||||||||||||
GCCTAAAGGATGGTTATGACACATCGTGTAGAGATAGAGGAGTGCAACTC 3400

TCTGGGGGTCAAAAGCAAAGAATTGCAATAGCTAGAGCCATATTGAAGAA 3450
||||||||||||||||||||||||||||||||||||||||||||||||||
TCTGGGGGTCAAAAGCAAAGAATTGCAATAGCTAGAGCCATATTGAAGAA 3450

TCCAGAAGTGTTGTTGTTGGATGAAGCCACAAGTGCCCTAGATAGCCAAT 3500
||||||||||||||||||||||||||||||||||||||||||||||||||
TCCAGAAGTGTTGTTGTTGGATGAAGCCACAAGTGCCCTAGATAGCCAAT 3500
```

FIG. 7E

```
CAGAAAAATTGGTGCAAGATGCTCTAGAAAGGGTGATGGTGGGGAGAACT 3550
||||||||||||||||||||||||||||||||||||||||||||||||||
CAGAAAAATTGGTGCAAGATGCTCTAGAAAGGGTGATGGTGGGGAGAACT 3550

AGTGTGGTGGTGGCTCACAGGTTAAGCACAATACAAAATTGTGACCTAAT 3600
||||||||||||||||||||||||||||||||||||||||||||||||||
AGTGTGGTGGTGGCTCACAGGTTAAGCACAATACAAAATTGTGACCTAAT 3600

TGCTGTGTTAGATAAGGGAAAAGTGGTGGAGAAAGGGACCCACTCATCTT 3650
||||||||||||||||||||||||||||||||||||||||||||||||||
TGCTGTGTTAGATAAGGGAAAAGTGGTGGAGAAAGGGACCCACTCATCTT 3650

TGTTGGCTCATGGACCAGGTGGAGCTTATTACTCTTTGATAAGTTTACAA 3700
||||||||||||||||||||||||||||||||||||||||||||||||||
TGTTGGCTCATGGACCAGGTGGAGCTTATTACTCTTTGATAAGTTTACAA 3700

AGAAGACCAGCAAATTAAACATGAATGTTAGTTTTACGCATGAAATCTCA 3750
||||||||||||||||||||||||||||||||||||||||||||||||||
AGAAGACCAGCAAATTAAACATGAATGTTAGTTTTACGCATGAAATCTCA 3750

GCTAGCTAATCAAAACAAACAAAATGTCACATTTATTGGTGATTAGTATT 3800
||||||||||||||||||||||||||||||||||||||||||||||||||
GCTAGCTAATCAAAACAAACAAAATGTCACATTTATTGGTGATTAGTATT 3800

AAACCTCTTTTGTGCTAACTTGTGAAAGTAAATTAAGAAAAATGAAAGAA 3850
||||||||||||||||||||||||||||||||||||||||||||||||||
AAACCTCTTTTGTGCTAACTTGTGAAAGTAAATTAAGAAAAATGAAAGAA 3850

AAGTAAATTAAGCAAAGATAGAAGCGAAGAACTATATAACAGTTGTAGTC 3900
|||||||||||||||||||||||||||| |||||||||||||||||||||
AAGTAAATTAAGCAAAGATAGAAGGGAAGAATTATATAACAGTTGTAGTC 3900

TCTCCCAACTTCCTAAATTC 3920
||||||||||||||||||||
TCTCCCAACTTCCTAAATTC 3920
```

FIG. 7F

```
        1                                                    50
SEQ127  MHADGLDWFL MIFGLFGAIG DGIGTPLVLF ITSKIMNNIG GFSSNIGSTF
SEQ126  MHADGLDWFL MIFGLFGAIG DGIGTPLVLF ITSKIMNNIG GFSSNIGSTF
SEQ128  MHADGLDWFL MIFGLFGAIG DGIGTPLVLF ITSKIMNNIG GFSSNIGSTF
SEQ129  MHADGLDWFL MIFGLFGAIG DGIGTPLVLF ITSKIMNNIG GFSSNIGSTF 51                                                   100
SEQ127  IHSINENAVV LLYLAGGSFI ACFLEGYCWT RTGERQAARM RVRYLKAVLR
SEQ126  IHSINENAVV LLYLAGGSFI ACFLEGYCWT RTGERQAARM RVRYLKAVLR
SEQ128  IHSINENAVV LLYLAGGSFI ACFLEGYCWT RTGERQAARM RVRYLKAVLR
SEQ129  IHSINENAVV LLYLAGGSFI ACFLEGYCWT RTGERQAARM RVRYLKAVLR 101                                                  150
SEQ127  QEVAYFDLHV TSTSEVITSV SNDSLVIQDC LSEKVPNFLM NASMFVGSYI
SEQ126  QEVAYFDLHV TSTSEVITSV SNDSLVIQDC LSEKVPNFLM NASMFVGSYI
SEQ128  QEVAYFDLHV TSTSEVITSV SNDSLVIQDC LSEKVPNFLM NASMFVGSYI
SEQ129  QEVAYFDLHV TSTSEVITSV SNDSLVIQDC LSEKVPNFLM NASMFVGSYI 151                                                  200
SEQ127  VAFALLWRLA IVGFPFVALL VIPGFMYGRT LMGLASKIRE EYNKAGTIAE
SEQ126  VAFALLWRLA IVGFPFVALL VIPGFMYGRT LMGLASKIRE EYNKAGTIAE
SEQ128  VAFALLWRLA IVGFPFVALL VIPGFMYGRT LMGLASKIRE EYNKAGTIAE
SEQ129  VAFALLWRLA IVGFPFVALL VIPGFMYGRT LMGLASKIRE EYNKAGTIAE 201                                                  250
SEQ127  QAISSIRTVY SFVGESKTID AFSEALQGSV ELGLRQGLAK GLAIGSNGVV
SEQ126  QAISSIRTVY SFVGESKTID AFSEALQGSV ELGLRQGLAK GLAIGSNGVV
SEQ128  QAISSIRTVY SFVGESKTID AFSEALQGSV ELGLRQGLAK GLAIGSNGVV
SEQ129  QAISSIRTVY SFVGESKTID AFSEALQGSV ELGLRQGLAK GLAIGSNGVV 251                                                  300
SEQ127  FAIWAFMSYY GSRLVMYHGA KGGTVFAVGA AIALGGLALG AGLSNVKYFS
SEQ126  FAIWAFMSYY GSRLVMYHGA KGGTVFAVGA AIALGGLALG AGLSNVKYFS
SEQ128  FAIWAFMSYY GSRLVMYHGA KGGTVFAVGA AIALGGLALG AGLSNVKYFS
SEQ129  FAIWAFMSYY GSRLVMYHGA KGGTVFAVGA AIALGGLALG AGLSNVKYFS 301                                                  350
SEQ127  EASTAGERIM EVIKRVPKID SDSMAEEILE NVSGEVEFNH VDFVYPSRPD
SEQ126  EASTAGERIM EVIKRVPKID SDSMAEEILE NVSGEVEFNH VDFVYPSRPD
SEQ128  EASTAGERIM EVIKRVPKID SDSMAEEILE NVSGEVEFNH VDFVYPSRPD
SEQ129  EASTAGERIM EVIKRVPKID SDSMAEEILE NVSGEVEFNH VDFVYPSRPD 351                                                  400
SEQ127  SVILNDFCLK IPAGKTVALV GGSGSGKSTV ISLLQRFYDP IEGEIFLDGV
SEQ126  SVILNDFCLK IPAGKTVALV GGSGSGKSTV ISLLQRFYDP IEGEIFLDGV
SEQ128  SVILNDFCLK IPAGKTVALV GGSGSGKSTV ISLLQRFYDP IEGEIFLDGV
SEQ129  SVILNDFCLK IPAGKTVALV GGSGSGKSTV ISLLQRFYDP IEGEIFLDGV 401                                                  450
SEQ127  AIHKLQLKWL RSQMGLVSQE PALFATSIKE NILFGREDAT QEEVVEAAKA
SEQ126  AIHKLQLKWL RSQMGLVSQE PALFATSIKE NILFGREDAT QEEVVEAAKA
SEQ128  AIHKLQLKWL RSQMGLVSQE PALFATSIKE NILFGREDAT QEEVVEAAKA
SEQ129  AIHKLQLKWL RSQMGLVSQE PALFATSIKE NILFGREDAT QEEVVEAAKA
```

FIG. 8A

```
             451                                                          500
SEQ127  SNAHNFISQL PQGYDTQVGE RGVQMSGGQK QRIAIARAII KKPRILLLDE
SEQ126  SNAHNFISQL PQGYDTQVGE RGVQMSGGQK QRIAIARAII KKPRILLLDE
SEQ128  SNAHNFISQL PQGYDTQVGE RGVQMSGGQK QRIAIARAII KKPRILLLDE
SEQ129  SNAHNFISQL PQGYDTQVGE RGVQMSGEQK QRIAIARAII KKPRILLLDE 501                                                          550
SEQ127  ATSALDSESE RVVQEALDKV AVGRTTIIIA HRLSTIRNAN VIAVVQSGKI
SEQ126  ATSALDSESE RVVQEALDKA AVGRTTIIIA HRLSTIRNAN VIAVVQSGKI
SEQ128  ATSALDSESE RVVQEALDKA AVGRTTILIA HRLSTIRNAN VIAVVQSGKI
SEQ129  ATSALDSESE RVVQEALDKV AVGRTTIIIA HRLSTIRNAN VIAVVQSGKI 551                                                          600
SEQ127  MEMGSHHELI QNDNGLYTSL VRLQQAKNEK EDTLFHPTPP SSISNKDNHN
SEQ126  MEMGSHHELI QNDNGLYTSL VRLQQAKNEK EDTIFHPTPP SSISNKDNHN
SEQ128  MEMGSHHELI QNDNGLYTSL VRLQQAKNEK EDTIFHPTPP SSISNKDNHN
SEQ129  MEMGSHHELI QNDNGLYTSL VRLQQAKNEK EDTLFHPTPP SSISNKDNHN 601                                                          650
SEQ127  TSSRRLSVVM SRSSSTNSIP RIGGGDDNNI VEEVVEDNKP PLPSFRRLLA
SEQ126  TSSRRLSVVM IRSSSTNSIP RIGGGDDNNI VEEVVEDNKP PLPSFRRLLA
SEQ128  TSSRRLSVVM IRSSSTNSIP RIGGGDDNNI VEEVVEDNKP PLPSFRRLLA
SEQ129  TSSRRLSVVM SRSSSTNSIP RIGGGDDNNI VEEVVEDNKP PLPSFRRLLA 651                                                          700
SEQ127  LNIPEWKQAC LGCLNAVLFG AIQPVYAFAM GSVISVYFLP DHNEIKKKTM
SEQ126  LNIPEWKQAC LGCLNAVLFG AIQPVYAFAM GSVISVYFLP DHNEIKKKTM
SEQ128  LNIPEWKQAC LGCLNAVLFG AIQPVYAFAM GSVISVYFLP DHNEIKKKTM
SEQ129  LNIPEWKQAC LGCLNAVLFG AIQPVYAFAM GSVISVYFLP DHNEIKKKTM 701                                                          750
SEQ127  IYSLCFLGLA VFSLVVNILQ HYNFAYIGEY LTKRIRERMF SKILTFEVGW
SEQ126  IYSLCFLGLA VFSLVVNILQ HYNFAYIGEY LTKRIRERMF SKILTFEVGW
SEQ128  IYSLCFLGLA VFSLVVNILQ HYNFAYIGEY LTKRIRERMF SKILTFEVGW
SEQ129  IYSLCFLGLA VFSLVVNILQ HYNFAYIGEY LTKRIRERMF SKILTFEVGW 751                                                          800
SEQ127  FDQDENSTGA VCSRLAKEAN V........N GLVVQTISAV VIAFTMGLII
SEQ126  FDQDENSTGA VCSRLAKEAN V........N GLVVQTISAV VIAFTMGLII
SEQ128  FDQDENSTGA VCSRLAKEAN VVRSLVGDRM ALVVQTISAV VIAFTMGLII
SEQ129  FDQDENSTGA VCSRLAKEAN VVRSLVGDRM ALVVQTISAV VIAFTMGLII 801                                                          850
SEQ127  AWRLAIVMIA VQPIIIACFY TRRVLLKSMS SKAIKAQDES SKIAVEAVSN
SEQ126  AWRLAIVMIA VQPIIIACFY TRRVLLKSMS SKAIKAQDES SKIAVEAVSN
SEQ128  AWRLAIVMIA VQPIIIACFY TRRVLLKSMS SKAIKAQDES SKIAVEAVSN
SEQ129  AWRLAIVMIA VQPIIIACFY TRRVLLKSMS SKAIKAQDES SKIAVEAVSN 851                                                          900
SEQ127  LRTITAFSSQ DRILKMLEKA QEGPSRESIR QSWFAGIGLA CSQSLTFCTW
SEQ126  LRTITAFSSQ DRILKMLEKA QEGPSRESIR QSWFAGIGLA CSQSLTFCTW
SEQ128  LRTITAFSSQ DRILKMLEKA QEGPSRESIR QSWFAGIGLA CSQSLTFCTW
SEQ129  LRTITAFSSQ DRILKMLEKA QEGPSRESIR QSWFAGIGLA CSQSLTFCTW
```

FIG. 8B

```
         901                                                          950
SEQ127 ALDFWYGGKL VFQGFINAKA LFETFMILVS TGRVIADAGS MTNDLAKGAD
SEQ126 ALDFWYGGKL VFQGFINAKA LFETFMILVS TGRVIADAGS MTNDLAKGAD
SEQ128 ALDFWYGGKL VFQGFINAKA LFETFMILVS TGRVIADAGS MTNDLAKGAD
SEQ129 ALDFWYGGKL VFQGFINAKA LFETFMILVS TGRVIADAGS MTNDLAKGAD 951                                                         1000
SEQ127 AVGSVFAILD KYTKIEPDDD IDGYKPEKLT GKIELHDVHF AYPARPNVMI
SEQ126 AVGSVFAILD RYTKIEPDDD IDGYKPEKLT GKIELHDVHF AYPARPNVMI
SEQ128 AVGSVFAILD RYTKIEPDDD IDGYKPEKLT GKIELHDVHF AYPARPNVMI
SEQ129 AVGSVFAILD KYTKIEPDDD IDGYKPEKLT GKIELHDVHF AYPARPNVMI 1001                                                         1050
SEQ127 FQGFSIKIDA GRSTALVGQS GSGKSTIIGL IERFYDPLKG IVTIDGRDIK
SEQ126 FQGFSIKIDA GRSTALVGQS GSGKSTIIGL IERFYDPMKG IVTIDGRDIK
SEQ128 FQGFSIKIDA GRSTALVGQS GSGKSTIIGL IERFYDPMKG IVTIDGRDIK
SEQ129 FQGFSIKIDA GRSTALVGQS GSGKSTIIGL IERFYDPLKG IVTIDGRDIK 1051                                                         1100
SEQ127 SYHLRSLRKH IALVSQEPTL FGGTIRENIA YGASNNNNKV DETEIIEAAR
SEQ126 SYHLRSLRKH IALVSQEPTL FGGTIRENIA YGASNNNNKV DETEIIEAAR
SEQ128 SYHLRSLRKH IALVSQEPTL FGGTIRENIA YGASNNNNKV DETEIIEAAR
SEQ129 SYHLRSLRKH IALVSQEPTL FGGTIRENIA YGASNNNNKV DETEIIEAAR 1101                                                         1150
SEQ127 AANAHDFIAS LKDGYDTSCG DRGVQLSGGQ KQRIAIARAI LKNPEVLLLD
SEQ126 AANAHDFIAS LKDGYDTSCR DRGVQLSGGQ KQRIAIARAI LKNPEVLLLD
SEQ128 AANAHDFIAS LKDGYDTSCR DRGVQLSGGQ KQRIAIARAI LKNPEVLLLD
SEQ129 AANAHDFIAS LKDGYDTSCG DRGVQLSGGQ KQRIAIARAI LKNPEVLLLD 1151                                                         1200
SEQ127 EATSALDSQS EKLVQDALER VMVGRTSVVV AHRLSTIQNC DLIAVLDKGK
SEQ126 EATSALDSQS EKLVQDALER VMVGRTSVVV AHRLSTIQNC DLIAVLDKGK
SEQ128 EATSALDSQS EKLVQDALER VMVGRTSVVV AHRLSTIQNC DLIAVLDKGK
SEQ129 EATSALDSQS EKLVQDALER VMVGRTSVVV AHRLSTIQNC DLIAVLDKGK 1201                                        1231
SEQ127 VVEKGTHSSL LAHGPGGAYY SLISLQRRPA N
SEQ126 VVEKGTHSSL LAHGPGGAYY SLISLQRRPA N
SEQ128 VVEKGTHSSL LAHGPGGAYY SLISLQRRPA N
SEQ129 VVEKGTHSSL LAHGPGGAYY SLISLQRRPA N
```

FIG. 8C

```
            1                                                            50
SEQ123   ~~~~~~~~~~ ~~~~~~~~~~ ~~ATGCATGC TGATGGCTTA GACTGGTTCC
SEQ122   ~~~~~~~~~~ ~~~~~~~~~~ ~~ATGCATGC TGATGGCTTA GACTGGTTCC
SEQ125   TGGCTCTCTT CGGTCTATTT TCATGCATGC TGATGGCTTA GACTGGTTCC
SEQ124   TGGCTCTCTT CGGTCTATTT TCATGCATGC TGATGGCTTA GACTGGTTCC 51                                                           100
SEQ123   TCATGATTTT TGGTCTCTTT GGGGCCATTG GTGATGGCAT AGGCACCCCT
SEQ122   TCATGATTTT TGGTCTCTTT GGGGCCATTG GTGATGGCAT AGGCACCCCT
SEQ125   TCATGATTTT TGGTCTCTTT GGGGCCATTG GTGATGGCAT AGGCACCCCT
SEQ124   TCATGATTTT TGGTCTCTTT GGGGCCATTG GTGATGGCAT AGGCACCCCT 101                                                          150
SEQ123   TTGGTGTTGT TTATCACCAG CAAAATTATG AACAATATTG GTGGTTTTTC
SEQ122   TTGGTGTTGT TTATCACCAG CAAAATTATG AACAATATTG GTGGTTTTTC
SEQ125   TTGGTGTTGT TTATCACCAG CAAAATTATG AACAATATTG GTGGTTTTTC
SEQ124   TTGGTGTTGT TTATCACCAG CAAAATTATG AACAATATTG GTGGTTTTTC 151                                                          200
SEQ123   TAGCAACATA GGCAGCACTT TCATCCACAG CATCAATGAG AATGCCGTGG
SEQ122   TAGCAACATA GGCAGCACTT TCATCCACAG CATCAATGAG AATGCCGTGG
SEQ125   TAGCAACATA GGCAGCACTT TCATCCACAG CATCAATGAG AATGCCGTGG
SEQ124   TAGCAACATA GGCAGCACTT TCATCCACAG CATCAATGAG AATGCCGTGG 201                                                          250
SEQ123   TTTTGTTATA TTTGGCTGGT GGGTCTTTCA TTGCTTGTTT CCTAGAGGGT
SEQ122   TTTTGTTATA TTTGGCTGGT GGGTCTTTCA TTGCTTGTTT CCTAGAGGGT
SEQ125   TTTTGTTATA TTTGGCTGGT GGGTCTTTCA TTGCTTGTTT CCTAGAGGGT
SEQ124   TTTTGTTATA TTTGGCTGGT GGGTCTTTCA TTGCTTGTTT CCTAGAGGGT 251                                                          300
SEQ123   TATTGTTGGA CAAGAACAGG AGAAAGGCAA GCTGCAAGAA TGAGAGTTAG
SEQ122   TATTGTTGGA CAAGAACAGG AGAAAGGCAA GCTGCAAGAA TGAGAGTTAG
SEQ125   TATTGTTGGA CAAGAACAGG AGAAAGGCAA GCTGCAAGAA TGAGAGTTAG
SEQ124   TATTGTTGGA CAAGAACAGG AGAAAGGCAA GCTGCAAGAA TGAGAGTTAG 301                                                          350
SEQ123   GTACCTTAAA GCAGTTCTCA GGCAAGAAGT AGCATACTTT GATTTGCATG
SEQ122   GTACCTTAAA GCAGTTCTCA GGCAAGAAGT AGCATACTTT GATTTGCATG
SEQ125   GTACCTTAAA GCAGTTCTCA GGCAAGAAGT AGCATACTTT GATTTGCATG
SEQ124   GTACCTTAAA GCAGTTCTCA GGCAAGAAGT AGCATACTTT GATTTGCATG 351                                                          400
SEQ123   TCACAAGCAC ATCGGAGGTC ATCACCAGCG TCTCTAATGA TAGCCTCGTA
SEQ122   TCACAAGCAC ATCGGAGGTC ATCACCAGCG TCTCTAATGA TAGCCTCGTA
SEQ125   TCACAAGCAC ATCGGAGGTC ATCACCAGCG TCTCTAATGA TAGCCTCGTA
SEQ124   TCACAAGCAC ATCGGAGGTC ATCACCAGCG TCTCTAATGA TAGCCTCGTA 401                                                          450
SEQ123   ATTCAAGATT GTCTTAGTGA AAAGGTCCCA AACTTTTTGA TGAATGCGTC
SEQ122   ATTCAAGATT GTCTTAGTGA AAAGGTCCCA AACTTTTTGA TGAATGCGTC
SEQ125   ATTCAAGATT GTCTTAGTGA AAAGGTCCCA AACTTTTTGA TGAATGCGTC
SEQ124   ATTCAAGATT GTCTTAGTGA AAAGGTCCCA AACTTTTTGA TGAATGCGTC
```

FIG. 9A

```
        451                                                    500
SEQ123  CATGTTTGTT GGGAGCTACA TAGTGGCTTT TGCATTATTG TGGAGATTGG
SEQ122  CATGTTTGTT GGGAGCTACA TAGTGGCTTT TGCATTATTG TGGAGATTGG
SEQ125  CATGTTTGTT GGGAGCTACA TAGTGGCTTT TGCATTATTG TGGAGATTGG
SEQ124  CATGTTTGTT GGGAGCTACA TAGTGGCTTT TGCATTATTG TGGAGATTGG 501                                                    550
SEQ123  CCATTGTGGG GTTCCCTTTT GTGGCCCTAC TTGTGATCCC CGGTTTCATG
SEQ122  CCATTGTGGG GTTCCCTTTT GTGGCCCTAC TTGTGATCCC CGGTTTCATG
SEQ125  CCATTGTGGG GTTCCCTTTT GTGGCCCTAC TTGTGATCCC CGGTTTCATG
SEQ124  CCATTGTGGG GTTCCCTTTT GTGGCCCTAC TTGTGATCCC CGGTTTCATG 551                                                    600
SEQ123  TATGGGAGGA CATTAATGGG GTTGGCTAGC AAGATAAGAG AAGAGTACAA
SEQ122  TATGGGAGGA CATTAATGGG GTTGGCTAGC AAGATAAGAG AAGAGTACAA
SEQ125  TATGGGAGGA CATTAATGGG GTTGGCTAGC AAGATAAGAG AAGAGTACAA
SEQ124  TATGGGAGGA CATTAATGGG GTTGGCTAGC AAGATAAGAG AAGAGTACAA 601                                                    650
SEQ123  TAAAGCAGGC ACAATAGCAG AACAAGCAAT ATCCTCCATC AGAACCGTTT
SEQ122  TAAAGCAGGC ACAATAGCAG AACAAGCAAT ATCCTCCATC AGAACCGTTT
SEQ125  TAAAGCAGGC ACAATAGCAG AACAAGCAAT ATCCTCCATC AGAACCGTTT
SEQ124  TAAAGCAGGC ACAATAGCAG AACAAGCAAT ATCCTCCATC AGAACCGTTT 651                                                    700
SEQ123  ATTCTTTTGT GGGGAAAGC AAGACTATTG ATGCTTTCTC TGAAGCCCTA
SEQ122  ATTCTTTTGT GGGGAAAGC AAGACTATTG ATGCTTTCTC TGAAGCCCTA
SEQ125  ATTCTTTTGT GGGGAAAGC AAGACTATTG ATGCTTTCTC TGAAGCCCTA
SEQ124  ATTCTTTTGT GGGGAAAGC AAGACTATTG ATGCTTTCTC TGAAGCCCTA 701                                                    750
SEQ123  CAAGGGTCTG TTGAGTTGGG ACTGAGACAA GGCTTAGCAA AAGGTTTAGC
SEQ122  CAAGGGTCTG TTGAGTTGGG ACTGAGACAA GGCTTAGCAA AAGGTTTAGC
SEQ125  CAAGGGTCTG TTGAGTTGGG ACTGAGACAA GGCTTAGCAA AAGGTTTAGC
SEQ124  CAAGGGTCTG TTGAGTTGGG ACTGAGACAA GGCTTAGCAA AAGGTTTAGC 751                                                    800
SEQ123  TATTGGAAGC AATGGTGTTG TCTTTGCTAT ATGGGCATTC ATGTCCTATT
SEQ122  TATTGGAAGC AATGGTGTTG TCTTTGCTAT ATGGGCATTC ATGTCCTATT
SEQ125  TATTGGAAGC AATGGTGTTG TCTTTGCTAT ATGGGCATTC ATGTCCTATT
SEQ124  TATTGGAAGC AATGGTGTTG TCTTTGCTAT ATGGGCATTC ATGTCCTATT 801                                                    850
SEQ123  ATGGTAGCAG ATTGGTCATG TACCATGGAG CTAAAGGTGG GACTGTATTT
SEQ122  ATGGTAGCAG ATTGGTCATG TACCATGGAG CTAAAGGTGG GACTGTATTT
SEQ125  ATGGTAGCAG ATTGGTCATG TACCATGGAG CTAAAGGTGG GACTGTATTT
SEQ124  ATGGTAGCAG ATTGGTCATG TACCATGGAG CTAAAGGTGG GACTGTATTT 851                                                    900
SEQ123  GCAGTTGGAG CAGCCATAGC TCTTGGAGGA TTGGCACTAG GTGCTGGTTT
SEQ122  GCAGTTGGAG CAGCCATAGC TCTTGGAGGA TTGGCACTAG GTGCTGGTTT
SEQ125  GCAGTTGGAG CAGCCATAGC TCTTGGAGGA TTGGCACTAG GTGCTGGTTT
SEQ124  GCAGTTGGAG CAGCCATAGC TCTTGGAGGA TTGGCACTAG GTGCTGGTTT
```

FIG. 9B

```
              901                                                       950
SEQ123  GTCGAACGTG  AAGTACTTCT  CAGAAGCAAG  TACCGCAGGA  GAACGCATAA
SEQ122  GTCGAACGTG  AAGTACTTCT  CAGAAGCAAG  TACCGCAGGA  GAACGCATAA
SEQ125  GTCGAACGTG  AAGTACTTCT  CAGAAGCAAG  TACCGCAGGA  GAACGCATAA
SEQ124  GTCGAACGTG  AAGTACTTCT  CAGAAGCAAG  TACCGCAGGA  GAACGCATAA 951                                                      1000
SEQ123  TGGAAGTGAT  AAAAAGGGTT  CCAAAGATTG  ATTCTGATAG  CATGGCTGAG
SEQ122  TGGAAGTGAT  AAAAAGGGTT  CCAAAGATTG  ATTCTGATAG  CATGGCTGAG
SEQ125  TGGAAGTGAT  AAAAAGGGTT  CCAAAGATTG  ATTCTGATAG  CATGGCTGAG
SEQ124  TGGAAGTGAT  AAAAAGGGTT  CCAAAGATTG  ATTCTGATAG  CATGGCTGAG 1001                                                      1050
SEQ123  GAGATTCTGG  AGAACGTTTC  AGGGGAAGTT  GAATTCAACC  ATGTGGACTT
SEQ122  GAGATTCTGG  AGAACGTTTC  AGGGGAAGTT  GAATTCAACC  ATGTGGACTT
SEQ125  GAGATTCTGG  AGAACGTTTC  AGGGGAAGTT  GAATTCAACC  ATGTGGACTT
SEQ124  GAGATTCTGG  AGAACGTTTC  AGGGGAAGTT  GAATTCAACC  ATGTGGACTT 1051                                                      1100
SEQ123  TGTGTACCCA  TCAAGGCCAG  ACAGTGTTAT  TCTGAATGAT  TTCTGCCTAA
SEQ122  TGTGTACCCA  TCAAGGCCAG  ACAGTGTTAT  TCTGAATGAT  TTCTGCCTAA
SEQ125  TGTGTACCCA  TCAAGGCCAG  ACAGTGTTAT  TCTGAATGAT  TTCTGCCTAA
SEQ124  TGTGTACCCA  TCAAGGCCAG  ACAGTGTTAT  TCTGAATGAT  TTCTGCCTAA 1101                                                      1150
SEQ123  AGATTCCAGC  AGGGAAAACA  GTGGCTTTGG  TTGGAGGGAG  TGGCTCTGGA
SEQ122  AGATTCCAGC  AGGGAAAACA  GTGGCTTTGG  TTGGAGGGAG  TGGCTCTGGA
SEQ125  AGATTCCAGC  AGGGAAAACA  GTGGCTTTGG  TTGGAGGGAG  TGGCTCTGGA
SEQ124  AGATTCCAGC  AGGGAAAACA  GTGGCTTTGG  TTGGAGGGAG  TGGCTCTGGA 1151                                                      1200
SEQ123  AAATCCACTG  TGATATCACT  TTTGCAGAGG  TTTTATGACC  CAATTGAGGG
SEQ122  AAATCCACTG  TGATATCACT  TTTGCAGAGG  TTTTATGACC  CAATTGAGGG
SEQ125  AAATCCACTG  TGATATCACT  TTTGCAGAGG  TTTTATGACC  CAATTGAGGG
SEQ124  AAATCCACTG  TGATATCACT  TTTGCAGAGG  TTTTATGACC  CAATTGAGGG 1201                                                      1250
SEQ123  AGAGATATTT  CTTGATGGTG  TGGCCATTCA  CAAGTTGCAA  CTCAAGTGGT
SEQ122  AGAGATATTT  CTTGATGGTG  TGGCCATTCA  CAAGTTGCAA  CTCAAGTGGT
SEQ125  AGAGATATTT  CTTGATGGTG  TGGCCATTCA  CAAGTTGCAA  CTCAAGTGGT
SEQ124  AGAGATATTT  CTTGATGGTG  TGGCCATTCA  CAAGTTGCAA  CTCAAGTGGT 1251                                                      1300
SEQ123  TGAGGTCTCA  AATGGGTTTG  GTCAGCCAAG  AGCCTGCACT  GTTTGCAACT
SEQ122  TGAGGTCTCA  AATGGGTTTG  GTCAGCCAAG  AGCCTGCACT  GTTTGCAACT
SEQ125  TGAGGTCTCA  AATGGGTTTG  GTCAGCCAAG  AGCCTGCACT  GTTTGCAACT
SEQ124  TGAGGTCTCA  AATGGGTTTG  GTCAGCCAAG  AGCCTGCACT  GTTTGCAACT 1301                                                      1350
SEQ123  AGCATTAAAG  AGAATATACT  TTTGGAAGA   GAAGATGCCA  CTCAAGAAGA
SEQ122  AGCATTAAAG  AGAATATACT  TTTGGAAGA   GAAGATGCCA  CTCAAGAAGA
SEQ125  AGCATTAAAG  AGAATATACT  TTTGGAAGA   GAAGATGCCA  CTCAAGAAGA
SEQ124  AGCATTAAAG  AGAATATACT  TTTGGAAGA   GAAGATGCCA  CTCAAGAAGA
```

FIG. 9C

```
           1351                                                   1400
SEQ123 GGTTGTGGAG GCAGCAAAAG CTTCCAATGC TCATAATTTC ATTTCACAGT
SEQ122 GGTTGTGGAG GCAGCAAAAG CTTCCAATGC TCATAATTTC ATTTCACAGT
SEQ125 GGTTGTGGAG GCAGCAAAAG CTTCCAATGC TCATAATTTC ATTTCACAGT
SEQ124 GGTTGTGGAG GCAGCAAAAG CTTCCAATGC TCATAATTTC ATTTCACAGT 1401                                                   1450
SEQ123 TGCCACAAGG ATATGATACT CAGGTTGGGG AGAGAGGAGT TCAAATGTCA
SEQ122 TGCCACAAGG ATATGATACT CAGGTTGGGG AGAGAGGAGT TCAAATGTCA
SEQ125 TGCCACAAGG ATATGATACT CAGGTTGGGG AGAGAGGAGT TCAAATGTCA
SEQ124 TGCCACAAGG ATATGATACT CAGGTTGGGG AGAGAGGAGT TCAAATGTCA 1451                                                   1500
SEQ123 GGTGGACAAA AGCAAAGAAT TGCAATAGCA CGAGCAATAA TAAAAAAGCC
SEQ122 GGTGGACAAA AGCAAAGAAT TGCAATAGCA CGAGCAATAA TAAAAAAGCC
SEQ125 GGTGAACAAA AGCAAAGAAT TGCAATAGCA CGAGCAATAA TAAAAAAGCC
SEQ124 GGTGGACAAA AGCAAAGAAT TGCAATAGCA CGAGCAATAA TAAAAAAGCC 1501                                                   1550
SEQ123 ACGGATTCTT CTATTAGATG AAGCAACAAG TGCACTAGAT TCTGAATCTG
SEQ122 ACGGATTCTT CTATTAGATG AAGCAACAAG TGCACTAGAT TCTGAATCTG
SEQ125 ACGGATTCTT CTATTAGATG AAGCAACAAG TGCACTAGAT TCTGAATCTG
SEQ124 ACGGATTCTT CTATTAGATG AAGCAACAAG TGCACTAGAT TCTGAATCTG 1551                                                   1600
SEQ123 AACGAGTTGT GCAAGAAGCA TTAGACAAAG TAGCAGTAGG GCGCACAACA
SEQ122 AACGAGTTGT GCAAGAAGCA TTAGACAAAG CAGCAGTAGG GCGCACAACA
SEQ125 AACGAGTTGT GCAAGAAGCA TTAGACAAAG TAGCAGTAGG GCGCACAACA
SEQ124 AACGAGTTGT GCAAGAAGCA TTAGACAAAG CAGCAGTAGG GCGCACAACA 1601                                                   1650
SEQ123 ATCATCATTG CACATAGATT ATCCACCATA ACGAATGCAA ATGTGATTGC
SEQ122 ATCATCATTG CACATAGATT ATCCACCATA AGGAATGCAA ATGTGATTGC
SEQ125 ATCATCATTG CACATAGATT ATCCACCATA AGGAATGCAA ATGTGATTGC
SEQ124 ATCATCATTG CACATAGATT ATCCACCATA AGGAATGCAA ATGTGATTGC 1651                                                   1700
SEQ123 TGTTGTGCAA AGTGGGAAAA TCATGGAGAT GGGATCACAC CATGAACTAA
SEQ122 TGTTGTGCAA AGTGGGAAAA TCATGGAGAT GGGATCACAC CATGAACTAA
SEQ125 TGTTGTGCAA AGTGGGAAAA TCATGGAGAT GGGATCACAC CATGAACTAA
SEQ124 TGTTGTGCAA AGTGGGAAAA TCATGGAGAT GGGATCACAC CATGAACTAA 1701                                                   1750
SEQ123 TCCAAAACGA CAATGGCCTT TACACCTCAC TAGTTCGTCT CCAACAAGCA
SEQ122 TCCAAAACGA CAATGGCCTT TACACCTCAC TAGTTCGTCT CCAACAAGCA
SEQ125 TCCAAAACGA CAATGGCCTT TACACCTCAC TAGTTCGTCT CCAACAAGCA
SEQ124 TCCAAAACGA CAATGGCCTT TACACCTCAC TAGTTCGTCT CCAACAAGCA 1751                                                   1800
SEQ123 AAAAATGAAA AAGAAGACAC CCTTTTTCAT CCTACTCCTC CTTCGTCCAT
SEQ122 AAAAATGAAA AAGAAGACAC CATTTTTCAT CCTACTCCTC CTTCGTCCAT
SEQ125 AAAAATGAAA AAGAAGACAC CCTTTTTCAT CCTACTCCTC CTTCGTCCAT
SEQ124 AAAAATGAAA AAGAAGACAC CATTTTTCAT CCTACTCCTC CTTCGTCCAT
```

FIG. 9D

```
           1801                                                   1850
SEQ123 ATCGAACAAA GACAATCACA ACACGAGTAG CCGTAGGCTC TCTGTTGTGA
SEQ122 ATCGAACAAA GACAATCACA ACACGAGTAG CCGTAGGCTC TCTGTTGTGA
SEQ125 ATCGAACAAA GACAATCACA ACACGAGTAG CCGTAGGCTC TCTGTTGTGA
SEQ124 ATCGAACAAA GACAATCACA ACACGAGTAG CCGTAGGCTC TCTGTTGTGA 1851                                                   1900
SEQ123 TGAGCCGTTC TAGCTCCACC AACTCGATAC CTCGTATTGG TGGTGGTGAC
SEQ122 TGATCCGTTC TAGCTCCACC AACTCGATAC CTCGTATTGG TGGTGGTGAC
SEQ125 TGAGCCGTTC TAGCTCCACC AACTCGATAC CTCGTATTGG TGGTGGTGAC
SEQ124 TGATCCGTTC TAGCTCCACC AACTCGATAC CTCGTATTGG TGGTGGTGAC 1901                                                   1950
SEQ123 GATAACAATA TTGTTGAAGA AGTAGTGGAA GATAACAAGC CACCACTTCC
SEQ122 GATAACAATA TTGTTGAAGA AGTAGTGGAA GATAACAAGC CACCACTTCC
SEQ125 GATAACAATA TTGTTGAAGA AGTAGTGGAA GATAACAAGC CACCACTTCC
SEQ124 GATAACAATA TTGTTGAAGA AGTAGTGGAA GATAACAAGC CACCACTTCC 1951                                                   2000
SEQ123 CTCATTTCGA AGGTTGCTCG CACTGAACAT TCCCGAGTGG AAGCAAGCAT
SEQ122 CTCGTTTCGA AGGTTGCTCG CACTGAACAT TCCCGAGTGG AAGCAAGCAT
SEQ125 CTCATTTCGA AGGTTGCTCG CACTGAACAT TCCCGAGTGG AAGCAAGCAT
SEQ124 CTCGTTTCGA AGGTTGCTCG CACTGAACAT TCCCGAGTGG AAGCAAGCAT 2001                                                   2050
SEQ123 GTTTAGGGTG TTTGAATGCG GTGTTGTTTG GTGCAATTCA GCCTGTGTAT
SEQ122 GTTTAGGGTG TTTGAATGCG GTGTTGTTTG GTGCAATTCA GCCTGTGTAT
SEQ125 GTTTAGGGTG TTTGAATGCG GTGTTGTTTG GTGCAATTCA GCCTGTGTAT
SEQ124 GTTTAGGGTG TTTGAATGCG GTGTTGTTTG GTGCAATTCA GCCTGTGTAT 2051                                                   2100
SEQ123 GCATTTGCAA TGGGGTCAGT GATATCTGTT TACTTCCTCC CAGACCATAA
SEQ122 GCATTTGCAA TGGGGTCAGT GATATCTGTT TACTTCCTCC CAGACCATAA
SEQ125 GCATTTGCAA TGGGGTCAGT GATATCTGTT TACTTCCTCC CAGACCATAA
SEQ124 GCATTTGCAA TGGGGTCAGT GATATCTGTT TACTTCCTCC CAGACCATAA 2101                                                   2150
SEQ123 TGAGATAAAG AAGAAAACTA TGATCTATTC ACTTTGTTTC CTAGGGTTGG
SEQ122 TGAGATAAAG AAGAAAACTA TGATCTATTC ACTTTGTTTC CTAGGGTTGG
SEQ125 TGAGATAAAG AAGAAAACTA TGATCTATTC ACTTTGTTTC CTAGGGTTGG
SEQ124 TGAGATAAAG AAGAAAACTA TGATCTATTC ACTTTGTTTC CTAGGGTTGG 2151                                                   2200
SEQ123 CTGTGTTCTC CTTAGTGGTT AATATCCTCC AGCATTACAA CTTTGCTTAC
SEQ122 CTGTGTTCTC CTTAGTGGTT AATATCCTCC AGCATTACAA CTTTGCTTAC
SEQ125 CTGTGTTCTC CTTAGTGGTT AATATCCTCC AGCATTACAA CTTTGCTTAC
SEQ124 CTGTGTTCTC CTTAGTGGTT AATATCCTCC AGCATTACAA CTTTGCTTAC 2201                                                   2250
SEQ123 ATAGGAGAGT ACTTGACTAA AAGGATCAGA GAAAGAATGT TTTCCAAGAT
SEQ122 ATAGGAGAGT ACTTGACTAA AAGGATCAGA GAAAGAATGT TTTCCAAGAT
SEQ125 ATAGGAGAGT ACTTGACTAA AAGGATCAGA GAAAGAATGT TTTCCAAGAT
SEQ124 ATAGGAGAGT ACTTGACTAA AAGGATCAGA GAAAGAATGT TTTCCAAGAT
```

FIG. 9E

```
        2251                                                2300
SEQ123 ACTCACTTTT GAAGTTGGAT GGTTTGATCA AGATGAAAAT TCCACAGGTG
SEQ122 ACTCACTTTT GAAGTTGGAT GGTTTGATCA AGATGAAAAT TCCACAGGTG
SEQ125 ACTCACTTTT GAAGTTGGAT GGTTTGATCA AGATGAAAAT TCCACAGGTG
SEQ124 ACTCACTTTT GAAGTTGGAT GGTTTGATCA AGATGAAAAT TCCACAGGTG 2301                                                2350
SEQ123 CTGTTTGTTC TAGACTTGCC AAAGAAGCCA ATGTG..... ..........
SEQ122 CTGTTTGTTC TAGACTTGCC AAAGAAGCCA ATGTG..... ..........
SEQ125 CTGTTTGTTC TAGACTTGCC AAAGAAGCCA ATGTGGTAAG GTCTTTAGTG
SEQ124 CTGTTTGTTC TAGACTTGCC AAAGAAGCCA ATGTGGTAAG GTCTTTAGTG 2351                                                2400
SEQ123 .........A ATGGTCTAGT GGTACAAACC ATTTCAGCAG TGGTAATAGC
SEQ122 .........A ATGGTCTAGT GGTACAAACC ATTTCAGCAG TGGTAATAGC
SEQ125 GGAGATAGAA TGGCTCTAGT GGTACAAACC ATTTCAGCAG TGGTAATAGC
SEQ124 GGAGATAGAA TGGCTCTAGT GGTACAAACC ATTTCAGCAG TGGTAATAGC 2401                                                2450
SEQ123 TTTTACAATG GGCCTAATCA TTGCATGGAG GTTGGCCATT GTTATGATAG
SEQ122 TTTTACAATG GGCCTAATCA TTGCATGGAG GTTGGCCATT GTTATGATAG
SEQ125 TTTTACAATG GGCCTAATCA TTGCATGGAG GTTGGCCATT GTTATGATAG
SEQ124 TTTTACAATG GGCCTAATCA TTGCATGGAG GTTGGCCATT GTTATGATAG 2451                                                2500
SEQ123 CAGTTCAACC CATTATCATA GCATGTTTCT ACACAAGGCG TGTCCTTCTC
SEQ122 CAGTTCAACC CATTATCATA GCATGTTTCT ACACAAGGCG TGTCCTTCTC
SEQ125 CAGTTCAACC CATTATCATA GCATGTTTCT ACACAAGGCG TGTCCTTCTC
SEQ124 CAGTTCAACC CATTATCATA GCATGTTTCT ACACAAGGCG TGTCCTTCTC 2501                                                2550
SEQ123 AAGAGCATGT CTAGTAAGGC CATCAAGGCC CAAGATGAAA GTAGCAAGAT
SEQ122 AAGAGCATGT CTAGTAAGGC CATCAAGGCC CAAGATGAAA GTAGCAAGAT
SEQ125 AAGAGCATGT CTAGTAAGGC CATCAAGGCC CAAGATGAAA GTAGCAAGAT
SEQ124 AAGAGCATGT CTAGTAAGGC CATCAAGGCC CAAGATGAAA GTAGCAAGAT 2551                                                2600
SEQ123 AGCTGTTGAA GCTGTTTCCA ACCTCAGAAC AATCACAGCA TTTTCTTCCC
SEQ122 AGCTGTTGAA GCTGTTTCCA ACCTCAGAAC AATCACAGCA TTTTCTTCCC
SEQ125 AGCTGTTGAA GCTGTTTCCA ACCTCAGAAC AATCACAGCA TTTTCTTCCC
SEQ124 AGCTGTTGAA GCTGTTTCCA ACCTCAGAAC AATCACAGCA TTTTCTTCCC 2601                                                2650
SEQ123 AAGATAGGAT CCTTAAAATG CTCGAAAAGG CCCAAGAAGG CCCGAGCCGT
SEQ122 AAGATAGGAT CCTTAAAATG CTCGAAAAGG CCCAAGAAGG CCCGAGCCGT
SEQ125 AAGATAGGAT CCTTAAAATG CTCGAAAAGG CCCAAGAAGG CCCGAGCCGT
SEQ124 AAGATAGGAT CCTTAAAATG CTCGAAAAGG CCCAAGAAGG CCCGAGCCGT 2651                                                2700
SEQ123 GAAAGCATTC GACAATCATG GTTTGCGGGC ATTGGGCTTG CATGTTCCCA
SEQ122 GAAAGCATTC GACAATCATG GTTTGCGGGC ATTGGGCTTG CATGTTCCCA
SEQ125 GAAAGCATTC GACAATCATG GTTTGCGGGC ATTGGGCTTG CATGTTCCCA
SEQ124 GAAAGCATTC GACAATCATG GTTTGCGGGC ATTGGGCTTG CATGTTCCCA
```

FIG. 9F

```
         2701                                                      2750
SEQ123 AAGCCTTACA TTTTGCACTT GGGCTTTGGA CTTTTGGTAT GGAGGCAAGC
SEQ122 AAGCCTTACA TTTTCCACTT GGGCTTTGGA CTTTTGGTAT GGAGGCAAGC
SEQ125 AAGCCTTACA TTTTGCACTT GGGCTTTGGA CTTTTGGTAT GGAGGCAAGC
SEQ124 AAGCCTTACA TTTTGCACTT GGGCTTTGGA CTTTTGGTAT GGAGGCAAGC 2751                                                      2800
SEQ123 TTGTGTTTCA GGGCTTCATA AATGCCAAAG CATTGTTTGA GACCTTCATG
SEQ122 TTGTGTTTCA GGGCTTCATA AACGCCAAAG CATTGTTTGA GACCTTCATG
SEQ125 TTGTGTTTCA GGGCTTCATA AATGCCAAAG CATTGTTTGA GACCTTCATG
SEQ124 TTGTGTTTCA GGGCTTCATA AACGCCAAAG CATTGTTTGA GACCTTCATG 2801                                                      2850
SEQ123 ATTTAGTGA GCACAGGTAG GGTTATTGCA GATGCTGGTA GCATGACCAA
SEQ122 ATTTAGTGA GCACAGGTAG GGTTATTGCA GATGCTGGTA GCATGACCAA
SEQ125 ATTTAGTGA GCACAGGTAG GGTTATTGCA GATGCTGGTA GCATGACCAA
SEQ124 ATTTAGTGA GCACAGGTAG GGTTATTGCA GATGCTGGTA GCATGACCAA 2851                                                      2900
SEQ123 TGACCTAGCT AAAGGGGCTG ATGCTGTGGG CTCAGTTTTT GCAATCTTAG
SEQ122 TGACCTAGCT AAAGGGGCTG ATGCTGTGGG CTCAGTTTTT GCAATCTTAG
SEQ125 TGACCTAGCT AAAGGGGCTG ATGCTGTGGG CTCAGTTTTT GCAATCTTAG
SEQ124 TGACCTAGCT AAAGGGGCTG ATGCTGTGGG CTCAGTTTTT GCAATCTTAG 2901                                                      2950
SEQ123 ATAAGTACAC AAAAATTGAG CCAGATGATG ACATAGATGG GTACAAGCCT
SEQ122 ATAGGTACAC AAAAATTGAG CCAGATGATG ACATAGATGG GTACAAGCCT
SEQ125 ATAAGTACAC AAAAATTGAG CCAGATGATG ACATAGATGG GTACAAGCCT
SEQ124 ATAGGTACAC AAAAATTGAG CCAGATGATG ACATAGATGG GTACAAGCCT 2951                                                      3000
SEQ123 GAAAAGCTAA CAGGGAAAAT AGAGCTTCAT GATGTCCATT TTGCATACCC
SEQ122 GAAAAGCTAA CAGGGAAAAT AGAGCTTCAT GATGTCCATT TTGCATACCC
SEQ125 GAAAAGCTAA CAGGGAAAAT AGAGCTTCAT GATGTCCATT TTGCATACCC
SEQ124 GAAAAGCTAA CAGGGAAAAT AGAGCTTCAT GATGTCCATT TTGCATACCC 3001                                                      3050
SEQ123 AGCTAGGCCC AATGTGATGA TCTTCCAAGG CTTCTCAATC AAAATTGATG
SEQ122 AGCTAGGCCC AATGTGATGA TCTTCCAAGG CTTCTCAATC AAAATTGATG
SEQ125 AGCTAGGCCC AATGTGATGA TCTTCCAAGG CTTCTCAATC AAAATTGATG
SEQ124 AGCTAGGCCC AATGTGATGA TCTTCCAAGG CTTCTCAATC AAAATTGATG 3051                                                      3100
SEQ123 CAGGCAGATC AACAGCATTG GTCGGGCAAA GTGGCTCTGG AAAATCAACA
SEQ122 CAGGCAGATC AACAGCATTG GTTGGGCAAA GTGGCTCTGG AAAATCAACA
SEQ125 CAGGCAGATC AACAGCATTG GTCGGGCAAA GTGGCTCTGG AAAATCAACA
SEQ124 CAGGCAGATC AACAGCATTG GTTGGGCAAA GTGGCTCTGG AAAATCAACA 3101                                                      3150
SEQ123 ATCATAGGCT TAATTGAGAG ATTCTATGAC CCTCTAAAAG GGATTGTGAC
SEQ122 ATCATAGGCT TAATTGAGAG ATTCTATGAC CCTATGAAAG GGATTGTGAC
SEQ125 ATCATAGGCT TAATTGAGAG ATTCTATGAC CCTCTAAAAG GGATTGTGAC
SEQ124 ATCATAGGCT TAATTGAGAG ATTCTATGAC CCTATGAAAG GGATTGTGAC
```

FIG. 9G

```
        3151                                                      3200
SEQ123  CATTGATGGT AGAGACATAA AATCATACCA CCTTAGGTCA CTAAGGAAGC
SEQ122  CATTGATGGT AGAGACATAA AATCATACCA CCTTAGGTCA CTAAGGAAGC
SEQ125  CATTGATGGT AGAGACATAA AATCATACCA CCTTAGGTCA CTAAGGAAGC
SEQ124  CATTGATGGT AGAGACATAA AATCATACCA CCTTAGGTCA CTAAGGAAGC 3201                                                      3250
SEQ123  ATATTGCTCT TGTAAGCCAA GAGCCAACAT TGTTTGGTGG GACCATAAGG
SEQ122  ATATTGCTCT TGTAAGCCAA GAGCCAACAT TGTTTGGTGG GACCATAAGG
SEQ125  ATATTGCTCT TGTAAGCCAA GAGCCAACAT TGTTTGGTGG GACCATAAGG
SEQ124  ATATTGCTCT TGTAAGCCAA GAGCCAACAT TGTTTGGTGG GACCATAAGG 3251                                                      3300
SEQ123  GAAAATATTG CATATGGGGC ATCTAATAAT AATAACAAGG TTGATGAAAC
SEQ122  GAAAATATTG CATATGGGGC ATCTAATAAT AATAACAAGG TTGATGAAAC
SEQ125  GAAAATATTG CATATGGGGC ATCTAATAAT AATAACAAGG TTGATGAAAC
SEQ124  GAAAATATTG CATATGGGGC ATCTAATAAT AATAACAAGG TTGATGAAAC 3301                                                      3350
SEQ123  TGAGATCATA GAAGCAGCTA GGGCAGCTAA TGCTCATGAT TTCATTGCAA
SEQ122  TGAGATCATA GAAGCAGCTA GGGCAGCTAA TGCTCATGAT TTCATTGCAA
SEQ125  TGAGATCATA GAAGCAGCTA GGGCAGCTAA TGCTCATGAT TTCATTGCAA
SEQ124  TGAGATCATA GAAGCAGCTA GGGCAGCTAA TGCTCATGAT TTCATTGCAA 3351                                                      3400
SEQ123  GCCTAAAGGA TGGTTATGAC ACATCGTGTG GAGATAGAGG AGTGCAACTC
SEQ122  GCCTAAAGGA TGGTTATGAC ACATCGTGTA GAGATAGAGG AGTGCAACTC
SEQ125  GCCTAAAGGA TGGTTATGAC ACATCGTGTG GAGATAGAGG AGTGCAACTC
SEQ124  GCCTAAAGGA TGGTTATGAC ACATCGTGTA GAGATAGAGG AGTGCAACTC 3401                                                      3450
SEQ123  TCTGGGGGTC AAAAGCAAAG AATTGCAATA GCTAGAGCCA TATTGAAGAA
SEQ122  TCTGGGGGTC AAAAGCAAAG AATTGCAATA GCTAGAGCCA TATTGAAGAA
SEQ125  TCTGGGGGTC AAAAGCAAAG AATTGCAATA GCTAGAGCCA TATTGAAGAA
SEQ124  TCTGGGGGTC AAAAGCAAAG AATTGCAATA GCTAGAGCCA TATTGAAGAA 3451                                                      3500
SEQ123  TCCAGAAGTG TTGTTGTTGG ATGAAGCCAC AAGTGCCCTA GATAGCCAAT
SEQ122  TCCAGAAGTG TTGTTGTTGG ATGAAGCCAC AAGTGCCCTA GATAGCCAAT
SEQ125  TCCAGAAGTG TTGTTGTTGG ATGAAGCCAC AAGTGCCCTA GATAGCCAAT
SEQ124  TCCAGAAGTG TTGTTGTTGG ATGAAGCCAC AAGTGCCCTA GATAGCCAAT 3501                                                      3550
SEQ123  CAGAAAAATT GGTGCAAGAT GCTCTAGAAA GGGTGATGGT GGGAGAACT
SEQ122  CAGAAAAATT GGTGCAAGAT GCTCTAGAAA GGGTGATGGT GGGAGAACT
SEQ125  CAGAAAAATT GGTGCAAGAT GCTCTAGAAA GGGTGATGGT GGGAGAACT
SEQ124  CAGAAAAATT GGTGCAAGAT GCTCTAGAAA GGGTGATGGT GGGAGAACT 3551                                                      3600
SEQ123  AGTGTGGTGG TGGCTCACAG GTTAAGCACA ATACAAAATT GTGACCTAAT
SEQ122  AGTGTGGTGG TGGCTCACAG GTTAAGCACA ATACAAAATT GTGACCTAAT
SEQ125  AGTGTGGTGG TGGCTCACAG GTTAAGCACA ATACAAAATT GTGACCTAAT
SEQ124  AGTGTGGTGG TGGCTCACAG GTTAAGCACA ATACAAAATT GTGACCTAAT
```

FIG. 9H

```
        3601                                                         3650
SEQ123  TGCTGTGTTA GATAAGGGAA AAGTGGTGGA GAAAGGGACC CACTCATCTT
SEQ122  TGCTGTGTTA GATAAGGGAA AAGTGGTGGA GAAAGGGACC CACTCATCTT
SEQ125  TGCTGTGTTA GATAAGGGAA AAGTGGTGGA GAAAGGGACC CACTCATCTT
SEQ124  TGCTGTGTTA GATAAGGGAA AAGTGGTGGA GAAAGGGACC CACTCATCTT 3651                                                         3700
SEQ123  TGTTGGCTCA TGGACCAGGT GGAGCTTATT ACTCTTTGAT AAGTTTACAA
SEQ122  TGTTGGCTCA TGGACCAGGT GGAGCTTATT ACTCTTTGAT AAGTTTACAA
SEQ125  TGTTGGCTCA TGGACCAGGT GGAGCTTATT ACTCTTTGAT AAGTTTACAA
SEQ124  TGTTGGCTCA TGGACCAGGT GGAGCTTATT ACTCTTTGAT AAGTTTACAA 3701                                                         3750
SEQ123  AGAAGACCAG CAAATTAA~~ ~~~~~~~~~~ ~~~~~~~~~~ ~~~~~~~~~~
SEQ122  AGAAGACCAG CAAATTAA~~ ~~~~~~~~~~ ~~~~~~~~~~ ~~~~~~~~~~
SEQ125  AGAAGACCAG CAAATTAAAC ATGAATGTTA GTTTTACGCA TGAAATCTCA
SEQ124  AGAAGACCAG CAAATTAAAC ATGAATGTTA GTTTTACGCA TGAAATCTCA 3751                                                         3800
SEQ123  ~~~~~~~~~~ ~~~~~~~~~~ ~~~~~~~~~~ ~~~~~~~~~~ ~~~~~~~~~~
SEQ122  ~~~~~~~~~~ ~~~~~~~~~~ ~~~~~~~~~~ ~~~~~~~~~~ ~~~~~~~~~~
SEQ125  GCTAGCTAAT CAAAACAAAC AAAATGTCAC ATTTATTGGT GATTAGTATT
SEQ124  GCTAGCTAAT CAAAACAAAC AAAATGTCAC ATTTATTGGT GATTAGTATT 3801                                                         3850
SEQ123  ~~~~~~~~~~ ~~~~~~~~~~ ~~~~~~~~~~ ~~~~~~~~~~ ~~~~~~~~~~
SEQ122  ~~~~~~~~~~ ~~~~~~~~~~ ~~~~~~~~~~ ~~~~~~~~~~ ~~~~~~~~~~
SEQ125  AAACCTCTTT TGTGGTAACT TGTGAAAGTA AATTAAGAAA AATGAAAGAA
SEQ124  AAACCTCTTT TGTGGTAACT TGTGAAAGTA AATTAAGAAA AATGAAAGAA 3851                                                         3900
SEQ123  ~~~~~~~~~~ ~~~~~~~~~~ ~~~~~~~~~~ ~~~~~~~~~~ ~~~~~~~~~~
SEQ122  ~~~~~~~~~~ ~~~~~~~~~~ ~~~~~~~~~~ ~~~~~~~~~~ ~~~~~~~~~~
SEQ125  AAGTAAATTA AGCAAAGATA GAAGGGAAGA ACTATATAAC AGTTGTAGTC
SEQ124  AAGTAAATTA AGCAAAGATA GAAGGGAAGA ATTATATAAC AGTTGTAGTC 3901                 3920
SEQ123  ~~~~~~~~~~ ~~~~~~~~~~
SEQ122  ~~~~~~~~~~ ~~~~~~~~~~
SEQ125  TCTCCCAACT TCCTAAATTC
SEQ124  TCTCCCAACT TCCTAAATTC
```

POLYNUCLEOTIDE AND POLYPEPTIDE SEQUENCES ASSOCIATED WITH HERBICIDE TOLERANCE

CROSS-REFERENCE TO RELATED APPLICATION

This Application claims priority to U.S. Provisional Application No. 61/298,528, filed Jan. 26, 2010; 61/298,523, filed Jan. 26, 2010; 61/371,392, filed Aug. 6, 2010; and 61/371,454, filed Aug. 6, 2010, each of which is incorporated by reference in its entirely.

FIELD OF THE INVENTION

This invention relates generally to the detection of genetic differences among soybeans.

BACKGROUND OF THE INVENTION

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications. Weed management in soybean fields is important to maximizing yields. A recent development in soybean technology has been the development of herbicide-tolerant soybean varieties. Glyphosate tolerant soybeans were commercially introduced in 1996 and accounted for more than 85% percent of U.S. soybean acreage in 2007.

Some weeds are starting to show increased tolerance to glyphosate. This increased tolerance decreases the effectiveness of glyphosate application and results in lower yields for farmers. As a result there is a need in the art for soybean varieties that are tolerant to other herbicide chemistry.

SUMMARY OF THE INVENTION

This invention relates generally to polynucleotide and polypeptide sequences related to tolerance to multiple herbicides, compositions comprising the same, and methods of their use. In certain examples, the invention relates to polynucleotide markers capable of discriminating between soybean that displays tolerance and soybean that displays susceptibility to one or more herbicides, such as one or more herbicides selected from the group consisting of an HPPD-inhibitor herbicide, such as mesotrione and isoxazole herbicides, and/or a PPO inhibitor herbicide. In certain other examples, the polynucleotide marker is capable of detecting a polynucleotide sequence with 80%, 90%, 95%, or better identity to a polynucleotide sequence provided herein, such as one of SEQ ID NOs: 122-125. In still further examples, the markers contain certain identified SNPs at given positions, such as a SNP at one or more of nucleotide position 1455, 1581, 1772, 1854, 1954, 2773, 2904, 3073, 3134, 3136, 3380, and 3882 of the sequence set forth in SEQ ID NO: 124 or SEQ ID NO: 125. Methods and compositions for use of these markers in genotyping of soybean and selection are also disclosed.

In still further examples, isolated polynucleotides encoding ABC transporter polypeptides are provided. In certain examples, the ABC transporter polypeptide displays 80%, 90%, 95%, or better identity to a polypeptide sequence provided herein, such as one of SEQ ID NOs: 126-129. In other examples, the polynucleotide sequence possesses certain identified amino acid substitutions at given amino acid positions, such as a substitution at one or more of positions E478X, V520X, L584X, S611X, K961X, L1038X, or G1120X, or positions equivalent thereto, including one or more of the amino acid substitutions E478G, V520A, L584I, S611I, K961R, L1038M, and G1120R. In still further examples, the polynucleotide comprises 80%, 90%, 95%, or better identity to a polynucleotide sequence provided herein, such as one of SEQ ID NOs:122-125; or the polynucleotide possesses certain identified SNPs at given positions, such as a SNP at one or more of nucleotide position 1455, 1581, 1772, 1854, 1954, 2773, 2904, 3073, 3134, 3136, 3380, and 3882 of the sequence set forth in SEQ ID NO: 124 or SEQ ID NO: 125. In certain examples, the one or more SNPs are selected from the group consisting of a G at position 1455; a C at position 1581; an A at position 1772; a T at position 1854; a G at position 1954; a C at position 2773; a G at position 2904; a T at position 3073; an A at position 3134; a G at position 3136; an A at position 3380; and a T at position 3882. In yet further examples, the polynucleotide sequence is operably linked to a promoter functional in a host cell.

In additional examples, isolated ABC transporter polypeptides are provided. In certain examples, the isolated polypeptide displays 80%, 90%, 95%, or better identity to a polypeptide sequence provided herein, such as one of SEQ ID NOs: 126-129. In other examples, the polynucleotide sequence possesses certain identified amino acid substitutions at given amino acid positions, such as a substitution at one or more of positions E478X, V520X, L584X, S611X, K961X, L1038X, and/or G1120X or positions equivalent thereto, including one or more of the amino acid substitutions E478G, V520A, L584I, S611I, K961R, L1038M, and G1120R.

Also described are isolated polynucleotides and isolated polypeptides relevant to tolerance or sensitivity to one or more herbicides. Additional traits may also be added to plants having such tolerance or sensitivity, such as additional herbicide tolerance traits, insect tolerance traits, or other transgenic traits. Also described are methods of introgressing a tolerance or susceptibility allele into a plant, such as by crossing a soybean plant tolerant to a given herbicide with a soybean plant susceptible to such herbicide herbicide in order to form a segregating population, screening the segregating population with one or more nucleic acid markers to determine if plants from the segregating population contains at least one SNP selected from the group consisting of an SNP at nucleotide position 1455, 1581, 1772, 1854, 1954, 2773, 2904, 3073, 3134, 3136, 3380, and 3882 of the sequence set forth as SEQ ID NOs: 124 or 125, for example as shown in FIGS. 7A-7F and FIGS. 9A-9I, or a sequence equivalent to SEQ ID NOs: 124 or 125, for example SEQ ID NOs: 122 or 123, and optionally selecting, if present, one or more soybean plants of the segregating population containing the at least one SNP. In some examples, soybean plant cells, plants, and/or seeds having a haplotype comprising SNPs at nucleotide positions 1455, 1581, 1772, 1854, 1954, 2773, 2904, 3073, 3134, 3136, 3380, and 3882, or their equivalent position(s), are selected. In some examples, soybean plant cells, plants, and/or seeds having a haplotype comprising a G at position 1455, a C at position 1581, an A at position 1772, a T at position 1854, a G at position 1954, a C at position 2773, a G at position 2904, a T at position 3073, an A at position 3134, a G at position 3136, an A at position 3380, and a T at position 3882, or their equivalent position(s), are selected. Alternatively, such tolerance may be transgenically provided by introducing into a plant cell a polynucleotide as disclosed herein operably linked to a promoter functional in the plant cell to produce a transformed plant cell, and optionally selecting a transformed plant cell having the polynucleotide stably incorporated into its genome.

Also useful are isolated polynucleotide variants, polynucleotides encoding polypeptide variants, and polypeptide variants having sequence identity to the appropriate reference sequence, such as an ABC transporter polypeptide, of at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.75%, or 100% identity.

Soybean plants, seeds, tissue cultures, variants, and mutants having herbicide tolerance produced by the foregoing methods are also provided. Also provided herein are methods for controlling weeds in a crop by applying to the crop and any weeds affecting such crop an effective amount of such herbicide(s), either pre-emergent or post-emergent, such that the weeds are substantially controlled without substantially negatively impacting the crop.

The invention can be more fully understood from the following detailed description and the accompanying drawings and Sequence Listing, which form a part of this application.

BRIEF DESCRIPTION OF THE DRAWINGS

FIG. 1A provides marker linkage information for linkage group L (LG-L) and depicts an integrated genetic map of soybean markers on LG-L, including the marker type (SSR, ASH, or SNP). The genetic map positions of the markers are indicated in centiMorgans (cM), typically with position zero being the first (most distal) marker on the chromosome. The map includes relative positions for some markers for which higher resolution genetic mapping data was not available, no position in cM is provided.

FIG. 1B is a continuation of FIG. 1A and depicts an integrated genetic map of soybean markers on LG-L.

FIG. 2 provides a table listing genetic markers that are linked to the herbicide tolerance markers identified on linkage group L. These markers are from the soybean public composite map of Jun. 18, 2008 for linkage group L.

FIG. 3A provides examples of primer and probe nucleic acid sequences that are useful for detecting SNP markers associated with the herbicide tolerance QTL on LG-L.

FIG. 3B is a continuation of FIG. 3A and provides examples of primer and probe nucleic acid sequences that are useful for detecting SNP markers associated with the herbicide tolerance QTL on LG-L.

FIG. 3C is a continuation of FIG. 3B and provides examples of primer and probe nucleic acid sequences that are useful for detecting SNP markers associated with the herbicide tolerance QTL on LG-L.

FIG. 3D is a continuation of FIG. 3C and provides examples of primer and probe nucleic acid sequences that are useful for detecting SNP markers associated with the herbicide tolerance QTL on LG-L.

FIG. 3E is a continuation of FIG. 3D and provides examples of primer and probe nucleic acid sequences that are useful for detecting SNP markers associated with the herbicide tolerance QTL on LG-L.

FIG. 6A is an exemplary alignment of Glyma19940 polypeptide sequences and provides a GAP alignment of tolerant (SEQ ID No: 128) vs. susceptible (SEQ ID NO: 129) polypeptide sequences.

FIG. 6B is a continuation of FIG. 6A and provides a GAP alignment of tolerant (SEQ ID No: 128) vs. susceptible (SEQ ID NO: 129) polypeptide sequences.

FIG. 7A is an exemplary alignment of Glyma19940 polynucleotide sequences and provides a GAP alignment of tolerant (SEQ ID NO: 124) vs. susceptible (SEQ ID NO: 125) polynucleotide sequences.

FIG. 7B is a continuation of FIG. 7A and provides a GAP alignment of tolerant (SEQ ID NO: 124) vs. susceptible (SEQ ID NO: 125) polynucleotide sequences.

FIG. 7C is a continuation of FIG. 7B and provides a GAP alignment of tolerant (SEQ ID NO: 124) vs. susceptible (SEQ ID NO: 125) polynucleotide sequences.

FIG. 7D is a continuation of FIG. 7C and provides a GAP alignment of tolerant (SEQ ID NO: 124) vs. susceptible (SEQ ID NO: 125) polynucleotide sequences.

FIG. 7E is a continuation of FIG. 7D and provides a GAP alignment of tolerant (SEQ ID NO: 124) vs. susceptible (SEQ ID NO: 125) polynucleotide sequences.

FIG. 7F is a continuation of FIG. 7E and provides a GAP alignment of tolerant (SEQ ID NO: 124) vs. susceptible (SEQ ID NO: 125) polynucleotide sequences.

FIG. 8A is an exemplary alignment of Glyma19940 polypeptide sequences and provides a PILEUP multiple sequence alignment of tolerant (SEQ ID NOs: 126 and 128) and susceptible (SEQ ID NOs: 127 and 129) polypeptide sequences.

FIG. 8B is a continuation of FIG. 8A and provides a PILEUP multiple sequence alignment of tolerant (SEQ ID NOs: 126 and 128) and susceptible (SEQ ID NOs: 127 and 129) polypeptide sequences.

FIG. 8C is a continuation of FIG. 8B and provides a PILEUP multiple sequence alignment of tolerant (SEQ ID NOs: 126 and 128) and susceptible (SEQ ID NOs: 127 and 129) polypeptide sequences.

FIG. 9A is an exemplary alignment of Glyma19940 polynucleotide sequences and provides a PILEUP multiple sequence alignment of tolerant (SEQ ID NOs: 122 and 124) and susceptible (SEQ ID NOs: 123 and 125) polynucleotide sequences.

FIG. 9B is a continuation of FIG. 9A and provides a PILEUP multiple sequence alignment of tolerant (SEQ ID NOs: 122 and 124) and susceptible (SEQ ID NOs: 123 and 125) polynucleotide sequences.

FIG. 9C is a continuation of FIG. 9B and provides a PILEUP multiple sequence alignment of tolerant (SEQ ID NOs: 122 and 124) and susceptible (SEQ ID NOs: 123 and 125) polynucleotide sequences.

FIG. 9D is a continuation of FIG. 9C and provides a PILEUP multiple sequence alignment of tolerant (SEQ ID NOs: 122 and 124) and susceptible (SEQ ID NOs: 123 and 125) polynucleotide sequences.

FIG. 9E is a continuation of FIG. 9D and provides a PILEUP multiple sequence alignment of tolerant (SEQ ID NOs: 122 and 124) and susceptible (SEQ ID NOs: 123 and 125) polynucleotide sequences.

FIG. 9F is a continuation of FIG. 9E and provides a PILEUP multiple sequence alignment of tolerant (SEQ ID NOs: 122 and 124) and susceptible (SEQ ID NOs: 123 and 125) polynucleotide sequences.

FIG. 9G is a continuation of FIG. 9F and provides a PILEUP multiple sequence alignment of tolerant (SEQ ID NOs: 122 and 124) and susceptible (SEQ ID NOs: 123 and 125) polynucleotide sequences.

FIG. 9H is a continuation of FIG. 9G and provides a PILEUP multiple sequence alignment of tolerant (SEQ ID NOs: 122 and 124) and susceptible (SEQ ID NOs: 123 and 125) polynucleotide sequences.

FIG. 9I is a continuation of FIG. 9H and provides a PILEUP multiple sequence alignment of tolerant (SEQ ID NOs: 122 and 124) and susceptible (SEQ ID NOs: 123 and 125) polynucleotide sequences.

SUMMARY OF THE SEQUENCES

Figure 4:
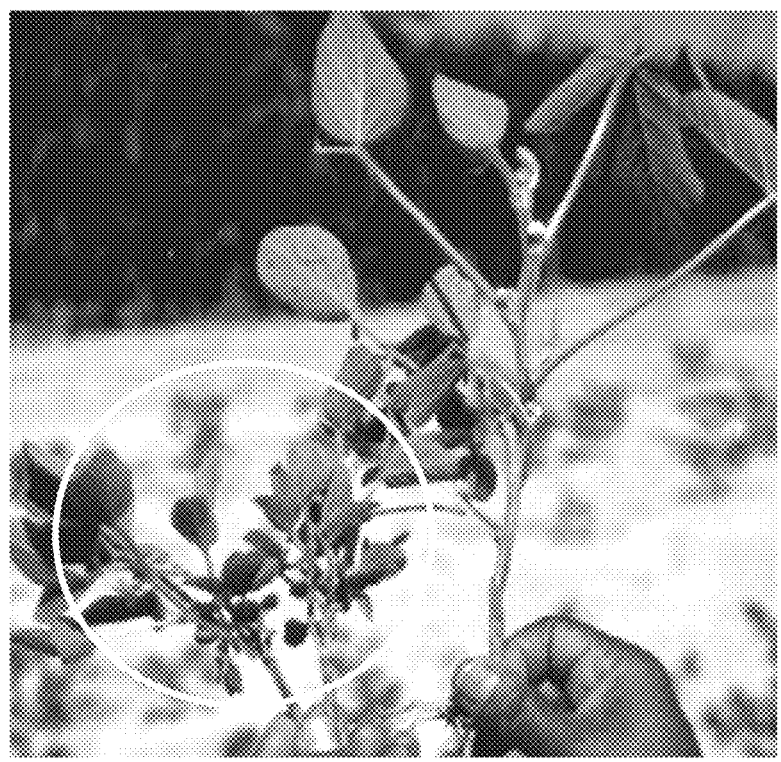
FIG. 4 provides an example of cultivars with vastly different protoporphyrinogen oxidase (PPO) inhibitor tolerance phenotypes. Shown are field samples, with a non-tolerant variety on the left (white circle: stunted, necrotic) and tolerant variety on the right (normal growth).

SEQ ID NOs: 1-5 comprise nucleotide sequences of regions of the Soybean genome, each capable of being used as a probe or primer, either alone or in combination, for the detection of marker locus P10649C-3 on LG-L. In certain examples, SEQ ID NOs: 1 and 2 are used as primers while SEQ ID NOs: 3-5 are used as probes.

SEQ ID NOs: 6-9 comprise nucleotide sequences of regions of the Soybean genome, each capable of being used as a probe or primer, either alone or in combination, for the detection of marker locus S00224-1 on LG-L. In certain examples, SEQ ID NOs: 6 and 7 are used as primers while SEQ ID NOs: 8 and 9 are used as probes.

SEQ ID NOs: 10-13 comprise nucleotide sequences of regions of the Soybean genome, each capable of being used as a probe or primer, either alone or in combination, for the detection of marker locus P5467-1 on LG-N. In certain examples, SEQ ID NOs: 10 and 11 are used as primers while SEQ ID NOs: 12 and 13 are used as probes.

SEQ ID NOs: 14-17 comprise nucleotide sequences of regions of the Soybean genome, each capable of being used as a probe or primer, either alone or in combination, for the detection of marker locus S08101-1-Q1 on LG-L. In certain examples, SEQ ID NOs: 14 and 15 are used as primers while SEQ ID NOs: 16 and 17 are used as probes.

SEQ ID NOs: 18-21 comprise nucleotide sequences of regions of the Soybean genome, each capable of being used as a probe or primer, either alone or in combination, for the detection of marker locus S08101-2-Q1 on LG-L. In certain examples, SEQ ID NOs: 18 and 19 are used as primers while SEQ ID NOs: 20 and 21 are used as probes.

SEQ ID NOs: 22-25 comprise nucleotide sequences of regions of the Soybean genome, each capable of being used as a probe or primer, either alone or in combination, for the detection of marker locus S08101-3-Q1 on LG-L. In certain examples, SEQ ID NOs: 22 and 23 are used as primers while SEQ ID NOs: 24 and 25 are used as probes.

SEQ ID NOs: 26-29 comprise nucleotide sequences of regions of the Soybean genome, each capable of being used as a probe or primer, either alone or in combination, for the detection of marker locus S08101-4-Q1 on LG-L. In certain examples, SEQ ID NOs: 26 and 27 are used as primers while SEQ ID NOs: 28 and 29 are used as probes.

SEQ ID NOs: 30-33 comprise nucleotide sequences of regions of the Soybean genome, each capable of being used as a probe or primer, either alone or in combination, for the detection of marker locus S08102-1-Q1 on LG-L. In certain examples, SEQ ID NOs: 30 and 31 are used as primers while SEQ ID NOs: 32 and 33 are used as probes.

SEQ ID NOs: 34-37 comprise nucleotide sequences of regions of the Soybean genome, each capable of being used as a probe or primer, either alone or in combination, for the detection of marker locus S08103-1-Q1 on LG-L. In certain examples, SEQ ID NOs: 34 and 35 are used as primers while SEQ ID NOs: 36 and 37 are used as probes.

SEQ ID NOs: 38-41 comprise nucleotide sequences of regions of the Soybean genome, each capable of being used as a probe or primer, either alone or in combination, for the detection of marker locus S08104-1-Q1 on LG-L. In certain examples, SEQ ID NOs: 38 and 39 are used as primers while SEQ ID NOs: 40 and 41 are used as probes.

SEQ ID NOs: 42-45 comprise nucleotide sequences of regions of the Soybean genome, each capable of being used as a probe or primer, either alone or in combination, for the detection of marker locus S08105-1-Q1 on LG-L. In certain examples, SEQ ID NOs: 42 and 43 are used as primers while SEQ ID NOs: 44 and 45 are used as probes.

SEQ ID NOs: 46-49 comprise nucleotide sequences of regions of the Soybean genome, each capable of being used as a probe or primer, either alone or in combination, for the detection of marker locus S08106-1-Q1 on LG-L. In certain examples, SEQ ID NOs: 46 and 47 are used as primers while SEQ ID NOs: 48 and 49 are used as probes.

SEQ ID NOs: 50-53 comprise nucleotide sequences of regions of the Soybean genome, each capable of being used as a probe or primer, either alone or in combination, for the detection of marker locus S08107-1-Q1 on LG-L. In certain examples, SEQ ID NOs: 50 and 51 are used as primers while SEQ ID NOs: 52 and 53 are used as probes.

SEQ ID NOs: 54-57 comprise nucleotide sequences of regions of the Soybean genome, each capable of being used as a probe or primer, either alone or in combination, for the detection of marker locus S08108-1-Q1 on LG-L. In certain examples, SEQ ID NOs: 54 and 55 are used as primers while SEQ ID NOs: 56 and 57 are used as probes.

SEQ ID NOs: 58-61 comprise nucleotide sequences of regions of the Soybean genome, each capable of being used as a probe or primer, either alone or in combination, for the detection of marker locus S08109-1-Q1 on LG-L. In certain examples, SEQ ID NOs: 58 and 59 are used as primers while SEQ ID NOs: 60 and 61 are used as probes.

SEQ ID NOs: 62-65 comprise nucleotide sequences of regions of the Soybean genome, each capable of being used as a probe or primer, either alone or in combination, for the detection of marker locus S08110-1-Q1 on LG-L. In certain examples, SEQ ID NOs: 62 and 63 are used as primers while SEQ ID NOs: 64 and 65 are used as probes.

SEQ ID NOs: 66-69 comprise nucleotide sequences of regions of the Soybean genome, each capable of being used as a probe or primer, either alone or in combination, for the detection of marker locus S08111-1-Q1 on LG-L. In certain examples, SEQ ID NOs: 66 and 67 are used as primers while SEQ ID NOs: 68 and 69 are used as probes.

SEQ ID NOs: 70-73 comprise nucleotide sequences of regions of the Soybean genome, each capable of being used as a probe or primer, either alone or in combination, for the detection of marker locus S08112-1-Q1 on LG-L. In certain examples, SEQ ID NOs: 70 and 71 are used as primers while SEQ ID NOs: 72 and 73 are used as probes.

SEQ ID NOs: 74-77 comprise nucleotide sequences of regions of the Soybean genome, each capable of being used as a probe or primer, either alone or in combination, for the detection of marker locus S08115-2-Q1 on LG-L. In certain examples, SEQ ID NOs: 74 and 75 are used as primers while SEQ ID NOs: 76 and 77 are used as probes.

SEQ ID NOs: 78-81 comprise nucleotide sequences of regions of the Soybean genome, each capable of being used as a probe or primer, either alone or in combination, for the detection of marker locus S08116-1-Q1 on LG-L. In certain examples, SEQ ID NOs: 78 and 79 are used as primers while SEQ ID NOs: 80 and 81 are used as probes.

SEQ ID NOs: 82-85 comprise nucleotide sequences of regions of the Soybean genome, each capable of being used as a probe or primer, either alone or in combination, for the detection of marker locus S08117-1-Q1 on LG-L. In certain examples, SEQ ID NOs: 82 and 83 are used as primers while SEQ ID NOs: 84 and 85 are used as probes.

SEQ ID NOs: 86-89 comprise nucleotide sequences of regions of the Soybean genome, each capable of being used as a probe or primer, either alone or in combination, for the detection of marker locus S08118-1-Q1 LG-L. In certain examples, SEQ ID NOs: 86 and 87 are used as primers while SEQ ID NOs: 88 and 89 are used as probes.

SEQ ID NOs: 90-93 comprise nucleotide sequences of regions of the Soybean genome, each capable of being used as a probe or primer, either alone or in combination, for the detection of marker locus S08119-1-Q1 on LG-L. In certain examples, SEQ ID NOs: 90 and 91 are used as primers while SEQ ID NOs: 92 and 93 are used as probes.

SEQ ID NOs: 94-97 comprise nucleotide sequences of regions of the Soybean genome, each capable of being used as a probe or primer, either alone or in combination, for the detection of marker locus S04867-1-A on LG-L. In certain examples, SEQ ID NOs: 94 and 95 are used as primers while SEQ ID NOs: 96 and 97 are used as probes.

SEQ ID NOs: 98-101 comprise nucleotide sequences of regions of the Soybean genome, each capable of being used as a probe or primer, either alone or in combination, for the detection of marker locus S03859-1-A on LG-L. In certain examples, SEQ ID NOs: 98 and 99 are used as primers while SEQ ID NOs: 100 and 101 are used as probes.

SEQ ID NOs: 102-105 comprise nucleotide sequences of regions of the Soybean genome, each capable of being used as a probe or primer, either alone or in combination, for the detection of marker locus S08010-1-Q1 on LG-L. In certain examples, SEQ ID NOs: 102 and 103 are used as primers while SEQ ID NOs: 104 and 105 are used as probes.

SEQ ID NOs: 106-109 comprise nucleotide sequences of regions of the Soybean genome, each capable of being used as a probe or primer, either alone or in combination, for the detection of marker locus S08010-2-Q1 on LG-L. In certain examples, SEQ ID NOs: 106 and 107 are used as primers while SEQ ID NOs: 108 and 109 are used as probes.

SEQ ID NOs: 110-113 comprise nucleotide sequences of regions of the Soybean genome, each capable of being used as a probe or primer, either alone or in combination, for the detection of marker locus S08114-1-Q1 on LG-L. In certain examples, SEQ ID NOs: 110 and 111 are used as primers while SEQ ID NOs: 112 and 113 are used as probes.

SEQ ID NOs: 114-117 comprise nucleotide sequences of regions of the Soybean genome, each capable of being used as a probe or primer, either alone or in combination, for the detection of marker locus S08113-1-Q1 on LG-L. In certain examples, SEQ ID NOs: 114 and 115 are used as primers while SEQ ID NOs: 116 and 117 are used as probes.

SEQ ID NOs: 118-121 comprise nucleotide sequences of regions of the Soybean genome, each capable of being used as a probe or primer, either alone or in combination, for the detection of marker locus S08007-1-Q1 on LG-L. In certain examples, SEQ ID NOs: 118 and 119 are used as primers while SEQ ID NOs: 120 and 121 are used as probes.

SEQ ID NO: 122 comprises the nucleotide sequence of approximately 95% of the coding region of Glyma19g1940.1 from a tolerant soybean line.

SEQ ID NO: 123 comprises the nucleotide sequence of approximately 95% of the coding region of Glyma19g1940.1 from a susceptible soybean line.

SEQ ID NO: 124 comprises the nucleotide sequence of a full length cDNA of Glyma19g1940.1 from tolerant soybean line GEID3495695.

SEQ ID NO: 125 comprises the nucleotide sequence of a full length cDNA of Glyma19g1940.1 from susceptible soybean line GEID1653063.

SEQ ID NO: 126 comprises the deduced amino acid sequence from the nucleotide sequence of SEQ ID NO: 122, which comprises the nucleotide sequence of approximately 95% of the coding region of Glyma19g1940.1 from a tolerant soybean line.

SEQ ID NO: 127 comprises the deduced amino acid sequence from the nucleotide sequence of SEQ ID NO: 123, which comprises the nucleotide sequence of approximately 95% of the coding region of Glyma19g1940.1 from a susceptible soybean line.

SEQ ID NO: 128 comprises the deduced amino acid sequence from the nucleotide sequence of SEQ ID NO: 124, which comprises the nucleotide sequence of a full length cDNA of Glyma19g1940.1 from tolerant soybean line GEID3495695.

SEQ ID NO: 129 comprises the deduced amino acid sequence from the nucleotide sequence of SEQ ID NO: 125, which comprises the nucleotide sequence of a full length cDNA of Glyma19g1940.1 from susceptible soybean line GEID1653063.

DETAILED DESCRIPTION

It is to be understood that this invention is not limited to particular embodiments or examples, which can, of course, vary. It is also to be understood that the terminology used herein is for the purpose of describing particular embodiments only, and is not intended to be limiting. Further, all publications referred to herein are incorporated by reference herein for the purpose cited to the same extent as if each was specifically and individually indicated to be incorporated by reference herein.

Definitions:

As used in this specification and the appended claims, terms in the singular and the singular forms "a," "an" and "the," for example, include plural referents unless the content clearly dictates otherwise. Thus, for example, reference to "plant," "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

Certain definitions used in the specification and claims are provided below. In order to provide a clear and consistent understanding of the specification and claims, including the scope to be given such terms, the following definitions are provided:

Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, insect resistance or tolerance, herbicide resistance or tolerance, branching, flowering, seed set, seed size, seed density, standability, threshability, and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods, such as the ligase chain reaction (LCR), and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

An "ancestral line" is a parent line used as a source of genes, e.g., for the development of elite lines.

An "ancestral population" is a group of ancestors that have contributed the bulk of the genetic variation that was used to develop elite lines.

"Backcrossing" is a process in which a breeder crosses a progeny variety back to one of the parental genotypes one or more times.

"Breeding" means the genetic manipulation of living organisms.

The term "chromosome segment" designates a contiguous linear span of genomic DNA that resides in planta on a single chromosome.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "equivalent position" in a polynucleotide and/or polypeptide sequence is a position that correlates to a position in the reference sequence when the sequences are aligned for a maximum correspondence. In some examples, the sequences are aligned across their whole length using a global alignment program. In other examples, a portion of the sequence or sequences may be aligned using a local alignment program or a global alignment program, for example a sequence may comprise exons and introns, conserved motifs or domains, or functional motifs or domains which may be aligned to the reference sequence(s) to identify equivalent positions. Equivalent positions in polynucleotides encoding a polypeptide can be determined using the encoded amino acid, and/or using a FrameAlign program to align the polynucleotide and polypeptide for maximal correspondence.

As used herein, the terms "exogenous" or "heterologous," as applied to polynucleotides or polypeptides, refer to molecules that have been artificially supplied to a biological system (e.g., a plant cell, a plant gene, a particular plant species or a plant chromosome under study) and are not native to that particular biological system. The terms indicate that the relevant material originated from a source other than the naturally occurring source, or refers to molecules having a non-natural configuration, genetic location or arrangement of parts. For example, exogenous polynucleotides includes polynucleotides from another organism or from the same organism which have been modified by linkage to a distinct non-endogenous polynucleotide and/or inserted to a distinct non-endogenous locus. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell. The term "introduced," when referring to a heterologous or exogenous nucleic acids, refers to the incorporation of a nucleic acid into a eukaryotic or prokaryotic cell using any type of suitable vector (e.g., naked linear DNA, plasmid, plastid, or virion), converted into an autonomous replicon, or transiently expressed (e.g., transfected mRNA). The term includes such nucleic acid introduction means as "transfection," "transformation," and "transduction." The term "host cell" means a cell that contains an exogenous nucleic acid, such as a vector, and supports the replication and/or expression of the nucleic acid. Host cells may be prokaryotic cells such as *E. coli*, or eukaryotic cells such as yeast, insect, amphibian or mammalian cells. In some examples, host cells are plant cells, including, but not limited to, dicot and monocot cells.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic linkage relationships among loci on one or more chromosomes (or linkage groups) within a given species, generally depicted in a diagrammatic or tabular form.

"Genotype" refers to the genetic constitution of a cell or organism.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Haplotype" means a combination of sequence polymorphisms that are located closely together on the same chromosome and that can discriminate between different genotypes. The combination represented by the haplotype tends to be inherited together, and this combination may represent sequence differences or alleles within a region. The region may contain one gene, or more than one gene.

The term "homologous" refers to nucleic acid sequences that are derived from a common ancestral gene through natural or artificial processes (e.g., are members of the same gene family), and thus, typically share sequence similarity. Typically, homologous nucleic acids have sufficient sequence identity that one of the sequences or a subsequence thereof or its complement is able to selectively hybridize to the other under selective (e.g., stringent) hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing nucleic acid sequences typically have about at least 70% sequence identity, at least 80% sequence identity, or about 90%, 91%, 92%, 93%, 94%, 95%, 96%, 97%, 98%, 99%, 99.5%, 99.75%, or 100% sequence identity with each other. A nucleic acid that exhibits at least some degree of homology to a reference nucleic acid can be unique or identical to the reference nucleic acid or its complementary sequence.

The term "introgression" refers to the transmission of a desired allele of a genetic locus from one genetic background to another by sexual crossing, transgenic means, or any other means known in the art. For example, introgression of a desired allele at a specified locus can be transmitted to at least one progeny plant via a sexual cross between two parent plants, at least one of the parent plants having the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a gene allele that imparts resistance to a plant pathogen.

The term "isolated" refers to material, such as polynucleotides or polypeptides, which are identified and separated from at least one contaminant with which it is ordinarily associated in its natural or original source. Furthermore, an isolated polynucleotide or polypeptide is typically present in a form or setting that is different from the form or setting that is normally found in nature. In some examples, the isolated molecule is substantially free from components that normally accompany or interact with it in its naturally occurring environment. In some embodiments, the isolated material optionally comprises material not found with the material in its natural environment, e.g., in a cell.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between two genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers lie to each other on the chromosome, the lower the frequency of recombination, and the greater the degree of linkage. Traits or markers are considered herein to be linked if they generally co-segregate. A 1/100 probability of recombination per generation is defined as a map distance of 1.0 centiMorgan (1.0 cM). For example, in soybean, 1 cM correlates, on average, to about 400,000 base pairs (400 Kb).

The genetic elements or genes located on a single chromosome segment are physically linked. Advantageously, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

"Linkage disequilibrium" refers to a phenomenon wherein alleles tend to remain together in linkage groups when segregating from parents to offspring, with a greater frequency than expected from their individual frequencies.

"Linkage group" refers to traits or markers that generally co-segregate. A linkage group generally corresponds to a chromosomal region containing genetic material that encodes the traits or markers.

"Locus" is a defined segment of DNA.

A "map location" is an assigned location on a genetic map relative to linked genetic markers where a specified marker can be found within a given species. Markers are frequently described as being "above" or "below" other markers on the same linkage group; a marker is "above" another marker if it appears earlier on the linkage group, whereas a marker is "below" another marker if it appears later on the linkage group.

"Mapping" is the process of defining the linkage relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Examples include Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs). Additionally, other types of molecular markers are known to the art, and phenotypic traits may also be used as markers. All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under specific conditions where the trait can be expressed. Molecular markers have been widely used to determine genetic composition in soybeans. Shoemaker and Olsen, ((1993) Molecular Linkage Map of Soybean (*Glycine max* L. Merr.). p. 6.131-6.138. In Si. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD, three classical markers, and four isozyme loci. See also Shoemaker R. C. (1994) RFLP Map of Soybean. pp. 299-309 in R. L. Phillips and I. K. Vasil (ed.) DNA-based markers in plants. Kluwer Academic Press Dordrecht, the Netherlands.

"Marker assisted selection" refers to the process of selecting a desired trait or desired traits in a plant or plants by detecting one or more molecular markers from the plant, where the molecular marker is linked to the desired trait.

The term "plant" includes reference to an immature or mature whole plant, including a plant from which seed or grain or anthers have been removed. Seed or embryo that will produce the plant is also considered to be the plant.

As used herein, the term "plant cell" includes, without limitation, cells within or derived from, for example and without limitation, plant seeds, plant tissue suspension cultures, plant tissue, plant tissue explants, plant embryos, meristematic tissue, callus tissue, leaves, roots, shoots, gametophytes, sporophytes, pollen and microspores.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleic acid comprising at least one nucleotide difference when compared to a related sequence when the two nucleic acids are aligned for maximal correspondence. A "genetic nucleotide polymorphism" refers to a nucleic acid comprising at least one nucleotide difference when compared to a related sequence when the two nucleic acids are aligned for maximal correspondence, where the two nucleic acids are genetically related, i.e., homologous, for example, where the nucleic acids are isolated from different strains of a soybean plant, or from different alleles of a single strain, or the like.

"Polynucleotide," "polynucleotide sequence," "nucleic acid sequence," "nucleic acid fragment," and "oligonucleotide" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

"Positional cloning" is a cloning procedure in which a target nucleic acid is identified and isolated by its genomic proximity to marker nucleic acid. For example, a genomic nucleic acid clone can include part or all of two more chromosomal regions that are proximal to one another. If a marker can be used to identify the genomic nucleic acid clone from a genomic library, standard methods such as sub-cloning or sequencing can be used to identify and or isolate subsequences of the clone that are located near the marker.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleic acids in length, but longer or shorter sequences can be employed. A probe can further contain a detectable label. The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, semiconductor nanocrystals, ligands (e.g., biotin, avidin, streptavidin, or haptens), and the like. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

"RAPD marker" means random amplified polymorphic DNA marker. Chance pairs of sites complementary to single octa- or decanucleotides may exist in the correct orientation and close enough to one another for PCR amplification. With some randomly chosen decanucleotides no sequences are amplified. With others, the same length products are generated from DNAs of different individuals. With still others, patterns of bands are not the same for every individual in a population. The variable bands are commonly called random amplified polymorphic DNA (RAPD) bands.

The term "recombinant" indicates that the material (e.g., a recombinant nucleic acid, gene, polynucleotide or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural text and cloned into any type of artificial nucleic acid vector. Protocols and reagents to produce recombinant molecules, especially recombinant nucleic acids, are common and routine in the art (see, e.g., Maniatis et al. (eds.), Molecular Cloning: A Laboratory Manual, Cold Spring Harbor Laboratory Press, NY, [1982]; Sambrook et al. (eds.), Molecular Cloning: A Laboratory Manual, Second Edition, Volumes 1-3, Cold Spring Harbor Laboratory Press, NY, [1989]; and Ausubel et al. (eds.), Current Protocols in Molecular Biology, Vol. 1-4, John Wiley & Sons, Inc., New York [1994]). The term recombinant can also refer to an organism that harbors a recombinant material, e.g., a plant that comprises a recombinant nucleic acid is considered a recombinant plant. In some embodiments, a recombinant organism is a transgenic organism.

"Recombination frequency" is the frequency of a crossing over event (recombination) between two genetic loci. Recombination frequency can be observed by following the segregation of markers and/or traits during meiosis. A marker locus is "associated with" another marker locus or some other locus (for example, a tolerance locus), when the relevant loci are part of the same linkage group and are in linkage disequilibrium. This occurs when the marker locus and a linked locus are found together in progeny plants more frequently than if the two loci segregated randomly. Similarly, a marker locus can also be associated with a trait, e.g., a marker locus can be "associated with tolerance or improved tolerance," when the marker locus is in linkage disequilibrium with the trait.

"RFLP" means restriction fragment length polymorphism. Any sequence change in DNA, including a single base substitution, insertion, deletion or inversion, can result in loss or gain of a restriction endonuclease recognition site. The size and number of fragments generated by one such enzyme is therefore altered. A probe that hybridizes specifically to DNA in the region of such an alteration can be used to rapidly and specifically identify a region of DNA that displays allelic variation between two plant varieties. Isozyme Electrophoresis and RFLPs have been widely used to determine genetic composition "Self crossing" or "self pollination" or "selfing" a process through which a breeder crosses progeny with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome. Many techniques for detecting SNPs are known in the art, including allele specific hybridization, primer extension, direct sequencing, and real-time PCR, such as the TaqMan™ assay.

"SSR" means short sequence repeats. "SSR markers" are genetic markers based on polymorphisms in repeated nucleotide sequences, such as microsatellites. A marker system based on SSRs can be highly informative in linkage analysis relative to other marker systems in that multiple alleles may be present. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

"Tolerance" and "improved tolerance" are used interchangeably herein and refer to plants in which higher doses of a herbicide are required to produce effects similar to those seen in non-tolerant plants. Tolerant plants typically exhibit fewer necrotic, lytic, chlorotic, or other lesions when subjected to the herbicide at concentrations and rates typically employed by the agricultural community. A "tolerant plant" or "tolerant plant variety" need not possess absolute or complete tolerance such that no detrimental effect to the plant or plant variety is observed when the given herbicide is applied. Instead, a "tolerant plant," "tolerant plant variety," or a plant or plant variety with "improved tolerance" will simply be less affected by the given herbicide than a comparable susceptible plant or variety.

"Transgenic plant" refers to a plant that comprises within its cells an exogenous polynucleotide, e.g., a polynucleotide from another organism (including a polynucleotide from another soybean plant). Generally, the exogenous polynucleotide is stably integrated within a genome such that the polynucleotide is passed on to successive generations. The exogenous polynucleotide may be integrated into the genome alone or as part of a recombinant expression cassette. "Transgenic" is used herein to refer to any cell, cell line, callus, tissue, plant part, or plant, the genotype of which has been altered by the presence of exogenous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"TRAP marker" means target region amplification polymorphism marker. The TRAP technique employs one fixed primer of known sequence in combination with a random primer to amplify genomic fragments. The differences in fragments between alleles can be detected by gel electrophoresis.

The term "vector" is used in reference to polynucleotide or other molecules that transfer nucleic acid segment(s) into a cell. A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

Mesotrione, Isoxazole, and PPO Inhibitor Herbicides

Mesotrione and isoxazole are two herbicide classes from different chemical families. Isoxazole is used as a pre-plant herbicide while mesotrione is used as either a pre-plant or post-emergent herbicide. Isoxazole is member of the isoxazole chemical family. Following either foliar or root uptake, isoxazole is rapidly converted to a diketonitrile derivative (2-cyclopropyl-3-(2-mesyl-4-trifluoromethylphenyl)-3-oxopropanenitrile) by opening of the isoxazole ring. This diketonitrile undergoes degradation to a benzoic acid derivative (2-mesyl-4-trifluoromethyl benzoic acid) in treated plants and the extent of this degradation is correlated to the degree of susceptibility, being most rapid in tolerant plants and slowest in susceptible plants.

Mesotrione belongs to the triketone family of herbicides, which are chemically derived from a natural phytotoxin produced by the bottlebrush plant *Callistemon citrinus*. Mesotrione works by inhibiting HPPD (p-hydroxyphenylpyruvate dioxygenase), an essential enzyme in the biosynthesis of carotenoids. Carotenoids protect chlorophyll from excess light energy Porphyrins are biologically important organic structures that are found in plants attached to chlorophyll and cytochrome pigments. An intermediate in the chlorophyll and cytochrome synthesis pathway is protoporphyrinogen IX which is converted to protoporphyrin IX by protoporphyrinogen oxidase. Inhibition of protoporphyrinogen oxidase prevents this conversion and results in a buildup of protoporphyrinogen IX in the cytoplasm of the plant. The protoporphyrinogen then undergoes non-enzymatic auto-oxidation and becomes protoporphyrin IX. When cytoplasmic protoporphyrin IX is exposed to sunlight, free radicals are formed which results in lipid peroxidation reactions that result in plant death. Protoporphyrinogen oxidase (PPO) inhibitor chemical families include diphenyl ether, triazolinone, N-phenylphthalimide, pyrimidindione and oxadiazole families. There are other families of chemistries that also belong to this group.

The diphenyl ether family is characterized by two benzene rings linked with an ether bridge and a nitro group bonded to the 4 position. Examples of diphenyl ether protoporphyrinogen oxidase inhibitors include acifluorfen, fomesafen, oxyfluorfen and lactofen. The diphenyl ethers are typically considered to be contact herbicides.

The triazolinone family is characterized by a 5-member ring containing three nitrogen atoms (two of which are adjacent) and two carbon atoms, one of the carbon atoms has a double bond with an oxygen atom and one of the nitrogen atoms is bonded to a benzene ring. Examples of triazolinone protoprophyrinogen oxidase inhibitors include sulfentrazone, carfentrasone, and azafeniden.

The N-phenylphthalimide family is characterized by pthalimide group wherein the nitrogen is bonded to a benzene ring. Examples of N-phenylphthalimide protoporphyrinogen oxidase inhibitors include flumiclorac and flumioxazin.

The oxadiazole family is characterized by a five member ring consisting of two adjacent nitrogen atoms, two carbon atoms, and an oxygen or sulfur atom. Examples of oxadiazole protoporphyrinogen oxidase inhibitors include oxadiazon and fluthiacet.

The various families of protoporphyrinogen oxidase inhibitors provide a wide variety in application options. Sulfentrazone, for example, has a relatively long half-life (approximately 280 days), is known to have residual soil activity and is frequently used as a pre-emergence herbicide. Carfentrazone has a considerably shorter half-life (approximately 4 days) has no residual soil activity, and is used as a contact/post-emergence herbicide. The pyrimidindiones family of PPO herbicides is a rather small class that includes benzfendizone, butagenacil and saflufenacil. This diversity in chemical characteristics combined with protoporphyrinogen oxidase inhibitor tolerance provides farmers with a wide variety of weed management options.

Mesotrione, isoxazole, and PPO inhibitor herbicides are each useful, for example, as a pre-emergent herbicide.

Molecular Markers and Genetic Linkage

In traditional linkage analysis, no direct knowledge of the physical relationship of genes on a chromosome is required. Mendel's first law is that factors of pairs of characteristics are segregated, meaning that alleles of a diploid trait separate into two gametes and then into different offspring. Classical linkage analysis can be thought of as a statistical description of the relative frequencies of cosegregation of different traits. Linkage analysis, as described previously, is the well-characterized descriptive framework of how traits are grouped together based upon the frequency with which they segregate together. Because chromosomal distance is approximately proportional to the frequency of crossing over events between traits, there is an approximate physical distance that correlates with recombination frequency.

Marker loci are traits, and can be assessed according to standard linkage analysis by tracking the marker loci during segregation. Thus, one cM is equal to a 1% chance that a marker locus will be separated from another locus (which can be any other trait, e.g., another marker locus, or another trait locus that encodes a QTL), due to crossing over in a single generation. Any detectible polymorphic trait can be used as a marker so long as it is inherited differentially and exhibits linkage disequilibrium with a phenotypic trait of interest. A number of soybean markers have been mapped and linkage groups created, as described in Cregan, P. B. et al., "An Integrated Genetic Linkage Map of the Soybean Genome" (1999) Crop Science 39:1464-90, and more recently in Choi et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website.

Most plant traits of agronomic importance are polygenic, otherwise known as quantitative traits. A quantitative trait is controlled by two or more genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicate greater linkage between the QTL and the molecular marker. The extent to which two features are linked is often referred to as the genetic distance. The genetic distance is also typically related to the physical distance between the marker and the QTL; however, certain biological phenomenon (including recombinational "hot spots") can affect the relationship between physical distance and genetic distance. Generally, the usefulness of a molecular marker is determined by the genetic and physical distance between the marker and the selectable trait of interest.

The method for determining the presence or absence of a QTL associated with tolerance or sensitivity to multiple herbicides, including one or more of a mesotrione, an isoxazole, and a PPO inhibitor herbicide, in soybean germplasm, comprises analyzing genomic DNA from a soybean germplasm for the presence of at least one molecular marker, wherein at least one molecular marker is linked to the QTL, and wherein the QTL maps to soybean major linkage group L and is associated with herbicide tolerance or sensitivity. The term "is associated with" in this context means that the QTL associated with herbicide tolerance or sensitivity has been found to be present in soybean plants showing herbicide tolerance or sensitivity as described herein.

Any marker that is linked to a trait of interest (e.g., in the present case, a tolerance or improved tolerance trait) can be used as a marker for that trait. Thus, in addition to the markers described herein, markers linked to the markers itemized herein can also be used to predict the tolerance, improved tolerance, or susceptibility/sensitivity trait. Such linked markers are particularly useful when they are sufficiently proximal to a given marker so that they display a low recombination frequency with the given marker. Markers linked and/or closely linked to the given markers are provided, for example, in FIGS. 1A and 1B. These include, for example, SATT495, SATT723, Sat_408, A169_1, EV2_1, Sle3_4s, BLT010_2, BLT007_1, SATT232, S04867-1-A, S08102-1-Q1, S08103-1-Q1, S08104-1-Q1, S08106-1-Q1, S08107-1-Q1, S08109-1-Q1, S08110-1-Q1, S08111-1-Q1, S08115-2-Q1, S08117-1-Q1, S08119-1-Q1, S08116-1-Q1, S08112-1-Q1, S08108-1-Q1, S08101-4-Q1, S08101-1-Q1, S08101-2-Q1, S08101-3-Q1, S08118-1-Q1, S08114-1-Q1, S08113-1-Q1, S03859-1-A, Sat_301, SATT446, P10649C-3, SATT232, S08105-1-Q1, SATT182, S08010-1-Q1, S08010-2-Q1, R176_1, JUBC090, SATT238, Sat_071, BLT039_1, Bng071_1, SATT388, A264_1, RGA_7, RGA7, SATT523, Sat_134, S00224-1, S01659-1, LbA, i8_2, A450_2, A106_1, Sat_405, SATT143, B124_2, A459_1, SATT398, SATT694, Sat_195, Sat_388, SATT652, SATT711, Sat_187, SATT418, SATT278, Sat_397, Sat_191, Sat_320, O109_1, A204_2, SATT497, G214_17, SATT313, B164_1, G214_16, SATT613, A023_1, SATT284, AW508247, SATT462, L050_7, E014_1, A071_5, B046_1, L1, and B162_2.

Marker loci are especially useful when they are closely linked to target loci (e.g., QTL for tolerance, or, alternatively, simply other marker loci, such as those identified herein, that are linked to such QTL) for which they are being used as markers. A marker more closely linked to a target locus is a better indicator for the target locus (due to the reduced cross-over frequency between the target locus and the marker). Thus, in one example, closely linked loci such as a marker locus and a second locus (e.g., a given marker or a QTL) display an inter-locus cross-over frequency of about 10% or less, about 9% or less, about 8% or less, about 7% or less, about 6% or less, about 5% or less, about 4% or less, about 3% or less, or about 2% or less. In some examples, the relevant loci (e.g., a marker locus and a target locus such as a QTL) display a recombination a frequency of about 1% or less, e.g., about 0.75% or less, about 0.5% or less, or about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of no more than 10% (e.g., about 9%, 8%, 7%, 6%, 5%, 4%, 3%, 2%, 1%, 0.75%, 0.5%, 0.25%, or less) are said to be proximal to each other.

Many marker alleles can be detected or selected for or against. Optionally, one, two, three, or more marker allele(s) can be identified in or introgressed into the plant. Plants or germplasm frequently are identified that have at least one favorable allele that positively correlates with tolerance or improved tolerance. However, it is useful for exclusionary purposes during breeding to also identify alleles that negatively correlate with tolerance, to eliminate such plants or germplasm from subsequent rounds of breeding.

The identification of favorable marker alleles may be germplasm-specific. The determination of which marker alleles correlate with tolerance (or non-tolerance) is determined for the particular germplasm under study. One of skill recognizes that methods for identifying favorable alleles are routine and well known, and, furthermore, that the identification and use of such favorable alleles is well within the scope of the invention.

Numerous markers disclosed herein have been found to be associated with or to correlate with tolerance, improved tolerance, or susceptibility/sensitivity to herbicides in soybean, including one or more of a mesotrione, an isoxazole, and a PPO inhibitor herbicide. Generally, markers that map closer to the QTL mapped to linkage group L and associated with herbicide tolerance or sensitivity are superior to markers that map farther from the QTL. In some examples, a marker used to determine the presence or absence of a QTL mapping to soybean linkage group L and associated with herbicide tolerance or sensitivity includes one or more of SATT495, P10649C-3, SATT182, S03859-1, S00224-1, SATT388, SATT313, and SATT613, or other markers above marker SATT613 on LG-L. Additional useful and/or relevant markers include S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1. Any marker assigned to soybean linkage group L and linked or closely linked to a marker disclosed herein as associated with herbicide tolerance or sensitivity may be used. Generally, a linked marker is within 50 cM of the referenced marker or trait, and a closely linked marker is within 10 cM of the referenced marker or trait. Updated information regarding markers assigned to soybean linkage group L may be found on the USDA's Soybase website. Further, linkage group L is now formally referred to as chromosome #19.

Intervals defined by markers flanking the QTL associated with herbicide tolerance or sensitivity are useful, as well. For interval determination, the genomic DNA of soybean germplasm is typically tested for the presence of at least two of the foregoing molecular markers, one marker on each side of the QTL. Examples of such intervals include the interval flanked by and including SATT613 and above on LG-L, the interval flanked by and including markers SATT495 and SATT613, the interval flanked by and including SATT313 and above on LG-L, the interval flanked by and including markers SATT495 and SATT313, the interval flanked by and including markers SATT495 and SATT388, the interval flanked by and including markers P10649C-3 and SATT182, the interval flanked by and including markers S04867-1-A and S03859-1-A, the interval flanked by and including markers S08110-1-Q1 and S08010-1-Q1, the interval flanked by and including markers S08117-1-Q1 and S08010-1-Q1, the interval flanked by and including markers S08110-1-Q1 and S08105-1-Q1, the interval flanked by and including markers S08117-1-Q1 and S08105-1-Q1, and the interval flanked by and including markers S08113-1-Q1 and S08105-1-Q1.

Initial fine mapping isolated the location of the QTL associated with herbicide tolerance/sensitivity to a ~56 kb interval between marker S08117-1-Q1 and S08105-1-Q1 on linkage group L. Further fine mapping refined the location of the QTL to a ~44 kb interval between marker S08113-1-Q1 and S08105-1-Q1 on linkage group L. Accordingly, markers that map within the interval defined by and including these markers are particularly useful for selecting for this QTL. These markers include S08117-1-Q1, S08119-1-Q1, S08118-1-Q1, S08116-1-Q1, S08101-1-Q1, S08112-1-Q1, S08108-1-Q1, S08101-1-Q1, S08101-2-Q1, S08101-3-Q1, S08101-4-Q1, and S08105-1-Q1. In some examples, the markers are S08112-1-Q1, S08108-1-Q1, S08101-2-Q1, S08101-3-Q1, and S08101-4-Q1.

Methods of introgressing herbicide tolerance into non-tolerant or less-tolerant soybean germplasm are provided. Any method for introgressing QTLs into soybean plants can be used. In some examples, a first soybean germplasm that contains herbicide tolerance or sensitivity derived from the QTL mapped to linkage group L which is associated with herbicide tolerance or sensitivity and a second soybean germplasm that lacks such tolerance or sensitivity are provided. The first soybean plant may be crossed with the second soybean plant to provide progeny soybeans. Phenotypic and/or marker screening is performed on the progeny plants to determine the presence of herbicide tolerance or sensitivity derived from the QTL mapped to linkage group L. Progeny that test positive for the presence of herbicide tolerance or sensitivity derived from the QTL mapped to linkage group L can be selected.

In some examples, the screening and selection are performed by using marker-assisted selection using any marker or combination of markers on major linkage group L provided. Any method of identifying the presence or absence of these markers may be used, including for example single-strand conformation polymorphism (SSCP) analysis, base excision sequence scanning (BESS), RFLP analysis, heteroduplex analysis, denaturing gradient gel electrophoresis, temperature gradient electrophoresis, allelic PCR, ligase chain reaction direct sequencing, mini sequencing, nucleic acid hybridization, or micro-array-type detection.

Amplification primers for amplifying marker loci and suitable marker probes to detect marker loci or to genotype SNP alleles are provided, for example, in FIGS. 3A-3E and the related sequence listing (SEQ ID NOs: 1-121). Optionally, other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. The configuration of the amplification primers and detection probes can, of course, vary. Thus, the invention is not limited to the primers and probes specifically recited herein.

Systems, including automated systems for selecting plants that comprise a marker of interest and/or for correlating presence of the marker with tolerance are also provided. These systems can include probes relevant to marker locus detection, detectors for detecting labels on the probes, appropriate fluid handling elements and temperature controllers that mix probes and templates and/or amplify templates, and systems and/or instructions that correlate label detection to the presence of a particular marker locus or allele.

Kits are also provided. For example, a kit can include appropriate primers or probes for detecting tolerance associated marker loci and instructions for using the primers or probes for detecting the marker loci and correlating the loci with predicted herbicide tolerance. The kits can further include packaging materials for packaging the probes, primers, or instructions; controls, such as control amplification reactions that include probes, primers, or template nucleic acids for amplifications; molecular size markers; or the like.

Isolated nucleic acid fragments comprising a nucleic acid sequence coding for herbicide tolerance or sensitivity are provided. The nucleic acid fragment comprises at least a portion of a nucleic acid belonging to linkage group L. The nucleic acid fragment is capable of hybridizing under stringent conditions to a nucleic acid of a soybean cultivar possessing a QTL associated with herbicide tolerance that is located on major linkage group L.

Vectors comprising such nucleic acid fragments, expression products of such vectors expressed in a host compatible therewith, antibodies to the expression product (both polyclonal and monoclonal), and antisense nucleic acid to the nucleic acid fragment are also provided.

Seed of a soybean produced by crossing a soybean variety having an herbicide tolerance QTL located on major linkage group L in its genome with another soybean variety, and progeny thereof, are provided.

Detection Methods

Any suitable detection method known in the art can be used to detect the markers, QTL, or traits discussed herein. In some examples, the presence of marker loci is directly detected in unamplified genomic DNA by performing a Southern blot on a sample of genomic DNA using probes to the marker loci. In other examples, amplification based techniques are employed. PCR, RT-PCR, and LCR are in particularly broad use as amplification and amplification-detection methods for amplifying nucleic acids of interest, thus facilitating detection of markers. Procedures for performing Southern blotting, amplification (PCR, LCR, or the like), and many other nucleic acid detection methods are well established and are taught, e.g., in Sambrook et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis et al. eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Typically, molecular markers are detected by any established method available, including, without limitation, allele specific hybridization (ASH), real-time PCR assays for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. While the exemplary markers provided in the tables herein are either SSR or SNP markers, any of the aforementioned marker types can be employed to identify chromosome segments encompassing genetic element that contribute to superior agronomic performance (e.g., tolerance or improved tolerance).

In another example, the presence or absence of a molecular marker is determined by nucleotide sequencing of the polymorphic marker region. This method is readily adapted to high throughput analysis, as are the other methods noted above, e.g., using available high throughput sequencing methods such as sequencing by hybridization.

In general, the majority of genetic markers rely on one or more properties of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York, as well as in Sambrook and Ausubel.

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction-digested genomic DNA. The restriction enzyme is selected to provide restriction fragments of at least two alternative (or polymorphic) lengths in different individuals or populations. Determining one or more restriction enzymes that produce informative fragments for each cross is a simple procedure. After separation by length in an appropriate matrix (e.g., agarose, polyacrylamide, etc.) and transfer to a membrane (e.g., nitrocellulose, nylon, etc.), the labeled probe is hybridized under conditions which result in equilibrium binding of the probe to the target followed by removal of excess probe by washing.

In some examples, molecular markers are detected using a suitable PCR-based detection method. This includes methods where the size or sequence of the PCR amplicon is indicative of the absence or presence of the marker (e.g., a particular marker allele), as well as methods where a labeled allele-specific probe is used for detection (e.g., a TaqMan® assay). In these types of methods, PCR primers and, optionally, probes are hybridized to the conserved regions flanking the polymorphic marker region. Suitable primers can be designed using any suitable method. It is not intended that the invention be limited to any particular primer or primer pair. For example, primers can be designed using any suitable software program, such as LASERGEN®.

In some examples, primers are labeled by any suitable means (e.g., using a non-radioactive fluorescent tag) to allow for rapid visualization of the different size amplicons following an amplification reaction without any additional labeling step or visualization step. In some examples, the primers are not labeled, and the amplicons are visualized following their size resolution, e.g., following agarose gel electrophoresis. In some examples, ethidium bromide staining of the PCR amplicons following size resolution allows visualization of the different size amplicons.

The primers used to amplify the marker loci and alleles herein are not limited to amplifying the entire region of the relevant locus. In some examples, marker amplification produces an amplicon at least 20 nucleotides in length, or alternatively, at least 50 nucleotides in length, or alternatively, at least 100 nucleotides in length, or alternatively, at least 200 nucleotides in length, or up to and including the full length of the amplicon.

Nucleic acid probes to the marker loci can also be cloned and/or synthesized. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Methods and reagents for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Real Time Amplification/Detection Methods:

In one aspect, real time PCR or LCR is performed on the amplification mixtures described herein, e.g., using molecular beacons or TaqMan™ probes. A molecular beacon (MB) is an oligonucleotide or peptide nucleic acid (PNA) which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched and signal is detected. Standard methods of making and using MBs are known and MBs and reagents are commercially available. See also, e.g., Leone et al. (1995) "Molecular beacon probes combined with amplification by NASBA enable homogenous real-time detection of RNA." Nucleic Acids Res. 26:2150-2155; Tyagi and Kramer (1996) "Molecular beacons: probes that fluoresce upon hybridization" Nature Biotechnology 14:303-308; Blok and Kramer (1997) "Amplifiable hybridization probes containing a molecular switch" Mol Cell Probes 11:187-194; Hsuih et al. (1997) "Novel, ligation-dependent PCR assay for detection of hepatitis C in serum" J Clin Microbiol 34:501-507; Kostrikis et al. (1998) "Molecular beacons: spectral genotyping of human alleles" Science 279:1228-1229; Sokol et al. (1998) "Real time detection of DNA:RNA hybridization in living cells" Proc. Natl. Acad. Sci. U.S.A. 95:11538-11543; Tyagi et al. (1998) "Multicolor molecular beacons for allele discrimination" Nature Biotechnology 16:49-53; Bonnet et al. (1999) "Thermodynamic basis of the chemical specificity of structured DNA probes" Proc. Natl. Acad. Sci. U.S.A. 96:6171-6176; Fang et al. (1999) "Designing a novel molecular beacon for surface-immobilized DNA hybridization studies" J. Am. Chem. Soc. 121:2921-2922; Marras et al. (1999) "Multiplex detection of single-nucleotide variation using molecular beacons" Genet. Anal. Biomol. Eng. 14:151-156; and Vet et al. (1999) "Multiplex detection of four pathogenic retroviruses using molecular beacons" Proc. Natl. Acad. Sci. U.S.A. 96:6394-6399. See also, e.g., U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits."

PCR detection and quantification using dual-labeled fluorogenic oligonucleotide probes can be done, using, for example, TaqMan® probes. These probes are composed of short (e.g., 10-40 bases) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher via FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TaqMan® probes are oligonucleotides that have a label and a quencher, where the label is released during amplification by the exonuclease action of the polymerase used in amplification. This provides a real time measure of amplification during synthesis. A variety of TaqMan® reagents are commercially available, e.g., from Applied Biosystems (Division Headquarters in Foster City, Calif.) as well as from a variety of specialty vendors such as Biosearch Technologies (e.g., black hole quencher probes).

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers (1981), Tetrahedron Letts 22:1859-1862, e.g., using a commercially available automated synthesizer. Oligonucleotides, including modified oligonucleotides and PNAs, can also be ordered from a variety of commercial sources known to persons of skill in the art.

Additional Details Regarding Amplified Variable Sequences SSR, AFLP ASH, SNPs, and Isozyme Markers Amplified variable sequences refer to amplified sequences of the plant genome, which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Typically, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNase H, and (3) a DNA-dependent RNA polymerase (Guatelli et al. (1990) Proc Natl Acad Sci USA 87:1874). By mimicking the retroviral strategy of RNA replication by means of cDNA intermediates, this reaction accumulates cDNA and RNA copies of the original target.

Amplified fragment length polymorphisms (AFLP), which are amplified before or after cleavage by a restriction endonuclease, can also be used as genetic markers (Vos et al. (1995) Nucl Acids Res 23:4407). The amplification step allows easier detection of specific restriction fragments. AFLP allows the detection large numbers of polymorphic markers and has been used for genetic mapping of plants (Becker et al. (1995) Mol Gen Genet 249:65; and Meksem et al. (1995) Mol Gen Genet 249:74).

Allele-specific hybridization (ASH) can be used to identify the genetic markers. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane. In one example, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on, e.g., an acrylamide gel. However, alternative modes of detection, such as hybridization, e.g., ASH, RFLP analysis, or real-time PCR analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid sequence, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes, which differ at the nucleic acid level, can be determined. In such cases any of the nucleic acid based methods described herein can be used to analyze isozyme markers.

Marker Assisted Selection and Breeding of Plants

The identification of markers associated with a particular phenotypic trait can allow for selection of plants possessing that trait, for example, via marker assisted selection (MAS). In general, the application of MAS uses the identification of a population of tolerant plants and genetic mapping of the tolerance trait. Polymorphic loci in the vicinity of the mapped tolerance trait are chosen as potential tolerance markers. Typically, a marker locus closest to the tolerance locus is a preferred marker. Linkage analysis is then used to determine which polymorphic marker allele sequence demonstrates a statistical likelihood of co-segregation with the tolerant phenotype (thus, a "tolerance marker allele"). Following identification of a marker allele for co-segregation with the tolerance allele, it is possible to use this marker for rapid, accurate screening of plant lines for the tolerance allele without the need to grow the plants through their life cycle and await phenotypic evaluations, and, furthermore, permits genetic selection for the particular tolerance allele even when the molecular identity of the actual tolerance QTL is anonymous. Tissue samples can be taken, for example, from the first leaf of the plant and screened with the appropriate molecular marker, and within days it is determined which progeny will advance. Linked markers also remove the impact of environmental factors that can often influence phenotypic expression.

After a desired phenotype (e.g., herbicide tolerance or sensitivity) and a polymorphic chromosomal marker locus are determined to cosegregate, the polymorphic marker locus can be used to select for marker alleles that segregate with the desired tolerance phenotype. This general process is typically called marker-assisted selection (MAS). In brief, a nucleic acid corresponding to the marker nucleic acid is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. After the presence (or absence) of a particular marker in the biological sample is verified, the plant is selected, e.g., used to make progeny plants by selective breeding.

Soybean plant breeders desire combinations of tolerance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein genetically linked to tolerance loci provide effective methods for selecting tolerant varieties in breeding programs. For example, one advantage of marker-assisted selection over field evaluations for tolerance is that MAS can be done at any time of year, regardless of the growing season. Moreover, environmental effects are largely irrelevant to marker-assisted selection.

When a population is segregating for multiple loci affecting one or multiple traits, e.g., multiple loci involved in tolerance, or multiple loci each involved in tolerance or tolerance to different herbicides, the efficiency of MAS compared to phenotypic screening becomes even greater, because all of the loci can be evaluated in the lab together from a single sample of DNA. In the present instance, for linkage group L, relevant markers include: SATT495, P10649C-3, SATT182, S03859-1, S00224-1, SATT388, SATT313, and SATT613 (or other markers above SATT613). Additional relevant markers on linkage group L include S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1. Markers for other traits, transgenes, and/or loci can be assayed simultaneously or sequentially in a single sample or population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait, such as herbicide tolerance.

The determination of the presence and/or absence of a particular genetic marker or allele, e.g., SATT495, P10649C-3, SATT182, S03859-1, S00224-1, SATT388, SATT313, SATT613 (including markers above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, or S08101-1-Q1, in the genome of a plant exhibiting a preferred phenotypic trait can be made by any method noted herein. If the nucleic acids from the plant are positive for a desired genetic marker, the plant can be self fertilized to create a true breeding line with the same genotype, or it can be crossed with a plant with the same marker or with other desired characteristics to create a sexually crossed hybrid generation.

Introgression of Favorable Alleles—Efficient Crossing of Tolerance Markers into Other Lines One application of MAS is to use the tolerance or improved tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite genetic background, one selects among progeny or backcross progeny for the donor trait.

Thus, the markers and methods can be utilized to guide marker assisted selection or breeding of soybean varieties with the desired complement (set) of allelic forms of chromosome segments associated with herbicide tolerance as well as markers associated with superior agronomic performance (tolerance, along with any other available markers for yield, disease tolerance, etc.). Any of the disclosed marker alleles can be introduced into a soybean line via, for example, introgression, traditional breeding, or transformation, or a combination thereof, to yield a soybean plant with superior agronomic performance. The number of alleles associated with herbicide tolerance that can be introduced or be present in a soybean plant ranges from 1 to the number of alleles disclosed herein, each integer of which is incorporated herein as if explicitly recited.

Methods of making a progeny soybean plant, and these progeny soybean plants having herbicide tolerance or susceptibility, are provided. These methods comprise crossing a first parent soybean plant with a second soybean plant and growing the female soybean plant under plant growth conditions to yield soybean plant progeny. Such soybean plant progeny can be assayed for alleles associated with herbicide tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant comprising at least one of the allelic forms of the markers provided, such that the progeny are capable of inheriting the allele.

Inheritance of the desired tolerance allele can be traced, such as from progenitor or descendant lines in the subject soybean plants pedigree such that the number of generations separating the soybean plants being subject to the methods will generally be from 1 to 20, commonly 1 to 5, and typically 1, 2, or 3 generations of separation, and quite often a direct descendant or parent of the soybean plant will be subject to the method (i.e., 1 generation of separation).

Positional Cloning

The molecular marker loci and alleles associated with herbicide tolerance or susceptibility, e.g., SATT495, P10649C-3, SATT182, S03859-1, S00224-1, SATT388, SATT313, SATT613 (including markers above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1, can be used, as indicated previously, to identify a tolerance QTL, which can be cloned by well-established procedures, e.g., as described in detail in Ausubel, Berger and Sambrook.

These tolerance clones are first identified by their genetic linkage to markers provided herein. Isolation of a nucleic acid of interest is achieved by any number of methods as discussed in detail in such references as Ausubel, Berger and Sambrook, herein, and Clark, ed. (1997) Plant Molecular Biology: A Laboratory Manual Springer-Verlag, Berlin.

For example, "positional gene cloning" uses the proximity of a tolerance marker to physically define an isolated chromosomal fragment containing a tolerance QTL gene. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication, and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the open reading frame is identified by successive rounds of screening and isolation of clones which together comprise a contiguous sequence of DNA, a process termed "chromosome walking", resulting in a "contig" or "contig map." Protocols sufficient to guide one of skill through the isolation of clones associated with linked markers are found in, e.g. Berger, Sambrook and Ausubel, all herein.

Variant sequences have a high degree of sequence similarity. For polynucleotides, conservative variants include those sequences that, because of the degeneracy of the genetic code, encode the amino acid sequence of one of the native recombinase polypeptides. Variants such as these can be identified with the use of well-known molecular biology techniques, as, for example, with polymerase chain reaction (PCR) and hybridization techniques. Variant polynucleotides also include synthetically derived nucleotide sequences, such as those generated, for example, by using site-directed mutagenesis but which still encode a recombinase protein. Generally, variants of a particular polynucleotide will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by known sequence alignment programs and parameters.

Variants of a particular polynucleotide (the reference nucleotide sequence) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described. Where any given pair of polynucleotides is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

Variant proteins include proteins derived from the native protein by deletion, addition, and/or substitution of one or more amino acids to the N-terminal, internal region(s), and/or C-terminal end of the native protein. Variant proteins can be biologically active, that is they continue to possess the desired biological activity of the native protein, for example a variant recombinase can implement a recombination event between appropriate recombination sites. Such variants may result from, for example, genetic polymorphism or from human manipulation. A biologically active variant of a protein may differ from that protein by as few as 1-15 amino acid residues, as few as 1-10, such as 6-10, as few as 5, as few as 4, 3, 2, or even 1 amino acid residue.

Sequence relationships can be analyzed and described using computer-implemented algorithms. The sequence relationship between two or more polynucleotides or two or more polypeptides can be determined by generating the best alignment of the sequences, and scoring the matches and the gaps in the alignment, which yields the percent sequence identity, and the percent sequence similarity. Polynucleotide relationships can also be described based on a comparison of the polypeptide each encodes. Many programs and algorithms for the comparison and analysis of sequences are available.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff & Henikoff (1989) Proc Natl Acad Sci USA 89:10915).

GAP uses the algorithm of Needleman & Wunsch (1970) J Mol Biol 48:443-453, to find an alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. GAP presents one member of the family of best alignments.

Sequence identity, or identity, is a measure of the residues in the two sequences that are the same when aligned for maximum correspondence. Sequences, particularly polypeptides, that differ by conservative substitutions are said to have sequence similarity or similarity. Means for making this adjustment are known, and typically involve scoring a conservative substitution as a partial rather than a full mismatch. For example, where an identical amino acid is given a score of 1 and a non-conservative substitution is given a score of zero, a conservative substitution is given a score between zero and 1. The scoring of conservative substitutions is calculated using the selected scoring matrix (BLOSUM62 by default for GAP).

Equivalent positions between two or more polynucleotides, and/or polypeptides can be identified using any searching, sequence assembly, and/or alignment tool including, but not limited to, BLAST, GAP, PILEUP, FrameAlign, Sequencher, or similar tools. In some examples, GAP alignment can be used to identify equivalent positions, using the following parameters: for a nucleotide sequence using a gap creation penalty weight of 50 and a gap length extension penalty weight of 3, and the nwsgapdna.cmp scoring matrix; for an amino acid sequence using a gap creation penalty weight of 8 and a gap length extension penalty of 2, and the BLOSUM62 scoring matrix (Henikoff & Henikoff (1989) Proc Natl. Acad Sci USA 89:10915). In some examples, PILEUP can be used to identify equivalent positions, using the following parameters for a nucleotide sequence: a gap weight of 5 and a gap length weight of 1, and the pileupdna.cmp scoring matrix; for an amino acid sequence using a gap weight of 8 and a gap length weight of 2, and the BLOSUM62 scoring matrix (Henikoff & Henikoff (1989) Proc Natl Acad Sci USA 89:10915).

Proteins may be altered in various ways including amino acid substitutions, deletions, truncations, and insertions. Methods for such manipulations are generally known. Methods for mutagenesis and nucleotide sequence alterations are described, for example, in Kunkel (1985) Proc Natl Acad Sci USA 82:488-492; Kunkel et al. (1987) Methods in Enzymol 154:367-382; U.S. Pat. No. 4,873,192; Walker & Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed Res Found, Washington, D.C.). Conservative substitutions, such as exchanging one amino acid with another having similar properties, may be preferable.

Generation of Transgenic Cells and Plants

In some embodiments, the activity and/or level of a polypeptide provided herein within a cell, such as a plant cell, is modulated (i.e., increased or decreased). An increase in the level and/or activity of the polypeptide can be achieved by providing the polypeptide to the plant. As discussed elsewhere herein, many methods are known in the art for providing a polypeptide to a plant, including, but not limited to, direct introduction of the polypeptide into the plant or introducing into the plant (transiently or stably) a polynucleotide construct encoding a polypeptide having the desired activity.

The present invention also relates to host cells and organisms which are transformed with nucleic acids corresponding to the tolerance, improved tolerance, or susceptibility/sensitivity markers, traits, or QTLs identified herein. For example, such nucleic acids include chromosome intervals (e.g., genomic fragments), ORFs, and/or cDNAs that encode an herbicide tolerance or improved tolerance trait. Additionally, production of polypeptides that provide tolerance or improved tolerance by recombinant techniques are provided.

General texts which describe molecular biological techniques for the cloning and manipulation of nucleic acids and production of encoded polypeptides include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2001 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 2004 or later) ("Ausubel")). These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors (e.g., vectors, such as expression vectors which comprise an ORF derived from or related to a tolerance QTL) which can be, for example, a cloning vector, a shuttle vector, or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells, or plant protoplasts by a variety of standard methods known in the art, including but not limited to electroporation (From et al. (1985) Proc. Natl. Acad. Sci. USA 82; 5824), infection by viral vectors such as cauliflower mosaic virus (CaMV) (Hohn et al. (1982) Molecular Biology of Plant Tumors (Academic Press, New York, pp. 549-560; Howell U.S. Pat. No. 4,407,956), high velocity ballistic penetration by small particles with the nucleic acid either within the matrix of small beads or particles or on the surface (Klein et al. (1987) Nature 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) Science 233:496; Fraley et al. (1983) Proc. Natl. Acad. Sci. USA 80:4803). Additional details regarding nucleic acid introduction methods are found in Sambrook, Berger and Ausubel. The method of introducing a nucleic acid into a host cell is not critical, and therefore should not be limited to any particular method for introducing exogenous genetic material into a host cell. Thus, any suitable method that provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, Plant regeneration from cultured protoplasts is described in Evans et al. (1983) "Protoplast Isolation and Culture," Handbook of Plant Cell Cultures 1, 124-176 (MacMillan Publishing Co., New York; Davey (1983) "Recent Developments in the Culture and Regeneration of Plant Protoplasts," Protoplasts, pp. 12-29, (Birkhauser, Basel); Dale (1983) "Protoplast Culture and Plant Regeneration of Cereals and Other Recalcitrant Crops," Protoplasts pp. 31-41, (Birkhauser, Basel); Binding (1985) "Regeneration of Plants," Plant Protoplasts, pp. 21-73, (CRC Press, Boca Raton, Fla.). Additional details regarding plant cell culture and regeneration include Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Plant Molecular Biology (1993) R. R. D. Croy, Ed. Bios Scientific Publishers, Oxford, U.K. ISBN 0 12 198370 6. Cell culture media in general are also set forth in Atlas and Parks (eds), The Handbook of Microbiological Media (1993) CRC Press, Boca Raton, Fla. Additional information for cell culture is found in available commercial literature such as the Life Science Research Cell Culture Catalogue (1998) from Sigma-Aldrich, Inc (St Louis, Mo.) ("Sigma-LSRCCC") and the Plant Culture Catalogue and supplement (e.g., 1997 or later), also from Sigma-Aldrich, Inc (St Louis, Mo.) ("Sigma-PCCS").

The production of transgenic organisms is provided, which may be bacteria, yeast, fungi, animals or plants, transduced with the nucleic acids (e.g., nucleic acids comprising the marker loci and/or QTL noted herein). A thorough discussion of techniques relevant to bacteria, unicellular eukaryotes, and cell culture is found in references enumerated herein. Several well-known methods of introducing target nucleic acids into bacterial cells are available, any of which may be used. These include: fusion of the recipient cells with bacterial protoplasts containing the DNA, treatment of the cells with liposomes containing the DNA, electroporation, microinjection, cell fusions, projectile bombardment (biolistics), carbon fiber delivery, and infection with viral vectors (discussed further, below). Bacterial cells can be used to amplify the number of plasmids containing DNA constructs. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors), and selection markers for both prokaryotic and eukaryotic systems. Vectors are suitable for replication and integration in prokaryotes, eukaryotes, or both. See, Giliman & Smith (1979) Gene 8:81; Roberts et al. (1987) Nature 328:731; Schneider et al. (1995) Protein Expr. Purif 6435:10; Ausubel, Sambrook, Berger (all infra). A catalogue of bacteria and bacteriophages useful for cloning are well known in the art, e.g., The ATCC Catalogue of Bacteria and Bacteriophage (1992) Ghema et al. (eds), published by the ATCC.

Polynucleotide Constructs:

In specific embodiments, one or more of the herbicide tolerant polynucleotides employed in the methods and compositions can be provided in an expression cassette for expression in the plant or other organism of interest. The cassette will include 5' and 3' regulatory sequences operably linked to an herbicide-tolerance polynucleotide. "Operably linked" is intended to mean a functional linkage between two or more elements. For example, an operable linkage between a polynucleotide of interest and a regulatory sequence (e.g., a promoter) is functional link that allows for expression of the polynucleotide of interest. Operably linked elements may be contiguous or non-contiguous. When used to refer to the joining of two protein coding regions, by "operably linked" is intended that the coding regions are in the same reading frame. When used to refer to the effect of an enhancer, "operably linked" indicates that the enhancer increases the expression of a particular polynucleotide or polynucleotides of interest. Where the polynucleotide or polynucleotides of interest encode a polypeptide, the encoded polypeptide is produced at a higher level.

The cassette may additionally contain at least one additional gene to be co-transformed into the organism. Alternatively, the additional gene(s) can be provided on multiple expression cassettes. Such an expression cassette is provided with a plurality of restriction sites and/or recombination sites for insertion of the herbicide-tolerance polynucleotide to be under the transcriptional regulation of the regulatory regions. The expression cassette may additionally contain other genes, including other selectable marker genes. Where a cassette contains more than one polynucleotide, the polynucleotides in the cassette may be transcribed in the same direction or in different directions (also called "divergent" transcription).

An expression cassette comprising an herbicide tolerance polynucleotide will include, in the 5'-3' direction of transcription, a transcriptional and translational initiation region (i.e., a promoter), an herbicide tolerance polynucleotide, and a transcriptional and translational termination region (i.e., termination region) functional in plants or the other organism of interest. Accordingly, plants having such expression cassettes are also provided. The regulatory regions (i.e., promoters, transcriptional regulatory regions, and translational termination regions) and/or the herbicide tolerance polynucleotide may be native (i.e., analogous) to the host cell or to each other. Alternatively, the regulatory regions and/or the herbicide tolerance polynucleotide may be heterologous to the host cell or to each other.

While it may be optimal to express polynucleotides using heterologous promoters, native promoter sequences may be used. Such constructs can change expression levels and/or expression patterns of the encoded polypeptide in the plant or plant cell. Expression levels and/or expression patterns of the encoded polypeptide may also be changed as a result of an additional regulatory element that is part of the construct, such as, for example, an enhancer. Thus, the phenotype of the plant or cell can be altered even though a native promoter is used.

The termination region may be native with the transcriptional initiation region, may be native with the operably linked herbicide tolerance polynucleotide of interest, may be native with the plant host, or may be derived from another source (i.e., foreign or heterologous) to the promoter, the herbicide tolerance polynucleotide of interest, the plant host, or any combination thereof. Convenient termination regions are available from the Ti-plasmid of *A. tumefaciens*, such as the octopine synthase and nopaline synthase termination regions, or can be obtained from plant genes such as the *Solarium tuberosum* proteinase inhibitor II gene. See Guerineau et al. (1991) Mol. Gen. Genet. 262: 141-144; Proudfoot (1991) Cell 64: 671-674; Sanfacon et al. (1991) Genes Dev. 5: 141-149; Mogen et al. (1990) Plant Cell 2: 1261-1272; Munroe et al. (1990) Gene 91: 151-158; Ballas et al. (1989) Nucleic Acids Res. 17: 7891-7903; and Joshi et al. (1987) Nucleic Acids Res. 15: 9627-9639.

A number of promoters can be used, including the native promoter of the polynucleotide sequence of interest. The promoters can be selected based on the desired outcome. The polynucleotides of interest can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); the maize actin promoter; the ubiquitin promoter (see, e.g., Christensen et al. (1989) Plant Mol. Biol. 12:619-632; Christensen et al. (1992) Plant Mol. Biol. 18:675-689; Callis et al. (1995) Genetics 139:921-39); pEMU (Last et al. (1991) Theor. Appl. Genet. 81:581-588); MAS (Velten et al. (1984) EMBO J. 3: 2723-2730); ALS promoter (U.S. Pat. No. 5,659,026), and the like. Other constitutive promoters include, for example, those described in U.S. Pat. Nos. 5,608,149; 5,608,144; 5,604,121; 5,569,597; 5,466,785; 5,399,680; 5,268,463; 5,608,142; and 6,177,611. Some promoters show improved expression when they are used in conjunction with a native 5' untranslated region and/or other elements such as, for example, an intron. For example, the maize ubiquitin promoter is often placed upstream of a polynucleotide of interest along with at least a portion of the 5' untranslated region of the ubiquitin gene, including the first intron of the maize ubiquitin gene.

Chemical-regulated promoters can be used to modulate the expression of a gene in a plant through the application of an exogenous chemical regulator. Depending upon the objective, the promoter may be a chemical-inducible promoter for which application of the chemical induces gene expression or the promoter may be a chemical-repressible promoter for which application of the chemical represses gene expression. Chemical-inducible promoters are known in the art and include, but are not limited to, the maize Int-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, e.g., the glucocorticoid-inducible promoter in Schena et al. (1991) Proc. Natl. Acad. Sci. USA 88:10421-10425 and McNellis et al. (1998) Plant J. 14:247-257) and tetracycline-inducible and tetracycline-repressible promoters (see, e.g., Gatz et al. (1991) Mol. Gen. Genet. 227:229-237, and U.S. Pat. Nos. 5,814,618 and 5,789,156), herein incorporated by reference.

Tissue-preferred promoters can be utilized to target enhanced herbicide tolerance polypeptide expression within a particular plant tissue. Tissue-preferred promoters include Yamamoto et al. (1997) Plant J. 12:255-265; Kawamata et al. (1997) Plant Cell Physiol. 38:792-803; Hansen et al. (1997) Mol. Gen Genet. 254:337-343; Russell et al. (1997) Transgenic Res. 6:157-168; Rinehart et al. (1996) Plant Physiol. 112:1331-1341; Van Camp et al. (1996) Plant Physiol. 112:525-535; Canevascini et al. (1996) Plant Physiol. 112:513-524; Yamamoto et al. (1994) Plant Cell Physiol. 35:773-778; Lam (1994) Results Probl. Cell Differ. 20:181-196; Orozco et al. (1993) Plant Mol. Biol. 23:1129-1138; Matsuoka et al. (1993) Proc Natl. Acad. Sci. USA 90:9586-9590; and Guevara-Garcia et al. (1993) Plant J. 4:495-505. Such promoters can be modified, if necessary, for weak expression.

Leaf-preferred promoters are known in the art. See, e.g., Yamamoto et al. (1997) Plant J. 12:255-265; Kwon et al. (1994) Plant Physiol. 105:357-67; Yamamoto et al. (1994) Plant Cell Physiol. 35:773-778; Gotor et al. (1993) Plant J. 3:509-18; Orozco et al. (1993) Plant Mol. Biol. 23:1129-1138; and Matsuoka et al. (1993) Proc. Natl. Acad. Sci. USA 90(20):9586-9590.

Root-preferred promoters are known and can be selected from the many available from the literature or isolated de novo from various compatible species. See, e.g., Hire et al. (1992) Plant Mol. Biol. 20:207-218 (soybean root-specific glutamine synthetase gene); Keller and Baumgartner (1991) Plant Cell 3:1051-1061 (root-specific control element in the GRP 1.8 gene of French bean); Sanger et al. (1990) Plant Mol. Biol. 14(3):433-443 (root-specific promoter of the mannopine synthase (MAS) gene of *Agrobacterium tumefaciens*); and Miao et al. (1991) Plant Cell 3:11-22 (full-length cDNA clone encoding cytosolic glutamine synthetase (GS), which is expressed in roots and root nodules of soybean). See also Bogusz et al. (1990) Plant Cell 2(7): 633-641, where two root-specific promoters are described. Leach and Aoyagi (1991) describe their analysis of the promoters of the highly expressed rolC and rolD root-inducing genes of *Agrobacterium rhizogenes* (see Plant Science (Limerick) 79:69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8:343-350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29:759-772); and rolB promoter (Capana et al. (1994) Plant Mol. Biol. 25:681-691. See also U.S. Pat. Nos. 5,837,876; 5,750,386; 5,633,363; 5,459,252; 5,401,836; 5,110,732; and 5,023,179.

Seed-preferred promoters include both seed-specific promoters (those promoters active during seed development such as promoters of seed storage proteins) as well as seed-germinating promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also WO 00/12733, where seed-preferred promoters from end1 and end2 genes are disclosed, herein incorporated by reference.

Additional promoters of interest include the SCP1 promoter (U.S. Pat. No. 6,072,050), the HB2 promoter (U.S. Pat. No. 6,177,611) and the SAMS promoter (US20030226166 and SEQ ID NO: 87 and biologically active variants and fragments thereof), each of which is herein incorporated by reference. In addition, as discussed elsewhere herein, various enhancers can be used with these promoters including, for example, the ubiquitin intron (i.e., the maize ubiquitin intron 1 (see, e.g., NCBI sequence S94464), the omega enhancer or the omega prime enhancer (Gallie et al. (1989) Molecular Biology of RNA ed. Cech (Liss, N.Y.) 237-256 and Gallie et al. Gene (1987) 60:217-25), or the 35S enhancer; each of which is incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as beta-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow fluorescent protein (PhiYFP from Evrogen, see, Bolte et al. (2004) J. Cell Science 117:943-54). For additional selectable markers, see generally Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Bairn et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference. The above list of selectable marker genes is not meant to be limiting. Any selectable marker gene can be used, including the GAT gene and/or HRA gene.

Methods are known in the art of increasing the expression level of a polypeptide in a plant or plant cell, for example, by inserting into the polypeptide coding sequence one or two G/C-rich codons (such as GCG or GCT) immediately adjacent to and downstream of the initiating methionine ATG codon. Where appropriate, the polynucleotides may be modified for increased expression in the transformed plant. That is, the polynucleotides can be synthesized substituting in the polypeptide coding sequence one or more codons which are less frequently utilized in plants for codons encoding the same amino acid(s) which are more frequently utilized in plants, and introducing the modified coding sequence into a plant or plant cell and expressing the modified coding sequence. See, e.g., Campbell and Gowri (1990) Plant Physiol. 92:1-11 for a discussion of host-preferred codon usage. Methods are available in the art for synthesizing plant-preferred genes. See, e.g., U.S. Pat. Nos. 5,380,831, and 5,436,391, and Murray et al. (1989) Nucleic Acids Res. 17:477-498, herein incorporated by reference. Embodiments comprising such modifications are also a feature disclosed.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. Enhancers such as the CaMV 35S enhancer may also be used (see, e.g., Benfey et al. (1990) EMBO J. 9:1685-96), or other enhancers may be used. For example, the sequence set forth in SEQ ID NO: 1, 72, 79, 84, 85, 88, or 89 or a biologically active variant or fragment thereof can be used. See also published application US2007/0061917. As used herein, an enhancer, when operably linked to an appropriate promoter, will modulate the level of transcription of an operably linked polynucleotide of interest. Biologically active fragments and variants of the enhancer domain may retain the biological activity of modulating (increase or decrease) the level of transcription when operably linked to an appropriate promoter. Generally, variants of a particular polynucleotides will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to another polynucleotides as determined by sequence alignment programs and parameters. Variants of a particular polynucleotides also include those encoding a polypeptide having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to a reference polypeptide as determined by sequence alignment programs and parameters. Polypeptide variants include those encoded by variant polynucleotides, and those having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to a reference polypeptide as determined by sequence alignment programs and parameters.

It is also recognized that the level and/or activity of a polypeptide of interest may be modulated by employing a polynucleotide that is not capable of directing, in a transformed plant, the expression of a protein or an RNA. For example, the polynucleotides may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96: 8774-8778; herein incorporated by reference.

The expression cassette may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) Proc. Natl. Acad. Sci. USA 86: 6126-6130); potyvirus leaders, for example, TEV leader (Tobacco Etch Virus) (Gallie et al. (1995) Gene 165(2): 233-238), MDMV leader (Maize Dwarf Mosaic Virus) (Kong et al. (1988) Arch Virol 143:1791-1799), and human immunoglobulin heavy-chain binding protein (BiP) (Macejak et al. (1991) Nature 353: 90-94); untranslated leader from the coat protein mRNA of alfalfa mosaic virus (AMV RNA 4) (Jobling et al. (1987) Nature 325: 622-625); tobacco mosaic virus leader (TMV) (Gallie et al. (1989) in Molecular Biology of RNA, ed. Cech (Liss, N.Y.), pp. 237-256); and maize chlorotic mottle virus leader (MCMV) (Lommel et al. (1991) Virology 81: 382-385). See also, Della-Cioppa et al. (1987) Plant Physiol. 84: 965-968.

In preparing the expression cassette, the various polynucleotide fragments may be manipulated, so as to provide for sequences to be in the proper orientation and, as appropriate, in the proper reading frame. Toward this end, adapters or linkers may be employed to join the fragments or other manipulations may be involved to provide for convenient restriction sites, removal of superfluous material such as the removal of restriction sites, or the like. For this purpose, in vitro mutagenesis, primer repair, restriction, annealing, resubstitutions, e.g., transitions and transversions, may be involved. Standard recombinant DNA and molecular cloning techniques used herein are well known in the art and are described more fully, for example, in Sambrook et al. (1989) Molecular Cloning: A Laboratory Manual (Cold Spring Harbor Laboratory Press, Cold Spring Harbor) (also known as "Maniatis").

In some embodiments, the polynucleotide of interest is targeted to the chloroplast for expression. In this manner, where the polynucleotide of interest is not directly inserted into the chloroplast, the expression cassette will additionally contain a nucleic acid encoding a transit peptide to direct the gene product of interest to the chloroplasts. Such transit peptides are known in the art. See, e.g., Von Heijne et al. (1991) Plant Mol. Biol. Rep. 9: 104-126; Clark et al. (1989)

J. Biol. Chem. 264: 17544-17550; Della-Cioppa et al. (1987) Plant Physiol. 84: 965-968; Romer et al. (1993) Biochem. Biophys. Res. Comm. 196: 1414-1421; and Shah et al. (1986) Science 233: 478-481.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30: 769-780; Schnell et al. (1991) J. Biol. Chem. 266(5): 3335-3342); 5-(enolpyruvyl)shikimate-3-phosphate synthase (EPSPS) (Archer et al. (1990) J. Bioenerg Biomemb. 22(6): 789-810); tryptophan synthase (Zhao et al. (1995) J. Biol. Chem. 270(11): 6081-6087); plastocyanin (Lawrence et al. (1997) J. Biol. Chem. 272(33): 20357-20363); chorismate synthase (Schmidt et al. (1993) J. Biol. Chem. 268(36): 27447-27457); and the light harvesting chlorophyll a/b binding protein (LHBP) (Lamppa et al. (1988) J. Biol. Chem. 263: 14996-14999). See also Von Heijne et al. (1991) Plant Mol. Biol. Rep. 9: 104-126; Clark et al. (1989) J. Biol. Chem. 264: 17544-17550; Della-Cioppa et al. (1987) Plant Physiol. 84: 965-968; Romer et al. (1993) Biochem. Biophys. Res. Comm. 196: 1414-1421; and Shah et al. (1986) Science 233: 478-481.

Methods for transformation of chloroplasts are known in the art. See, e.g., Svab et al. (1990) Proc. Natl. Acad. Sci. USA 87: 8526-8530; Svab and Maliga (1993) Proc. Natl. Acad. Sci. USA 90: 913-917; Svab and Maliga (1993) EMBO J. 12: 601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91: 7301-7305.

The polynucleotides of interest to be targeted to the chloroplast may be optimized for expression in the chloroplast to account for differences in codon usage between the plant nucleus and this organelle. In this manner, the polynucleotide of interest may be synthesized using chloroplast-preferred codons. See, e.g., U.S. Pat. No. 5,380,831, herein incorporated by reference.

Introducing Nucleic Acids into Plants:

Methods for the production of transgenic plants comprising the cloned nucleic acids, e.g., isolated ORFs and cDNAs encoding herbicide tolerance genes, are provided. Techniques for transforming plant cells with nucleic acids are widely available and can be readily adapted. In addition to the Berger, Ausubel, and Sambrook references, useful general references for plant cell cloning, culture and regeneration include Jones (ed) (1995) Plant Gene Transfer and Expression Protocols—Methods in Molecular Biology, Volume 49 Humana Press Towata N.J.; Payne et al. (1992) Plant Cell and Tissue Culture in Liquid Systems John Wiley & Sons, Inc. New York, N.Y. (Payne); and Gamborg and Phillips (eds) (1995) Plant Cell, Tissue and Organ Culture; Fundamental Methods Springer Lab Manual, Springer-Verlag (Berlin Heidelberg N.Y.) (Gamborg). A variety of cell culture media are described in Atlas and Parks (eds) The Handbook of Microbiological Media (1993) CRC Press, Boca Raton, Fla. (Atlas). Additional information for plant cell culture is found in available commercial literature such as the Life Science Research Cell Culture Catalogue (1998) from Sigma-Aldrich, Inc (St Louis, Mo.) (Sigma-LSRCCC) and, e.g., the Plant Culture Catalogue and supplement (1997) also from Sigma-Aldrich, Inc (St Louis, Mo.) (Sigma-PCCS). Additional details regarding plant cell culture are found in Croy, (ed.) (1993) Plant Molecular Biology, Bios Scientific Publishers, Oxford, U.K.

The nucleic acid constructs, e.g., DNA molecules plasmids, cosmids, artificial chromosomes, DNA, and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acid acids can be introduced into plants according to any of a variety of techniques known in the art. Techniques for transforming a wide variety of higher plant species are also well known and described in widely available technical, scientific, and patent literature. See, e.g., Weising et al. (1988) Ann. Rev. Genet. 22:421-477.

Such methods for introducing polynucleotide or polypeptides into plants include stable transformation methods, transient transformation methods, virus-mediated methods, and breeding. "Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

The DNA constructs, for example DNA fragments, plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Transformation protocols as well as protocols for introducing polypeptides or polynucleotide sequences into plants may vary depending on the type of plant or plant cell (i.e., monocot or dicot) targeted for transformation. Suitable methods of introducing polypeptides and polynucleotides into plant cells include microinjection (Crossway et al. (1986) Biotechniques 4:320-334), electroporation (Riggs et al. (1986) Proc. Natl. Acad. Sci. USA 83: 5602-5606, Agrobacterium-mediated transformation (U.S. Pat. No. 5,563,055 and U.S. Pat. No. 5,981,840), direct gene transfer (Paszkowski et al. (1984) EMBO J. 3: 2717-2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) Biotechnology 6: 923-926); and Lec1 transformation (WO 00/28058). Also see Weissinger et al. (1988) Ann. Rev. Genet. 22: 421-477; Sanford et al. (1987) Particulate Science and Technology 5: 27-37 (onion); Christou et al. (1988) Plant Physiol. 87: 671-674 (soybean); McCabe et al. (1988) Bio/Technology 6: 923-926 (soybean); Finer and McMullen (1991) In Vitro Cell Dev. Biol. 27P: 175-182 (soybean); Singh et al. (1998) Theor. Appl. Genet. 96:319-324 (soybean); Datta et al. (1990) Biotechnology 8: 736-740 (rice); Klein et al. (1988) Proc. Natl. Acad. Sci. USA 85:4305-4309 (maize); Klein et al. (1988) Biotechnology 6:559-563 (maize); U.S. Pat. Nos. 5,240,855; 5,322,783; and, 5,324, 646; Klein et al (1988) Plant Physiol. 91: 440-444 (maize); Fromm et al. (1990) Biotechnology 8: 833-839 (maize);

protocols published electronically by "IP.com" under the permanent publication identifiers IPCOM000033402D, IPCOM000033402D, and IPCOM000033402D and available at the "IP.com" website (cotton); Hooykaas-Van Slogteren et al. (1984) Nature (London) 311: 763-764; U.S. Pat. No. 5,736,369 (cereals); Bytebier et al. (1987) Proc. Natl. Acad. Sci. USA 84: 5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) Plant Cell Reports 9: 415-418 and Kaeppler et al. (1992) Theor. Appl. Genet. 84: 560-566 (whisker-mediated transformation); D'Halluin et al. (1992) Plant Cell 4: 1495-1505 (electroporation); Li et al. (1993) Plant Cell Reports 12: 250-255 and Christou and Ford (1995) Annals of Botany 75: 407-413 (rice); Osjoda et al. (1996) Nature Biotechnology 14: 745-750 (maize via *Agrobacterium tumefaciens*); all of which are herein incorporated by reference.

Microinjection techniques for injecting plant, e.g., cells, embryos, callus, and protoplasts, are known in the art and well described in the scientific and patent literature. For example, a number of methods are described in Jones (ed) (1995) Plant Gene Transfer and Expression Protocols—Methods in Molecular Biology, Volume 49 Humana Press, Towata, N.J., as well as in the other references noted herein and available in the literature.

For example, the introduction of DNA constructs using polyethylene glycol precipitation is described in Paszkowski et al., EMBO J. 3:2717 (1984). Electroporation techniques are described in Fromm et al., Proc. Natl. Acad. Sci. USA 82:5824 (1985). Ballistic transformation techniques are described in Klein et al., Nature 327:70-73 (1987). Additional details are found in Jones (1995) and Gamborg and Phillips (1995), supra, and in U.S. Pat. No. 5,990,387.

Alternatively, *Agrobacterium*-mediated transformation is employed to generate transgenic plants. *Agrobacterium*-mediated transformation techniques, including disarming and use of binary vectors, are also well described in the scientific literature. See, e.g., Horsch, et al. (1984) Science 233:496; and Fraley et al. (1984) Proc. Natl. Acad. Sci. USA 80:4803 and recently reviewed in Hansen and Chilton (1998) Current Topics in Microbiology 240:22 and Das (1998) Subcellular Biochemistry 29: Plant Microbe Interactions, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller (1987) In: Genetic Engineering, vol. 6, P W J Rigby, Ed., London, Academic Press; and Lichtenstein; C. P., and Draper (1985) In: DNA Cloning, Vol. II, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) Plant Cell Physiol. 25:1353), (3) the vortexing method (see, e.g., Kindle (1990) Proc. Natl. Acad. Sci., (USA) 87:1228.

DNA can also be introduced into plants by direct DNA transfer into pollen as described by Zhou et al. (1983) Methods in Enzymology, 101:433; D. Hess (1987) Intern Rev. Cytol. 107:367; Luo et al. (1988) Plant Mol. Biol. Reporter 6:165. Expression of polypeptide coding genes can be obtained by injection of the DNA into reproductive organs of a plant as described by Pena et al. (1987) Nature 325:274. DNA can also be injected directly into the cells of immature embryos and the desiccated embryos rehydrated as described by Neuhaus et al. (1987) Theor. Appl. Genet. 75:30; and Benbrook et al. (1986) in Proceedings Bio Expo Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Methods are known in the art for the targeted insertion of a polynucleotide at a specific location in the plant genome. In one embodiment, the insertion of the polynucleotide at a desired genomic location is achieved using a site-specific recombination system. See, e.g., WO99/25821, WO99/25854, WO99/25840, WO99/25855, and WO99/25853, all of which are herein incorporated by reference. Briefly, a polynucleotide can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

Generation/Regeneration of Transgenic Plants:

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); Evans et al. (1983) Protoplasts Isolation and Culture, Handbook of Plant Cell Culture pp. 124-176, Macmillian Publishing Company, New York; and Binding (1985) Regeneration of Plants, Plant Protoplasts pp. 21-73, CRC Press, Boca Raton. Regeneration can also be obtained from plant callus, explants, somatic embryos (Dandekar et al. (1989) J. Tissue Cult. Meth. 12:145; McGranahan, et al. (1990) Plant Cell Rep. 8:512) organs, or parts thereof. Such regeneration techniques are described generally in Klee et al. (1987)., Ann. Rev. of Plant Phys. 38:467-486. Additional details are found in Payne (1992) and Jones (1995), both supra, and Weissbach and Weissbach, eds. (1988) Methods for Plant Molecular Biology Academic Press, Inc., San Diego, Calif. This regeneration and growth process includes the steps of selection of transformant cells and shoots, rooting the transformant shoots and growth of the plantlets in soil. These methods are adapted to produce transgenic plants bearing QTLs and other genes isolated according to the methods.

In addition, the regeneration of plants containing polynucleotides introduced by *Agrobacterium* into cells of leaf explants can be achieved as described by Horsch et al.

(1985) Science 227:1229-1231. In this procedure, transformants are grown in the presence of a selection agent and in a medium that induces the regeneration of shoots in the plant species being transformed as described by Fraley et al. (1983) Proc. Natl. Acad. Sci. (U.S.A.) 80:4803. This procedure typically produces shoots within two to four weeks and these transformant shoots are then transferred to an appropriate root-inducing medium containing the selective agent and an antibiotic to prevent bacterial growth. Transgenic plants may be fertile or sterile.

It is not intended that plant transformation and expression of polypeptides that provide herbicide tolerance be limited to soybean species. Indeed, it is contemplated that the polypeptides that provide herbicide tolerance in soybean can also provide a similar phenotype when transformed and expressed in other plants. Examples of plant genuses and species of interest include, but are not limited to, monocots and dicots such as corn (*Zea mays*), *Brassica* sp. (e.g., *B. napus, B. rapa, B. juncea*), particularly those *Brassica* species useful as sources of seed oil, alfalfa (*Medicago saliva*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annum*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Oleo europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena*), barley (*Hordeum*), palm, legumes including beans and peas such as guar, locust bean, fenugreek, garden beans, cowpea, mungbean, lima bean, fava bean, lentils, chickpea, and castor, *Arabidopsis*, vegetables, ornamentals, grasses, conifers, crop and grain plants that provide seeds of interest, oil-seed plants, and other leguminous plants. Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pukherrima*), and chrysanthemum. Conifers include, for example, pines such as loblolly pine (*Pinus taeda*), slash pine (*Pinus elliotil*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Promoters of bacterial origin that operate in plants include the octopine synthase promoter, the nopaline synthase promoter and other promoters derived from native Ti plasmids. See, Herrara-Estrella et al. (1983), Nature, 303:209. Viral promoters include the 35S and 19S RNA promoters of cauliflower mosaic virus. See, Odell et al. (1985) Nature, 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) EMBO J. 7:3315. Many other promoters are in current use and can be coupled to an exogenous DNA sequence to direct expression of the nucleic acid.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorsulforon, or phosphinothricin (the active ingredient in the herbicides bialaphos or Basta). See, e.g., Padgette et al. (1996) In: Herbicide-Resistant Crops (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See Vasil (1996) In: Herbicide-Resistant Crops (Duke, ed.), pp 85-91, CRC Lewis Publishers, Boca Raton) ("Vasil", 1996).

One of skill will recognize that, after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included, provided that these parts comprise cells comprising the isolated nucleic acid. Progeny and variants, and mutants of the regenerated plants are also included, provided that these parts comprise the introduced nucleic acid sequences.

Transgenic or introgressed plants expressing a polynucleotide can be screened for transmission of the nucleic acid by, for example, standard nucleic acid detection methods or by immunoblot protocols. Expression at the RNA level can be determined to identify and quantitate expression-positive plants. Standard techniques for RNA analysis can be employed and include RT-PCR amplification assays using oligonucleotide primers designed to amplify only heterologous or introgressed RNA templates and solution hybridization assays using marker or linked QTL specific probes. Plants can also be analyzed for protein expression, e.g., by Western immunoblot analysis using antibodies that recognize the encoded polypeptides. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

In one example a transgenic plant that is homozygous for the added heterologous nucleic acid; e.g., a transgenic plant that contains two added nucleic acid sequence copies, such as a gene at the same locus on each chromosome of a homologous chromosome pair, is provided. A homozygous transgenic plant can be obtained by sexually mating (self-fertilizing) a heterozygous transgenic plant that contains a single added heterologous nucleic acid, germinating some of the seed produced and analyzing the resulting plants produced for altered expression of a polynucleotide relative to a control plant (e.g., a native, non-transgenic plant). Backcrossing to a parental plant and out-crossing with a non-transgenic plant can be used to introgress the heterologous nucleic acid into a selected background (e.g., an elite or exotic soybean line).

Plants may be produced by any suitable method, including breeding. Plant breeding can be used to introduce desired characteristics (e.g., a stably incorporated transgene or a genetic variant or genetic alteration of interest) into a particular plant line of interest, and can be performed in any of several different ways. Pedigree breeding starts with the crossing of two genotypes, such as an elite line of interest and one other elite inbred line having one or more desirable characteristics (i.e., having stably incorporated a polynucleotide of interest, having a modulated activity and/or level of the polypeptide of interest, etc.) which complements the elite plant line of interest. If the two original parents do not provide all the desired characteristics, other sources can be included in the breeding population. In the pedigree method, superior plants are selfed and selected in successive filial generations. After a sufficient amount of inbreeding, successive filial generations will serve to increase seed of the developed inbred. In specific embodiments, the inbred line comprises homozygous alleles at about 95% or more of its loci. Various techniques known in the art can be used to facilitate and accelerate the breeding (e.g., backcrossing) process, including, for example, the use of a greenhouse or growth chamber with accelerated day/night cycles, the analysis of molecular markers to identify desirable progeny, and the like.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, a method of making a backcross conversion of an inbred line of interest comprising the steps of crossing a plant from the inbred line of interest with a donor plant comprising at least one mutant gene or transgene conferring a desired trait (e.g., herbicide tolerance), selecting an F1 progeny plant comprising the mutant gene or transgene conferring the desired trait, and backcrossing the selected F1 progeny plant to a plant of the inbred line of interest is provided. This method may further comprise the step of obtaining a molecular marker profile of the inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of the inbred line of interest with a different plant to make F1 hybrid seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation such as X-rays, Gamma rays (e.g., cobalt 60 or cesium 137), neutrons, (product of nuclear fission of uranium 235 in an atomic reactor), Beta radiation (emitted from radioisotopes such as phosphorus 32 or carbon 14), or ultraviolet radiation (typically from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

Methods for Identifying Herbicide Tolerant or Susceptible Soybean Plants

Experienced plant breeders can recognize tolerant soybean plants in the field, and can select the tolerant individuals or populations for breeding purposes or for propagation. In this context, the plant breeder recognizes tolerant and non-tolerant soybean plants. In some examples, the tolerance is observed in the context of herbicide carryover from the previous crop season.

The screening and selection may also be performed by exposing plants containing said progeny germplasm to a desired herbicide, for example, a mesotrione, isoxazole, or PPO inhibitor herbicide, in an assay and selecting those plants showing herbicide tolerance or sensitivity as containing soybean germplasm into which germplasm having tolerance or sensitivity to the given herbicide(s) derived from the QTL mapped to linkage group L has been introgressed. The live assay may be any such assay known to the art, e.g., Taylor-Lovell et al. (2001) Weed Tech 15:95-102.

However, plant tolerance is a phenotypic spectrum consisting of extremes of high tolerance to non-tolerance with a continuum of intermediate tolerance phenotypes. Evaluation of these intermediate phenotypes using reproducible assays are of value to scientists who seek to identify genetic loci that impart tolerance, conduct marker assisted selection for tolerant population, and for introgression techniques to breed a tolerance trait into an elite soybean line, for example. Describing the continuum of tolerance can be done using any known scoring system or derivative thereof, including the scoring systems described in the Examples.

Automated Detection/Correlation Systems

In some examples, the methods include an automated system for detecting markers and or correlating the markers with a desired phenotype (e.g., tolerance or susceptibility). Thus, a typical system can include a set of marker probes or primers configured to detect at least one favorable allele of one or more marker locus associated with herbicide tolerance, improved tolerance, or sensitivity, such as to one or more of a mesotrione herbicide, an isoxazole herbicide, or a PPO inhibitor herbicide. These probes or primers are configured to detect the marker alleles, such as the marker alleles noted in the tables and examples herein, e.g., using any available allele detection format, such as solid or liquid phase array based detection, microfluidic-based sample detection, etc.

In some examples, markers involving linkage group L are used. In some examples a marker linked or closely linked to the marker locus of SATT495, P10649C-3, SATT182, S03859-1, S00224-1, SATT388, SATT313, SATT613 (or another marker above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1 is used, and the probe set is configured to detect the closely linked marker(s). In some examples, the marker locus is SATT495, P10649C-3, SATT182, S03859-1, S00224-1, SATT388, SATT313, SATT613 (or another marker above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1, and the probe set is configured to detect the locus. Similarly, alleles of SATT495, P10649C-3, SATT182, S03859-1, S00224-1, SATT388, SATT313, SATT613 (or another marker above SATT613), S03859-1-A, S08103-1-Q1, S08104-1-Q1, S08106-1-Q1, S08110-1-Q1, S08111-1-Q1, S08115-2-Q1, S08117-1-Q1, S08119-1-Q1, S08118-1-Q1, S08116-1-Q1, S08114-1-Q1, S08113-1-Q1, S08112-1-Q1, S08108-1-Q1, S08101-2-Q1, S08101-3-Q1, S08101-4-Q1, S08105-1-Q1, S08102-1-Q1, S08107-1-Q1, S08109-1-Q1, and S08101-1-Q1 can be detected.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele. The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also provided. For example, the instructions can include at least one look-up table that includes a correlation between the presence or absence of the favorable alleles and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected, e.g., in an automated system. The computer readable media can include cache, main, and storage memory and/or other electronic data storage components (hard drives, floppy drives, storage drives, etc.) for storage of computer code. Data representing alleles detected can also be electronically, optically, magnetically o transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele, is transformed to output data, e.g., the identification of the allelic form of a chromosome segment. The process within the computer is a set of instructions, or "program," by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database. Data regarding genotype for one or more molecular markers, e.g, ASH, SSR, RFLP, RAPD, AFLP, SNP, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like, for, e.g., selecting files, retrieving data, reviewing tables of maker information, etc., and an output device (e.g., a monitor, a printer, etc.) for viewing or recovering the product of the statistical analysis.

Integrated systems comprising a computer or computer readable medium comprising set of files and/or a database with at least one data set that corresponds to the marker alleles herein are provided. The systems optionally also includes a user interface allowing a user to selectively view one or more of these databases. In addition, standard text manipulation software such as word processing software (e.g., Microsoft Word™ or Corel Wordperfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent technologies (Palo Alto, Calif.).

Systems for molecular marker analysis can include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of soybean plants with favorable allelic forms of chromosome segments involved in agronomic performance (e.g., tolerance or improved tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image.

Stacking of Traits and Additional Traits of Interest

In some embodiments, the polynucleotide conferring the herbicide tolerance in the plants are engineered into a molecular stack with at least one additional polynucleotide. The additional polynucleotide may confer any additional trait of interest, such as tolerance to an additional herbicide, insects, disease, or any other desirable trait. A trait, as used herein, refers to the phenotype derived from a particular sequence or groups of sequences. For example, herbicide tolerance polynucleotides may be stacked with any other polynucleotides encoding polypeptides having pesticidal and/or insecticidal activity, such as *Bacillus thuringiensis* toxic proteins (described in U.S. Pat. Nos. 5,366,892; 5,747,450; 5,737,514; 5,723,756; 5,593,881; Geiser et al. (1986) Gene 48:109; Lee et al. (2003) Appl. Environ. Microbiol. 69:4648-4657 (Vip3A); Galitzky et al. (2001) Acta Crystallogr. D. Biol. Crystallogr. 57:1101-1109 (Cry3Bb1); and Herman et al. (2004) J. Agric. Food Chem. 52:2726-2734 (Cry1F)), lectins (Van Damme et al. (1994) Plant Mol. Biol. 24: 825, pentin (described in U.S. Pat. No. 5,981,722), and the like. The combinations generated can also include multiple copies of any one of the polynucleotides of interest.

In some embodiments, an herbicide tolerance polynucleotide described herein may be stacked with other herbicide tolerance traits to create a transgenic plant with further improved properties. Other herbicide-tolerance polynucleotides that could be used in such embodiments include those conferring tolerance to the same herbicide by other modes of action, or a different herbicide. Other traits that could be combined with herbicide tolerance polynucleotides include those derived from polynucleotides that confer on the plant the capacity to produce a higher level of 5-enolpyruvylshikimate-3-phosphate synthase (EPSPS), for example, as more fully described in U.S. Pat. Nos. 6,248,876 B1; 5,627,061; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; U.S. Pat. No. Re. 36,449; U.S. Pat. Nos. RE 37,287 E; and 5,491,288; and WO 97/04103; WO 00/66746; WO 01/66704; and WO 00/66747. Other traits that could be combined with herbicide tolerance polynucleotides include those conferring tolerance to sulfonylurea and/or imidazolinone, for example, as described more fully in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

In some embodiments, herbicide tolerance polynucleotides of the plants may be stacked with, for example, hydroxyphenylpyruvatedioxygenases which are enzymes that catalyze the reaction in which para-hydroxyphenylpyruvate (HPP) is transformed into homogentisate. Molecules which inhibit this enzyme and which bind to the enzyme in order to inhibit transformation of the HPP into homogentisate are useful as herbicides. Traits conferring tolerance to such herbicides in plants are described in U.S. Pat. Nos. 6,245,968 B1; 6,268,549; and 6,069,115; and WO 99/23886. Other examples of suitable herbicide tolerance traits that could be stacked with herbicide tolerance polynucleotides include aryloxyalkanoate dioxygenase polynucleotides (which reportedly confer tolerance to 2,4-D and other phenoxy auxin herbicides as well as to aryloxyphenoxypropionate herbicides as described, for example, in WO2005/107437) and dicamba-tolerance polynucleotides as described, for example, in Herman et al. (2005) J. Biol. Chem. 280: 24759-24767.

Other examples of herbicide tolerance traits that could be combined with herbicide tolerance polynucleotides include those conferred by polynucleotides encoding an exogenous phosphinothricin acetyltransferase, as described in U.S. Pat. Nos. 5,969,213; 5,489,520; 5,550,318; 5,874,265; 5,919,675; 5,561,236; 5,648,477; 5,646,024; 6,177,616; and 5,879,903. Plants containing an exogenous phosphinothricin acetyltransferase can exhibit improved tolerance to glufosinate herbicides, which inhibit the enzyme glutamine synthase. Other examples of herbicide tolerance traits that could be combined with the herbicide tolerance polynucleotides include those conferred by polynucleotides conferring altered protoporphyrinogen oxidase (protox) activity, as described in U.S. Pat. Nos. 6,288,306 B1; 6,282,837 B1; and 5,767,373; and WO 01/12825. Plants containing such polynucleotides can exhibit improved tolerance to any of a variety of herbicides which target the protox enzyme (also referred to as protox inhibitors).

Other examples of herbicide-tolerance traits that could be combined with herbicide tolerance polynucleotides include those conferring tolerance to at least one herbicide in a plant such as, for example, a maize plant or horseweed. Herbicide tolerant weeds are known in the art, as are plants that vary in their tolerance to particular herbicides. See, e.g., Green and Williams (2004) "Correlation of Corn (*Zea mays*) Inbred Response to Nicosulfuron and Mesotrione," poster presented at the WSSA Annual Meeting in Kansas City, Mo., Feb. 9-12, 2004; Green (1998) Weed Technology 12:474-477; Green and Ulrich (1993) Weed Science 41:508-516. The trait(s) responsible for these tolerances can be combined by breeding or via other methods with herbicide-tolerance polynucleotides to provide a plant as well as methods of use thereof.

In this manner, plants that are more tolerant to multiple herbicides are disclosed. Accordingly, methods for growing a crop (i.e., for selectively controlling weeds in an area of cultivation) that comprise treating an area of interest (e.g., a field or area of cultivation) with at least one herbicide to which the plant is tolerant are likewise disclosed. In some embodiments, methods further comprise treatment with additional herbicides to which the plant is tolerant. In such embodiments, generally the methods permit selective control of weeds without significantly damaging the crop. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

Herbicide tolerant traits can also be combined with at least one other trait to produce plants that further comprise a variety of desired trait combinations including, but not limited to, traits desirable for animal feed such as high oil content (e.g., U.S. Pat. No. 6,232,529); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference. Desired trait combinations also include LLNC (low linolenic acid content; see, e.g., Dyer et al. (2002) Appl. Microbiol. Biotechnol. 59:224-230) and OLCH (high oleic acid content; see, e.g., Fernandez-Moya et al. (2005) J. Agric. Food Chem. 53:5326-5330).

Herbicide tolerant traits of interest can also be combined with other desirable traits such as, for example, fumonisim detoxification genes (U.S. Pat. No. 5,792,931), avirulence and disease resistance genes (Jones et al. (1994) Science 266:789; Martin et al. (1993) Science 262:1432; Mindrinos et al. (1994) Cell 78:1089), and traits desirable for processing or process products such as modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference. One could also combine herbicide tolerant polynucleotides with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

In another embodiment, the herbicide tolerant traits of interest can also be combined with the Rcg1 sequence or biologically active variant or fragment thereof. The Rcg1 sequence is an anthracnose stalk rot resistance gene in corn. See, e.g., U.S. patent application Ser. No. 11/397,153, 11/397,275, and 11/397,247, each of which is herein incorporated by reference.

These stacked combinations can be created by any method including, but not limited to, breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, e.g., WO99/25821, WO99/25854, WO99/25840, WO99/25855, and WO99/25853, all of which are herein incorporated by reference.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) Gene 48: 109); and the like.

Genes encoding disease resistance traits include detoxification genes, such as against fumonosin (U.S. Pat. No. 5,792,931); avirulence (avr) and disease resistance (R) genes (Jones et al. (1994) Science 266: 789; Martin et al. (1993) Science 262: 1432; and Mindrinos et al. (1994) Cell 78: 1089); and the like.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Methods of Controlling Weeds

Methods are provided for controlling weeds in an area of cultivation, preventing the development or the appearance of herbicide resistant weeds in an area of cultivation, producing a crop, and increasing crop safety. The term "controlling," and derivations thereof, for example, as in "controlling weeds" refers to one or more of inhibiting the growth, germination, reproduction, and/or proliferation of and/or killing, removing, destroying, or otherwise diminishing the occurrence and/or activity of a weed.

The herbicide tolerant plants display a modified tolerance to herbicides, such as mesotrione, isoxazole, or PPO inhibitor herbicides, and therefore allow for the application of one or more herbicides at rates that would significantly damage control plants and further allow for the application of combinations of herbicides at lower concentrations than normally applied which still continue to selectively control weeds. In addition, the herbicide tolerant plants can be used in combination with herbicide blends technology and thereby make the application of chemical pesticides more convenient, economical, and effective for the producer.

The methods comprise planting the area of cultivation with herbicide tolerant crop seeds or plants, and applying to any crop, crop part, weed or area of cultivation thereof an effective amount of an herbicide of interest. It is recognized that the herbicide can be applied before or after the crop is planted in the area of cultivation. Such herbicide applications can include an application of a mesotrione chemistry, an isoxazole chemistry, or a PPO inhibitor chemistry, or any combination thereof.

In certain examples, a diphenyl ether, triazolinone, N-phenylphthalimide, pyrimidindione and/or oxadiazole containing herbicide formulation is applied. In some examples the herbicide formulation comprises acifluorfen, fomesafen, oxyfluorfen, lactofen, sulfentrazone, carfentrasone, azafeniden flumiclorac, flumioxazin, oxadiazon, fluthiacet, benzfendizone, butagenacil and/or saflufenacil. In certain other examples, the combination of herbicides comprises a glyphosate, a glufosinate, a dicamba, a bialaphos, a phosphinothricin, a protox inhibitor, a sulfonylurea, an imidazolinone, a chlorsulfuron, an imazapyr, a chlorimuron-ethyl, a quizalofop, an HPPD, a PPO, and/or a fomesafen, or combinations thereof, wherein said effective amount is tolerated by the crop and controls weeds. Any effective amount of these herbicides can be applied, wherein the effective amount is any amount that differentiates between plant cells, plants, and/or seed comprising an herbicide tolerance allele, an herbicide tolerance polynucleotide, and/or a polynucleotide encoding an ABC transporter protein that confers tolerance to herbicide formulations, including one or more of mesotrione, isoxazole, and PPO inhibitor herbicides. In some examples the herbicides are applied simultaneously, in some examples the herbicides are applied sequentially, in some examples the herbicides are applied as pre-emergent treatments, in some examples the herbicides are applied as post-emergent treatments, in some examples the herbicides are applied as a combination of pre- and post-emergent treatments.

In some examples, the method of controlling weeds comprises planting the area with herbicide tolerant crop seeds or plants and applying to the crop, crop part, seed of said crop or the area under cultivation, an effective amount of an herbicide, wherein said effective amount comprises an amount that is not tolerated by a control crop when applied to the control crop, crop part, seed or the area of cultivation, wherein the control crop does not express a polynucleotide that encodes an herbicide tolerance polypeptide. In specific embodiments, combinations of herbicides may be used, such as when an additional tolerance trait is incorporated into the plant.

In another embodiment, the method of controlling weeds comprises planting the area with herbicide tolerant crop seeds or plant and applying to the crop, crop part, seed of said crop or the area under cultivation, an effective amount of an herbicide, wherein said effective amount comprises a level that is above the recommended label use rate for the crop, wherein said effective amount is tolerated when applied to the herbicide tolerant crop, crop part, seed, or the area of cultivation thereof.

Any herbicide can be applied to the tolerant crop, crop part, or the area of cultivation containing said crop plant. Classifications of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) Weed Technology 11: 384-393). An abbreviated version of the HRAC classification (with notes regarding the corresponding WSSA group) is set forth in Table 1.

TABLE 1

Abbreviated HRAC classification table.

| HRAC Group | Mode of Action | Chemical Family | Active Ingredient | WSSA Group |
|---|---|---|---|---|
| A | Inhibition of acetyl CoA carboxylase (ACCase) | Aryloxyphenoxy-propionate "FOPs" | clodinafop-propargyl cyhalofop-butyl diclofop-methyl fenoxaprop-P-ethyl fluazifop-P-butyl haloxyfop-R-methyl propaquizafop quizalofop-P-ethyl | 1 |
| | | Cyclohexanedione "DIMs" | alloxydim butroxydim clethodim cycloxydim profoxydim sethoxydim tepraloxydin tralkoxydim | |
| B | Inhibition of acetolactate synthase ALS (acetohydroxyacid synthase AHAS) | Phenylpyrazoline "DEN" Sulfonylurea | pinoxaden amidosulfuron azimsulfuron bensulfuron-methyl chlorimuron-ethyl chlorsulfuron cinosulfuron cyclosulfamuron ethametsulfuron-methyl ethoxysulfuron flazasulfuron flupyrsulfuron-methyl-Na foramsulfuron halosulfuron-methyl imazosulfuron iodosulfuron mesosulfuron metsulfuron-methyl nicosulfuron oxasulfuron primisulfuron-methyl prosulfuron pyrazosulfuron-ethyl rimsulfuron sulfometuron- | 2 |

TABLE 1-continued

Abbreviated HRAC classification table.

| HRAC Group | Mode of Action | Chemical Family | Active Ingredient | WSSA Group |
|---|---|---|---|---|
| | | | methyl sulfosulfuron | |
| | | | thifensulfuron-methyl | |
| | | | triasulfuron | |
| | | | tribenuron-methyl | |
| | | | trifloxysulfuron | |
| | | | triflusulfuron-methyl | |
| | | | tritosulfuron | |
| | | Imidazolinone | imazapic | |
| | | | imazamethabenz-methyl | |
| | | | imazamox | |
| | | | imazapyr | |
| | | | imazaquin | |
| | | | imazethapyr | |
| | | Triazolopyrimidine | cloransulam-methyl | |
| | | | diclosulam | |
| | | | florasulam | |
| | | | flumetsulam | |
| | | | metosulam | |
| | | | penoxsulam | |
| | | Pyrimidinyl(thio)benzoate | bispyribac-Na | |
| | | | pyribenzoxim | |
| | | | pyriftalid | |
| | | | pyrithiobac-Na | |
| | | | pyriminobac-methyl | |
| | | Sulfonylaminocarbonyl-triazolinone | flucarbazone-Na | |
| | | | propoxycarbazone-Na | |
| C1 | Inhibition of photosynthesis at photosystem II | Triazine | ametryne | 5 |
| | | | atrazine | |
| | | | cyanazine | |
| | | | desmetryne | |
| | | | dimethametryne | |
| | | | prometon | |
| | | | prometryne | |
| | | | propazine | |
| | | | simazine | |
| | | | simetryne | |
| | | | terbumeton | |
| | | | terbuthylazine | |
| | | | terbutryne | |
| | | | trietazine | |
| | | Triazinone | hexazinone | |
| | | | metamitron | |
| | | | metribuzin | |
| | | Triazolinone | amicarbazone | |
| | | Uracil | bromacil | |
| | | | lenacil | |
| | | | terbacil | |
| | | Pyridazinone | pyrazon = chloridazon | |
| | | Phenyl-carbamate | desmedipham | |
| | | | phenmedipham | |
| C2 | Inhibition of photosynthesis at photosystem II | Urea | chlorobromuron | 7 |
| | | | chlorotoluron | |
| | | | chloroxuron | |
| | | | dimefuron | |
| | | | diuron | |
| | | | ethidimuron | |
| | | | fenuron | |
| | | | fluometuron (see F3) | |
| | | | isoproturon | |
| | | | isouron | |
| | | | linuron | |
| | | | methabenzthiazuron | |
| | | | metobromuron | |
| | | | metoxuron | |
| | | | monolinuron | |
| | | | neburon | |
| | | | siduron | |

TABLE 1-continued

Abbreviated HRAC classification table.

| HRAC Group | Mode of Action | Chemical Family | Active Ingredient | WSSA Group |
|---|---|---|---|---|
| | | Amide | tebuthiuron propanil pentanochlor | |
| C3 | Inhibition of photosynthesis at photosystem II | Nitrile | bromofenoxim bromoxynil ioxynil | 6 |
| | | Benzothiadiazinone | bentazon | |
| | | Phenyl-pyridazine | pyridate pyridafol | |
| D | Photosystem-I-electron diversion | Bipyridylium | diquat paraquat | 22 |
| E | Inhibition of protoporphyrinogen oxidase (PPO) | Diphenylether | acifluorfen-Na bifenox chlomethoxyfen fluoroglycofen-ethyl fomesafen halosafen lactofen oxyfluorfen | 14 |
| | | Phenylpyrazole | fluazolate pyraflufen-ethyl | |
| | | N-phenylphthalimide | cinidon-ethyl flumioxazin flumiclorac-pentyl | |
| | | Thiadiazole | fluthiacet-methyl thidiazimin | |
| | | Oxadiazole | oxadiazon oxadiargyl | |
| | | Triazolinone | azafenidin carfentrazone-ethyl sulfentrazone | |
| | | Oxazolidinedione | pentoxazone | |
| | | Pyrimidindione | benzfendizone butafenacil | |
| | | Other | pyraclonil profluazol flufenpyr-ethyl | |
| F1 | Bleaching: Inhibition of carotenoid biosynthesis at the phytoene desaturase step (PDS) | Pyridazinone | norflurazon | 12 |
| | | Pyridinecarboxamide | diflufenican picolinafen | |
| | | Other | beflubutamid fluridone flurochloridone flurtamone | |
| F2 | Bleaching: Inhibition of 4-hydroxyphenyl-pyruvate-dioxygenase (4-HPPD) | Triketone | mesotrione sulcotrione | 27 |
| | | Isoxazole | isoxachlortole isoxazole | |
| | | Pyrazole | benzofenap pyrazolynate pyrazoxyfen | |
| | | Other | benzobicyclon | |
| F3 | Bleaching: Inhibition of carotenoid biosynthesis (unknown target) | Triazole | amitrole (in vivo inhibition of lycopene cyclase | 11 |
| | | Isoxazolidinone | clomazone | 13 |
| | | Urea | fluometuron (see C2) | |
| | | Diphenylether | aclonifen | |
| G | Inhibition of EPSP synthase | Glycine | glyphosate sulfosate | 9 |

TABLE 1-continued

Abbreviated HRAC classification table.

| HRAC Group | Mode of Action | Chemical Family | Active Ingredient | WSSA Group |
|---|---|---|---|---|
| H | Inhibition of glutamine synthetase | Phosphinic acid | glufosinate-ammonium bialaphos = bilanaphos | 10 |
| I | Inhibition of DHP (dihydropteroate) synthase | Carbamate | asulam | 18 |
| K1 | Microtubule assembly inhibition | Dinitroaniline | benefin = benfluralin butralin dinitramine ethalfluralin oryzalin pendimethalin trifluralin | 3 |
| | | Phosphoroamidate | amiprophos-methyl butamiphos | |
| | | Pyridine | dithiopyr thiazopyr | |
| | | Benzamide | propyzamide = pronamide tebutam | |
| | | Benzoic acid | DCPA = chlorthal-dimethyl | |
| K2 | Inhibition of mitosis/microtubule organisation | Carbamate | chlorpropham propham carbetamide | 23 |
| K3 | Inhibition of VLCFAs (Inhibition of cell division) | Chloroacetamide | acetochlor alachlor butachlor dimethachlor dimethanamid metazachlor metolachlor pethoxamid pretilachlor propachlor propisochlor thenylchlor | 15 |
| | | Acetamide | diphenamid napropamide naproanilide | |
| | | Oxyacetamide | flufenacet mefenacet | |
| | | Tetrazolinone | fentrazamide | |
| | | Other | anilofos cafenstrole piperophos | |
| L | Inhibition of cell wall (cellulose) synthesis | Nitrile | dichlobenil chlorthiamid | 20 |
| | | Benzamide | isoxaben | 21 |
| | | Triazolocarboxamide | flupoxam | |
| | | Quinoline carboxylic acid | quinclorac (for monocots) (also group O) | 26 |
| M | Uncoupling (Membrane disruption) | Dinitrophenol | DNOC dinoseb dinoterb | 24 |
| N | Inhibition of lipid synthesis - not ACCase inhibition | Thiocarbamate | butylate cycloate dimepiperate EPTC esprocarb molinate orbencarb pebulate prosulfocarb thiobencarb = benthiocarb tiocarbazil triallate vernolate | 8 |

TABLE 1-continued

Abbreviated HRAC classification table.

| HRAC Group | Mode of Action | Chemical Family | Active Ingredient | WSSA Group |
|---|---|---|---|---|
| | | Phosphorodithioate | bensulide | |
| | | Benzofuran | benfuresate | |
| | | | ethofumesate | |
| | | Chloro-Carbonic-acid | TCA | 26 |
| | | | dalapon | |
| | | | flupropanate | |
| O | Action like indole acetic acid (synthetic auxins) | Phenoxy-carboxylic-acid | clomeprop | 4 |
| | | | 2,4-D | |
| | | | 2,4-DB | |
| | | | dichlorprop = 2,4-DP | |
| | | | MCPA | |
| | | | MCPB | |
| | | | mecoprop = MCPP = CMPP | |
| | | Benzoic acid | chloramben | |
| | | | dicamba | |
| | | | TBA | |
| | | Pyridine carboxylic acid | clopyralid | |
| | | | fluroxypyr | |
| | | | picloram | |
| | | | triclopyr | |
| | | Quinoline carboxylic acid | quinclorac (also group L) | |
| | | | quinmerac | |
| | | Other | benazolin-ethyl | |
| P | Inhibition of auxin transport | Phthalamate | naptalam | 19 |
| | | Semicarbazone | diflufenzopyr-Na | |
| Z | Unknown (actual mode of action unknown, but likely that they differ in mode of action between themselves and from other groups) | Arylaminopropionic acid | Flamprop-M-methyl/-isopropyl | 25 |
| | | Pyrazolium | difenzoquat | 26 |
| | | Organoarsenical | DSMA | 17 |
| | | | MSMA | |
| | | Other | bromobutide | 27 |
| | | | (chloro)-flurenol | |
| | | | cinmethylin | |
| | | | cumyluron | |
| | | | dazomet | |
| | | | dymron = daimuron = methyl-dimuron = methyl-dymron | |
| | | | etobenzanid | |
| | | | fosamine | |
| | | | indanofan | |
| | | | metam | |
| | | | oxaziclomefone | |
| | | | oleic acid | |
| | | | pelargonic acid | |
| | | | pyributicarb | |

Herbicides can be classified by their mode of action and/or site of action and can also be classified by the time at which they are applied (e.g., pre-emergent or post-emergent), by the method of application (e.g., foliar application or soil application), or by how they are taken up by or affect the plant. Mode of action generally refers to the metabolic or physiological process within the plant that the herbicide inhibits or otherwise impairs, whereas site of action generally refers to the physical location or biochemical site within the plant where the herbicide acts or directly interacts. Herbicides can be classified in various ways, including by mode of action and/or site of action. Often, an herbicide-tolerance gene that confers tolerance to a particular herbicide or other chemical on a plant expressing it will also confer tolerance to other herbicides or chemicals in the same class or subclass, for example, a class or subclass set forth in the table above. Thus, in some examples, a transgenic plant is tolerant to more than one herbicide or chemical in the same class or subclass, such as, for example, an inhibitor of PPO, an inhibitor of HPPD (hydroxyphenyl pyruvate dioxygenase), a sulfonylurea, a glyphosate, or a synthetic auxin. In other examples, a transgenic plant is tolerant to more than one of mesotrione, isoxazole, and PPO inhibitor herbicides. In some examples the plant is transgenic for one or more of the herbicide tolerance traits, non-transgenic for one of more of the tolerance traits, or any combination thereof.

Typically, the plants provided can tolerate treatment with different types of herbicides (i.e., herbicides having different modes of action and/or different sites of action) as well as with higher amounts of herbicides than previously known plants, thereby permitting improved weed management strategies that are recommended in order to reduce the incidence and prevalence of herbicide-tolerant weeds. Specific herbicide combinations can be employed to effectively control weeds.

A transgenic crop plant which can be selected for use in crop production based on the prevalence of herbicide tolerant weed species in the area where the transgenic crop is to be grown is provided. Methods are known in the art for assessing the herbicide tolerance of various weed species. Weed management techniques are also known in the art, such as for example, crop rotation using a crop that is tolerant to an herbicide to which the local weed species are not tolerant. A number of entities monitor and publicly report the incidence and characteristics of herbicide-tolerant weeds, including the Herbicide Resistance Action Committee (HRAC), the Weed Science Society of America, and various state agencies (see, e.g., herbicide tolerance scores for various broadleaf weeds from the 2004 Illinois Agricultural Pest Management Handbook), and one of skill in the art would be able to use this information to determine which crop and herbicide combinations should be used in a particular location.

These entities also publish advice and guidelines for preventing the development and/or appearance of and controlling the spread of herbicide tolerant weeds (see, e.g., Owen and Hartzler (2004), 2005 Herbicide Manual for Agricultural Professionals, Pub. WC 92 Revised (Iowa State University Extension, Iowa State University of Science and Technology, Ames, Iowa); Weed Control for Corn, Soybeans, and Sorghum, Chapter 2 of "2004 Illinois Agricultural Pest Management Handbook" (University of Illinois Extension, University of Illinois at Urbana-Champaign, Ill.); Weed Control Guide for Field Crops, MSU Extension Bulletin E434 (Michigan State University, East Lansing, Mich.)).

Also included are plant cells, plants, and/or seeds produced by any of the foregoing methods.

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLES

Example 1

Identification of Isoxafutole Tolerant and Sensitive Soybean Lines—Herbicide Screening Bioassay and Intergroup Association Marker Based Diagnostic Two soybean mapping populations were used to confirm significant QTLs related to tolerance and susceptibility to mesotrione and/or isoxazole herbicides (HPPD-inhibitors), to identify any potential QTLs associated with the tolerance or susceptibility to these herbicides, and to identify any varietal variation due to differences between the two herbicide chemistries used in the study. The mesotrione herbicide used in this study was CALLISTO® (referred to as Herbicide B); the isoxazole herbicide used in this study was BALANCE PRO® (referred to as Herbicide A).

Part 1:

Studies were conducted using herbicides A and B and were performed at two locations, Princeton, Ill. and Johnston, Iowa. Herbicide screening protocols developed in the summer of 2008 determined the optimum herbicide rate, application timing and the best time to evaluate soybean injury following application.

Herbicide A and B were applied as a pre-plant incorporated herbicide. The application rate for Herbicide A was based on soil organic matter and was applied at half the recommended labeled rate. Herbicide B was applied at half the pre-plant incorporated label rate. Both herbicides were applied using an ATV sprayer outfitted with a 10-foot boom, GPS and a Raven control system. The herbicides were applied at a rate of 30 gallons of water per acre and a spray pressure of 35-40 psi. An agitation system was used to maintain herbicide suspension in the water spray solution. Since both herbicides A and B were used in the same field, the sprayer was cleaned out between applications and a 10-foot buffer strip was used to help separate the two herbicides in the field to ensure no spray overlap.

The herbicides were incorporated into the soil to a depth of 1-2 inches using a field cultivator with rolling baskets 2-5 days following application (Table 2). Incorporation was performed in two directions to ensure even distribution of the herbicide in the soil.

The soybeans were planted into the soil to a depth of 1-1.5 inches using an Almaco 4-row index planter set on 30-inch row spacing. All plots were planted as single row plots with 25 seeds for 4.5 feet of planted row with a three-foot alleyway. The planted population was approximately 90,000 seeds per acre. Both Princeton and Johnston locations were planted on June 4. The herbicide application, planting, and rating dates for both Princeton and Johnston locations are presented in Table 2.

TABLE 2

Herbicide Application, tillage, planting and rating dates

| Location | Herbicide Application | Tilled In | Planting Date | 1st Rating | Untreated Crop Stage | 2nd Rating | Untreated Crop Stage |
| --- | --- | --- | --- | --- | --- | --- | --- |
| Princeton, IL | May 29, 2009 | Jun. 4, 2009 | Jun. 4, 2009 | Jun. 29, 2009 | V3 | Jul. 8, 2009 | V6 |
| Johnston, IA | Jun. 2, 2009 | Jun. 4, 2009 | Jun. 4, 2009 | Jun. 30, 2009 | V3 | Jul. 7, 2009 | V5 |

Soybean varietal herbicide reactions were evaluated using visual scores for plant growth reduction (STNT) and crop injury rating (HERSC) using descriptions defined below. Two ratings were conducted at both locations; the initial rating (V3) was based off of the clearest distinction of symptoms across the experiments. A second rating (V5 or V6) was conducted to ensure accuracy and note any varietal variation over time. An untreated check was used as a guide for the expected plant growth and development over time.

Plant Growth Reduction Rating (STNT)
1-9 herbicide reaction scale for plant growth reduction:
- 9=no plant growth reduction from the herbicide
- 8=<5% plant growth reduction
- 7=>5% and <20% plant growth reduction
- 6=>20% and <35% plant growth reduction
- 5=>35% and <50% plant growth reduction
- 4=>50 and <65% plant growth reduction
- 3=>65 and <80% plant growth reduction
- 2=>80 and <95% plant growth reduction
- 1=>95% plant growth reduction Crop Injury Rating (HERSC)
1-9 herbicide reaction scale for crop injury (both chlorotic and necrotic tissue):
- 9=no crop injury
- 8=<5% crop injury
- 7=>5% and <20% crop injury
- 6=>20% and <35% crop injury
- 5=>35% and <50% crop injury
- 4=>50 and <65% crop injury
- 3=>65 and <80% crop injury
- 2=>80 and <95% crop injury
- 1=>95% crop injury Two mapping populations were used that contained known susceptible and tolerant parents that were fixed and carried different alleles for two QTLs identified on linkage group L. The mapping populations were screened using herbicide A and the herbicide screening protocol described above. Two populations (Pop A and Pop B) of 90 randomly selected F3:F5 lines were used in the study. Four replications of the populations were placed in a row by column design to help adjust means due to field variation. The parents of each population were replicated 3 times per replication for a total of 12 times per location. An analysis of variance (ANOVA) was conducted to identify significant differences between the varieties within the populations.

A variety trial was conducted using 144 varieties with herbicides A and B and the herbicide screening protocol described above. Four replications of the varieties were placed in a row by column design to help adjust means due to field variation for both herbicides. The 144 lines included 52 susceptible and 61 tolerant lines identified previously as well as lines identified as moderate but containing the susceptible or tolerant allele for the QTLs.

An ANOVA was run on the STNT and HERSC data to determine any significant differences between soybean varieties. The herbicide response and the varieties were classified into tolerant and susceptible groups to be analyzed using available SSR and SNP markers for identification of other potential QTLs associated with the trait. The tolerant and susceptible classes were analyzed to observe marker trait associations by comparing the allelic frequencies of tolerant and susceptible varieties. This analysis used all available genome wide data produced for the markers and the varieties to run the analysis. Significant markers were then identified and potential QTL regions were recognized for candidates causing tolerant reactions. This data was used to help identify additional polymorphic markers within the mapping populations. Table 3 indicates the results of the various varieties tested.

TABLE 3

Mapping population analysis

| Grouping | HERSC score | Adjusted mean |
| --- | --- | --- |
| SUS | 1 | 2.2915 |
| SUS | 1 | 2.3105 |
| SUS | 1 | 2.333 |
| SUS | 1 | 2.3955 |
| SUS | 1 | 2.4045 |
| SUS | 1 | 2.4155 |
| SUS | 2 | 2.4825 |
| SEG | 2 | 2.547 |
| SUS | 2 | 2.577 |
| SUS | 2 | 2.888 |
| SUS | 2 | 2.9185 |
| SUS | 3 | 3.083 |
| SEG | 3 | 3.091 |
| SUS | 3 | 3.1775 |
| SEG | 3 | 3.207 |
| SUS | 3 | 3.252 |
| SUS | 3 | 3.3115 |
| SEG | 4 | 3.427 |
| SEG? | 4 | 3.5305 |
| SEG | 4 | 3.544 |
| SUS | 4 | 3.5845 |
| SEG | 4 | 3.589 |
| SUS | 4 | 3.6135 |
| SUS | 4 | 3.6575 |
| SEG | 4 | 3.662 |
| SEG | 5 | 3.729 |
| SEG | 5 | 3.73 |
| SUS | 5 | 3.7435 |
| SEG | 5 | 3.843 |
| TOL | 5 | 3.89 |
| SEG | 5 | 3.9255 |
| SEG | 5 | 3.9925 |
| SEG | 5 | 4.0415 |
| SEG | 5 | 4.0755 |
| SEG | 5 | 4.1025 |
| TOL | 5 | 4.1315 |
| TOL | 5 | 4.171 |
| SEG | 6 | 4.273 |
| SEG | 6 | 4.276 |
| SEG | 6 | 4.325 |
| SEG? | 4 | 4.331 |
| SEG | 4 | 4.375 |
| TOL | 6 | 4.4225 |
| SEG | 6 | 4.436 |
| SEG | 6 | 4.456 |
| SEG | 6 | 4.4955 |
| TOL | 6 | 4.5525 |
| TOL | 6 | 4.5905 |
| TOL | 6 | 4.6135 |
| SEG | 6 | 4.627 |
| TOL | 6 | 4.652 |
| SEG | 6 | 4.652 |
| SEG | 6 | 4.7305 |
| TOL | 6 | 4.7785 |
| TOL | 6 | 4.7805 |
| TOL | 6 | 4.814 |
| SEG? | 6 | 4.815 |
| TOL | 6 | 4.827 |
| TOL | 6 | 4.883 |
| SEG | 6 | 4.955 |
| SEG | 7 | 5.005 |
| SEG | 7 | 5.018 |
| TOL | 7 | 5.0185 |
| SEG | 7 | 5.048 |
| TOL | 7 | 5.053 |
| TOL | 7 | 5.0635 |
| TOL | 7 | 5.0895 |
| TOL | 7 | 5.151 |
| TOL | 6 | 5.239 |
| SEG | 7 | 5.2525 |
| TOL | 7 | 5.258 |

TABLE 3-continued

Mapping population analysis

| Grouping | HERSC score | Adjusted mean |
|---|---|---|
| SEG | 7 | 5.263 |
| TOL | 5 | 5.312 |
| TOL | 7 | 5.357 |
| TOL | 7 | 5.358 |
| SEG? | 8 | 5.4165 |
| TOL | 8 | 5.4475 |
| SEG? | 8 | 5.512 |
| TOL | 8 | 5.5645 |
| TOL | 8 | 5.5975 |
| TOL | 8 | 5.6185 |
| TOL | 8 | 5.707 |
| TOL | 8 | 5.713 |
| TOL | 9 | 5.8935 |
| TOL | 9 | 5.904 |
| TOL | 9 | 6.022 |
| TOL | 7 | 6.0235 |
| SEG? | 9 | 6.1865 |
| TOL | 9 | 6.591 |
| TOL | 9 | 6.842 |
| SUS | 1 | 2.049 |
| TOL | 9 | 5.9145 |
| SUS | 2 | 2.733 |
| SUS | 2 | 2.748 |
| SUS | 2 | 2.801 |
| SUS | 2 | 2.883 |
| SUS | 2 | 2.938 |
| SUS | 2 | 2.9515 |
| SUS | 2 | 2.9955 |
| SEG? | 2 | 3.0555 |
| SUS | 1 | 2.4295 |
| SUS | 1 | 2.5185 |
| SUS | 1 | 2.6205 |
| SUS | 1 | 2.6395 |
| SUS | 3 | 3.1315 |
| SEG? | 3 | 3.1925 |
| SUS | 3 | 3.193 |
| SEG | 3 | 3.216 |
| SEG | 3 | 3.267 |
| SUS | 3 | 3.2875 |
| SUS | 3 | 3.2885 |
| SUS | 3 | 3.3375 |
| SUS | 4 | 3.3435 |
| SUS | 4 | 3.3555 |
| SUS | 4 | 3.361 |
| SUS | 4 | 3.428 |
| SUS | 4 | 3.449 |
| SUS | 4 | 3.539 |
| SUS | 4 | 3.5505 |
| SUS | 4 | 3.6335 |
| SUS | 5 | 3.681 |
| SUS | 5 | 3.793 |
| SUS | 5 | 3.8215 |
| SUS | 4 | 3.8395 |
| SUS | 5 | 4.01 |
| SEG? | 5 | 4.0635 |
| SUS | 5 | 4.072 |
| SEG | 5 | 4.1245 |
| SUS | 5 | 4.1535 |
| TOL | 5 | 4.239 |
| SEG | 6 | 4.3385 |
| SEG | 6 | 4.489 |
| TOL | 6 | 4.5315 |
| SEG | 6 | 4.5915 |
| SEG | 6 | 4.721 |
| TOL | 6 | 4.7345 |
| TOL | 6 | 4.8215 |
| TOL | 6 | 4.8495 |
| TOL | 6 | 4.8625 |
| TOL | 6 | 4.867 |
| TOL | 6 | 4.944 |
| TOL | 4 | 4.973 |
| TOL | 7 | 5.0845 |
| TOL | 7 | 5.0885 |
| TOL | 5 | 5.0955 |
| TOL | 7 | 5.1245 |
| TOL | 7 | 5.1505 |
| TOL | 7 | 5.1695 |
| TOL | 4 | 5.1885 |
| TOL | 7 | 5.221 |
| TOL | 7 | 5.228 |
| SEG | 7 | 5.2285 |
| SEG | 7 | 5.2805 |
| TOL | 7 | 5.3305 |
| SEG | 7 | 5.3345 |
| TOL | 8 | 5.381 |
| TOL | 8 | 5.3835 |
| TOL | 8 | 5.414 |
| TOL | 8 | 5.5165 |
| TOL | 8 | 5.535 |
| TOL | 8 | 5.55 |
| TOL | 8 | 5.5925 |
| TOL | 8 | 5.6125 |
| TOL | 8 | 5.617 |
| TOL | 8 | 5.6275 |
| TOL | 8 | 5.6435 |
| TOL | 8 | 5.67 |
| TOL | 8 | 5.7255 |
| TOL | 8 | 5.7645 |
| TOL | 8 | 5.8155 |
| TOL | 8 | 5.8245 |
| TOL | 8 | 5.8835 |
| TOL | 9 | 5.885 |
| TOL | 9 | 5.8885 |
| TOL | 9 | 5.9165 |
| TOL | 9 | 5.964 |
| TOL | 9 | 6.0095 |
| TOL | 9 | 6.2345 |
| TOL | 9 | 6.2655 |
| TOL | 9 | 6.286 |
| TOL | 7 | 6.3875 |
| TOL | 9 | 6.599 |
| SUS | 3 | 3.069 |
| TOL | 7 | 5.359 |

The experimental means for Herbicide A across both locations for HERSC2 was 4.695 with a standard deviation of 1.94. The coefficient of variation across the locations was 26.7.

Example 2

Determination of QTL and Marker Associations/Intergroup Analysis

There was significant (P<0.001) difference across varieties for Herbicide A. The LSD was 1.316 across all varieties. Predicted means by location were calculated using a linear model for the locations. The varieties were looked at individually by the adjusted means by location, the LSD value, the average score by location, and the 2008 data for each variety. This gave an overall view of each variety and allowed for a simple classification across all varieties. Any variety that showed a high rate of variability across the data was automatically placed in the segregating group.

The results of the ANOVA for both Herbicides A and B are reported in Table 4. The model used for the analysis was the incomplete block design and the affect of the model is described through the relative efficiency and the Czekanowski Coefficient (Czek Coeff). The relative efficiency is comparing the error terms of the more complex block (incomplete block, ICB) to the less complex model (randomized complete block, RCB). The relative efficiency for the variety trial using herbicide A was 111% and herbicide B was 123%. The Czek Coeff which reports the top 10 and 20 percent of the entries that were the same for both the RCB and ICB designs was 73 and 83% for the top 10% of entries and 86 and 90% for the top 20% of the entries for the variety trials using herbicides A and B, respectfully.

TABLE 4

Analysis of variance for the variety trial

|  | Herbicide A HERSC | Herbicide B HERSC |
|---|---|---|
| Experiment Mean | 4.695 | 4.585 |
| CV(%) | 26.7 | 26.6 |
| Model | IB | IB |
| Rel Eff | 111 | 123 |
| Czek Coeff .10 | 0.73 | 0.87 |
| Czek Coeff .20 | 0.86 | 0.9 |
| # Environments | 2 | 2 |
| Total Blocks | 8 | 8 |
| p.val (Entry) | 0 | 0 |
| % V | 85.7 | 82.9 |
| % VL | 0.8 | 2.9 |
| % E | 13.5 | 14.1 |
| SED between 2 entry means | 0.658 | 0.637 |
| 2'SED between 2 entry means (LSD) | 1.316 | 1.274 |

Using this method of classification the varieties were grouped according to their reactions to herbicides A and B. For herbicide A there were 32 tolerant, 67 moderate, 37 susceptible and 8 segregating lines. For herbicide B there were 29 tolerant, 75 moderate, 32 susceptible and 8 segregating lines.

An Intergroup Allele Frequency Distribution analysis was conducted using GeneFlow™ version 7.0 software. An intergroup allele frequency distribution analysis provides a method for finding non-random distributions of alleles between two phenotypic groups.

During processing, a contingency table of allele frequencies was constructed and from this a G-statistic and probability were calculated. The G-statistic was adjusted by using the William's correction factor. The probability value was adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the tolerance phenotype and the marker will co-segregate. A more complete discussion of the derivation of the probability values can be found in the GeneFlow™ version 7.0 software documentation. See also Sokal and Rolf (1981), Biometry: The Principles and Practices of Statistics in Biological Research, 2nd ed., San Francisco, W. H. Freeman and Co.

The underlying logic is that markers with significantly different allele distributions between the tolerant and non-tolerant groups (i.e., non-random distributions) might be associated with the trait and can be used to separate them for purposes of marker assisted selection of soybean lines with previously uncharacterized tolerance or non-tolerance or sensitivity to mesotrione and/or isoxazole herbicides. The present analysis examined one marker locus at a time and determined if the allele distribution within the tolerant group is significantly different from the allele distribution within the non-tolerant group. A statistically different allele distribution is an indication that the marker is linked to a locus that is associated with tolerance or non-tolerance or sensitivity to mesotrione and/or isoxazole herbicides. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 1043 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

For the herbicide A variety trial, the analysis identified 275 markers (P<0.05), of these 275 markers identified, 243 of the markers had been previously mapped to a particular genomic position. This allowed for further analysis to identify potential genomic regions for genes and to eliminate marker regions that are likely not associated with the native tolerance to the herbicide. There were a total of 6 regions identified where multiple markers were pointing to a particular genomic region (Table 5). The regions identified included regions on B2, D2, E, G, L and 7 unmapped (UM) markers. Of the original 275 markers identified, 112 markers were used to identify the 6 genomic regions.

TABLE 5

Potential genomic regions for Herbicide A

| Linkage group | cM (position) | Markers | Comment |
|---|---|---|---|
| B2 | 92.2-111.86 | 31 |  |
| D2 | 88.11-92.58 | 6 |  |
| E | 82.16-100.51 | 37 |  |
| G | 78.6-85.82 | 22 |  |
| L | 10.1-14.31 | 4 | Highest significance |
| L | 41.09-46.35 | 5 |  |
| UM |  | 7 | Highly significant <.008 |

A similar analysis was conducted for the tolerant and susceptible classes to Herbicide B where 274 markers were identified (P<0.05). Of the 274 markers identified 239 markers had been previously mapped to a particular genomic position. Similar regions to Herbicide A were identified that included B2, E, G, L, and 10 UM markers (Table 6). A potential region on N was added and the region on D2 was taken off for Herbicide B tolerance. Of the original 274 markers identified 116 markers were used to help identify the 6 regions.

TABLE 6

Potential genomic regions for Herbicide B

| Linkage group | cM (position) | Markers | Comment |
|---|---|---|---|
| B2 | 92.2-111.86 | 20 |  |
| E | 82.16-100.51 | 41 |  |
| G | 77.87-85.82 | 17 |  |
| L | 10.1-14.31 | 4 | Highest significance |
| L | 41.09-42.17 | 3 |  |
| N | 37.11-53.27 | 21 |  |
| UM |  | 10 | Highly significant <.008 |

Additional observations were made through looking at the tolerant, moderate, susceptible and segregating classes to each herbicide as assigned through the variety trial. Of the 144 varieties in the herbicide trial, 21 were tolerant to both herbicides, 54 displayed moderate tolerance to both herbicides, and 28 displayed susceptible reactions to both herbicides. There were a total of 31 varieties that were classified one class higher or lower to herbicide A or B. For example 11 varieties were tolerant to herbicide A and moderate to herbicide B, where they were lowered I class from herbicide A classification to herbicide B classification. There were zero lines that were tolerant to one herbicide and susceptible to the other. This is summarized in Table 7.

TABLE 7

Variety reactions to both herbicides

|  |  | Herbicide B (mesotrione) | | | |
|---|---|---|---|---|---|
|  | Class | Tol | Moderate | Sus | Seg |
| Herbicide A (isoxazole) | Tol | 21 | 11 | 0 | 0 |
|  | Moderate | 8 | 54 | 3 | 2 |
|  | Sus | 0 | 9 | 28 | 0 |
|  | Seg | 0 | 1 | 1 | 6 |

The significant markers were observed for both variety classes to each of the chemistries. Of the 275 and 274 markers that were significant for the Herbicide A and Herbicide B reactions, 144 markers were significant for both variety reactions. As observed in the variety trial analysis, the regions of potential QTLs were observed for both classes on B2, E, G, and L; with the most significant markers on L from 10.1-14.31 cM (Tables 5 and 6).

Table 8 shows the allele distribution for marker 503859, which is closely linked to this region, among the 144 lines analyzed; 32 tolerant lines, 37 non-tolerant (susceptible) lines, 67 moderate, and 8 segregating lines analyzed. Marker calls for the 503859 locus were available for 111 of the 144 lines.

TABLE 8

Allele distribution

| S03859 allele (LG-L) | Phenotype | Adjusted mean |
|---|---|---|
| 1, 1 | Susceptible | 1.6085 |
| 1, 1 | Susceptible | 1.7085 |
| 1, 1 | Susceptible | 1.8675 |
|  | Susceptible | 1.9175 |
| 1, 1 | Susceptible | 2.006 |
| 1, 1 | Susceptible | 2.212 |
|  | Susceptible | 2.272 |
|  | Susceptible | 2.283 |
| 1, 1 | Susceptible | 2.2845 |
| 1, 1 | Susceptible | 2.327 |
| 1, 1 | Susceptible | 2.4255 |
| 1, 1 | Susceptible | 2.643 |
|  | Susceptible | 2.6815 |
| 1, 1 | Susceptible | 2.781 |
|  | Susceptible | 2.8325 |
| 1, 1 | Susceptible | 2.838 |
| 1, 1 | Susceptible | 2.881 |
| 1, 1 | Susceptible | 2.883 |
| 1, 1 | Susceptible | 2.9005 |
| 1, 1 | Susceptible | 2.927 |
| 1, 1 | Susceptible | 2.992 |
| 1, 1 | Susceptible | 2.994 |
|  | Susceptible | 3.056 |
| 1, 1 | Susceptible | 3.1475 |
| 3, 3 | Susceptible | 3.215 |
| 1, 1 | Susceptible | 3.2835 |
| 1, 3 | Susceptible | 3.3085 |
|  | Susceptible | 3.3385 |
| 1, 1 | Susceptible | 3.3875 |
| 1, 1 | Susceptible | 3.3885 |
| 1, 1 | Susceptible | 3.4085 |

TABLE 8-continued

Allele distribution

| S03859 allele (LG-L) | Phenotype | Adjusted mean |
|---|---|---|
| 1, 1 | Segregating | 3.5095 |
| 1, 1 | Susceptible | 3.6345 |
| 1, 1 | Susceptible | 3.711 |
| 1, 1 | Susceptible | 3.7595 |
| 1, 1 | Moderate | 3.851 |
| 1, 3 | Moderate | 3.919 |
|  | Susceptible | 3.9385 |
| 1, 1 | Moderate | 3.967 |
| 3, 3 | Moderate | 4.067 |
|  | Moderate | 4.107 |
| 3, 3 | Susceptible | 4.1605 |
| 1, 1 | Susceptible | 4.1645 |
| 1, 3 | Moderate | 4.17 |
| 3, 3 | Moderate | 4.179 |
| 3, 3 | Moderate | 4.3415 |
| 3, 3 | Moderate | 4.35 |
| 1, 1 | Moderate | 4.357 |
| 3, 3 | Moderate | 4.4295 |
| 3, 3 | Moderate | 4.4495 |
|  | Moderate | 4.4765 |
| 3, 3 | Moderate | 4.524 |
| 1, 1 | Moderate | 4.555 |
|  | Moderate | 4.6375 |
| 3, 3 | Moderate | 4.6615 |
| 3, 3 | Moderate | 4.676 |
| 3, 3 | Moderate | 4.678 |
|  | Segregating | 4.723 |
|  | Moderate | 4.7575 |
| 3, 3 | Segregating | 4.7645 |
| 3, 3 | Moderate | 4.7675 |
|  | Moderate | 4.771 |
|  | Moderate | 4.7875 |
| 3, 3 | Moderate | 4.797 |
| 1, 3 | Moderate | 4.846 |
|  | Tolerant | 4.85 |
|  | Moderate | 4.891 |
| 1, 1 | Moderate | 4.9085 |
| 3, 3 | Moderate | 4.9095 |
| 3, 3 | Moderate | 4.9395 |
| 3, 3 | Tolerant | 4.943 |
| 1, 1 | Moderate | 4.961 |
| 1, 1 | Moderate | 5.015 |
| 3, 3 | Moderate | 5.0195 |
| 3, 3 | Moderate | 5.051 |
| 3, 3 | Moderate | 5.1305 |
|  | Tolerant | 5.1475 |
| 3, 3 | Moderate | 5.1495 |
|  | Moderate | 5.2105 |
| 3, 3 | Tolerant | 5.2125 |
| 3, 3 | Moderate | 5.214 |
| 3, 3 | Tolerant | 5.215 |
| 3, 3 | Moderate | 5.2565 |
| 3, 3 | Moderate | 5.2795 |
| 3, 3 | Moderate | 5.2945 |
| 3, 3 | Moderate | 5.3125 |
| 3, 3 | Moderate | 5.3145 |
| 3, 3 | Moderate | 5.3345 |
| 3, 3 | Moderate | 5.335 |
| 3, 3 | Tolerant | 5.3365 |
|  | Tolerant | 5.377 |
| 3, 3 | Moderate | 5.39 |
| 3, 3 | Segregating | 5.3905 |
| 3, 3 | Segregating | 5.4675 |
| 3, 3 | Moderate | 5.4835 |
| 3, 3 | Segregating | 5.4925 |
| 3, 3 | Moderate | 5.4975 |
| 3, 3 | Tolerant | 5.518 |
| 3, 3 | Moderate | 5.524 |
|  | Segregating | 5.541 |
|  | Tolerant | 5.574 |
| 1, 1 | Moderate | 5.5895 |
| 3, 3 | Moderate | 5.6025 |
|  | Moderate | 5.616 |
| 3, 3 | Tolerant | 5.6685 |
| 3, 3 | Tolerant | 5.6925 |
| 3, 3 | Moderate | 5.7005 |

TABLE 8-continued

Allele distribution

| S03859 allele (LG-L) | Phenotype | Adjusted mean |
|---|---|---|
| 3, 3 | Moderate | 5.7095 |
|  | Tolerant | 5.7165 |
| 3, 3 | Moderate | 5.7315 |
|  | Moderate | 5.741 |
|  | Moderate | 5.75 |
| 3, 3 | Tolerant | 5.7545 |
| 3, 3 | Moderate | 5.7625 |
| 3, 3 | Moderate | 5.7705 |
| 3, 3 | Moderate | 5.7715 |
| 3, 3 | Moderate | 5.7835 |
| 3, 3 | Segregating | 5.7875 |
| 3, 3 | Moderate | 5.798 |
| 3, 3 | Moderate | 5.851 |
| 3, 3 | Moderate | 5.852 |
| 3, 3 | Tolerant | 5.857 |
| 3, 3 | Tolerant | 5.87 |
| 3, 3 | Moderate | 5.8705 |
|  | Tolerant | 5.914 |
|  | Tolerant | 5.948 |
| 3, 3 | Tolerant | 5.9525 |
| 3, 3 | Tolerant | 5.9675 |
|  | Tolerant | 6.0245 |
| 3, 3 | Moderate | 6.026 |
| 3, 3 | Moderate | 6.0275 |
| 3, 3 | Tolerant | 6.034 |
| 3, 3 | Tolerant | 6.042 |
| 3, 3 | Tolerant | 6.054 |
|  | Tolerant | 6.092 |
|  | Tolerant | 6.1295 |
| 3, 3 | Moderate | 6.2395 |
| 3, 3 | Tolerant | 6.2475 |
| 3, 3 | Tolerant | 6.2695 |
|  | Tolerant | 6.275 |
| 3, 3 | Tolerant | 6.387 |
| 3, 3 | Tolerant | 6.431 |
| 3, 3 | Tolerant | 6.6535 |
|  | Tolerant | 6.674 |

The non-random distribution of alleles between the tolerant and non-tolerant plant groups at the marker loci in Table 8 is good evidence that a QTL influencing tolerance or sensitivity to mesotrione and/or isoxazole herbicides is linked to these marker loci.

QTLs related to tolerance and susceptibility to mesotrione and/or isoxazole herbicides were found to essentially co-localize with QTLs related to tolerance to PPO inhibitor herbicides to linkage group L, as shown in the Examples below. Thus, PPO tolerance could be used to fine map the QTL and to identify putative candidate genes as shown below.

Example 3

Identification of Sulfentrazone Tolerant and Sensitive Soybean Lines—Herbicide Screening Bioassay and Intergroup Association Marker Based Diagnostic Sulfentrazone is a PPO inhibitor and is the active ingredient in AUTHORITY® herbicide. AUTHORITY® 75DF (FMC Corp., Philadelphia, Pa., USA) is a 75% active ingredient formulation of sulfentrazone containing no other active ingredients.

Part 1: Herbicide Bioassay

One hundred sixteen (116) elite soybean lines were screened for sulfentrazone tolerance using the following protocol. Seed of soybean varieties with adequate seed quality, having greater than 85% warm germination were used.

DESIGN AND REPLICATION: After planting, entries were set up in a randomized complete block design, blocked by replication. Three replications per experiment were used. One or more of well established check variety were included in the experiment, such as available public sector check lines.

Non-tolerant check: Pioneer 9692, Asgrow A4715
Tolerant check: Pioneer 9584, Syngenta S5960

Growing conditions were as follows (greenhouse/growth chamber): 16 hr photoperiod @ 85° F. (w/75° nighttime set back). Lighting is critical to the success of the screening as stated below.

METHOD OF SCREENING: Four inch plastic pots were filled with a high quality universal potting soil. Entries were planted 1 inch deep at the rate of 5 seeds/pot. A bar-coded plastic stake was used to identify each entry. After planting the pots were allowed to sit in greenhouse overnight to acclimate to soil and improve germination. The following day a sulfentrazone herbicide solution was slowly poured over each pot and allowed to evenly soak through entire soil profile. This ensured that each seed was exposed to an equal amount of sulfentrazone. Pots were placed on aluminum trays and placed in a greenhouse or growth chamber under high intensity light conditions with photosynthetic photon flux density (PPFD) of at least 500 µmol/m/s. Proper lighting conditions were necessary for this screening due to the nature of the PPO inhibitor used. Pots were lightly watered so that herbicide was not leached from the soil profile. After soybean emergence the pots were watered by keeping aluminum trays filled with ¾" of water under each pot.

Herbicide Solution:

A) Mix a stock solution of 0.926 g AUTHORITY® 75DF (FMC Corp.), thoroughly dissolved in 1000 ml of water.
B) Mix 10 ml of STOCK SOLUTION in 1000 ml of water to create final solution.
C) Pour 100 ml of FINAL SOLUTION over each pot.

RECORDING DATA: 10-14 days after treatment, plants were ready to be scored. All scores were based on a comparison to the checks and evaluated as follows:

9=Equivalent or better when compared to the tolerant check
7=Very little damage or response noted.
5=Intermediate response or damage
3=Major damage, including stunting and foliar necrosis
1=Severe damage, including severe stunting and necrosis; equivalent or worse when compared to the non-tolerant check Of the 116 soybean lines screened, 102 showed at least some tolerance to sulfentrazone based herbicides and 11 showed high sensitivity. A reference relevant to this protocol would be: Dayan et al. (1997) 'Soybean (*Glycine max*) cultivar differences in response to sulfentrazone' Weed Science 45:634-641.

Part 2: Intergroup Analysis

An "Intergroup Allele Frequency Distribution" analysis was conducted using GeneFlow™ version 7.0 software. An intergroup allele frequency distribution analysis provides a method for finding non-random distributions of alleles between two phenotypic groups.

During processing, a contingency table of allele frequencies was constructed and from this a G-statistic and probability were calculated. The G statistic was adjusted by using the William's correction factor. The probability value was adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the tolerance phenotype and the marker will co-segregate. A more complete discussion of the derivation of the probability values can be found in the GeneFlow™ version 7.0 software documentation. See also Sokal and Rolf (1981), Biometry: The Principles and Practices of Statistics in Biological Research, 2nd ed., San Francisco, W. H. Freeman and Co.

The underlying logic is that markers with significantly different allele distributions between the tolerant and non-tolerant groups (i.e., non-random distributions) might be associated with the trait and can be used to separate them for purposes of marker assisted selection of soybean lines with previously uncharacterized tolerance or non-tolerance to protoporphyrinogen oxidase inhibitors. The present analysis examined one marker locus at a time and determined if the allele distribution within the tolerant group is significantly different from the allele distribution within the non-tolerant group. A statistically different allele distribution is an indication that the marker is linked to a locus that is associated with tolerance or non-tolerance to protoporphyrinogen oxidase inhibitors. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 1043 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

RESULTS: Table 9 lists the soybean markers that demonstrated linkage disequilibrium with the tolerance to protoporphyrinogen oxidase inhibitor phenotype. There were 1043 markers used in this analysis. Also indicated in that table are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the Adjusted Probability values. Out of 584 loci studied in 38 sensitive and 160 tolerant soybean lines, QTLs on Lg-L were highly significant, as shown in the table below.

TABLE 9

Intergroup analysis results for Lg-L markers

| Locus | Test | Linkage Group | Position | G-value | df | Prob(G) | Adj Prob |
|---|---|---|---|---|---|---|---|
| S00224-1 | GW | L | 12.03 | 89.87 | −1 | 0 | 0 |
| P10649C-3 | ASH | L | 3.6 | 86.01 | −1 | 0 | 0 |
| SATT523 | SSR | L | 32.4 | 24.02 | −1 | 0.000001 | 0.000592 |

Table 10 shows the allele distribution between 101 tolerant lines and 32/33 non-tolerant lines analyzed. Lines exhibiting tolerance are indicated in the first column as "TOL," and lines exhibiting non-tolerance are indicated in the first column as "NON." Marker calls for the P10649C-3 locus and the S60167-TB locus were available for 132 and 63 of the lines respectively.

TABLE 10

Allele distribution

| Phenotype | P10649C-3 allele LG-L |
|---|---|
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |

TABLE 10-continued

Allele distribution

| Phenotype | P10649C-3 allele LG-L |
|---|---|
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL | 1 |
| TOL |  |
| TOL | 1 |
| TOL | 1 |
| TOL | 2 |
| TOL | 1 |
| TOL | 1 |
| TOL | 1 |
| NON | 3 |
| NON | 3 |
| NON | 1 |
| NON | 1_2 |
| NON | 3 |
| NON | 3 |
| NON | 1 |
| NON | 3 |
| NON | 2 |
| NON | 3 |
| NON | 2 |
| NON | 2 |
| NON | 2 |
| NON | 1 |
| NON | 2_3 |
| NON | 3 |
| NON | 3 |
| NON | 2_3 |
| NON | 3 |
| NON | 3 |
| NON | 1 |
| NON | 2 |
| NON | 3 |
| NON | 3 |
| NON | 2 |
| NON | 3 |
| NON | 1_3 |
| NON | 3 |
| NON | 2 |
| NON | 1 |
| NON | 3 |

The non-random distribution of alleles between the tolerant and non-tolerant plant groups at the marker loci in Table 10 is good evidence that a QTL influencing tolerance to protoporphyrinogen oxidase inhibitors is linked to these marker loci.

Example 4

Predication and Confirmation of Marker Based Selection for Response to PPO Chemistries in a Set of Diverse Public Soybean Lines Marker haplotype data for a set of 17 diverse public soybean lines was determined for two QTL identified in Example 3 for Linkage Group L molecular markers P10649C-3 (approximate position 3.6) and S00224-1 (approximate position 12.0). The response of these lines to sulfentrazone herbicide was published by Hulting et al. (Soybean (*Glycine max* (L.) Merr.) cultivar tolerance to sulfentrazone. 2001 Science Direct, Vol. 20(8): 679-683). The phenotypic response was reported as a growth reduction index: plant height and visual injury as expressed as a percentage of check plot of each cultivar. Data for the marker haplotype on Linkage Group L and the herbicide bioassay results are presented in Table 11. Use of the molecular diagnostic P10649C-3 (linked QTL on Linkage Group L, approximate position 3.6) for this set of phentoyped soybean lines is 92% predictive of tolerance to sulfentrazone when injury is set at 39% or less GRI and is 100% predictive of non-tolerance to sulfentrazone when injury is set at 40% or higher GRI. Use of the S00224-1 marker (approximate position 12.0) for this set of soybean lines is 88% predictive of tolerance to sulfentrazone when injury is set at 39% or less GRI and is 100% predictive of non-tolerance to sulfentrazone when injury is set at 40% or more GRI.

TABLE 11

Marker haplotype at/near QTL on Linkage Group L for PPO herbicide (sulfentrazone) response and phenotypic measure of crop response, expressed in terms of Growth Reduction Index, for soybean cultivars (italicized items indicate deviations from expected)

| | | Linkage Group L QTLs | |
|---|---|---|---|
| Cultivar | Growth Reduction Index* | Position 3.6 P10649C-3 | Position 12.0 S00224-1 |
| PI88788 | 2 | 1, 1 | 3, 3 |
| Richland | 4 | 1, 1 | 3, 3 |
| Lincoln | 5 | 1, 1 | 3, 3 |
| PI180501 | 8 | 1, 1 | 3, 3 |
| Illini | 8 | 1, 1 | 3, 3 |
| S100 | 8 | 1, 1 | 3, 3 |
| Mukden | 8 | 1, 1 | 3, 3 |
| Arksoy | 10 | 1, 1 | 3, 3 |
| Capital | 10 | 1, 1 | 3, 3 |
| Haberlandt | 10 | *3, 3* | *2, 2* |
| Ralsoy | 13 | 1, 1 | *2, 3* |
| Dunfield | 16 | 1, 1 | 3, 3 |
| Peking | 22 | 1, 1 | 3, 3 |
| Roanoke | 40 | 3, 3 | 2, 2 |
| Ogden | 42 | 3, 3 | 2, 2 |
| Hutcheson | 46 | 3, 3 | 2, 2 |
| Ransom | 52 | 3, 3 | 2, 2 |
| allele call load percent accuracy correct tolerant | | (alleles 1) 24/26 = 92% | (allele 3) 23/26 = 88% |
| correct non-tolerant | | (allele 3) 8/8 = 100% | (allele 2) = 8/8 = 100% |

*growth reduction index (plant height and visual injury as expressed as a percentage of check plot of each cultivar); Pre-emergence sulfentrazone application of 0.28 kg ai/ha, from Hulting, et al. (supra)

Example 5

Predication and Confirmation of Marker Based Selection for Response to PPO Chemistries in a Set of Soybean Commercial Lines Haplotype data for a set of 7 commercial soybean lines was determined for two QTL identified in the previous example for Linkage Group L molecular markers P10649C-3 (position 3.6) and S00224-1 (position 12.0). The response of these lines to sulfentrazone herbicide was determined by method used in Example 3. In addition, the same scale was used for scoring such that:

9=Equivalent or better when compared to the tolerant check
7=Very little damage or response noted.
5=Intermediate response or damage
3=Major damage, including stunting and foliar necrosis
1=Severe damage, including severe stunting and necrosis; equivalent or worse when compared to the non-tolerant check Data for the marker haplotype on Linkage Group L and the herbicide bioassay results are presented in Table 12. Use of either/both of these markers for this set of phentoyped soybean lines is 100% predictive of both tolerance (score of a 7 or 9) and non-tolerance (score of a 1 for the non-tolerant check).

TABLE 12

Prediction and confirmation of marker based selection at QTL for linkage group L for response to PPO chemistry (sulfentrazone) in a set of commercial soybean varieties.

| Variety | sulfentrazone injury score | Position 3.6 P10649C-3 | Position 12.0 S00224-1 |
|---|---|---|---|
| 93B41 | 9 | 1, 1 | 3, 3 |
| 93B82 | 9 | 1, 1 | 3, 3 |
| 9281 | 9 | 1, 1 | 3, 3 |
| 9584 | 9 | 1, 1 | 3, 3 |
| 92B52 | 7 | 1, 1 | 3, 3 |
| 92B61 | 7 | 1, 1 | 3, 3 |
| 9692 | 1 | 3, 3 | 2, 2 |

Example 6

Predication and Confirmation of Marker Based Selection for Response to PPO Chemistries (Sulfentrazone) in Ten Lines from a Set of Soybean Lines Phenotyped at the University of Illinois A comparison for the marker predictiveness of PPO response was conducted. The herbicide bioassay experiment used is described in Phytoxic Response and Yield of Soybean (*Glycine max*) Varieties Treated with Sulfentrazone or Flumioxazin (Taylor-Lovell et al., 2001 Weed Technology 15:96-102). Phenotypic data was taken from Table 2 of the publication for those varieties for which in-house marker data was available. Phenotypic score and haplotype data for a set of 10 soybean lines (1 public and 9 commercial) in the chromosomal regions around the QTL for Linkage group L is presented in Table 13. The phenotypic score was determined as percent injury which is defined as visible injury ratings including stunting, chlorosis, and bronzing symptomology (0=no injury; 100=complete death) with 448 g ai/ha field application. Ratings were taken 12 days after treatment. Use of marker P10649C (linked QTL on Linkage Group L, approximate position 3.6, allele call 1) for this set of phentoyped soybean lines is 100% predictive of tolerance (allele call 1) to sulfentrazone when injury is 21% or less and is 100% predictive of non-tolerance (allele call 2 or 3) to sulfentrazone when injury is 43% or greater. The predictiveness of marker S00224-1 is also 100% accurate for tolerance (allele 3) and non-tolerance (allele 2) for this set of material.

TABLE 13

Marker haplotype at/near QTL on Linkage Group L for PPO herbicide (sulfentrazone) response and phenotypic measure of crop injury

| Variety | sulfentrazone injury score | Position 3.6 P10649C-3 | Position 12.0 S00224-1 |
|---|---|---|---|
| P9584 | 5 | 1, 1 | 3, 3 |
| P9671 | 5 | 1, 1 | 3, 3 |
| P9151 | 8 | 1, 1 | 3, 3 |
| P9306 | 15 | 1, 1 | 3, 3 |
| Elgin | 18 | 1, 1 | 3, 3 |
| P9282 | 19 | 1, 1 | 3, 3 |
| P9352 | 21 | 1, 1 | 3, 3 |
| P9362 | 43 | 2, 2 | 2, 2 |
| 91B01 | 58 | 3, 3 | 2, 2 |
| P9552 | 61 | 3, 3 | 2, 2 |
| LSD (0.05) | 8 | | |

| | allele call load percent accuracy | |
|---|---|---|
| correct tolerant | (alleles 1 or 2) 14/14 = 100% | (allele 3) 14/14 = 100% |
| correct non-tolerant | (allele 3) 8/8 = 100% | (allele 2) = 8/8 = 100% |

Example 7

Figure 5:
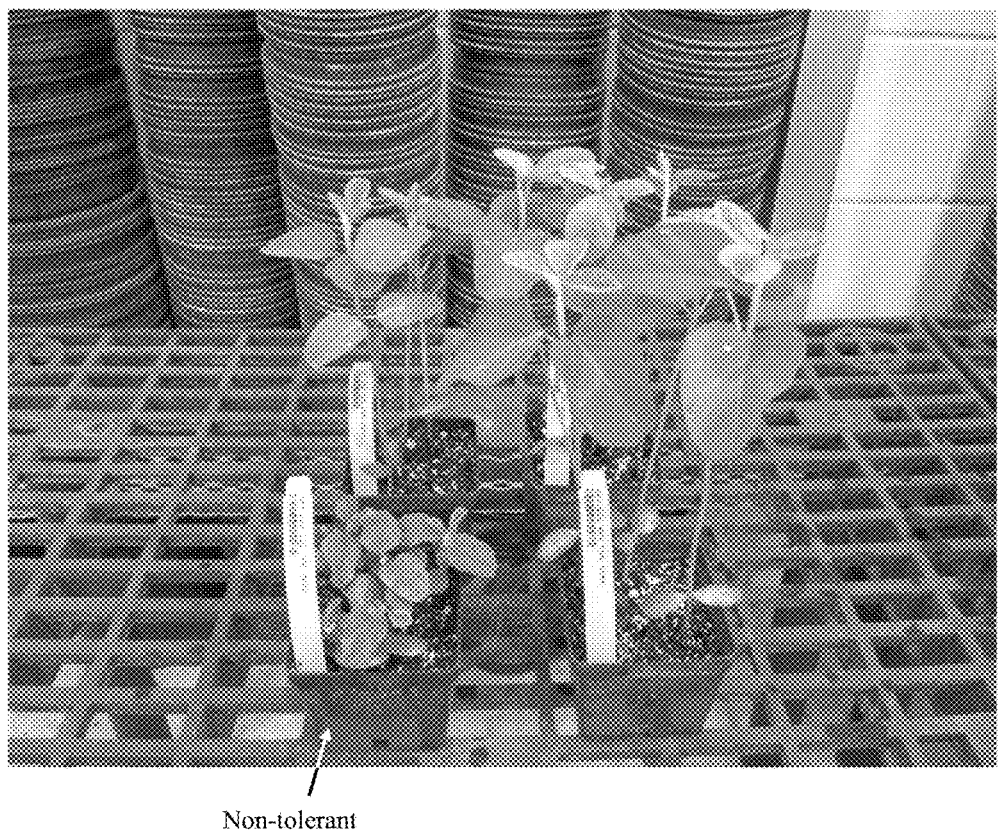
FIG. 5 provides an example of cultivars with vastly different PPO inhibitor tolerance phenotypes. Shown are greenhouse samples, with a non-tolerant variety with non-tolerant (arrow, left side) and tolerant (right side) variety checks, showing treated plants in the foreground, and untreated plants in the background.

Pictures of Soybean Variety Response (Tolerant and Non-Tolerant Check Varieties) to Sulfentrazone Injury in the Field and in the Greenhouse/Growth Chamber Bioassay Known non-tolerant (i.e., Pioneer variety 9692, Asgrow variety A4715) and tolerant (i.e., Pioneer variety 9584, Syngenta variety S5960) germplasm can exhibit severe differences in symptomology when field conditions are conducive to damage and when lab conditions for bioassays are optimized for selection purposes. FIGS. 4 and 5 show these differences in phenotype. FIG. 4 shows a field sample, with a non-tolerant variety on the left (stunted, necrotic) and tolerant variety on the right (normal growth). FIG. 5 shows a greenhouse sample, with non-tolerant (left side) and tolerant (right side) variety checks, treated in the foreground, untreated in the background.

Example 8

Fine Mapping of the LG-L Herbicide Tolerance QTL

The herbicide tolerance QTL on LG-L was initially mapped in two different soybean mapping populations: GEID1653063×GEID3495695 (F4-derived F6) and GEID4520632×GEID7589905 (F3-derived F5). From these populations, 184 and 180 lines respectively were genotyped and scored for PPO herbicide tolerance as described above. This data was used to map the herbicide tolerance QTL to chromosome GM19 near the closely linked marker S03859-1-A, which explains 80% of the phenotypic variation. From these two populations, lines with recombination breakpoints near S03859-1-A were identified to define the borders of the QTL and to facilitate fine-mapping.

Subsequent analysis of the recombinants indicated that the closely linked marker S03859-1-A was actually the left flanking marker. The GEID1653063×GEID3495695 population had 37 recombinants that set the flanking markers for the herbicide tolerance QTL as S04867-1-A (GM19: 841543-841958) and S03859-1-A (GM19: 1634882-1635399) (Table 17). The GEID4520632×GEID7589905 population bad 42 recombinants that delimit the QTL to the same interval (Table 18).

Because 503859-1-A was determined to be closely linked to the herbicide tolerance QM, annotated loci in the vicinity of this marker were targeted for SNP discovery and marker development. Primers were designed from target loci using Primer3 (open source software available from The Source Forge website) and checked for uniqueness using bioinformatics software. A panel composed of 20 PPO tolerant and 8 PPO susceptible lines, including the four mapping parents from the mapping population, was re-sequenced at the target loci to identify informative SNPs. DNA was extracted using the urea extraction protocol below and PCR amplified using standard lab protocols (see Tables 14-15). The PCR was then cleaned up using the EXOSAP-IT® protocol (USB-Cleveland, Ohio, USA) (Table 15) before being sequenced by Sanger sequencing.

In total, 104 loci were re-sequenced and 235 informative SNPs were identified. From these SNPs, 22 TAQMAN® probe markers were designed to distinguish between tolerant versus susceptible alleles in the mapping populations. TAQMAN® assays were designed generally following ABI suggested parameters. These markers were then run on 86 select recombinants combined from the two mapping populations to facilitate fine-mapping and to further delimit the herbicide tolerance QTL interval (Table 19).

Urea Extraction Protocol
1. Grind 2 g fresh tissue or 0.5 g lyophilized tissue and add it to 6 mL Urea Extraction Buffer and mix well.
2. Add RNase A (100 mg/mL) and incubate @ 37° C. for 20 min.
   a. 3 uL—Leaf
   b. 12 uL—Seed
3. Add 4-5 mL Phenol:Chloroform:Isoamyl 25:24:1. Mix well. (Sigma P3803)
4. Put on rocker inside hood.
   a. Fresh—15 min
   b. Lyophilized—30 min
5. Centrifuge @ 8000 rpm at 10° C. for 10 min.
6. Transfer supernatant to clean tube.
7. Add 700 uL of 3M NaOAC (pH 5.0) and 5 mL cold isopropanol. Mix well.
8. Hook DNA and wash in 70% EtOH.
9. Repeat 70% wash.
10. Transfer pellet to 1.5 mL tube and allow to dry.
11. Dissolve pellet in 1 mL 10 mM Tris.

7 M Urea Extraction Buffer
Water 350 mL
Urea 336 g
5M NaCl 50 mL (14.61 g)
1M Tris 40 mL (pH 8.0)
0.5M EDTA 32 mL (pH 8.0)
20% Sarcosine Sol. 40 mL (8 g)
Adjust volume to 800 mL with ddH2O

TABLE 14

PCR Reaction Mix for SNP Discovery

|  | 1X (uL) | 24 plate (ul) | 36 plate (uL) | 48 plate (uL) |
|---|---|---|---|---|
| gDNA (~50-100 ng) | 2.0 | — | — | — |
| 10x PCR Buffer | 2.0 | 5,952 | 7,680 | 10,944 |
| 1 mM dNTP | 2.0 | 5,952 | 7,680 | 10,944 |
| Taq | 0.1 | 297.6 | 384 | 547.2 |
| 0.5 uM Primer (F + R) | 4.0 | — | — | — |
| ddH2O | 9.9 | 29,462 | 38,016 | 54,173 |
| Total | 20.0 | 41,664 | 53,760 | 76,608 |

TABLE 15

PCR Setup for SNP Discovery Dipper Setup

| PCR conditions | Temp | Time | #Cycles |
|---|---|---|---|
| initial denature | 94 C. | 3 min | 1X |
| denature | 94 C. | 45 sec |  |
| anneal | 65 C. | 60 sec | 35X |
| extension | 72 C. | 75 sec |  |
| final extension end | 72 C. | 5 min | 1X |

TABLE 16

Protocol for PCR clean up
PCR clean up Exo/SAP Mix (pre-sequencing) add 3.6ul of mastermix to 7 μl final PCR product

|  | 24 plate (μl) | 36 plate (μl) | 48 plate (μl) |
|---|---|---|---|
| ddH2O | 4,285.4 | 5,944.3 | 7,326.7 |
| SAP | 4,285.4 | 5,944.3 | 7,326.7 |
| Exo | 2,142.7 | 2,972.2 | 3,663.4 |
| total | 10,714 | 14,861 | 18,317 |

TABLE 17

Initial recombinants identified from GEID1653063 × GEID3495695 mapping population that delimited herbicide tolerance QTL to interval between S04867-1-A and S03859-1-A

| SAMPLE | S04867-1-A | S03859-1-A | Call | Average | Comment |
|---|---|---|---|---|---|
| Genetic Pos | 7.81 | 10.00 |  |  |  |
| GEID1653063 | A | A | SUS | 1 | Control |
| GEID3495695 | B | B | TOL | 9 | Control |
| SJ22185567 | A | B | TOL | 9 | L border |
| SJ22185980 | A | B | TOL | 9 | L border |
| SJ22186045 | A | B | TOL | 9 | L border |
| SJ22186929 | A | B | TOL | 9 | L border |
| SJ22186019 | B | H | TOL | 9 | R border |
| SJ22185608 | H | B | TOL | 9 | L border |
| SJ22186913 | H | B | TOL | 9 | L border |
| SJ22185928 | H | B | TOL | 9 | L border |
| SJ22186923 | H | B | TOL | 8.333333 | L border |
| SJ22185569 | A | H | SEG | 5 | L border |
| SJ22186052 | A | H | SEG | 6.333333 | L border |
| SJ22186882 | A | H | SEG | 5 | L border |
| SJ22186919 | B | H | SEG | 5.666667 | L border |
| SJ22186968 | B | H | SEG | 6.333333 | L border |
| SJ22186824 | B | H | SEG | 6.333333 | L border |
| SJ22185604 | H | B | SEG | 6.333333 | R border |
| SJ22185573 | H | A | SEG? | 3.666667 | R border |
| SJ22185983 | A | B | SUS | 1 | R border |
| SJ22186894 | A | B | SUS | 2.333333 | R border |

TABLE 17-continued

Initial recombinants identified from GEID1653063 × GEID3495695 mapping population that delimited herbicide tolerance QTL to interval between S04867-1-A and S03859-1-A

| SAMPLE | S04867-1-A | S03859-1-A | Call | Average | Comment |
|---|---|---|---|---|---|
| SJ22185562 | A | H | SUS | 1.666667 | R border |
| SJ22185941 | A | H | SUS | 1 | R border |
| SJ22185534 | B | A | SUS | 3 | L border |
| SJ22185545 | B | A | SUS | 1.666667 | L border |
| SJ22185559 | B | A | SUS | 2.333333 | L border |
| SJ22186023 | B | A | SUS | 3 | L border |
| SJ22186057 | B | A | SUS | 1 | L border |
| SJ22186065 | B | A | SUS | 1 | L border |
| SJ22186837 | B | A | SUS | 3 | L border |
| SJ22185957 | B | A | SUS | 1 | L border |
| SJ22186846 | B | A | SUS | 1.666667 | L border |
| SJ22186840 | H | A | SUS | 1 | L border |
| SJ22186950 | H | A | SUS | 1 | L border |
| SJ22186872 | H | A | SUS | 2.333333 | L border |
| SJ22186836 | H | A | SUS | 1.666667 | L border |
| SJ22186074 | H | A | SUS | 1 | L border |
| SJ22186906 | H | A | SUS | 1 | L border |
| SJ22185984 | H | A | SUS | 1 | L border |

TABLE 18

Initial recombinants identified from GEID4520632 × GEID7589905 mapping population that delimited herbicide tolerance QTL to interval between S04867-1-A and S03859-1-A

| SAMPLE | S04867-1-A | S03859-1-A | Call | Ave | Comment |
|---|---|---|---|---|---|
| Genetic Pos | 7.81 | 10.00 | | | |
| GEID7589905 | A | A | SUS | 1 | Control |
| GEID4520632 | B | B | TOL | 9 | Control |
| SP21669231 | A | B | TOL | 9 | L border |
| SP21669401 | A | B | TOL | 9 | L border |
| SP21669240 | A | B | TOL | 9 | L border |
| SP21669613 | A | B | TOL | 9 | L border |
| SP21669249 | H | B | TOL | 9 | L border |
| SP21669645 | H | B | TOL | 9 | L border |
| SP21669670 | H | B | TOL | 9 | L border |
| SP21669563 | H | B | TOL | 9 | L border |
| SP21669592 | H | B | TOL | 9 | L border |
| SP21669260 | B | A | SUS | 1 | L border |
| SP21669265 | B | A | SUS | 1 | L border |
| SP21669778 | B | A | SUS | 1.666667 | L border |
| SP21669590 | B | A | SUS | 1 | L border |
| SP21669751 | A | H | SUS | 1 | R border |
| SP21669380 | H | A | SUS | 2.666667 | L border |
| SP21669679 | H | A | SUS | 1 | L border |
| SP21669708 | H | A | SUS | 1 | L border |
| SP21669755 | H | A | SUS | 1 | L border |
| SP21669214 | H | A | SUS | 1 | L border |
| SP21669573 | H | A | SUS | 1.666667 | L border |
| SP21669612 | H | A | SUS | 2.333333 | L border |
| SP21669336 | H | A | SUS | 3.666667 | L border |
| SP21669201 | B | H | SEG | 5 | L border |
| SP21669503 | B | H | SEG | 5 | L border |
| SP21669664 | B | H | SEG | 5 | L border |
| SP21669540 | B | H | SEG | 5 | L border |
| SP21669752 | B | H | SEG | 5.666667 | L border |
| SP21669230 | B | H | SEG | 5.666667 | L border |
| SP21669331 | A | H | SEG | 6.333333 | L border |
| SP21669371 | A | H | SEG | 5 | L border |
| SP21669542 | A | H | SEG | 6.333333 | L border |
| SP21669584 | A | H | SEG | 5 | L border |
| SP21669694 | A | H | SEG | 5.666667 | L border |
| SP21669763 | A | H | SEG | 5 | L border |
| SP21669533 | A | H | SEG | 5 | L border |
| SP21669417 | A | H | SEG | 6.333333 | L border |
| SP21669647 | A | H | SEG? | 7.666667 | L border |
| SP21669651 | A | H | SEG? | 7.666667 | L border |
| SP21669541 | H | B | SEG? | 7.666667 | R border |
| SP21669749 | H | A | SEG | 5 | R border |
| SP21669356 | H | A | SEG | 5 | R border |
| SP21669674 | H | A | SEG? | 3.666667 | R border |

In an initial analysis of the GEID1653063×GEID3495695 mapping population, four key recombinants were identified which served to further fine-map the herbicide tolerance QTL interval (Table 20). A recombination breakpoint at S08110-1-Q1 in line SJ22186052 set the left border, while breakpoints at S08105-1-Q1 in SJ22186019, SJ22186894, and SJ22185941 set the right border. These recombinants delimit the herbicide tolerance QTL to an ~70 kb interval. Initial analysis of the GEID4520632×GEID7589905 mapping population identified eight key recombinants (Table 13). A recombination breakpoint in line SP21669503 at S08117-1-Q1 set the left border, while breakpoints in SP21669249, SP21669332, SP21669615, SP21669616, SP21669670, SP21669458, and SP21669760 set the right border at S08010-1-Q1. These recombinants delimit the herbicide tolerance QTL to a ~526 kb interval. However, when the data from these two mapping populations are combined into a single set, the herbicide tolerance QTL interval was delimited to a ~56 kb interval between S08117-1-Q1 and S08105-1-Q1 (Table 19 and Table 20).

To facilitate higher resolution mapping of the herbicide tolerance QTL interval, lines from the initial set of 86 recombinants were re-scored for herbicide tolerance to confirm their phenotype. Moreover, new markers were developed and used to genotype these recombinants. Consequently, this further analysis resulted in the identification of a key recombinant (SP21669417) from the GEID4520632×GEID7589905 mapping population which set the left border of the herbicide tolerance QTL interval at S08113-1-Q1 (Table 13). In summary, key recombinants from the two mapping populations, scored in two fine-mapping experiments, define the herbicide tolerance QTL to a ~44 kb interval between S08113-1-Q1 and S08105-1-Q1 (Table 19 and Table 20).

TABLE 19

Summary of SNP markers used for initial QTL mapping and fine-mapping of herbicide tolerance QTL.

| Marker | Amplicon | Loci | First Base Coordinate | Last base coordinate | Population Fine-mapping | Comment |
|---|---|---|---|---|---|---|
| S04867-1-A | | Glyma19g01220.1 | 841543 | 841958 | Both | |
| S08102-1-Q1 | PPO_Gm19_1487k3-1 | Glyma19g01860.1 | 1489113 | 1489545 | Both | |
| S08103-1-Q1 | PPO_Gm19_1491k1-1 | X | 1491603 | 1492136 | Both | |
| S08104-1-Q1 | PPO_Gm19_1491k2-1 | Glyma19g01870.1 | 1492364 | 1492948 | Both | |

TABLE 19-continued

Summary of SNP markers used for initial QTL mapping and fine-mapping of herbicide tolerance QTL.

| Marker | Amplicon | Loci | First Base Coordinate | Last base coordinate | Population | Fine-mapping | Comment |
|---|---|---|---|---|---|---|---|
| S08106-1-Q1 | PPO_Gm19_1499k2-1 | Glyma19g01880.1 | 1500732 | 1501392 | A | | |
| S08107-1-Q1 | PPO_Gm19_1541k3-1 | Glyma19g01900.1 | 1542880 | 1543693 | A | | |
| S08109-1-Q1 | PPO_Gm19_1541k4-1 | Glyma19g01900.1 | 1543868 | 1544588 | A | | |
| S08110-1-Q1 | PPO_Gm19_1548k1-1 | Glyma19g01910.1 | 1548367 | 1548822 | A | L border Pop A | |
| S08111-1-Q1 | PPO_Gm19_1548k2-1 | Glyma19g01910.1 | 1548902 | 1549558 | A | | |
| S08115-2-Q1 | PPO_Gm19_1563k1-1 | X | 1563958 | 1564512 | Both | | |
| S08117-1-Q1 | PPO_Gm19_1563k2-1 | X | 1564563 | 1564960 | Both | L border Pop B | |
| S08119-1-Q1 | PPO_Gm19_1566k2-1 | Glyma19g01920.1 | 1567791 | 1568282 | Both | | histone deacetylase |
| S08118-1-Q1 | PPO_Gm19_1566k4-1 | Glyma19g01920.1 | 1569273 | 1569748 | Both | | histone deacetylase |
| S08116-1-Q1 | PPO_Gm19_1566k5-1 | Glyma19g01920.1 | 1570198 | 1570729 | Both | | histone deacetylase |
| S08101-1-Q1 | PPO_Gm19_1586k1-1 | Glyma19g01940.1 | 1587051 | 1587687 | Both | | multidrug/pheromone exporter, ABC superfamily |
| S08112-1-Q1 | PPO_Gm19_1586k1-1 | Glyma19g01940.1 | 1587051 | 1587687 | Both | | multidrug/pheromone exporter, ABC superfamily |
| S08108-1-Q1 | PPO_Gm19_1586k2-1 | Glyma19g01940.1 | 1587805 | 1588500 | Both | | multidrug/pheromone exporter, ABC superfamily |
| S08101-1-Q1 | PPO_Gm19_1586k4-1 | Glyma19g01940.1 | 1589409 | 1590062 | Both | | multidrug/pheromone exporter, ABC superfamily |
| S08101-2-Q1 | PPO_Gm19_1586k4-1 | Glyma19g01940.1 | 1589409 | 1590062 | Both | | multidrug/pheromone exporter, ABC superfamily |
| S08101-3-Q1 | PPO_Gm19_1586k4-1 | Glyma19g01940.1 | 1589409 | 1590062 | Both | | multidrug/pheromone exporter, ABC superfamily |
| S08101-4-Q1 | PPO_Gm19_1586k4-1 | Glyma19g01940.1 | 1589409 | 1590062 | Both | | multidrug/pheromone exporter, ABC superfamily |
| S08105-1-Q1 | PPO_Gm19_1618k2-1 | X | 1619657 | 1620279 | Both | R border Pop A | |
| S03859-1-A | sbacm.pk005.c3.f | X | 1634882 | 1635399 | Both | | |
| S08010-1-Q1 | PPO_Gm19_2089k4-1 | Glyma19g02370.1 | 2091644 | 2092359 | Both | R border Pop B | |
| S08010-2-Q2 | PPO_Gm19_2089k4-1 | Glyma19g02370.1 | 2091644 | 2092359 | Both | | |

Combined data from the two populations delimits the QTL to a ~44 kb interval between S08113-1-Q1 and S8105-1-Q1
* Population A = GEID1653063/GEID3495695; Population B = GEID4520632/GEID7589905

Tables 20-27. Fine-mapping of the herbicide tolerance QTL interval with recombinants from the GEID1653063× GEID3495695 population. Key recombinants delimit the QTL to the ~70 kb interval between 508110-1-Q1 and S08105-1-Q1.

TABLE 20

| | Marker | | | |
|---|---|---|---|---|
| | S04867-1-A | S08102-1-Q1 | S08103-1-Q1 | S08104-1-Q1 |
| | | Amplicon/Pos | | |
| Sample | Gm19:841750 | PPO_Gm19_1487k3-1 | PPO_Gm19_1491k1-1 | PPO_Gm19_1491k2-1 |
| SJ22185925 | B | B | B | B |
| SJ22186974 | B | B | B | B |
| SJ22185946 | B | B | B | B |
| SJ22186019 | B | B | B | B |
| SJ22186923 | H | H | H | H |
| SJ22185604 | H | H | H | H |
| SJ22186029 | H | H | H | H |
| SJ22186052 | A | A | A | A |
| SJ22185534 | B | A | A | A |

TABLE 20-continued

| | Marker | | | |
|---|---|---|---|---|
| | S04867-1-A | S08102-1-Q1 | S08103-1-Q1 | S08104-1-Q1 |
| | Amplicon/Pos | | | |
| Sample | Gm19:841750 | PPO_Gm19_1487k3-1 | PPO_Gm19_1491k1-1 | PPO_Gm19_1491k2-1 |
| SJ22185552 | A | A | A | A |
| SJ22186842 | A | A | — | A |
| SJ22186924 | A | A | A | A |
| SJ22186873 | A | A | A | A |
| SJ22186894 | A | A | A | A |
| SJ22185957 | B | A | A | A |
| SJ22185941 | A | A | A | A |
| SJ22186872 | H | A | A | A |
| SJ22185984 | H | H | H | H |
| SJ22186045 | — | — | H | H |
| SJ22186913 | — | — | H | H |
| SJ22186891 | — | — | H | H |
| SJ22186879 | — | — | H | H |
| SJ22186841 | — | — | H | H |
| SJ22186057 | — | — | H | H |
| SJ22186065 | — | — | H | H |
| SJ22186951 | — | — | H | H |
| SJ22186840 | — | — | H | H |
| SJ22186070 | — | — | A | A |

TABLE 21

| | Marker | | | |
|---|---|---|---|---|
| | S08106-1-Q1 | S08107-1-Q1 | S08109-1-Q1 | S08110-1-Q1 |
| | Amplicon/Pos | | | |
| Sample | PPO_Gm19_1499k2-1 | PPO_Gm19_1541k3-1 | PPO_Gm19_1541k4-1 | PPO_Gm19_1548k1-1 |
| SJ22185925 | B2 | B | B | B |
| SJ22186974 | B1 | B | B | B |
| SJ22185946 | B2 | B | B | B |
| SJ22186019 | B2 | B | B | B |
| SJ22186923 | H | B | — | B |
| SJ22185604 | H | H | H | H |
| SJ22186029 | H | H | H | H |
| SJ22186052 | A | A | A | A |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | H | A | A | A |
| SJ22185957 | A | A | A | A |
| SJ22185941 | A | A | A | A |
| SJ22186872 | A | A | A | A |
| SJ22185984 | H | A | A | A |
| SJ22186045 | H | — | — | H |
| SJ22186913 | H | — | — | B |
| SJ22186891 | H | — | — | H |
| SJ22186879 | H | — | — | H |
| SJ22186841 | H | — | — | H |
| SJ22186057 | H | — | — | H |
| SJ22186065 | H | — | — | H |
| SJ22186951 | H | — | — | H |
| SJ22186840 | H | — | — | A |
| SJ22186070 | A | — | — | A |

TABLE 22

| | Marker | | | |
|---|---|---|---|---|
| | S08111-1-Q1 | S08115-2-Q1 | S08117-1-Q1 | S08119-1-Q1 |
| | Amplicon/Pos | | | |
| Sample | PPO_Gm19_1548k2-1 | PPO_Gm19_1563k1-1 | PPO_Gm19_1563k2-1 | PPO_Gm19_1566k2-1 |
| SJ22185925 | B | B | B | B |
| SJ22186974 | B | B/H | B | B |

TABLE 22-continued

| | Marker | | | |
|---|---|---|---|---|
| | S08111-1-Q1 | S08115-2-Q1 | S08117-1-Q1 | S08119-1-Q1 |
| | Amplicon/Pos | | | |
| Sample | PPO_Gm19_1548k2-1 | PPO_Gm19_1563k1-1 | PPO_Gm19_1563k2-1 | PPO_Gm19_1566k2-1 |
| SJ22185946 | B | B | B | B |
| SJ22186019 | B | B | B | B |
| SJ22186923 | B | B | B | B |
| SJ22185604 | H | H | H | H |
| SJ22186029 | H | H | H | H |
| SJ22186052 | — | H | H | H |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | A | A | A | A |
| SJ22185957 | A | A | A | — |
| SJ22185941 | A | A | A | A |
| SJ22186872 | A | A | A | — |
| SJ22185984 | A | A | A | A |
| SJ22186045 | H | B | B | B |
| SJ22186913 | B | B | B | B |
| SJ22186891 | H | H | H | H |
| SJ22186879 | H | H | H | H |
| SJ22186841 | H | H | H | H |
| SJ22186057 | H | H | H | H |
| SJ22186065 | H | H | H | H |
| SJ22186951 | H | H | H | H |
| SJ22186840 | A | A | A | A |
| SJ22186070 | A | A | A | A |

TABLE 23

| | Marker | | | |
|---|---|---|---|---|
| | S08118-1-Q1 | S08116-1-Q1 | S08114-1-Q1 | S08113-1-Q1 |
| | Amplicon/Pos | | | |
| Sample | PPO_Gm19_1566k4-1 | PPO_Gm19_1566k5-1 | PPO_Gm19_1571k3-1 | PPO_Gm19_1571k3-1 |
| SJ22185925 | B | B | — | — |
| SJ22186974 | — | B | — | — |
| SJ22185946 | B | B | — | — |
| SJ22186019 | — | B | B | B |
| SJ22186923 | B | B | B | B |
| SJ22185604 | H | H | — | — |
| SJ22186029 | H | H | — | — |
| SJ22186052 | — | H | — | — |
| SJ22185534 | A | A | — | — |
| SJ22185552 | A | A | — | — |
| SJ22186842 | A | A | — | — |
| SJ22186924 | A | A | — | — |
| SJ22186873 | A | A | — | — |
| SJ22186894 | A | A | A | A |
| SJ22185957 | A | A | A | A |
| SJ22185941 | A | A | A | A |
| SJ22186872 | A | A | — | — |
| SJ22185984 | A | A | A | A |
| SJ22186045 | B | B | B | B |
| SJ22186913 | B | B | B | B |
| SJ22186891 | H | H | H | H |
| SJ22186879 | H | H | H | H |
| SJ22186841 | H | H | — | — |
| SJ22186057 | H | H | H | H |
| SJ22186065 | H | H | H | H |
| SJ22186951 | H | H | H | H |
| SJ22186840 | A | A | A | A |
| SJ22186070 | A | A | A | A |

TABLE 24

| Sample | Marker | | | |
|---|---|---|---|---|
| | S08101-1-Q1 | S08112-1-Q1 | S08108-1-Q1 | S08101-2-Q1 |
| | Amplicon/Pos | | | |
| | PPO_Gm19_1586k1-1 | PPO_Gm19_1586k1-1 | PPO_Gm19_1586k2-1 | PPO_Gm19_1586k4-1 |
| SJ22185925 | B | B | B | B |
| SJ22186974 | B | B | B | B |
| SJ22185946 | B | B | B | B |
| SJ22186019 | B | B | B | B |
| SJ22186923 | B | B | B | B |
| SJ22185604 | H | H | H | H |
| SJ22186029 | H | H | H | H |
| SJ22186052 | H | H | H | H |
| SJ22185534 | A | A | A | A |
| SJ22185552 | A | A | A | A |
| SJ22186842 | A | A | A | A |
| SJ22186924 | A | A | A | A |
| SJ22186873 | A | A | A | A |
| SJ22186894 | A | A | A | A |
| SJ22185957 | A | A | A | A |
| SJ22185941 | A | A | A | A |
| SJ22186872 | A | A | A | A |
| SJ22185984 | A | A | A | A |
| SJ22186045 | — | B | B | B |
| SJ22186913 | — | B | B | B |
| SJ22186891 | — | H | H | H |
| SJ22186879 | — | H | H | H |
| SJ22186841 | — | H | H | H |
| SJ22186057 | — | H | H | H |
| SJ22186065 | — | H | H | H |
| SJ22186951 | — | H | H | H |
| SJ22186840 | — | A | A | A |
| SJ22186070 | — | A | A | A |

TABLE 25

| Sample | Marker | | | |
|---|---|---|---|---|
| | S08101-1-Q1 | S08101-2-Q1 | S08101-3-Q1 | S08101-4-Q1 |
| | Amplicon/Pos | | | |
| | PPO_Gm19_1586k4-1 | PPO_Gm19_1586k4-1 | PPO_Gm19_1586k4-1 | PPO_Gm19_1586k4-1 |
| SJ22185925 | B | — | B | B |
| SJ22186974 | B | — | B | B |
| SJ22185946 | B | — | B | B |
| SJ22186019 | B | B | B | B |
| SJ22186923 | B | B | B | B |
| SJ22185604 | H | — | H | H |
| SJ22186029 | H | — | H | H |
| SJ22186052 | H | — | H | H |
| SJ22185534 | A | — | A | A |
| SJ22185552 | A | — | A | A |
| SJ22186842 | A | — | A | A |
| SJ22186924 | A | — | A | A |
| SJ22186873 | A | — | A | A |
| SJ22186894 | A | A | A | A |
| SJ22185957 | A | A | A | A |
| SJ22185941 | A | A | A | A |
| SJ22186872 | A | — | A | A |
| SJ22185984 | A | A | A | A |
| SJ22186045 | — | B | B | B |
| SJ22186913 | — | B | B | B |
| SJ22186891 | — | H | H | H |
| SJ22186879 | — | H | H | H |
| SJ22186841 | — | H | H | H |
| SJ22186057 | — | H | H | H |
| SJ22186065 | — | H | H | H |
| SJ22186951 | — | H | H | H |
| SJ22186840 | — | A | A | A |
| SJ22186070 | — | A | A | A |

TABLE 26

| | Marker | | | |
|---|---|---|---|---|
| | S08105-1-Q1 | S08007-1-Q1 | S03859-1-A | S08010-1-Q1 |
| | Amplicon/Pos | | | |
| Sample | PPO_Gm19_1618k2-1 | PPO_Gm19_2089k3-1 | PPO_Gm19_1635140 | PPO_Gm19_2089k4-1 |
| SJ22185925 | B | — | B | A |
| SJ22186974 | B | — | B | A |
| SJ22185946 | B | — | B | A |
| SJ22186019 | H | H | H | H |
| SJ22186923 | B | B | B | B |
| SJ22185604 | B | — | B | B |
| SJ22186029 | H | — | H | B |
| SJ22186052 | H | — | H | H |
| SJ22185534 | A | — | A | B |
| SJ22185552 | A | — | A | B |
| SJ22186842 | A | — | A | B |
| SJ22186924 | A | — | A | B |
| SJ22186873 | A | — | A | B |
| SJ22186894 | B | B | B | B |
| SJ22185957 | A | B | A | B |
| SJ22185941 | H | H | H | H |
| SJ22186872 | A | — | A | B |
| SJ22185984 | A | A | A | A |
| SJ22186045 | B | B | — | B |
| SJ22186913 | B | B | — | B |
| SJ22186891 | H | A | — | A |
| SJ22186879 | H | B | — | B |
| SJ22186841 | H | A | — | A |
| SJ22186057 | H | A | — | A |
| SJ22186065 | H | H | — | A |
| SJ22186951 | H | H | — | A |
| SJ22186840 | A | A | — | A |
| SJ22186070 | A | H | — | H |

TABLE 27

| Marker Amplicon/Pos | 508010-2-Q2 PPO_Gm19_2089k4-1 | Comment | Phenotype |
|---|---|---|---|
| SJ22185925 | A | | TOL |
| SJ22186974 | A | | TOL |
| SJ22185946 | H | | TOL |
| SJ22186019 | H | R Border | TOL |
| SJ22186923 | B | | TOL |
| SJ22185604 | B | | SEG |
| SJ22186029 | B | | SEG |
| SJ22186052 | H | L Border | SEG |
| SJ22185534 | B | | SUS |
| SJ22185552 | B | | SUS |
| SJ22186842 | B | | SUS |
| SJ22186924 | B | | SUS |
| SJ22186873 | B | | SUS |
| SJ22186894 | B | R Border | SUS |
| SJ22185957 | B | | SUS |
| SJ22185941 | H | R Border | SUS |
| SJ22186872 | B | | SUS |
| SJ22185984 | A | | SUS |
| SJ22186045 | B | | TOL |
| SJ22186913 | B | | TOL |
| SJ22186891 | A | | SEG |
| SJ22186879 | B | | SEG |
| SJ22186841 | A | | SEG |
| SJ22186057 | A | | SEG |
| SJ22186065 | A | | SEG |
| SJ22186951 | A | | SEG |
| SJ22186840 | A | | SUS |
| SJ22186070 | H | | SUS |

Tables 28-31. Fine-mapping of the herbicide tolerance QTL interval with recombinants from the GEID4520632× GEID7589905 population

TABLE 28

| | | | Marker | | | | | | |
|---|---|---|---|---|---|---|---|---|---|
| Sample | Comment | Phenotype | S04867-1-A | S08102-1-Q1 | S08103-1-Q1 | S08104-1-Q1 | S08115-2-Q1 | S08115-1-Q1 | S08117-1-Q1 |
| SP21669249 | R Border | TOL | H | B | B | B | B | — | B |
| SP21669332 | R Border | TOL | B | B | — | B | B | — | B |
| SP21669615 | R Border | TOL | B | — | B | B | B | — | B |
| SP21669616 | R Border | TOL | B | B | — | B | B/H | — | B |
| SP21669670 | R Border | TOL | H | B | B | B | — | — | B |
| SP21669503 | L Border | SEG | B | B | B | B | B | — | B |
| SP21669458 | R Border | SUS | A | A | A | A | A | — | A |
| SP21669760 | R Border | SUS | A | A | A | A | A | — | A |
| SP21669417 | L Border | SEG | — | — | A | A | — | A | A |

TABLE 28-continued

| | | | Marker | | | | | | |
| --- | --- | --- | --- | --- | --- | --- | --- | --- | --- |
| Sample | Comment | Phenotype | S04867-1-A | S08102-1-Q1 | S08103-1-Q1 | S08104-1-Q1 | S08115-2-Q1 | S08115-1-Q1 | S08117-1-Q1 |
| SP21669560 | | SEG | — | — | B | B | — | H | H |
| SP21669331 | | SEG | — | — | H | H | — | H | H |

TABLE 29

| | | | Marker | | | | | | |
| --- | --- | --- | --- | --- | --- | --- | --- | --- | --- |
| Sample | Comment | Phenotype | S08119-1-Q1 | S08118-1-Q1 | S08116-1-Q1 | S08114-1-Q1 | S08113-1-Q1 | S08101-1-Q1 | S08112-1-Q1 |
| SP21669249 | R Border | TOL | B | B | B | — | — | B | B |
| SP21669332 | R Border | TOL | B | B | B | — | — | B | B |
| SP21669615 | R Border | TOL | B | B | B | — | — | B | B |
| SP21669616 | R Border | TOL | B | B | B | — | — | B | B/H |
| SP21669670 | R Border | TOL | B | B | B | — | — | B | B |
| SP21669503 | L Border | SEG | H | H | H | — | — | H | H |
| SP21669458 | R Border | SUS | A | A | A | — | — | A | A |
| SP21669760 | R Border | SUS | A | A | A | — | — | A | A |
| SP21669417 | L Border | SEG | A | A | A | A | A | — | H |
| SP21669560 | | SEG | — | H | H | H | H | — | H |
| SP21669331 | | SEG | H | H | H | H | H | — | H |

TABLE 30

| | | | Marker | | | | | | |
| --- | --- | --- | --- | --- | --- | --- | --- | --- | --- |
| Sample | Comment | Phenotype | S08108-1-Q1 | S08101-1-Q1 | S08101-2-Q1 | S08101-3-Q1 | S08101-4-Q1 | S08105-1-Q1 | S03859-1-A |
| SP21669249 | R Border | TOL | B | B | B | B | B | B | B |
| SP21669332 | R Border | TOL | B | B | B | B | - | B | B |
| SP21669615 | R Border | TOL | B | B | B | B | B | B | B |
| SP21669616 | R Border | TOL | B | B | B | B | B | B | B |
| SP21669670 | R Border | TOL | B | B | B | B | B | B | B |
| SP21669503 | L Border | SEG | H | H | H | H | H | H | H |
| SP21669458 | R Border | SUS | A | A | A | A | A | A | A |
| SP21669760 | R Border | SUS | A | A | A | A | A | A | A |
| SP21669417 | L Border | SEG | H | — | H | H | H | H | — |
| SP21669560 | | SEG | H | — | H | H | H | H | — |
| SP21669331 | | SEG | H | — | H | H | H | H | — |

TABLE 31

| Sample | Comment | Phenotype | Marker | | |
| --- | --- | --- | --- | --- | --- |
| | | | S08007-1-Q1 | S08010-1-Q1 | S08010-2-Q2 |
| SP21669249 | R Border | TOL | — | H | H |
| SP21669332 | R Border | TOL | — | H | H |
| SP21669615 | R Border | TOL | — | B | B |
| SP21669616 | R Border | TOL | — | H | H |
| SP21669670 | R Border | TOL | — | B | B |
| SP21669503 | L Border | SEG | — | H | H |
| SP21669458 | R Border | SUS | — | H | H |
| SP21669760 | R Border | SUS | — | H | H |
| SP21669417 | L Border | SEG | H | H | H |
| SP21669560 | | SEG | H | — | H |
| SP21669331 | | SEG | A | A | A |

Example 9

SNP Haplotype Association Analysis

Association analysis of SNP haplotypes across the herbicide tolerance QTL region provides an independent method of validating the herbicide tolerance interval. From the panel of susceptible and tolerant lines used to identify SNPs for TAQMAN® probe development, 235 SNPs from 49 amplicons were identified in the vicinity of the closely linked marker S03859-1-A. The resulting SNP haplotype data was analyzed to identify an interval in which all of the haplotypes from the susceptible and tolerant lines co-segregated with each other (Table 32).

TABLE 32

SNP haplotype association analysis of the herbicide tolerance QTL interval.

| GEID | Amplicon | 1563k1 | 1563k1 | 1563k1 | 1563k1 | 1618k2 | 1618k2 |
|---|---|---|---|---|---|---|---|
| 627002 | TOL (PPO) | G | G | A | C | * | C |
| 3911338 | TOL (PPO) | G | G | A | C | * | C |
| 1564727 | TOL (PPO) | G | G | A | C | * | C |
| 4230314 | TOL (PPO) | G | G | A | C | * | C |
| 4135359 | TOL (PPO) | G | G | A | C | * | C |
| 4611588 | TOL (PPO) | G | G | A | C | * | C |
| 1590166 | TOL (PPO) | G | G | A | C | * | C |
| 3395451 | TOL (PPO) | G | G | A | C | * | C |
| 2322432 | TOL (PPO) | G | G | A | C | * | C |
| 4520632 | TOL (PPO) | G | G | A | C | * | C |
| 632343 | TOL (PPO) | G | G | A | C | * | C |
| 1770139 | TOL (PPO) | G | G | A | C | * | C |
| 3587853 | TOL (PPO) | G | G | A | C | * | C |
| 4553991 | TOL (PPO) | G | G | A | C | * | C |
| 5183219 | TOL (PPO) | G | G | A | C | * | C |
| 2636517 | TOL (PPO) | G | G | A | C | * | C |
| 3495695 | TOL (PPO) | G | G | A | C | * | C |
| 1737165 | SUS (PPO) | A | * | G | T | A | A |
| 1653063 | SUS (PPO) |   |   |   |   | A | A |
| 4501774 | SUS (PPO) | A | * | G | T | A | A |
| 7589905 | SUS (PPO) | A | * | G | T | N | A |
| 4832982 | SUS (PPO) | A | * | G | T | N | A |
| 2839548 | SUS (PPO) | A | * | G | T |   |   |
| 3958440 | SUS (PPO) | A | * | G | T | A | A |
| 6116656 | SUS (PPO) | A | * | G | T | A | A |

Perfect association between haplotype and phenotype between amplicons 1563k1 and 1618k2 defines the QTL interval Although it is difficult to definitively define the co-segregating region, it can conservatively be estimated to reside between amplicons PPO_Gm19_1563k1 and PPO_Gm19_1618k2-1. Within the borders defined by these loci, there are 38 SNP differences that are shared between all of the susceptible lines as compared to all the tolerant lines. This interval overlaps with the ~44 kb QTL interval identified by fine-mapping.

Example 10

Identification of Herbicide Tolerance Candidate Genes

The ~44 kb QTL interval defined by fine-mapping with key recombinants includes only two annotated gene loci based on the Phytozome database (see, e.g., phytozome.net): Glyma19g01920.1 and Glyma19g01940.1. The former is functionally annotated as a Histone deacetylase complex (SIN3 component) while the latter is annotated as a multi-drug/pheromone exporter (ABC superfamily). Given the nature of the herbicide tolerance trait and the role of plant ABC transporters in detoxification and cellular export processes, Glyma19g01940.1, the ABC transporter gene, may be considered the more likely candidate gene. Moreover, all but ~1.2 kb of genomic sequence at the 5' end of and promoter of the histone deacetylase are excluded from the QTL interval.

Based on a gene prediction model for the soybean reference genome (Williams82), Glyma19g01940.1 appeared to be a 3672 base pair coding region which encoded a 1224 amino acid polypeptide (FIGS. 6A-9I, SEQ ID NOs:114-117). To examine sequence differences between the two susceptible lines (GEID1653063 and GEID7589905) and the two tolerant lines (GEID3495695 and GEID4520632) used for mapping, the coding region from Glyma19g01940.1 was targeted for re-sequencing in these four lines. With 95% of the coding region re-sequenced, 10 SNPs, which result in 6 amino acid substitutions, were observed between susceptible and tolerant lines (SED ID NOs: 114-117).

In an effort to obtain the actual coding sequence from the tolerant and susceptible lines from one of the mapping populations, full-length cDNAs for Glyma19g01940.1 were isolated and sequenced for GEID3495695 (Tol) and GEID1653063 (Sus). For each of these lines, sequence analysis of the cDNAs from Glyma19g01940.1 identified a 3696 base pair coding region which encodes a 1231 amino acid polypeptide (SED ID NOs: 118-121), which differs slightly from the putative sequence obtained from the initial gene prediction model. These sequence differences did not any indicate a frameshift in the coding region of the initial sequence as compared to the full insert sequence obtained. A sequence comparison between the two sequenced cDNAs identified 11 SNPs between the susceptible and tolerant lines, which led to seven differences in the 1231 amino acids that comprise the ABC transporter protein (Glyma19g1940.1, see FIGS. 6A-9I). None of these SNPs or amino acid substitutions result in a truncated protein. These amino acid differences for Glyma19g01940.1 between tolerant and susceptible lines are summarized in Table 33 for SEQ ID NOs: 119 and 121, and equivalent positions in SEQ ID NOs: 115 and 117. These nucleotide differences for Glyma19g01940.1 between tolerant and susceptible lines are summarized in Table 34 for SEQ ID NOs: 118 and 120, and equivalent positions in SEQ ID NOs: 114 and 116.

TABLE 33

Amino acid differences for Glyma19g01940.1 between tolerant and susceptible lines

| AA Position SEQ ID NOs: 128 or 129 | AA Position SEQ ID NOs: 126 or 127 | Tolerant | Susceptible |
|---|---|---|---|
| 478 | — | Glycine (G) | Glutamine (E) |
| 520 | 520 | Alanine (A) | Valine (V) |
| 584 | 584 | Isoleucine (I) | Leucine (L) |
| 611 | 611 | Isoleucine (I) | Serine (S) |
| 961 | 953 | Arginine (R) | Lysine (K) |

TABLE 33-continued

Amino acid differences for Glyma19g01940.1 between tolerant and susceptible lines

| AA Position SEQ ID NOs: 128 or 129 | AA Position SEQ ID NOs: 126 or 127 | Tolerant | Susceptible |
|---|---|---|---|
| 1038 | 1030 | Methionine (M) | Leucine (L) |
| 1120 | 1112 | Arginine (R) | Glycine (G) |

TABLE 34

Nucleotide differences for Glyma19g01940.1 between tolerant and susceptible lines

| Nucleotide Position SEQ ID NOs: 124 or 125 | Nucleotide Position SEQ ID NOs: 112 or 113 | Tolerant | Susceptible |
|---|---|---|---|
| 1455 | — | G | A |
| 1581 | 1559 | C | T |
| 1772 | 1750 | A | C |
| 1854 | 1832 | T | G |
| 1954 | 1932 | G | A |
| 2773 | 2727 | C | T |
| 2904 | 2858 | G | A |
| 3073 | 3027 | T | C |
| 3134 | 3088 | A | C |
| 3136 | 3090 | G | A |
| 3380 | 3334 | A | G |
| 3882 | n/a | T | C |

Example 11

QTL Analysis

The F2 population derived from GEID1653063×GEID6461257 consisting of 251 progeny and segregating for the herbicide tolerance trait was used for mapping. The trait has been previously mapped to LG-L. The population was screened with a total of 15 polymorphic markers from LG-L (Ch 19). Five of these 19 markers showed severe segregation distortion and were excluded in the mapping analysis. A significant QTL for herbicide tolerance was detected on the LG-L (LRS=364) which was closely linked with the PPO production marker S08101-2-Q1 and flanked by markers S04867-1-A (7.81 cM) and S03859-1-A (10.00 cM). The QTL explained around 76% of phenotypic variation.

Material and Methods

Population: An F2 mapping population GEID1653063/GEID6461257 consisting of 251 F2 progeny was used. DNA extraction of the tissue was prepared using a citrate extraction protocol and quantified using the GW DNA quantification protocol.

Phenotype: The herbicide tolerance phenotypes were for each line were evaluated using chi-square analysis to establish a goodness to fit to the expected 1:2:1 genetic segregation ratio. The goodness of fit test indicated that the phenotypic data for the 251 progeny follows the expected 1:2:1 genetic ratio (p-value=0.769).

Genotype: PolyM was used to identify polymorphic markers between the two parents. A total of 15 polymorphic markers from LG-L were assayed. Allele nomenclature used were maternal alleles were assigned "A" and paternal alleles "B", and heterozygous "H". The 10 of 15 markers were linked together on LG-L with 5 markers showing severe segregation distortion in the population. The 5 markers showing severe segregation distortion were excluded for mapping analysis.

Linkage Analysis: Map Manager QTX.b20 (Manly et al. (2001) Mammalian Genome 12:930-932) was used to construct the linkage map and perform the QTL analysis. A 1000 permutation test was used to establish the threshold for statistical significance (LOD ratio statistic—LRS) to declare a putative QTL.

Map Manager parameters were set to:
1) Linkage Evaluation: Intercross
2) Search Criteria: P=1e-5
3) Map Function: Kosambi
4) Cross Type: Line Cross QTL Analysis Permutation Test: The thresholds at, 0.01 and 0.05 level based on a 1000 permutation test for herbicide tolerance trait are 7.0 and 17.3, respectively. The marker regression analysis showed that the QTL associated with herbicide tolerance could locate on the LG-L. Interval mapping showed a highly significant region on LG L (LRS=346). The QTL was closely linked with marker S08101-2-Q1 and flanked by markers S04867-1-A (7.81 cM) and S03859-1-A (10.00 cM). This region was estimated to explain ~76% of the phenotypic variation.

Example 12

Characterization of the Glycine max ABC Transporter 1 (GM ABCT1) Resistant and Susceptible Alleles in Transgenic Soy and Transgenic Tobacco Expression of the soybean ABC Transporter 1 Tolerant Allele (GM-ABCT1 TOL) can be used to engineer plants with multiple herbicide tolerance. This can be done by controlling expression of the gene with a plant gene promoter, preferably a constitutive promoter, such as the Arabidopsis polyubiquitin 10 promoter (AT-UBQ10 PRO) or the corn polyubiquitin 1 promoter (UBI1ZM PRO), and joining the promoter to the GM-ABCT1 TOL coding sequence with a plant derived 5' untranslated leader. Examples of such a leader include the Arabidopsis polyubiquitin 10 5' untranslated leader or the corn polyubiquitin 1 5' untranslated leader. 5' untranslated leaders may contain introns; inclusion of an intron would be the preferred configuration, particularly for monocot species. The gene expression cassette would be completed by addition of a 3' untranslated region and poly-adenylation signal.

The several genetic elements could be joined by ligation, GATEWAY® Cloning (Invitrogen), or by In-Fusion™ (Clontech, www.clonetech.com). Alternatively, part or all of the expression cassette DNA sequence could be synthesized. The expression cassette can then be introduced to plant cells by agrobacterium mediated transformation or by direct DNA transfer, e.g. BIOLISTIC™ (DuPont) bombardment.

Soybean Experiments:

Soybean was transformed essentially as described in Li et al. (2007) Plant Mol Biol 65:329-341. Soybean (cv. Jack) embryogenic cultures were transformed by particle bombardment with plant expression vectors using a strong constitutive promoter to control the GM ABCT1 SUS (susceptible allele, SEQ ID NO:125) or GM ABCT1 TOL (resistant allele, SEQ ID NO: 124) genes. Stable transgenic events were tested for presence of the transgene by PCR, but no confirmation of expression was performed. Three clonal plants were produced from each transgenic event.

These T0 plants were grown to the V2 to V8 growth stage and then sprayed with saflufenacil at a rate of 3 g/ha. All treatments were applied in a spray volume of 280 L/ha. The spray mixture contained acetone, water, glycerin and surfactant. Treated plants were compared to untreated plants of similar genetic background and evaluated for herbicide injury at seven days after treatment. Visual injury was on a scale of 0 to 100% injury (0=no effect to 100=dead plant). Plants are also visually evaluated for agronomic effects such as interveinal and veinal chlorosis, reddening, leaf malformation, necrosis, apical withering/death/regrowth, and whole plant height.

T0 plants carrying the susceptible allele showed a mean visual injury score of 59% while plants carrying the resistant allele showed a mean visual injury of 72%. Wild type soy plants showed a mean visual injury of 84%.

There are numerous reasons why this result may have been obtained, including:

1. T0 plants are highly variable coming out of tissue culture, so the plants being compared are not uniform in age, size, or vigor.
2. The phenotype observed for these native soy gene alleles was only for pre-emergence treatment with saflufenacil; resistance to foliar application of this herbicide was not tested. Thus, these foliar spray experiments were performed without evidence the gene would provide protection for this herbicide under such conditions. Pre-emergence experiments were not performed because seed for these transgenic lines had not yet been produced.
3. The soybean genotype used in this experiment, Jack, carries the resistant allele of GM ABCT1, so the resistance gene was endogenously present in this experiment. Thus, while it was possible that adding an additional copy of the gene and expressing it with a constitutive promoter would have produced a quantitative change in herbicide tolerance, it was equally possible that the addition would not produce any measureable difference as compared to the two copies of the resistant allele already present. This soybean line was used because a reproducible transformation procedure for this soybean genotype was known to the inventors.
4. To date only 15 T0 plants carrying the resistant allele, representing 11 events, have been tested. This low number of replicates could have caused skewed the results of this study.
5. As no confirmation of expression was performed, it is possible that no transcription and/or translation is taking place.
6. The putative events were not subjected to quality control for single and/or intact insertion of the transgene construct. Therefore, some events may contain deletions, duplications, and/or rearrangements of all or part of the transgene construct elements.

Tobacco Experiments:

Tobacco (cv. Petite Havana) was transformed by particle bombardment with plant expression vectors using a strong constitutive promoter to control the GM ABCT1 SUS (susceptible allele, SEQ ID NO: 125) or GM ABCT1 RES (resistant allele, SEQ ID NO: 124) genes using the following protocol:

1) Weigh 1 mg 0.6 micron gold powder (for 8 shots). Add 1 ml 100% ethanol Sonicate 2 min. Centrifuge at 13,000 rpm×5 sec. Remove Supernatant. Repeat 3 times.
2) Add 1 ml sterile double-deionized water. Sonicate 2 min. Centrifuge at 13,000 rpm×5 sec. Remove Supernatant. Repeat 2 times.
3) Add 321 µl sterile water. Vortex and sonicate 2 min.
4) Add 4 µl of DNA (1 µg/µl concentration) and vortex briefly.
5) Add 100 µl of 5M $CaCl_2$ and 80 µl of 0.1M Spermidine (14 µl of Spermidine+985.6 µl water prepared freshly). Mix with finger and vortex 2 sec.
6) Incubate on ice for 1 min. Spin down at 13,000 rpm for 2 sec and remove supernatant.
7) Add 500 µl of 100% ethanol. Pipette up and down a few times to wash. (It is important to break all big aggregates at this stage). Vortex 2 sec. Spin down at 13,000 rpm for 2 sec and remove supernatant.
8) Re-suspend in 85 µl of 100% ethanol. Keep on ice. Vortex solution before spreading 10 µl of DNA prep on flying disk. (Sterilize in 100% ethanol for 5-10 min and air dry, also sterilize and air dry 1100 psi rupture disk).
9) Place tobacco leaf (cv. Petit Havana) abaxial side up in the center of a petri plate containing MS01 medium (MS+B5 vitamins (Phytotechnology M519), Sucrose 30 g/l, agar 8 g/l, BA 2 mg/L, NAA 0.05 mg/L).
10) Bombard with 28 mm Hg vacuum, position plate at 9 cm (2nd position from bottom), 1100 psi rupture disk. After bombardment, invert leaves so bombarded side and petioles are in contact with medium.
11) Maintain leaves under 16 hrs/day dim light (<5 µEinstein) for 2-3 days.
12) Cut leaves into small pieces (0.5 cm×0.5 cm) in MSB-Co (MS+Vit, Glucose 10 g/L, BA 50 mg/L, pH5.2), then blot dry on sterile filter paper and place with bombarded side in contact with the MS01 medium containing hygromycin 25 mg/L under 16 hrs/day light (80-120 µEinstein). When shoots appear, cut and place directly in selection media.
13) Until shoots appear, change selection medium every 2 weeks.
14) When entire plantlets are formed (1-2 cm high), leaves are cut into approx. 1-2 mm segments and re-cultured on MS01 medium containing hygromycin 25 mg/L and 8 g/L agar. Subculture to fresh medium every 3 weeks. When new shoots appear, isolate single shoots and transfer onto ½ MS media (M519 2.22 g/L, sucrose 15 g/L, agar 6 g/L).

Stable transgenic events were tested for presence of the transgene by PCR, and transcription of the genes was confirmed by qRT-PCR. Three clonal plants were produced from each transgenic event; two plants from each event were used for the spray experiment.

Plants were grown until 3 to 5 expanded true leaves were present and then sprayed with saflufenacil at a rate of 12.5 g/ha. All treatments were applied in a spray volume of 140 L/ha. Ammonium sulfate was included at 1% w/v. Treated plants were compared to untreated plants of similar genetic background and evaluated for herbicide injury at seven and seventeen days after treatment. Visual injury was on a scale of 0 to 100% injury (0=no effect to 100=dead plant).

At seven days after treatment T0 plants carrying the susceptible allele showed a mean visual injury score of 77% while plants carrying the resistant allele showed a mean visual injury of 63%. Transgenic control plants carrying an unrelated transgene showed a mean visual injury of 63%.

At seventeen days after treatment many plants had shown partial recovery from herbicide damage. T0 plants carrying the susceptible allele now showed a mean visual injury score of 61% while plants carrying the resistant allele showed a mean visual injury of 46%. Transgenic control plants carrying an unrelated transgene showed a mean visual injury of 53%.

Again, there are several reasons why this result may have been obtained, including:
1. T0 plants are highly variable coming out of tissue culture, so the plants being compared are not uniform in age, size, or vigor.
2. The phenotype observed for these native soy gene alleles was only for pre-emergence treatment with saflufenacil; resistance to foliar application of this herbicide was not tested. Thus, these foliar spray experiments were performed without evidence the gene would provide protection for this herbicide under such conditions. Pre-emergence experiments were not performed because seed for these transgenic lines had not yet been produced.
3. Expression of the GM ABCT1 peptide was not tested, so it is possible that no peptide translation is taking place.

Unsprayed clones of the transgenic tobacco plants described above were grown in a greenhouse until flowering and were allowed to self pollinate. Seeds were harvested and used for further experiments. Transgene insertion copy number was not determined for these plants, but for single copy plants the seeds would be expected to segregate 1homozygous:2hemizygous:1null for the transgene.

T1 seeds from multiple transgenic events carrying the resistant and susceptible alleles, and wild type seeds, were germinated on 1.5% Gelrite (no nutrients or minerals) plates and kept in a growth chamber at 26° C. under a 16 hr light regime. Plate media contained saflufenacil at concentrations down to 0.45 parts per billion (ppb). At concentrations above 0.91 ppb no germination was observed; at 0.91 ppb and 0.45 ppb seeds germinated but were bleached and failed to grow. No visible difference was observed between transgenic seed with either GM ABCT1 allele or wild type seed. All seed germinated and grew normally on Gelrite plates lacking saflufenacil.

T1 seeds were sown in four inch pots containing soil and allowed to germinate for five days. At this point, with cotyledons visible above the soil, pots were drenched with 100 mls saflufenacil in water at 0.45 ppb. The solution was applied to soil, avoiding direct contact with plant cotyledons. Three days after treatment all seedlings were severely bleached and appeared dead. No visible differences were observed between any transgenic lines and wild type seed.

It will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All publications referred to herein are incorporated by reference herein for the purpose cited to the same extent as if each was specifically and individually indicated to be incorporated by reference herein.

What is claimed is:

1. An isolated labeled polynucleotide, wherein the polynucleotide discriminates between a soybean that displays tolerance and a soybean that displays susceptibility to one or more herbicides, and wherein the polynucleotide detects at least one SNP within a genomic sequence set forth in SEQ ID NO: 124 or SEQ ID NO: 125.

2. The polynucleotide of claim 1, wherein the one or more herbicides are selected from the group consisting of a mesotrione herbicide, an isoxazole herbicide, and a PPO inhibitor herbicide.

3. The polynucleotide of claim 1, wherein the SNP is selected from the group consisting of a SNP at position 1455, 1581, 1772, 1854, 1954, 2773, 2904, 3073, 3134, 3136, 3380, and 3882 based on the nucleotide positions of the sequence set forth in SEQ ID NO:125.

4. The polynucleotide of claim 3, wherein the SNP is selected from the group consisting of:
(a) a G at position 1455;
(b) a C at position 1581;
(c) an A at position 1772;
(d) a T at position 1854;
(e) a G at position 1954;
(f) a C at position 2773;
(g) a G at position 2904;
(h) a T at position 3073;
(i) an A at position 3134;
(j) a G at position 3136;
(k) an A at position 3380; and
(l) a T at position 3882.

5. A method of selecting a soybean plant or germplasm that displays tolerance, susceptibility, or increased susceptibility to one or more herbicides, the method comprising:
a) detecting in a soybean plant a locus associated with a polynucleotide, wherein the polynucleotide discriminates between a soybean that displays tolerance and a soybean that displays susceptibility to one or more herbicides, and wherein the polynucleotide detects at least one SNP within a genomic sequence set forth in SEQ ID NO: 124 or SEQ ID NO: 125; and
b) selecting the soybean plant or germplasm comprising the detected locus, thereby selecting a soybean plant with tolerance, improved tolerance, susceptibility, or increased susceptibility to one or more herbicides.

6. The method of claim 5, wherein the one or more herbicides are selected from the group consisting of a mesotrione herbicide, an isoxazole herbicide, and a PPO inhibitor herbicide.

7. The method of claim 5, wherein the at least one SNP is selected from the group consisting of:
(a) a G at position 1455;
(b) a C at position 1581;
(c) an A at position 1772;
(d) a T at position 1854;
(e) a G at position 1954;
(f) a C at position 2773;
(g) a G at position 2904;
(h) a T at position 3073;
(i) an A at position 3134;
(j) a G at position 3136;
(k) an A at position 3380; and
(l) a T at position 3882.

8. A method of introgressing an herbicide resistance allele into a soybean plant, the method comprising:
a) crossing at least one soybean plant tolerant to one or more herbicides with at least one soybean plant susceptible to said one or more herbicides in order to form a segregating population;
b) screening the segregating population with one or more polynucleotides, wherein the one or more polynucleotides discriminates between a soybean that displays tolerance and a soybean that displays susceptibility to one or more herbicides, and wherein the one or more polynucleotides detects at least one SNP within a genomic sequence set forth in SEQ ID NO: 124 or SEQ ID NO: 125; and
c) selecting, if present, one or more soybean plants of the segregating population containing the detected locus.

9. The method of claim 8, wherein the one or more herbicides are selected from the group consisting of a mesotrione herbicide, an isoxazole herbicide, and a PPO inhibitor herbicide.

10. The method of claim 8, wherein the at least one SNP is selected from the group consisting of:
(a) a G at position 1455;
(b) a C at position 1581;
(c) an A at position 1772;
(d) a Tat position 1854;
(e) a G at position 1954;
(f) a C at position 2773;
(g) a G at position 2904;
(h) a T at position 3073;
(i) an A at position 3134;
(j) a G at position 3136;
(k) an A at position 3380; and
(l) a T at position 3882.

* * * * *

SEQUENCE LISTING

```
<160> NUMBER OF SEQ ID NOS: 129

<210> SEQ ID NO 1
<211> LENGTH: 30
<212> TYPE: DNA
<213> ORGANISM: Artificial Sequence
<220> FEATURE:
<223> OTHER INFORMATION: Primer/Probe Sequence

<400> SEQUENCE: 1
gagggctatg ttttcttctc cagatgtgag                              30

<210> SEQ ID NO 2
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 2
aaggtcggct tggtggttaa aggcag                                  26

<210> SEQ ID NO 3
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 3
tcatctgtga taa                                                13
```

```
<210> SEQ ID NO 4
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 4
tcatgtgtga taa                                                        13

<210> SEQ ID NO 5
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 5
tcatctctga taa                                                        13

<210> SEQ ID NO 6
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 6
ctggacctac ccgggatgaa aa                                              22

<210> SEQ ID NO 7
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 7
tcttcctctc ccttcctctc gc                                              22

<210> SEQ ID NO 8
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 8
cgcgactctc ctc                                                        13

<210> SEQ ID NO 9
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 9
cgcgagtctc ctc                                                        13

<210> SEQ ID NO 10
<211> LENGTH: 27
<212> TYPE: DNA
<213> ORGANISM: Artificial Sequence
<220> FEATURE:
<223> OTHER INFORMATION: Primer/Probe Sequence
```

<400> SEQUENCE: 10
tcccaggtta gattttctga acgaaga                      27

<210> SEQ ID NO 11
<211> LENGTH: 24
<212> TYPE: DNA
<213> ORGANISM: Artificial Sequence
<220> FEATURE:
<223> OTHER INFORMATION: Primer/Probe Sequence

<400> SEQUENCE: 11
catcagcaca aagggcatc ctca                          24

<210> SEQ ID NO 12
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 12
cactccttaa ggtaat                                  16

<210> SEQ ID NO 13
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 13
cactccttaa gataat                                  16

<210> SEQ ID NO 14
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 14
gttatcgtca ccaccaccaa                              20

<210> SEQ ID NO 15
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 15
cacaacacga gtagccgtag g                            21

<210> SEQ ID NO 16
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 16
aacggatcat cacaac                                  16

<210> SEQ ID NO 17
<211> LENGTH: 15

```
<212> TYPE: DNA
<213> ORGANISM: Artificial Sequence
<220> FEATURE:
<223> OTHER INFORMATION: Primer/Probe Sequence

<400> SEQUENCE: 17
aacggctcat cacaa                                                    15

<210> SEQ ID NO 18
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 18
cgacaatggc ctttacacct                                               20

<210> SEQ ID NO 19
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 19
tcgatatgga cgaaggagga                                               20

<210> SEQ ID NO 20
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 20
acaccatttt tcatcc                                                   16

<210> SEQ ID NO 21
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 21 acacccttttt tcatcc                                                  16

<210> SEQ ID NO 22
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 22
gcaatcacat ttgcattcct ta                                            22

<210> SEQ ID NO 23
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 23
```
tctgaacgag ttgtgcaaga a                                              21

<210> SEQ ID NO 24
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 24
actgctgctt tgtcta                                                    16

<210> SEQ ID NO 25
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 25
ctactgctac tttgtc                                                    16

<210> SEQ ID NO 26
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 26
acctcgtatt ggtggtggtg                                                20

<210> SEQ ID NO 27
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 27
gaatgttcag tgcgagcaac                                                20

<210> SEQ ID NO 28
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 28
acttccctcg tttcg                                                     15

<210> SEQ ID NO 29
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 29
cttccctcat ttcg                                                      14

<210> SEQ ID NO 30
<211> LENGTH: 22
<212> TYPE: DNA
<213> ORGANISM: Artificial Sequence

```
<220> FEATURE:
<223> OTHER INFORMATION: Primer/Probe Sequence

<400> SEQUENCE: 30
caaaaggaaa gaagaaccgt gt                                              22

<210> SEQ ID NO 31
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 31
tccaacctat gtgttggtgt g                                               21

<210> SEQ ID NO 32
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 32
atgattgaag caggaaa                                                    17

<210> SEQ ID NO 33
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 33
tcatgattga agcagcaa                                                   18

<210> SEQ ID NO 34
<211> LENGTH: 27
<212> TYPE: DNA
<213> ORGANISM: Artificial Sequence
<220> FEATURE:
<223> OTHER INFORMATION: Primer/Probe Sequence

<400> SEQUENCE: 34
ggagacttga cttaaagaga aagaaaa                                         27

<210> SEQ ID NO 35
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 35
cggaaagaaa aacaatagat tgaatg                                          26

<210> SEQ ID NO 36
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 36
cttgttctag actgatcat                                                  19
```

<210> SEQ ID NO 37
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 37
ctagactgat aattca                                                        16

<210> SEQ ID NO 38
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 38
tcattcaaga ctacatgaaa gacaaa                                             26

<210> SEQ ID NO 39
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 39
caagggagag caatccttga                                                    20

<210> SEQ ID NO 40
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 40
atagtctccc aaacac                                                        16

<210> SEQ ID NO 41
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 41
atagtctctc aaacacc                                                       17

<210> SEQ ID NO 42
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 42
gaaactttcc attttgccct tc                                                 22

<210> SEQ ID NO 43
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 43
agaacgcagg ggagaagc                                                          18

<210> SEQ ID NO 44
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 44
cttcttccac tcttac                                                            16

<210> SEQ ID NO 45
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 45
ccttcttaca ctcttac                                                           17

<210> SEQ ID NO 46
<211> LENGTH: 28
<212> TYPE: DNA
<213> ORGANISM: Artificial Sequence
<220> FEATURE:
<223> OTHER INFORMATION: Primer/Probe Sequence

<400> SEQUENCE: 46
tgatatgaca ctctactaag atgtgttg                                               28

<210> SEQ ID NO 47
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 47
tgattcatcc gcaaacttga                                                        20

<210> SEQ ID NO 48
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 48
cactctccta tattgtc                                                           17

<210> SEQ ID NO 49
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 49
ctctcctaca ttgtca                                                            16

<210> SEQ ID NO 50

```
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 50
agatccttgt tccaaattcc aa                                              22

<210> SEQ ID NO 51
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 51
ccttggctta atgggtgtgt                                                 20

<210> SEQ ID NO 52
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 52
ccaacacaat ctaact                                                     16

<210> SEQ ID NO 53
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 53
ccaacacaat cgaa                                                       14

<210> SEQ ID NO 54
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 54
atggaggcaa gcttgtgttt                                                 20

<210> SEQ ID NO 55
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 55
catgctacca gcatctgcaa                                                 20

<210> SEQ ID NO 56
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 56
```

-continued cttcataaac gccaaag                                                                                    17

<210> SEQ ID NO 57
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 57
cataaatgcc aaagca                                                                                     16

<210> SEQ ID NO 58
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 58
aatgagcaag ggagaggaca                                                                                 20

<210> SEQ ID NO 59
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 59
tcgccgctgc tatttaattt                                                                                 20

<210> SEQ ID NO 60
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 60
aagcactact ttcaattg                                                                                   18

<210> SEQ ID NO 61
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 61
aagcaccact ttca                                                                                       14

<210> SEQ ID NO 62
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 62
agatgccttg ctcagtggac                                                                                 20

<210> SEQ ID NO 63
<211> LENGTH: 22
<212> TYPE: DNA

```
<213> ORGANISM: Artificial Sequence
<220> FEATURE:
<223> OTHER INFORMATION: Primer/Probe Sequence

<400> SEQUENCE: 63
atgatgaatg tgttgagcca at                                              22

<210> SEQ ID NO 64
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 64
ccccatcacc atac                                                       14

<210> SEQ ID NO 65
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 65
accccaccac cata                                                       14

<210> SEQ ID NO 66
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 66
agaaaccttc caaagctctt gg                                              22

<210> SEQ ID NO 67
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 67
tagggaggca cttgacaacc                                                 20

<210> SEQ ID NO 68
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 68
caacatccga gtcca                                                      15

<210> SEQ ID NO 69
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 69
caacatcaga gtcca                                                      15
```

<210> SEQ ID NO 70
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 70
ttttgacccc cagagagttg                              20

<210> SEQ ID NO 71
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 71
ttgcaagcct aaaggatggt                              20

<210> SEQ ID NO 72
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 72
ctatctctac acgatgtgt                               19

<210> SEQ ID NO 73
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 73
ctatctccac acgatg                                  16

<210> SEQ ID NO 74
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 74
tcccacttga tcttgcagaa                              20

<210> SEQ ID NO 75
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 75
tacggtgggt ggattattcg                              20

<210> SEQ ID NO 76
<211> LENGTH: 15
<212> TYPE: DNA
<213> ORGANISM: Artificial Sequence
<220> FEATURE:

```
<223> OTHER INFORMATION: Primer/Probe Sequence

<400> SEQUENCE: 76
cctccaatgg catac                                                         15

<210> SEQ ID NO 77
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 77
cctccaatag catacat                                                       17

<210> SEQ ID NO 78
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 78
agaaaagcag cagaaagagg ac                                                 22

<210> SEQ ID NO 79
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 79
cttcatgaat cccaacatca ga                                                 22

<210> SEQ ID NO 80
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 80
ctctaattcc acatctg                                                       17

<210> SEQ ID NO 81
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 81
cctctaattt cacatctg                                                      18

<210> SEQ ID NO 82
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 82
tcaaaccatt ttgtttccca gt                                                 22
```

```
<210> SEQ ID NO 83
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 83
tgctagcctt tgatacccaa c                                              21

<210> SEQ ID NO 84
<211> LENGTH: 16
<212> TYPE: DNA
<213> ORGANISM: Artificial Sequence
<220> FEATURE:
<223> OTHER INFORMATION: Primer/Probe Sequence

<400> SEQUENCE: 84
ttgcattgta ttctct                                                    16

<210> SEQ ID NO 85
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 85
ttgcattgta ttttc                                                     15

<210> SEQ ID NO 86
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 86
gtctcaggca gtgaatctgc t                                              21

<210> SEQ ID NO 87
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 87
cagccttacc atcaacatcg                                                20

<210> SEQ ID NO 88
<211> LENGTH: 13
<212> TYPE: DNA
<213> ORGANISM: Artificial Sequence
<220> FEATURE:
<223> OTHER INFORMATION: Primer/Probe Sequence

<400> SEQUENCE: 88
ttccgtgaag atc                                                       13

<210> SEQ ID NO 89
<211> LENGTH: 15
<212> TYPE: DNA
<213> ORGANISM: Artificial Sequence
<220> FEATURE:
<223> OTHER INFORMATION: Primer/Probe Sequence
```

```
<400> SEQUENCE: 89
atgcttccgc gaaga                                                      15

<210> SEQ ID NO 90
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 90
ggtagcagtt actttgtgat gtaagc                                          26

<210> SEQ ID NO 91
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 91
catgcaataa aatccaaaac ca                                              22

<210> SEQ ID NO 92
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 92
tactgatcac aggttat                                                    17

<210> SEQ ID NO 93
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 93
tactgaccac aggttat                                                    17

<210> SEQ ID NO 94
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 94
ttgctttgga aaggactcca                                                 20

<210> SEQ ID NO 95
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 95
cctcatcaac tcctgctgct                                                 20

<210> SEQ ID NO 96
<211> LENGTH: 14
```

```
<212> TYPE: DNA
<213> ORGANISM: Artificial Sequence
<220> FEATURE:
<223> OTHER INFORMATION: Primer/Probe Sequence

<400> SEQUENCE: 96
ctcggtgctg tttt                                                         14

<210> SEQ ID NO 97
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 97
ctcggtgctg tctt                                                         14

<210> SEQ ID NO 98
<211> LENGTH: 23
<212> TYPE: DNA
<213> ORGANISM: Artificial Sequence
<220> FEATURE:
<223> OTHER INFORMATION: Primer/Probe Sequence

<400> SEQUENCE: 98
gaaaccaatt ttgatgtgaa gga                                               23

<210> SEQ ID NO 99
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 99
aagtgagagg ggtgcaaaga                                                   20

<210> SEQ ID NO 100
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 100
cagccctatc tcac                                                         14

<210> SEQ ID NO 101
<211> LENGTH: 14
<212> TYPE: DNA
<213> ORGANISM: Artificial Sequence
<220> FEATURE:
<223> OTHER INFORMATION: Primer/Probe Sequence

<400> SEQUENCE: 101
agccctgtct cact                                                         14

<210> SEQ ID NO 102
<211> LENGTH: 21
<212> TYPE: DNA
<213> ORGANISM: Artificial Sequence
<220> FEATURE:
<223> OTHER INFORMATION: Primer/Probe Sequence

<400> SEQUENCE: 102
```
gcaaatgaga aggctgaagc t                                          21

<210> SEQ ID NO 103
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 103
gctgtccctc agtccatcc                                             19

<210> SEQ ID NO 104
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 104
cggtatcgct cgtca                                                 15

<210> SEQ ID NO 105
<211> LENGTH: 15
<212> TYPE: DNA
<213> ORGANISM: Artificial Sequence
<220> FEATURE:
<223> OTHER INFORMATION: Primer/Probe Sequence

<400> SEQUENCE: 105
tatcgctcgc caacg                                                 15

<210> SEQ ID NO 106
<211> LENGTH: 23
<212> TYPE: DNA
<213> ORGANISM: Artificial Sequence
<220> FEATURE:
<223> OTHER INFORMATION: Primer/Probe Sequence

<400> SEQUENCE: 106
atccacttgc aagataggac act                                        23

<210> SEQ ID NO 107
<211> LENGTH: 26
<212> TYPE: DNA
<213> ORGANISM: Artificial Sequence
<220> FEATURE:
<223> OTHER INFORMATION: Primer/Probe Sequence

<400> SEQUENCE: 107
gtgtaagtac tgatgtgcag ttttga                                     26

<210> SEQ ID NO 108
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 108
cttgacatta agactatcc                                             19

<210> SEQ ID NO 109
<211> LENGTH: 19
<212> TYPE: DNA
<213> ORGANISM: Artificial Sequence

```
<220> FEATURE:
<223> OTHER INFORMATION: Primer/Probe Sequence

<400> SEQUENCE: 109
agactaatcc ttaaacaag                                              19

<210> SEQ ID NO 110
<211> LENGTH: 27
<212> TYPE: DNA
<213> ORGANISM: Artificial Sequence
<220> FEATURE:
<223> OTHER INFORMATION: Primer/Probe Sequence

<400> SEQUENCE: 110
tcaacaggtt atgaatatac aggtcaa                                     27

<210> SEQ ID NO 111
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 111
catcaccaat tgtttggagt tc                                          22

<210> SEQ ID NO 112
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 112
ctattactct ccgttattt                                              19

<210> SEQ ID NO 113
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 113
ctattactcc ccgttatt                                               18

<210> SEQ ID NO 114
<211> LENGTH: 18
<212> TYPE: DNA
<213> ORGANISM: Artificial Sequence
<220> FEATURE:
<223> OTHER INFORMATION: Primer/Probe Sequence

<400> SEQUENCE: 114
ttgttgaatg ggggcact                                               18

<210> SEQ ID NO 115
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 115
ctcgagcaaa tctcgatggt                                             20
```

```
<210> SEQ ID NO 116
<211> LENGTH: 17
<212> TYPE: DNA
<213> ORGANISM: Artificial Sequence
<220> FEATURE:
<223> OTHER INFORMATION: Primer/Probe Sequence

<400> SEQUENCE: 116
ttgaatgctt actctct                                                    17

<210> SEQ ID NO 117
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 117
ttgaatgttt actctcttt                                                  19

<210> SEQ ID NO 118
<211> LENGTH: 20
<212> TYPE: DNA
<213> ORGANISM: Artificial Sequence
<220> FEATURE:
<223> OTHER INFORMATION: Primer/Probe Sequence

<400> SEQUENCE: 118
ctgtggagga ggagcttgag                                                 20

<210> SEQ ID NO 119
<211> LENGTH: 22
<212> TYPE: DNA
<213> ORGANISM: Artificial Sequence
<220> FEATURE:
<223> OTHER INFORMATION: Primer/Probe Sequence

<400> SEQUENCE: 119
acaagtcaca accgtcaatg at                                              22

<210> SEQ ID NO 120
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 120
agtctttgtt ttctctttt                                                  19

<210> SEQ ID NO 121
<211> LENGTH: 19
<212> TYPE: DNA
<213> ORGANISM: Artificial Sequence
<220> FEATURE:
<223> OTHER INFORMATION: Primer/Probe Sequence

<400> SEQUENCE: 121
agtctttgtt ttctctctt                                                  19

<210> SEQ ID NO 122
<211> LENGTH: 3672
<212> TYPE: DNA
<213> ORGANISM: Glycine max

<400> SEQUENCE: 122
```

```
atgcatgctg atggcttaga ctggttcctc atgattttg gtctctttgg ggccattggt      60
gatggcatag gcaccccttt ggtgttgttt atcaccagca aaattatgaa caatattggt     120
ggttttcta gcaacatagg cagcactttc atccacagca tcaatgagaa tgccgtggtt     180
ttgttatatt tggctggtgg gtctttcatt gcttgtttcc tagagggtta ttgttggaca     240
agaacaggag aaaggcaagc tgcaagaatg agagttaggt accttaaagc agttctcagg     300
caagaagtag catactttga tttgcatgtc acaagcacat cggaggtcat caccagcgtc     360
tctaatgata gcctcgtaat tcaagattgt cttagtgaaa aggtcccaaa cttttttgatg    420
aatgcgtcca tgtttgttgg gagctacata gtggcttttg cattattgtg agattggcc      480
attgtggggt tccttttgt ggccctactt gtgatccccg gtttcatgta tgggaggaca      540
ttaatggggt tggctagcaa gataagagaa gagtacaata aagcaggcac aatagcagaa     600
caagcaatat cctccatcag aaccgtttat tcttttgtgg gggaaagcaa gactattgat     660
gctttctctg aagccctaca agggtctgtt gagttgggac tgagacaagg cttagcaaaa     720
ggtttagcta ttggaagcaa tggtgttgtc tttgctatat gggcattcat gtcctattat     780
ggtagcagat tggtcatgta ccatggagct aaaggtggga ctgtatttgc agttggagca     840
gccatagctc ttggaggatt ggcactaggt gctggtttgt cgaacgtgaa gtacttctca     900
gaagcaagta ccgcaggaga acgcataatg gaagtgataa aaagggttcc aaagattgat     960
tctgatagca tggctgagga gattctggag aacgtttcag gggaagttga attcaaccat    1020
gtggactttg tgtacccatc aaggccagac agtgttattc tgaatgattt ctgcctaaag    1080
attccagcag ggaaaacagt ggctttggtt ggagggagtg gctctggaaa atccactgtg    1140
atatcacttt tgcagaggtt ttatgaccca attgagggag agatatttct tgatggtgtg    1200
gccattcaca agttgcaact caagtggttg aggtctcaaa tgggtttggt cagccaagag    1260
cctgcactgt ttgcaactag cattaaagag aatatacttt ttggaagaga gatgccact     1320
caagaagagg ttgtggaggc agcaaaagct tccaatgctc ataatttcat ttcacagttg    1380
ccacaaggat atgatactca ggttggggag agaggagttc aaatgtcagg tggacaaaag    1440
caaagaattg caatagcacg agcaataata aaaaagccac ggattcttct attagatgaa    1500
gcaacaagtg cactagattc tgaatctgaa cgagttgtgc aagaagcatt agacaaagca    1560
gcagtagggc gcacaacaat catcattgca catagattat ccaccataag gaatgcaaat    1620
gtgattgctg ttgtgcaaag tgggaaaatc atggagatgg atcacacca tgaactaatc     1680
caaaacgaca atggccttta cacctcacta gttcgtctcc aacaagcaaa aaatgaaaaa    1740
gaagacacca tttttcatcc tactcctcct tcgtccatat cgaacaaaga caatcacaac    1800
acgagtagcc gtaggctctc tgttgtgatg atccgttcta gctccaccaa ctcgatacct    1860
cgtattggtg gtggtgacga taacaatatt gttgaagaag tagtggaaga taacaagcca    1920
ccacttccct cgtttcgaag gttgctcgca ctgaacattc ccgagtggaa gcaagcatgt    1980
ttagggtgtt tgaatgcggt gttgtttggt gcaattcagc ctgtgtatgc atttgcaatg    2040
gggtcagtga tatctgtta cttcctccca gaccataatg agataaagaa gaaaactatg    2100
atctattcac tttgtttcct agggttggct gtgttctcct tagtggttaa tatcctccag    2160
cattacaact ttgcttacat aggagagtac ttgactaaaa ggatcagaga agaatgtttt    2220
tccaagatac tcacttttga agttggatgg tttgatcaag atgaaaattc cacaggtgct    2280
gtttgttcta gacttgccaa agaagccaat gtgaatggtc tagtggtaca aaccatttca    2340
```

```
gcagtggtaa tagcttttac aatgggccta atcattgcat ggaggttggc cattgttatg   2400
atagcagttc aacccattat catagcatgt ttctacacaa ggcgtgtcct tctcaagagc   2460
atgtctagta aggccatcaa ggcccaagat gaaagtagca agatagctgt tgaagctgtt   2520
tccaacctca gaacaatcac agcatttttct tcccaagata ggatccttaa aatgctcgaa   2580
aaggcccaag aaggcccgag ccgtgaaagc attcgacaat catggtttgc gggcattggg   2640
cttgcatgtt cccaaagcct tacattttgc acttgggctt tggacttttg gtatggaggc   2700
aagcttgtgt ttcagggctt cataaacgcc aaagcattgt ttgagacctt catgatttta   2760
gtgagcacag gtagggttat tgcagatgct ggtagcatga ccaatgacct agctaaaggg   2820
gctgatgctg tgggctcagt ttttgcaatc ttagataggt acacaaaaat tgagccagat   2880
gatgacatag atgggtacaa gcctgaaaag ctaacaggga aaatagagct tcatgatgtc   2940
cattttgcat acccagctag gcccaatgtg atgatcttcc aaggcttctc aatcaaaatt   3000
gatgcaggca gatcaacagc attggttggg caaagtggct ctggaaaatc aacaatcata   3060
ggcttaattg agagattcta tgaccctatg aaagggattg tgaccattga tggtagagac   3120
ataaaatcat accaccttag gtcactaagg aagcatattg ctcttgtaag ccaagagcca   3180
acattgtttg gtgggaccat aagggaaaat attgcatatg gggcatctaa taataataac   3240
aaggttgatg aaactgagat catagaagca gctagggcag ctaatgctca tgatttcatt   3300
gcaagcctaa aggatggtta tgacacatcg tgtagagata gaggagtgca actctctggg   3360
ggtcaaaagc aaagaattgc aatagctaga gccatattga agaatccaga agtgttgttg   3420
ttggatgaag ccacaagtgc cctagatagc caatcagaaa aattggtgca agatgctcta   3480
gaaagggtga tggtggggag aactagtgtg gtggtggctc acaggttaag cacaatacaa   3540
aattgtgacc taattgctgt gttagataag ggaaaagtgg tggagaaagg gacccactca   3600
tctttgttgg ctcatggacc aggtggagct tattactctt tgataagttt acaaagaaga   3660
ccagcaaatt aa                                                       3672
```

<210> SEQ ID NO 123
<211> LENGTH: 3672
<212> TYPE: DNA
<213> ORGANISM: Glycine max

<400> SEQUENCE: 123

```
atgcatgctg atggcttaga ctggttcctc atgattttg gtctctttgg ggccattggt     60
gatggcatag caccccttt ggtgttgttt atcaccagca aaattatgaa caatattggt    120 ggttttttcta gcaacatagg cagcactttc atccacagca tcaatgagaa tgccgtggtt    180
ttgttatatt tggctggtgg gtctttcatt gcttgtttcc tagagggtta ttgttggaca    240
agaacaggag aaaggcaagc tgcaagaatg agagttaggt accttaaagc agttctcagg    300
caagaagtag catactttga tttgcatgtc acaagcacat cggaggtcat caccagcgtc    360
tctaatgata gcctcgtaat tcaagattgt cttagtgaaa aggtcccaaa cttttttgatg    420 aatgcgtcca tgtttgttgg gagctacata gtggcttttg cattattgtg gagattggcc    480 attgtgggt tcccttttgt ggccctactt gtgatcccg gtttcatgta tgggaggaca    540
ttaatggggt tggctagcaa gataagagaa gagtacaata agcaggcac aatagcagaa    600 caagcaatat cctccatcag aaccgtttat tcttttgtgg gggaaagcaa gactattgat    660
gctttctctg aagccctaca agggtctgtt gagttgggac tgagacaagg cttagcaaaa    720
ggtttagcta ttgaagcaa tggtgttgtc tttgctatat gggcattcat gtcctattat    780
```

```
ggtagcagat tggtcatgta ccatggagct aaaggtggga ctgtatttgc agttggagca    840
gccatagctc ttggaggatt ggcactaggt gctggtttgt cgaacgtgaa gtacttctca    900
gaagcaagta ccgcaggaga acgcataatg gaagtgataa aaagggttcc aaagattgat    960
tctgatagca tggctgagga gattctggag aacgtttcag gggaagttga attcaaccat   1020
gtggactttg tgtacccatc aaggccagac agtgttattc tgaatgattt ctgcctaaag   1080
attccagcag ggaaaacagt ggctttggtt ggagggagtg gctctggaaa atccactgtg   1140
atatcacttt tgcagaggtt ttatgaccca attgagggag agatatttct tgatggtgtg   1200
gccattcaca agttgcaact caagtggttg aggtctcaaa tgggtttggt cagccaagag   1260
cctgcactgt ttgcaactag cattaaagag aatatacttt ttggaagaga gatgccact    1320
caagaagagg ttgtggaggc agcaaaagct tccaatgctc ataatttcat ttcacagttg   1380
ccacaaggat atgatactca ggttggggag agaggagttc aaatgtcagg tggacaaaag   1440
caaagaattg caatagcacg agcaataata aaaaagccac ggattcttct attagatgaa   1500
gcaacaagtg cactagattc tgaatctgaa cgagttgtgc aagaagcatt agacaaagta   1560
gcagtagggc gcacaacaat catcattgca catagattat ccaccataag gaatgcaaat   1620
gtgattgctg ttgtgcaaag tgggaaaatc atggagatgg gatcacacca tgaactaatc   1680
caaaacgaca atggccttta cacctcacta gttcgtctcc aacaagcaaa aaatgaaaaa   1740
gaagacaccc ttttcatcc tactcctcct tcgtccatat cgaacaaaga caatcacaac   1800
acgagtagcc gtaggctctc tgttgtgatg agccgttcta gctccaccaa ctcgatacct   1860
cgtattggtg gtggtgacga taacaatatt gttgaagaag tagtggaaga taacaagcca   1920
ccacttccct catttcgaag gttgctcgca ctgaacattc ccgagtggaa gcaagcatgt   1980
ttagggtgtt tgaatgcggt gttgtttggt gcaattcagc ctgtgtatgc atttgcaatg   2040
gggtcagtga tatctgttta cttcctccca gaccataatg agataaagaa gaaaactatg   2100
atctattcac tttgtttcct agggttggct gtgttctcct tagtggttaa tatcctccag   2160
cattacaact tgcttacat aggagagtac ttgactaaaa ggatcagaga agaatgtttt   2220
tccaagatac tcacttttga agttggatgg tttgatcaag atgaaaattc cacaggtgct   2280
gtttgttcta gacttgccaa agaagccaat gtgaatggtc tagtggtaca aaccatttca   2340
gcagtggtaa tagcttttac aatgggccta atcattgcat ggaggttggc cattgttatg   2400
atagcagttc aacccattat catagcatgt ttctacacaa ggcgtgtcct tctcaagagc   2460
atgtctagta aggccatcaa ggcccaagat gaaagtagca gatagctgt tgaagctgtt   2520
tccaacctca gaacaatcac agcatttctt tcccaagata ggatccttaa aatgctcgaa   2580
aaggcccaag aaggcccgag ccgtgaaagc attcgacaat catggtttgc gggcattggg   2640
cttgcatgtt cccaaagcct tacattttgc acttgggctt tggactttg tatggaggc    2700
aagcttgtgt ttcagggctt cataaatgcc aaagcattgt ttgagacctt catgatttta   2760
gtgagcacag gtagggttat tgcagatgct ggtagcatga ccaatgacct agctaaaggg   2820
gctgatgctg tgggctcagt ttttgcaatc ttagataagt acacaaaaat tgagccagat   2880
gatgacatag atgggtacaa gcctgaaaag ctaacaggga aatagagct tcatgatgtc   2940
cattttgcat acccagctag gcccaatgtg atgatcttcc aaggcttctc aatcaaaatt   3000
gatgcaggca atcaacagc attggtcggg caaagtggct ctggaaaatc aacaatcata   3060
ggcttaattg agagattcta tgaccctcta aaagggattg tgaccattga tggtagagac   3120
```

| | |
|---|---|
| ataaaatcat accaccttag gtcactaagg aagcatattg ctcttgtaag ccaagagcca | 3180 |
| acattgtttg gtgggaccat aagggaaaat attgcatatg gggcatctaa taataataac | 3240 |
| aaggttgatg aaactgagat catagaagca gctagggcag ctaatgctca tgatttcatt | 3300 |
| gcaagcctaa aggatggtta tgacacatcg tgtggagata gaggagtgca actctctggg | 3360 |
| ggtcaaaagc aaagaattgc aatagctaga gccatattga agaatccaga agtgttgttg | 3420 |
| ttggatgaag ccacaagtgc cctagatagc caatcagaaa aattggtgca agatgctcta | 3480 |
| gaaagggtga tggtggggag aactagtgtg gtggtggctc acaggttaag cacaatacaa | 3540 |
| aattgtgacc taattgctgt gttagataag ggaaaagtgg tggagaaagg gacccactca | 3600 |
| tctttgttgg ctcatggacc aggtggagct tattactctt tgataagttt acaagaaga | 3660 |
| ccagcaaatt aa | 3672 |

<210> SEQ ID NO 124
<211> LENGTH: 3920
<212> TYPE: DNA
<213> ORGANISM: Glycine max

<400> SEQUENCE: 124

| | |
|---|---|
| tggctctctt cggtctattt tcatgcatgc tgatggctta gactggttcc tcatgatttt | 60 |
| tggtctcttt ggggccattg gtgatggcat aggcacccct ttggtgttgt ttatcaccag | 120 |
| caaaattatg aacaatattg gtggttttc tagcaacata ggcagcactt tcatccacag | 180 |
| catcaatgag aatgccgtgg ttttgttata tttggctggt gggtctttca ttgcttgttt | 240 |
| cctagagggt tattgttgga caagaacagg agaaaggcaa gctgcaagaa tgagagttag | 300 |
| gtaccttaaa gcagttctca ggcaagaagt agcatacttt gatttgcatg tcacaagcac | 360 |
| atcggaggtc atcaccagcg tctctaatga tagcctcgta attcaagatt gtcttagtga | 420 |
| aaaggtccca aactttttga tgaatgcgtc catgtttgtt gggagctaca tagtggcttt | 480 |
| tgcattattg tggagattgg ccattgtggg gttccctttt gtggccctac ttgtgatccc | 540 |
| cggtttcatg tatgggagga cattaatggg gttggctagc aagataagag aagagtacaa | 600 |
| taaagcaggc acaatagcag aacaagcaat atcctccatc agaaccgttt attcttttgt | 660 |
| gggggaaagc aagactattg atgctttctc tgaagcccta caagggtctg ttgagttggg | 720 |
| actgagacaa ggcttagcaa aaggtttagc tattggaagc aatggtgttg tctttgctat | 780 |
| atgggcattc atgtcctatt atggtagcag attggtcatg taccatggag ctaaaggtgg | 840 |
| gactgtattt gcagttggag cagccatagc tcttggagga ttggcactag gtgctggttt | 900 |
| gtcgaacgtg aagtacttct cagaagcaag taccgcagga gaacgcataa tggaagtgat | 960 |
| aaaaagggtt ccaaagattg attctgatag catggctgag gagattctgg agaacgtttc | 1020 |
| aggggaagtt gaattcaacc atgtggactt tgtgtaccca tcaaggccag acagtgttat | 1080 |
| tctgaatgat ttctgcctaa agattccagc agggaaaaca gtggctttgg ttggagggag | 1140 |
| tggctctgga aaatccactg tgatatcact tttgcagagg ttttatgacc caattgaggg | 1200 |
| agagatattt cttgatggtg tggccattca caagttgcaa ctcaagtggt tgaggtctca | 1260 |
| aatgggtttg gtcagccaag agcctgcact gtttgcaact agcattaaag agaatatact | 1320 |
| ttttggaaga gaagatgcca ctcaagaaga ggttgtggag gcagcaaaag cttccaatgc | 1380 |
| tcataatttc atttcacagt tgccacaagg atatgatact caggttgggg agagaggagt | 1440 |
| tcaaatgtca ggtggacaaa agcaaagaat tgcaatagca cgagcaataa taaaaaagcc | 1500 |
| acggattctt ctattagatg aagcaacaag tgcactagat tctgaatctg aacgagttgt | 1560 |

```
gcaagaagca ttagacaaag cagcagtagg gcgcacaaca atcatcattg cacatagatt    1620
atccaccata aggaatgcaa atgtgattgc tgttgtgcaa agtgggaaaa tcatggagat    1680
gggatcacac catgaactaa tccaaaacga caatggcctt tacacctcac tagttcgtct    1740
ccaacaagca aaaaatgaaa aagaagacac cattttttcat cctactcctc cttcgtccat    1800
atcgaacaaa gacaatcaca acacgagtag ccgtaggctc tctgttgtga tgatccgttc    1860
tagctccacc aactcgatac ctcgtattgg tggtggtgac gataacaata ttgttgaaga    1920
agtagtggaa gataacaagc caccacttcc ctcgtttcga aggttgctcg cactgaacat    1980
tcccgagtgg aagcaagcat gtttagggtg tttgaatgcg gtgttgtttg gtgcaattca    2040
gcctgtgtat gcatttgcaa tggggtcagt gatatctgtt tacttcctcc cagaccataa    2100
tgagataaag aagaaaacta tgatctattc actttgtttc ctagggttgg ctgtgttctc    2160
cttagtggtt aatatcctcc agcattacaa ctttgcttac ataggagagt acttgactaa    2220
aaggatcaga gaaagaatgt tttccaagat actcactttt gaagttggat ggtttgatca    2280
agatgaaaat tccacaggtg ctgtttgttc tagacttgcc aaagaagcca atgtggtaag    2340
gtctttagtg ggagatagaa tggctctagt ggtacaaacc atttcagcag tggtaatagc    2400
ttttacaatg ggcctaatca ttgcatggag gttggccatt gttatgatag cagttcaacc    2460
cattatcata gcatgtttct acacaaggcg tgtccttctc aagagcatgt ctagtaaggc    2520
catcaaggcc caagatgaaa gtagcaagat agctgttgaa gctgtttcca acctcagaac    2580
aatcacagca ttttcttccc aagataggat ccttaaaatg ctcgaaaagg cccaagaagg    2640
cccgagccgt gaaagcattc gacaatcatg gtttgcgggc attgggcttg catgttccca    2700
aagccttaca ttttgcactt gggctttgga cttttggtat ggaggcaagc ttgtgtttca    2760
gggcttcata aacgccaaag cattgtttga gaccttcatg atttagtga gcacaggtag    2820 ggttattgca gatgctggta gcatgaccaa tgacctagct aaaggggctg atgctgtggg    2880 ctcagtttttt gcaatcttag ataggtacac aaaaaattgag ccagatgatg acatagatgg    2940
gtacaagcct gaaaagctaa cagggaaaat agagcttcat gatgtccatt ttgcataccc    3000
agctaggccc aatgtgatga tcttccaagg cttctcaatc aaaattgatg caggcagatc    3060
aacagcattg gttgggcaaa gtggctctgg aaaatcaaca atcataggct taattgagag    3120
attctatgac cctatgaaag ggattgtgac cattgatggt agagacataa aatcatacca    3180
ccttaggtca ctaaggaagc atattgctct tgtaagccaa gagccaacat tgtttggtgg    3240
gaccataagg gaaaatattg catatggggc atctaataat aataacaagg ttgatgaaac    3300
tgagatcata gaagcagcta gggcagctaa tgctcatgat ttcattgcaa gcctaaagga    3360
tggttatgac acatcgtgta gagatagagg agtgcaactc tctgggggtc aaaagcaaag    3420
aattgcaata gctagagcca tattgaagaa tccagaagtg ttgttgttgg atgaagccac    3480
aagtgcccta gatagccaat cagaaaaatt ggtgcaagat gctctagaaa gggtgatggt    3540
ggggagaact agtgtggtgg tggctcacag gttaagcaca atacaaaatt gtgacctaat    3600
tgctgtgtta gataagggaa aagtggtgga gaaagggacc cactcatctt tgttggctca    3660
tggaccaggt ggagcttatt actctttgat aagtttacaa agaagaccag caaattaaac    3720
atgaatgtta gttttacgca tgaaatctca gctagctaat caaaacaaac aaaatgtcac    3780
atttattggt gattagtatt aaacctcttt tgtggtaact tgtgaaagta aattaagaaa    3840
aatgaaagaa aagtaaatta agcaaagata gaagggaaga attatataac agttgtagtc    3900
```

```
tctcccaact tcctaaattc                                              3920

<210> SEQ ID NO 125
<211> LENGTH: 3920
<212> TYPE: DNA
<213> ORGANISM: Glycine max

<400> SEQUENCE: 125
tggctctctt cggtctattt tcatgcatgc tgatggctta gactggttcc tcatgatttt      60
tggtctcttt ggggccattg gtgatggcat aggcacccct ttggtgttgt ttatcaccag     120
caaaattatg aacaatattg gtggtttttc tagcaacata gcagcactt tcatccacag      180 catcaatgag aatgccgtgg ttttgttata tttggctggt gggtctttca ttgcttgttt     240
cctagagggt tattgttgga caagaacagg agaaaggcaa gctgcaagaa tgagagttag     300
gtaccttaaa gcagttctca ggcaagaagt agcatacttt gatttgcatg tcacaagcac     360
atcggaggtc atcaccagcg tctctaatga tagcctcgta attcaagatt gtcttagtga     420
aaaggtccca aactttttga tgaatgcgtc catgtttgtt gggagctaca tagtggcttt     480
tgcattattg tggagattgg ccattgtggg gttccctttt gtggccctac ttgtgatccc     540
cggtttcatg tatgggagga cattaatggg gttggctagc aagataagag aagagtacaa     600
taaagcaggc acaatagcag aacaagcaat atcctccatc agaaccgttt attcttttgt     660
gggggaaagc aagactattg atgctttctc tgaagcccta caagggtctg ttgagttggg     720
actgagacaa ggcttagcaa aaggtttagc tattggaagc aatggtgttg tctttgctat     780
atgggcattc atgtcctatt atggtagcag attggtcatg taccatggag ctaaaggtgg     840
gactgtattt gcagttggag cagccatagc tcttggagga ttggcactag gtgctggttt     900
gtcgaacgtg aagtacttct cagaagcaag taccgcagga gaacgcataa tggaagtgat     960
aaaaagggtt ccaaagattg attctgatag catggctgag gagattctgg agaacgtttc    1020
aggggaagtt gaattcaacc atgtggactt tgtgtaccca tcaaggccag acagtgttat    1080
tctgaatgat ttctgcctaa agattccagc agggaaaaca gtggctttgg ttggagggag    1140
tggctctgga aaatccactg tgatatcact tttgcagagg ttttatgacc caattgaggg    1200
agagatattt cttgatggtg tggccattca caagttgcaa ctcaagtggt tgaggtctca    1260
aatgggtttg gtcagccaag agcctgcact gtttgcaact agcattaaag agaatatact    1320
ttttggaaga gaagatgcca ctcaagaaga ggttgtggag gcagcaaaag cttccaatgc    1380
tcataatttc atttcacagt tgccacaagg atatgatact caggttgggg agagaggagt    1440
tcaaatgtca ggtgaacaaa agcaaagaat tgcaatagca cgagcaataa taaaaaagcc    1500
acggattctt ctattagatg aagcaacaag tgcactagat tctgaatctg aacgagttgt    1560
gcaagaagca ttagacaaag tagcagtagg gcgcacaaca atcatcattg cacatagatt    1620
atccaccata aggaatgcaa atgtgattgc tgttgtgcaa agtgggaaaa tcatggagat    1680
gggatcacac catgaactaa tccaaaacga caatggccta tacacctcac tagttcgtct    1740
ccaacaagca aaaaatgaaa aagaagacac cttttttcat cctactcctc cttcgtccat    1800
atcgaacaaa gacaatcaca acacgagtag ccgtaggctc tctgttgtga tgagccgttc    1860
tagctccacc aactcgatac ctcgtattgg tggtggtgac gataacaata ttgttgaaga    1920
agtagtggaa gataacaagc caccacttcc ctcattccga aggttgctcg cactgaacat    1980
tcccgagtgg aagcaagcat gtttagggtg tttgaatgcg tgttgtttg gtgcaattca     2040 gcctgtgtat gcatttgcaa tggggtcagt gatatctgtt tacttcctcc cagaccataa    2100
```

-continued

```
tgagataaag aagaaaacta tgatctattc actttgtttc ctagggttgg ctgtgttctc    2160
cttagtggtt aatatcctcc agcattacaa ctttgcttac ataggagagt acttgactaa    2220
aaggatcaga gaaagaatgt tttccaagat actcactttt gaagttggat ggtttgatca    2280
agatgaaaat tccacaggtg ctgtttgttc tagacttgcc aaagaagcca atgtggtaag    2340
gtctttagtg ggagatagaa tggctctagt ggtacaaacc atttcagcag tggtaatagc    2400
ttttacaatg ggcctaatca ttgcatggag gttggccatt gttatgatag cagttcaacc    2460
cattatcata gcatgtttct acacaaggcg tgtccttctc aagagcatgt ctagtaaggc    2520
catcaaggcc caagatgaaa gtagcaagat agctgttgaa gctgtttcca acctcagaac    2580
aatcacagca ttttcttccc aagataggat ccttaaaatg ctcgaaaagg cccaagaagg    2640
cccgagccgt gaaagcattc gacaatcatg gtttgcgggc attgggcttg catgttccca    2700
aagccttaca ttttgcactt gggctttgga cttttggtat ggaggcaagc ttgtgtttca    2760
gggcttcata aatgccaaag cattgtttga gaccttcatg attttagtga gcacaggtag    2820
ggttattgca gatgctggta gcatgaccaa tgacctagct aaaggggctg atgctgtggg    2880
ctcagttttt gcaatcttag ataagtacac aaaaattgag ccagatgatg acatagatgg    2940
gtacaagcct gaaaagctaa cagggaaaat agagcttcat gatgtccatt ttgcataccc    3000
agctaggccc aatgtgatga tcttccaagg cttctcaatc aaaattgatg caggcagatc    3060
aacagcattg gtcgggcaaa gtggctctgg aaaatcaaca atcataggct taattgagag    3120
attctatgac cctctaaaag ggattgtgac cattgatggt agagacataa aatcatacca    3180
ccttaggtca ctaaggaagc atattgctct tgtaagccaa gagccaacat tgtttggtgg    3240
gaccataagg gaaaatattg catatggggc atctaataat aataacaagg ttgatgaaac    3300
tgagatcata gaagcagcta gggcagctaa tgctcatgat ttcattgcaa gcctaaagga    3360
tggttatgac acatcgtgtg gagatagagg agtgcaactc tctgggggtc aaaagcaaag    3420
aattgcaata gctagagcca tattgaagaa tccagaagtg ttgttgttgg atgaagccac    3480
aagtgcccta gatagccaat cagaaaaatt ggtgcaagat gctctagaaa gggtgatggt    3540
ggggagaact agtgtggtgg tggctcacag gttaagcaca atacaaaatt gtgacctaat    3600
tgctgtgtta gataagggaa aagtggtgga gaaagggacc cactcatctt tgttggctca    3660
tggaccaggt ggagcttatt actctttgat aagtttacaa agaagaccag caaattaaac    3720
atgaatgtta gttttacgca tgaaatctca gctagctaat caaaacaaac aaaatgtcac    3780
atttattggt gattagtatt aaacctcttt tgtggtaact tgtgaaagta aattaagaaa    3840
aatgaaagaa aagtaaatta agcaaagata gaagggaaga actatataac agttgtagtc    3900
tctcccaact tcctaaattc                                                 3920
```

<210> SEQ ID NO 126
<211> LENGTH: 1223
<212> TYPE: PRT
<213> ORGANISM: Glycine max

<400> SEQUENCE: 126

```
Met His Ala Asp Gly Leu Asp Trp Phe Leu Met Ile Phe Gly Leu Phe
1               5                   10                  15

Gly Ala Ile Gly Asp Gly Ile Gly Thr Pro Leu Val Leu Phe Ile Thr
            20                  25                  30

Ser Lys Ile Met Asn Asn Ile Gly Gly Phe Ser Ser Asn Ile Gly Ser
        35                  40                  45
```

-continued

```
Thr Phe Ile His Ser Ile Asn Glu Asn Ala Val Val Leu Leu Tyr Leu
 50                  55                  60
Ala Gly Gly Ser Phe Ile Ala Cys Phe Leu Glu Gly Tyr Cys Trp Thr
 65                  70                  75                  80
Arg Thr Gly Glu Arg Gln Ala Ala Arg Met Arg Val Arg Tyr Leu Lys
                 85                  90                  95
Ala Val Leu Arg Gln Glu Val Ala Tyr Phe Asp Leu His Val Thr Ser
                100                 105                 110
Thr Ser Glu Val Ile Thr Ser Val Ser Asn Asp Ser Leu Val Ile Gln
                115                 120                 125
Asp Cys Leu Ser Glu Lys Val Pro Asn Phe Leu Met Asn Ala Ser Met
130                 135                 140
Phe Val Gly Ser Tyr Ile Val Ala Phe Ala Leu Leu Trp Arg Leu Ala
145                 150                 155                 160
Ile Val Gly Phe Pro Phe Val Ala Leu Leu Val Ile Pro Gly Phe Met
                165                 170                 175
Tyr Gly Arg Thr Leu Met Gly Leu Ala Ser Lys Ile Arg Glu Glu Tyr
                180                 185                 190
Asn Lys Ala Gly Thr Ile Ala Glu Gln Ala Ile Ser Ser Ile Arg Thr
                195                 200                 205
Val Tyr Ser Phe Val Gly Glu Ser Lys Thr Ile Asp Ala Phe Ser Glu
210                 215                 220
Ala Leu Gln Gly Ser Val Glu Leu Gly Leu Arg Gln Gly Leu Ala Lys
225                 230                 235                 240
Gly Leu Ala Ile Gly Ser Asn Gly Val Val Phe Ala Ile Trp Ala Phe
                245                 250                 255
Met Ser Tyr Tyr Gly Ser Arg Leu Val Met Tyr His Gly Ala Lys Gly
                260                 265                 270
Gly Thr Val Phe Ala Val Gly Ala Ala Ile Ala Leu Gly Gly Leu Ala
                275                 280                 285
Leu Gly Ala Gly Leu Ser Asn Val Lys Tyr Phe Ser Glu Ala Ser Thr
290                 295                 300
Ala Gly Glu Arg Ile Met Glu Val Ile Lys Arg Val Pro Lys Ile Asp
305                 310                 315                 320
Ser Asp Ser Met Ala Glu Glu Ile Leu Glu Asn Val Ser Gly Glu Val
                325                 330                 335
Glu Phe Asn His Val Asp Phe Val Tyr Pro Ser Arg Pro Asp Ser Val
                340                 345                 350
Ile Leu Asn Asp Phe Cys Leu Lys Ile Pro Ala Gly Lys Thr Val Ala
                355                 360                 365
Leu Val Gly Gly Ser Gly Ser Gly Lys Ser Thr Val Ile Ser Leu Leu
                370                 375                 380
Gln Arg Phe Tyr Asp Pro Ile Glu Gly Glu Ile Phe Leu Asp Gly Val
385                 390                 395                 400
Ala Ile His Lys Leu Gln Leu Lys Trp Leu Arg Ser Gln Met Gly Leu
                405                 410                 415
Val Ser Gln Glu Pro Ala Leu Phe Ala Thr Ser Ile Lys Glu Asn Ile
                420                 425                 430
Leu Phe Gly Arg Glu Asp Ala Thr Gln Glu Glu Val Val Glu Ala Ala
                435                 440                 445
Lys Ala Ser Asn Ala His Asn Phe Ile Ser Gln Leu Pro Gln Gly Tyr
450                 455                 460
```

```
Asp Thr Gln Val Gly Glu Arg Gly Val Gln Met Ser Gly Gly Gln Lys
465                 470                 475                 480

Gln Arg Ile Ala Ile Ala Arg Ala Ile Ile Lys Lys Pro Arg Ile Leu
            485                 490                 495

Leu Leu Asp Glu Ala Thr Ser Ala Leu Asp Ser Glu Ser Glu Arg Val
        500                 505                 510

Val Gln Glu Ala Leu Asp Lys Ala Ala Val Gly Arg Thr Thr Ile Ile
    515                 520                 525

Ile Ala His Arg Leu Ser Thr Ile Arg Asn Ala Asn Val Ile Ala Val
530                 535                 540

Val Gln Ser Gly Lys Ile Met Glu Met Gly Ser His His Glu Leu Ile
545                 550                 555                 560

Gln Asn Asp Asn Gly Leu Tyr Thr Ser Leu Val Arg Leu Gln Gln Ala
                565                 570                 575

Lys Asn Glu Lys Glu Asp Thr Ile Phe His Pro Thr Pro Pro Ser Ser
            580                 585                 590

Ile Ser Asn Lys Asp Asn His Asn Thr Ser Ser Arg Arg Leu Ser Val
        595                 600                 605

Val Met Ile Arg Ser Ser Ser Thr Asn Ser Ile Pro Arg Ile Gly Gly
    610                 615                 620

Gly Asp Asp Asn Asn Ile Val Glu Glu Val Val Glu Asp Asn Lys Pro
625                 630                 635                 640

Pro Leu Pro Ser Phe Arg Arg Leu Leu Ala Leu Asn Ile Pro Glu Trp
                645                 650                 655

Lys Gln Ala Cys Leu Gly Cys Leu Asn Ala Val Leu Phe Gly Ala Ile
            660                 665                 670

Gln Pro Val Tyr Ala Phe Ala Met Gly Ser Val Ile Ser Val Tyr Phe
        675                 680                 685

Leu Pro Asp His Asn Glu Ile Lys Lys Lys Thr Met Ile Tyr Ser Leu
    690                 695                 700

Cys Phe Leu Gly Leu Ala Val Phe Ser Leu Val Val Asn Ile Leu Gln
705                 710                 715                 720

His Tyr Asn Phe Ala Tyr Ile Gly Glu Tyr Leu Thr Lys Arg Ile Arg
                725                 730                 735

Glu Arg Met Phe Ser Lys Ile Leu Thr Phe Glu Val Gly Trp Phe Asp
            740                 745                 750

Gln Asp Glu Asn Ser Thr Gly Ala Val Cys Ser Arg Leu Ala Lys Glu
        755                 760                 765

Ala Asn Val Asn Gly Leu Val Val Gln Thr Ile Ser Ala Val Val Ile
    770                 775                 780

Ala Phe Thr Met Gly Leu Ile Ile Ala Trp Arg Leu Ala Ile Val Met
785                 790                 795                 800

Ile Ala Val Gln Pro Ile Ile Ile Ala Cys Phe Tyr Thr Arg Arg Val
                805                 810                 815

Leu Leu Lys Ser Met Ser Ser Lys Ala Ile Lys Ala Gln Asp Glu Ser
            820                 825                 830

Ser Lys Ile Ala Val Glu Ala Val Ser Asn Leu Arg Thr Ile Thr Ala
        835                 840                 845

Phe Ser Ser Gln Asp Arg Ile Leu Lys Met Leu Glu Lys Ala Gln Glu
    850                 855                 860

Gly Pro Ser Arg Glu Ser Ile Arg Gln Ser Trp Phe Ala Gly Ile Gly
865                 870                 875                 880

Leu Ala Cys Ser Gln Ser Leu Thr Phe Cys Thr Trp Ala Leu Asp Phe
```

885                 890                 895
Trp Tyr Gly Gly Lys Leu Val Phe Gln Gly Phe Ile Asn Ala Lys Ala
            900                 905                 910

Leu Phe Glu Thr Phe Met Ile Leu Val Ser Thr Gly Arg Val Ile Ala
        915                 920                 925

Asp Ala Gly Ser Met Thr Asn Asp Leu Ala Lys Gly Ala Asp Ala Val
    930                 935                 940

Gly Ser Val Phe Ala Ile Leu Asp Arg Tyr Thr Lys Ile Glu Pro Asp
945                 950                 955                 960

Asp Asp Ile Asp Gly Tyr Lys Pro Gly Lys Leu Thr Gly Lys Ile Glu
            965                 970                 975

Leu His Asp Val His Phe Ala Tyr Pro Ala Arg Pro Asn Val Met Ile
        980                 985                 990

Phe Gln Gly Phe Ser Ile Lys Ile Asp Ala Gly Arg Ser Thr Ala Leu
    995                 1000                1005

Val Gly Gln Ser Gly Ser Gly Lys Ser Thr Ile Ile Gly Leu Ile
    1010                1015                1020

Glu Arg Phe Tyr Asp Pro Met Lys Gly Ile Val Thr Ile Asp Gly
    1025                1030                1035

Arg Asp Ile Lys Ser Tyr His Leu Arg Ser Leu Arg Lys His Ile
    1040                1045                1050

Ala Leu Val Ser Gln Glu Pro Thr Leu Phe Gly Gly Thr Ile Arg
    1055                1060                1065

Glu Asn Ile Ala Tyr Gly Ala Ser Asn Asn Asn Lys Val Asp
    1070                1075                1080

Glu Thr Glu Ile Ile Glu Ala Ala Arg Ala Ala Asn Ala His Asp
    1085                1090                1095

Phe Ile Ala Ser Leu Lys Asp Gly Tyr Asp Thr Ser Cys Arg Asp
    1100                1105                1110

Arg Gly Val Gln Leu Ser Gly Gly Gln Lys Gln Arg Ile Ala Ile
    1115                1120                1125

Ala Arg Ala Ile Leu Lys Asn Pro Glu Val Leu Leu Leu Asp Glu
    1130                1135                1140

Ala Thr Ser Ala Leu Asp Ser Gln Ser Glu Lys Leu Val Gln Asp
    1145                1150                1155

Ala Leu Glu Arg Val Met Val Gly Arg Thr Ser Val Val Ala
    1160                1165                1170

His Arg Leu Ser Thr Ile Gln Asn Cys Asp Leu Ile Ala Val Leu
    1175                1180                1185

Asp Lys Gly Lys Val Val Glu Lys Gly Thr His Ser Ser Leu Leu
    1190                1195                1200

Ala His Gly Pro Gly Gly Ala Tyr Tyr Ser Leu Ile Ser Leu Gln
    1205                1210                1215

Arg Arg Pro Ala Asn
    1220

<210> SEQ ID NO 127
<211> LENGTH: 1223
<212> TYPE: PRT
<213> ORGANISM: Glycine max

<400> SEQUENCE: 127

Met His Ala Asp Gly Leu Asp Trp Phe Leu Met Ile Phe Gly Leu Phe
1               5                   10                  15

-continued

```
Gly Ala Ile Gly Asp Gly Ile Gly Thr Pro Leu Val Leu Phe Ile Thr
             20                  25                  30
Ser Lys Ile Met Asn Asn Ile Gly Gly Phe Ser Ser Asn Ile Gly Ser
         35                  40                  45
Thr Phe Ile His Ser Ile Asn Glu Asn Ala Val Val Leu Leu Tyr Leu
     50                  55                  60
Ala Gly Gly Ser Phe Ile Ala Cys Phe Leu Glu Gly Tyr Cys Trp Thr
 65                  70                  75                  80
Arg Thr Gly Glu Arg Gln Ala Ala Arg Met Arg Val Arg Tyr Leu Lys
                 85                  90                  95
Ala Val Leu Arg Gln Glu Val Ala Tyr Phe Asp Leu His Val Thr Ser
             100                 105                 110
Thr Ser Glu Val Ile Thr Ser Val Ser Asn Asp Ser Leu Val Ile Gln
         115                 120                 125
Asp Cys Leu Ser Glu Lys Val Pro Asn Phe Leu Met Asn Ala Ser Met
     130                 135                 140
Phe Val Gly Ser Tyr Ile Val Ala Phe Ala Leu Leu Trp Arg Leu Ala
145                 150                 155                 160
Ile Val Gly Phe Pro Phe Val Ala Leu Leu Val Ile Pro Gly Phe Met
                 165                 170                 175
Tyr Gly Arg Thr Leu Met Gly Leu Ala Ser Lys Ile Arg Glu Glu Tyr
             180                 185                 190
Asn Lys Ala Gly Thr Ile Ala Glu Gln Ala Ile Ser Ser Ile Arg Thr
         195                 200                 205
Val Tyr Ser Phe Val Gly Glu Ser Lys Thr Ile Asp Ala Phe Ser Glu
     210                 215                 220
Ala Leu Gln Gly Ser Val Glu Leu Gly Leu Arg Gln Gly Leu Ala Lys
225                 230                 235                 240
Gly Leu Ala Ile Gly Ser Asn Gly Val Val Phe Ala Ile Trp Ala Phe
                 245                 250                 255
Met Ser Tyr Tyr Gly Ser Arg Leu Val Met Tyr His Gly Ala Lys Gly
             260                 265                 270
Gly Thr Val Phe Ala Val Gly Ala Ala Ile Ala Leu Gly Gly Leu Ala
         275                 280                 285
Leu Gly Ala Gly Leu Ser Asn Val Lys Tyr Phe Ser Glu Ala Ser Thr
     290                 295                 300
Ala Gly Glu Arg Ile Met Glu Val Ile Lys Arg Val Pro Lys Ile Asp
305                 310                 315                 320
Ser Asp Ser Met Ala Glu Glu Ile Leu Glu Asn Val Ser Gly Glu Val
                 325                 330                 335
Glu Phe Asn His Val Asp Phe Val Tyr Pro Ser Arg Pro Asp Ser Val
             340                 345                 350
Ile Leu Asn Asp Phe Cys Leu Lys Ile Pro Ala Gly Lys Thr Val Ala
         355                 360                 365
Leu Val Gly Gly Ser Gly Ser Gly Lys Ser Thr Val Ile Ser Leu Leu
     370                 375                 380
Gln Arg Phe Tyr Asp Pro Ile Glu Gly Glu Ile Phe Leu Asp Gly Val
385                 390                 395                 400
Ala Ile His Lys Leu Gln Leu Lys Trp Leu Arg Ser Gln Met Gly Leu
                 405                 410                 415
Val Ser Gln Glu Pro Ala Leu Phe Ala Thr Ser Ile Lys Glu Asn Ile
             420                 425                 430
Leu Phe Gly Arg Glu Asp Ala Thr Gln Glu Glu Val Val Glu Ala Ala
```

```
            435                 440                 445
Lys Ala Ser Asn Ala His Asn Phe Ile Ser Gln Leu Pro Gln Gly Tyr
450                 455                 460

Asp Thr Gln Val Gly Glu Arg Gly Val Gln Met Ser Gly Gly Gln Lys
465                 470                 475                 480

Gln Arg Ile Ala Ile Ala Arg Ala Ile Lys Lys Pro Arg Ile Leu
                    485                 490                 495

Leu Leu Asp Glu Ala Thr Ser Ala Leu Asp Ser Glu Ser Glu Arg Val
                500                 505                 510

Val Gln Glu Ala Leu Asp Lys Val Ala Val Gly Arg Thr Thr Ile Ile
    515                 520                 525

Ile Ala His Arg Leu Ser Thr Ile Arg Asn Ala Asn Val Ile Ala Val
    530                 535                 540

Val Gln Ser Gly Lys Ile Met Glu Met Gly Ser His His Glu Leu Ile
545                 550                 555                 560

Gln Asn Asp Asn Gly Leu Tyr Thr Ser Leu Val Arg Leu Gln Gln Ala
                565                 570                 575

Lys Asn Glu Lys Glu Asp Thr Leu Phe His Pro Thr Pro Ser Ser
                580                 585                 590

Ile Ser Asn Lys Asp Asn His Asn Thr Ser Ser Arg Leu Ser Val
                595                 600                 605

Val Met Ser Arg Ser Ser Thr Asn Ser Ile Pro Arg Ile Gly Gly
610                 615                 620

Gly Asp Asn Asn Ile Val Glu Val Val Glu Asp Asn Lys Pro
625                 630                 635                 640

Pro Leu Pro Ser Phe Arg Arg Leu Leu Ala Leu Asn Ile Pro Glu Trp
                645                 650                 655

Lys Gln Ala Cys Leu Gly Cys Leu Asn Ala Val Leu Phe Gly Ala Ile
                660                 665                 670

Gln Pro Val Tyr Ala Phe Ala Met Gly Ser Val Ile Ser Val Tyr Phe
                675                 680                 685

Leu Pro Asp His Asn Glu Ile Lys Lys Lys Thr Met Ile Tyr Ser Leu
                690                 695                 700

Cys Phe Leu Gly Leu Ala Val Phe Ser Leu Val Val Asn Ile Leu Gln
705                 710                 715                 720

His Tyr Asn Phe Ala Tyr Ile Gly Glu Tyr Leu Thr Lys Arg Ile Arg
                725                 730                 735

Glu Arg Met Phe Ser Lys Ile Leu Thr Phe Glu Val Gly Trp Phe Asp
                740                 745                 750

Gln Asp Glu Asn Ser Thr Gly Ala Val Cys Ser Arg Leu Ala Lys Glu
                755                 760                 765

Ala Asn Val Asn Gly Leu Val Val Gln Thr Ile Ser Ala Val Val Ile
                770                 775                 780

Ala Phe Thr Met Gly Leu Ile Ile Ala Trp Arg Leu Ala Ile Val Met
785                 790                 795                 800

Ile Ala Val Gln Pro Ile Ile Ile Ala Cys Phe Tyr Thr Arg Arg Val
                805                 810                 815

Leu Leu Lys Ser Met Ser Ser Lys Ala Ile Lys Ala Gln Asp Glu Ser
                820                 825                 830

Ser Lys Ile Ala Val Glu Ala Val Ser Asn Leu Arg Thr Ile Thr Ala
                835                 840                 845

Phe Ser Ser Gln Asp Arg Ile Leu Lys Met Leu Glu Lys Ala Gln Glu
                850                 855                 860
```

```
Gly Pro Ser Arg Glu Ser Ile Arg Gln Ser Trp Phe Ala Gly Ile Gly
865                 870                 875                 880

Leu Ala Cys Ser Gln Ser Leu Thr Phe Cys Thr Trp Ala Leu Asp Phe
                885                 890                 895

Trp Tyr Gly Gly Lys Leu Val Phe Gln Gly Phe Ile Asn Ala Lys Ala
            900                 905                 910

Leu Phe Glu Thr Phe Met Ile Leu Val Ser Thr Gly Arg Val Ile Ala
        915                 920                 925

Asp Ala Gly Ser Met Thr Asn Asp Leu Ala Lys Gly Ala Asp Ala Val
    930                 935                 940

Gly Ser Val Phe Ala Ile Leu Asp Lys Tyr Thr Lys Ile Glu Pro Asp
945                 950                 955                 960

Asp Asp Ile Asp Gly Tyr Lys Pro Glu Lys Leu Thr Gly Lys Ile Glu
                965                 970                 975

Leu His Asp Val His Phe Ala Tyr Pro Ala Arg Pro Asn Val Met Ile
            980                 985                 990

Phe Gln Gly Phe Ser Ile Lys Ile Asp Ala Gly Arg Ser Thr Ala Leu
        995                 1000                1005

Val Gly Gln Ser Gly Ser Gly Lys Ser Thr Ile Ile Gly Leu Ile
    1010                1015                1020

Glu Arg Phe Tyr Asp Pro Leu Lys Gly Ile Val Thr Ile Asp Gly
    1025                1030                1035

Arg Asp Ile Lys Ser Tyr His Leu Arg Ser Leu Arg Lys His Ile
    1040                1045                1050

Ala Leu Val Ser Gln Glu Pro Thr Leu Phe Gly Gly Thr Ile Arg
    1055                1060                1065

Glu Asn Ile Ala Tyr Gly Ala Ser Asn Asn Asn Lys Val Asp
    1070                1075                1080

Glu Thr Glu Ile Ile Glu Ala Arg Ala Ala Asn Ala His Asp
    1085                1090                1095

Phe Ile Ala Ser Leu Lys Asp Gly Tyr Asp Thr Ser Cys Gly Asp
    1100                1105                1110

Arg Gly Val Gln Leu Ser Gly Gln Lys Gln Arg Ile Ala Ile
    1115                1120                1125

Ala Arg Ala Ile Leu Lys Asn Pro Glu Val Leu Leu Leu Asp Glu
    1130                1135                1140

Ala Thr Ser Ala Leu Asp Ser Gln Ser Glu Lys Leu Val Gln Asp
    1145                1150                1155

Ala Leu Glu Arg Val Met Val Gly Arg Thr Ser Val Val Val Ala
    1160                1165                1170

His Arg Leu Ser Thr Ile Gln Asn Cys Asp Leu Ile Ala Val Leu
    1175                1180                1185

Asp Lys Gly Lys Val Val Glu Lys Gly Thr His Ser Ser Leu Leu
    1190                1195                1200

Ala His Gly Pro Gly Gly Ala Tyr Tyr Ser Leu Ile Ser Leu Gln
    1205                1210                1215

Arg Arg Pro Ala Asn
    1220

<210> SEQ ID NO 128
<211> LENGTH: 1231
<212> TYPE: PRT
<213> ORGANISM: Glycine max
```

-continued

```
<400> SEQUENCE: 128

Met His Ala Asp Gly Leu Asp Trp Phe Leu Met Ile Phe Gly Leu Phe
1               5                   10                  15

Gly Ala Ile Gly Asp Gly Ile Gly Thr Pro Leu Val Leu Phe Ile Thr
            20                  25                  30

Ser Lys Ile Met Asn Asn Ile Gly Phe Ser Ser Asn Ile Gly Ser
        35                  40                  45

Thr Phe Ile His Ser Ile Asn Glu Asn Ala Val Val Leu Leu Tyr Leu
    50                  55                  60

Ala Gly Gly Ser Phe Ile Ala Cys Phe Leu Glu Gly Tyr Cys Trp Thr
65                  70                  75                  80

Arg Thr Gly Glu Arg Gln Ala Ala Arg Met Arg Val Arg Tyr Leu Lys
                85                  90                  95

Ala Val Leu Arg Gln Glu Val Ala Tyr Phe Asp Leu His Val Thr Ser
            100                 105                 110

Thr Ser Glu Val Ile Thr Ser Val Ser Asn Asp Ser Leu Val Ile Gln
        115                 120                 125

Asp Cys Leu Ser Glu Lys Val Pro Asn Phe Leu Met Asn Ala Ser Met
    130                 135                 140

Phe Val Gly Ser Tyr Ile Val Ala Phe Ala Leu Leu Trp Arg Leu Ala
145                 150                 155                 160

Ile Val Gly Phe Pro Phe Val Ala Leu Leu Val Ile Pro Gly Phe Met
                165                 170                 175

Tyr Gly Arg Thr Leu Met Gly Leu Ala Ser Lys Ile Arg Glu Glu Tyr
            180                 185                 190

Asn Lys Ala Gly Thr Ile Ala Glu Gln Ala Ile Ser Ser Ile Arg Thr
        195                 200                 205

Val Tyr Ser Phe Val Gly Glu Ser Lys Thr Ile Asp Ala Phe Ser Glu
    210                 215                 220

Ala Leu Gln Gly Ser Val Glu Leu Gly Leu Arg Gln Gly Leu Ala Lys
225                 230                 235                 240

Gly Leu Ala Ile Gly Ser Asn Gly Val Val Phe Ala Ile Trp Ala Phe
                245                 250                 255

Met Ser Tyr Tyr Gly Ser Arg Leu Val Met Tyr His Gly Ala Lys Gly
            260                 265                 270

Gly Thr Val Phe Ala Val Gly Ala Ala Ile Ala Leu Gly Gly Leu Ala
        275                 280                 285

Leu Gly Ala Gly Leu Ser Asn Val Lys Tyr Phe Ser Glu Ala Ser Thr
    290                 295                 300

Ala Gly Glu Arg Ile Met Glu Val Ile Lys Arg Val Pro Lys Ile Asp
305                 310                 315                 320

Ser Asp Ser Met Ala Glu Glu Ile Leu Glu Asn Val Ser Gly Glu Val
                325                 330                 335

Glu Phe Asn His Val Asp Phe Val Tyr Pro Ser Arg Pro Asp Ser Val
            340                 345                 350

Ile Leu Asn Asp Phe Cys Leu Lys Ile Pro Ala Gly Lys Thr Val Ala
        355                 360                 365

Leu Val Gly Gly Ser Gly Ser Gly Lys Ser Thr Val Ile Ser Leu Leu
    370                 375                 380

Gln Arg Phe Tyr Asp Pro Ile Glu Gly Glu Ile Phe Leu Asp Gly Val
385                 390                 395                 400

Ala Ile His Lys Leu Gln Leu Lys Trp Leu Arg Ser Gln Met Gly Leu
                405                 410                 415
```

-continued

```
Val Ser Gln Glu Pro Ala Leu Phe Ala Thr Ser Ile Lys Glu Asn Ile
                420                 425                 430

Leu Phe Gly Arg Glu Asp Ala Thr Gln Glu Val Glu Ala Ala
        435                 440                 445

Lys Ala Ser Asn Ala His Asn Phe Ile Ser Gln Leu Pro Gln Gly Tyr
    450                 455                 460

Asp Thr Gln Val Gly Glu Arg Val Gln Met Ser Gly Gln Lys
465                 470                 475             480

Gln Arg Ile Ala Ile Ala Arg Ala Ile Lys Lys Pro Arg Ile Leu
            485                 490                 495

Leu Leu Asp Glu Ala Thr Ser Ala Leu Asp Ser Glu Ser Glu Arg Val
                500                 505                 510

Val Gln Glu Ala Leu Asp Lys Ala Ala Val Gly Arg Thr Thr Ile Ile
            515                 520                 525

Ile Ala His Arg Leu Ser Thr Ile Arg Asn Ala Asn Val Ile Ala Val
            530                 535                 540

Val Gln Ser Gly Lys Ile Met Glu Met Gly Ser His His Glu Leu Ile
545                 550                 555                 560

Gln Asn Asp Asn Gly Leu Tyr Thr Ser Leu Val Arg Leu Gln Gln Ala
                565                 570                 575

Lys Asn Glu Lys Glu Asp Thr Ile Phe His Pro Thr Pro Ser Ser
            580                 585                 590

Ile Ser Asn Lys Asp Asn His Asn Thr Ser Ser Arg Arg Leu Ser Val
            595                 600                 605

Val Met Ile Arg Ser Ser Ser Thr Asn Ser Ile Pro Arg Ile Gly Gly
            610                 615                 620

Gly Asp Asp Asn Asn Ile Val Glu Val Val Glu Asp Asn Lys Pro
625                 630                 635             640

Pro Leu Pro Ser Phe Arg Arg Leu Leu Ala Leu Asn Ile Pro Glu Trp
                645                 650                 655

Lys Gln Ala Cys Leu Gly Cys Leu Asn Ala Val Leu Phe Gly Ala Ile
                660                 665                 670

Gln Pro Val Tyr Ala Phe Ala Met Gly Ser Val Ile Ser Val Tyr Phe
            675                 680                 685

Leu Pro Asp His Asn Glu Ile Lys Lys Lys Thr Met Ile Tyr Ser Leu
            690                 695                 700

Cys Phe Leu Gly Leu Ala Val Phe Ser Leu Val Val Asn Ile Leu Gln
705                 710                 715                 720

His Tyr Asn Phe Ala Tyr Ile Gly Glu Tyr Leu Thr Lys Arg Ile Arg
                725                 730                 735

Glu Arg Met Phe Ser Lys Ile Leu Thr Phe Glu Val Gly Trp Phe Asp
            740                 745                 750

Gln Asp Glu Asn Ser Thr Gly Ala Val Cys Ser Arg Leu Ala Lys Glu
            755                 760                 765

Ala Asn Val Val Arg Ser Leu Val Gly Asp Arg Met Ala Leu Val Val
            770                 775                 780

Gln Thr Ile Ser Ala Val Val Ile Ala Phe Thr Met Gly Leu Ile Ile
785                 790                 795                 800

Ala Trp Arg Leu Ala Ile Val Met Ile Ala Val Gln Pro Ile Ile Ile
                805                 810                 815

Ala Cys Phe Tyr Thr Arg Arg Val Leu Leu Lys Ser Met Ser Ser Lys
            820                 825                 830
```

-continued

Ala Ile Lys Ala Gln Asp Glu Ser Lys Ile Ala Val Glu Ala Val
835                 840                 845

Ser Asn Leu Arg Thr Ile Thr Ala Phe Ser Ser Gln Asp Arg Ile Leu
850                 855                 860

Lys Met Leu Glu Lys Ala Gln Glu Gly Pro Ser Arg Glu Ser Ile Arg
865                 870                 875                 880

Gln Ser Trp Phe Ala Gly Ile Gly Leu Ala Cys Ser Gln Ser Leu Thr
                885                 890                 895

Phe Cys Thr Trp Ala Leu Asp Phe Trp Tyr Gly Gly Lys Leu Val Phe
                900                 905                 910

Gln Gly Phe Ile Asn Ala Lys Ala Leu Phe Glu Thr Phe Met Ile Leu
                915                 920                 925

Val Ser Thr Gly Arg Val Ile Ala Asp Ala Gly Ser Met Thr Asn Asp
930                 935                 940

Leu Ala Lys Gly Ala Asp Ala Val Gly Ser Val Phe Ala Ile Leu Asp
945                 950                 955                 960

Arg Tyr Thr Lys Ile Glu Pro Asp Asp Ile Asp Gly Tyr Lys Pro
                965                 970                 975

Glu Lys Leu Thr Gly Lys Ile Glu Leu His Asp Val His Phe Ala Tyr
                980                 985                 990

Pro Ala Arg Pro Asn Val Met Ile Phe Gln Gly Phe Ser Ile Lys Ile
                995                 1000                1005

Asp Ala Gly Arg Ser Thr Ala Leu Val Gly Gln Ser Gly Ser Gly
        1010                1015                1020

Lys Ser Thr Ile Ile Gly Leu Ile Glu Arg Phe Tyr Asp Pro Met
        1025                1030                1035

Lys Gly Ile Val Thr Ile Asp Gly Arg Asp Ile Lys Ser Tyr His
        1040                1045                1050

Leu Arg Ser Leu Arg Lys His Ile Ala Leu Val Ser Gln Glu Pro
        1055                1060                1065

Thr Leu Phe Gly Gly Thr Ile Arg Glu Asn Ile Ala Tyr Gly Ala
        1070                1075                1080

Ser Asn Asn Asn Lys Val Asp Glu Thr Glu Ile Ile Glu Ala
        1085                1090                1095

Ala Arg Ala Ala Asn Ala His Asp Phe Ile Ala Ser Leu Lys Asp
        1100                1105                1110

Gly Tyr Asp Thr Ser Cys Arg Asp Arg Gly Val Gln Leu Ser Gly
        1115                1120                1125

Gly Gln Lys Gln Arg Ile Ala Ile Ala Arg Ala Ile Leu Lys Asn
        1130                1135                1140

Pro Glu Val Leu Leu Leu Asp Glu Ala Thr Ser Ala Leu Asp Ser
        1145                1150                1155

Gln Ser Glu Lys Leu Val Gln Asp Ala Leu Glu Arg Val Met Val
        1160                1165                1170

Gly Arg Thr Ser Val Val Val Ala His Arg Leu Ser Thr Ile Gln
        1175                1180                1185

Asn Cys Asp Leu Ile Ala Val Leu Asp Lys Gly Lys Val Val Glu
        1190                1195                1200

Lys Gly Thr His Ser Ser Leu Leu Ala His Gly Pro Gly Gly Ala
        1205                1210                1215

Tyr Tyr Ser Leu Ile Ser Leu Gln Arg Arg Pro Ala Asn
        1220                1225                1230

-continued

```
<210> SEQ ID NO 129
<211> LENGTH: 1231
<212> TYPE: PRT
<213> ORGANISM: Glycine max

<400> SEQUENCE: 129
```

| | | | | | | | | | | | | | | | |
|---|---|---|---|---|---|---|---|---|---|---|---|---|---|---|---|
| Met | His | Ala | Asp | Gly | Leu | Asp | Trp | Phe | Leu | Met | Ile | Phe | Gly | Leu | Phe |
| 1 | | | | 5 | | | | | 10 | | | | | 15 | |
| Gly | Ala | Ile | Gly | Asp | Gly | Ile | Gly | Thr | Pro | Leu | Val | Leu | Phe | Ile | Thr |
| | | | 20 | | | | | 25 | | | | | 30 | | |
| Ser | Lys | Ile | Met | Asn | Asn | Ile | Gly | Gly | Phe | Ser | Ser | Asn | Ile | Gly | Ser |
| | | | 35 | | | | | 40 | | | | | 45 | | |
| Thr | Phe | Ile | His | Ser | Ile | Asn | Glu | Asn | Ala | Val | Val | Leu | Leu | Tyr | Leu |
| | 50 | | | | | 55 | | | | | 60 | | | | |
| Ala | Gly | Gly | Ser | Phe | Ile | Ala | Cys | Phe | Leu | Glu | Gly | Tyr | Cys | Trp | Thr |
| 65 | | | | | 70 | | | | | 75 | | | | | 80 |
| Arg | Thr | Gly | Glu | Arg | Gln | Ala | Ala | Arg | Met | Arg | Val | Arg | Tyr | Leu | Lys |
| | | | | 85 | | | | | 90 | | | | | 95 | |
| Ala | Val | Leu | Arg | Gln | Glu | Val | Ala | Tyr | Phe | Asp | Leu | His | Val | Thr | Ser |
| | | | 100 | | | | | 105 | | | | | 110 | | |
| Thr | Ser | Glu | Val | Ile | Thr | Ser | Val | Ser | Asn | Asp | Ser | Leu | Val | Ile | Gln |
| | | | 115 | | | | | 120 | | | | | 125 | | |
| Asp | Cys | Leu | Ser | Glu | Lys | Val | Pro | Asn | Phe | Leu | Met | Asn | Ala | Ser | Met |
| | 130 | | | | | 135 | | | | | 140 | | | | |
| Phe | Val | Gly | Ser | Tyr | Ile | Val | Ala | Phe | Ala | Leu | Leu | Trp | Arg | Leu | Ala |
| 145 | | | | | 150 | | | | | 155 | | | | | 160 |
| Ile | Val | Gly | Phe | Pro | Phe | Val | Ala | Leu | Leu | Val | Ile | Pro | Gly | Phe | Met |
| | | | | 165 | | | | | 170 | | | | | 175 | |
| Tyr | Gly | Arg | Thr | Leu | Met | Gly | Leu | Ala | Ser | Lys | Ile | Arg | Glu | Glu | Tyr |
| | | | 180 | | | | | 185 | | | | | 190 | | |
| Asn | Lys | Ala | Gly | Thr | Ile | Ala | Glu | Gln | Ala | Ile | Ser | Ser | Ile | Arg | Thr |
| | | | 195 | | | | | 200 | | | | | 205 | | |
| Val | Tyr | Ser | Phe | Val | Gly | Glu | Ser | Lys | Thr | Ile | Asp | Ala | Phe | Ser | Glu |
| | 210 | | | | | 215 | | | | | 220 | | | | |
| Ala | Leu | Gln | Gly | Ser | Val | Glu | Leu | Gly | Leu | Arg | Gln | Gly | Leu | Ala | Lys |
| 225 | | | | | 230 | | | | | 235 | | | | | 240 |
| Gly | Leu | Ala | Ile | Gly | Ser | Asn | Gly | Val | Val | Phe | Ala | Ile | Trp | Ala | Phe |
| | | | | 245 | | | | | 250 | | | | | 255 | |
| Met | Ser | Tyr | Tyr | Gly | Ser | Arg | Leu | Val | Met | Tyr | His | Gly | Ala | Lys | Gly |
| | | | 260 | | | | | 265 | | | | | 270 | | |
| Gly | Thr | Val | Phe | Ala | Val | Gly | Ala | Ala | Ile | Ala | Leu | Gly | Gly | Leu | Ala |
| | | | 275 | | | | | 280 | | | | | 285 | | |
| Leu | Gly | Ala | Gly | Leu | Ser | Asn | Val | Lys | Tyr | Phe | Ser | Glu | Ala | Ser | Thr |
| | 290 | | | | | 295 | | | | | 300 | | | | |
| Ala | Gly | Glu | Arg | Ile | Met | Glu | Val | Ile | Lys | Arg | Val | Pro | Lys | Ile | Asp |
| 305 | | | | | 310 | | | | | 315 | | | | | 320 |
| Ser | Asp | Ser | Met | Ala | Glu | Glu | Ile | Leu | Glu | Asn | Val | Ser | Gly | Glu | Val |
| | | | | 325 | | | | | 330 | | | | | 335 | |
| Glu | Phe | Asn | His | Val | Asp | Phe | Val | Tyr | Pro | Ser | Arg | Pro | Asp | Ser | Val |
| | | | 340 | | | | | 345 | | | | | 350 | | |
| Ile | Leu | Asn | Asp | Phe | Cys | Leu | Lys | Ile | Pro | Ala | Gly | Lys | Thr | Val | Ala |
| | | | 355 | | | | | 360 | | | | | 365 | | |
| Leu | Val | Gly | Gly | Ser | Gly | Ser | Gly | Lys | Ser | Thr | Val | Ile | Ser | Leu | Leu |
| | 370 | | | | | 375 | | | | | 380 | | | | |

-continued

```
Gln Arg Phe Tyr Asp Pro Ile Glu Gly Glu Ile Phe Leu Asp Gly Val
385                 390                 395                 400

Ala Ile His Lys Leu Gln Leu Lys Trp Leu Arg Ser Gln Met Gly Leu
            405                 410                 415

Val Ser Gln Glu Pro Ala Leu Phe Ala Thr Ser Ile Lys Glu Asn Ile
        420                 425                 430

Leu Phe Gly Arg Glu Asp Ala Thr Gln Glu Glu Val Val Glu Ala Ala
    435                 440                 445

Lys Ala Ser Asn Ala His Asn Phe Ile Ser Gln Leu Pro Gln Gly Tyr
450                 455                 460

Asp Thr Gln Val Gly Glu Arg Gly Val Gln Met Ser Gly Glu Gln Lys
465                 470                 475                 480

Gln Arg Ile Ala Ile Ala Arg Ala Ile Ile Lys Lys Pro Arg Ile Leu
            485                 490                 495

Leu Leu Asp Glu Ala Thr Ser Ala Leu Asp Ser Glu Ser Glu Arg Val
        500                 505                 510

Val Gln Glu Ala Leu Asp Lys Val Ala Val Gly Arg Thr Thr Ile Ile
    515                 520                 525

Ile Ala His Arg Leu Ser Thr Ile Arg Asn Ala Asn Val Ile Ala Val
530                 535                 540

Val Gln Ser Gly Lys Ile Met Glu Met Gly Ser His His Glu Leu Ile
545                 550                 555                 560

Gln Asn Asp Asn Gly Leu Tyr Thr Ser Leu Val Arg Leu Gln Gln Ala
            565                 570                 575

Lys Asn Glu Lys Glu Asp Thr Leu Phe His Pro Thr Pro Ser Ser
        580                 585                 590

Ile Ser Asn Lys Asp Asn His Asn Thr Ser Ser Arg Arg Leu Ser Val
    595                 600                 605

Val Met Ser Arg Ser Ser Ser Thr Asn Ser Ile Pro Arg Ile Gly Gly
610                 615                 620

Gly Asp Asp Asn Asn Ile Val Glu Glu Val Val Glu Asp Asn Lys Pro
625                 630                 635                 640

Pro Leu Pro Ser Phe Arg Arg Leu Leu Ala Leu Asn Ile Pro Glu Trp
            645                 650                 655

Lys Gln Ala Cys Leu Gly Cys Leu Asn Ala Val Leu Phe Gly Ala Ile
        660                 665                 670

Gln Pro Val Tyr Ala Phe Ala Met Gly Ser Val Ile Ser Val Tyr Phe
    675                 680                 685

Leu Pro Asp His Asn Glu Ile Lys Lys Lys Thr Met Ile Tyr Ser Leu
690                 695                 700

Cys Phe Leu Gly Leu Ala Val Phe Ser Leu Val Val Asn Ile Leu Gln
705                 710                 715                 720

His Tyr Asn Phe Ala Tyr Ile Gly Glu Tyr Leu Thr Lys Arg Ile Arg
            725                 730                 735

Glu Arg Met Phe Ser Lys Ile Leu Thr Phe Glu Val Gly Trp Phe Asp
        740                 745                 750

Gln Asp Glu Asn Ser Thr Gly Ala Val Cys Ser Arg Leu Ala Lys Glu
    755                 760                 765

Ala Asn Val Val Arg Ser Leu Val Gly Asp Arg Met Ala Leu Val Val
770                 775                 780

Gln Thr Ile Ser Ala Val Val Ile Ala Phe Thr Met Gly Leu Ile Ile
785                 790                 795                 800

Ala Trp Arg Leu Ala Ile Val Met Ile Ala Val Gln Pro Ile Ile Ile
```

-continued

```
                805                 810                 815
Ala Cys Phe Tyr Thr Arg Arg Val Leu Leu Lys Ser Met Ser Ser Lys
                    820                 825                 830

Ala Ile Lys Ala Gln Asp Glu Ser Lys Ile Ala Val Glu Ala Val
                    835                 840                 845

Ser Asn Leu Arg Thr Ile Thr Ala Phe Ser Ser Gln Asp Arg Ile Leu
                    850                 855                 860

Lys Met Leu Glu Lys Ala Gln Glu Gly Pro Ser Arg Glu Ser Ile Arg
865                 870                 875                 880

Gln Ser Trp Phe Ala Gly Ile Gly Leu Ala Cys Ser Gln Ser Leu Thr
                    885                 890                 895

Phe Cys Thr Trp Ala Leu Asp Phe Trp Tyr Gly Gly Lys Leu Val Phe
                    900                 905                 910

Gln Gly Phe Ile Asn Ala Lys Ala Leu Phe Glu Thr Phe Met Ile Leu
                    915                 920                 925

Val Ser Thr Gly Arg Val Ile Ala Asp Ala Gly Ser Met Thr Asn Asp
                    930                 935                 940

Leu Ala Lys Gly Ala Asp Ala Val Gly Ser Val Phe Ala Ile Leu Asp
945                 950                 955                 960

Lys Tyr Thr Lys Ile Glu Pro Asp Asp Ile Asp Gly Tyr Lys Pro
                    965                 970                 975

Glu Lys Leu Thr Gly Lys Ile Glu Leu His Asp Val His Phe Ala Tyr
                    980                 985                 990

Pro Ala Arg Pro Asn Val Met Ile Phe Gln Gly Phe Ser Ile Lys Ile
                    995                1000                1005

Asp Ala  Gly Arg Ser Thr Ala  Leu Val Gly Gln Ser  Gly Ser Gly
    1010                1015                1020

Lys Ser  Thr Ile Ile Gly Leu  Ile Glu Arg Phe Tyr  Asp Pro Leu
    1025                1030                1035

Lys Gly  Ile Val Thr Ile Asp  Gly Arg Asp Ile Lys  Ser Tyr His
    1040                1045                1050

Leu Arg  Ser Leu Arg Lys His  Ile Ala Leu Val Ser  Gln Glu Pro
    1055                1060                1065

Thr Leu  Phe Gly Gly Thr Ile  Arg Glu Asn Ile Ala  Tyr Gly Ala
    1070                1075                1080

Ser Asn  Asn Asn Asn Lys Val  Asp Glu Thr Glu Ile  Ile Glu Ala
    1085                1090                1095

Ala Arg  Ala Ala Asn Ala His  Asp Phe Ile Ala Ser  Leu Lys Asp
    1100                1105                1110

Gly Tyr  Asp Thr Ser Cys Gly  Asp Arg Gly Val Gln  Leu Ser Gly
    1115                1120                1125

Gly Gln  Lys Gln Arg Ile Ala  Ile Ala Arg Ala Ile  Leu Lys Asn
    1130                1135                1140

Pro Glu  Val Leu Leu Leu Asp  Glu Ala Thr Ser Ala  Leu Asp Ser
    1145                1150                1155

Gln Ser  Glu Lys Leu Val Gln  Asp Ala Leu Glu Arg  Val Met Val
    1160                1165                1170

Gly Arg  Thr Ser Val Val Val  Ala His Arg Leu Ser  Thr Ile Gln
    1175                1180                1185

Asn Cys  Asp Leu Ile Ala Val  Leu Asp Lys Gly Lys  Val Val Glu
    1190                1195                1200
```

```
Lys Gly Thr His Ser Ser Leu Leu Ala His Gly Pro Gly Gly Ala
    1205                1210                1215

Tyr Tyr Ser Leu Ile Ser Leu Gln Arg Arg Pro Ala Asn
    1220                1225                1230
```